United States Patent [19]
Rio et al.

[11] Patent Number: 5,981,218
[45] Date of Patent: Nov. 9, 1999

[54] ISOLATED NUCLEIC ACID MOLECULES USEFUL AS LEUKEMIA MARKERS AND IN BREAST CANCER PROGNOSIS AND ENCODED POLYPEPTIDES

[75] Inventors: Marie-Christine Rio, Illkirch; Catherine Tomasetto; Paul Basset, both of Strasbourg, all of France; Jennifer Byrne, Ashfield, Australia

[73] Assignees: Bristol-Myers Squibb Company, Princeton, N.J.; Institut National de la Santé et de la Recherche Médicale; Centre National de la Recherche Scientifique, both of Paris Cedex, France; Université Louis Pasteur, Strasbourg Cedex, France

[21] Appl. No.: 08/691,814

[22] Filed: Jul. 31, 1996

Related U.S. Application Data

[60] Provisional application No. 60/002,183, Aug. 9, 1995.

[51] Int. Cl.$^6$ ............ C12N 15/11; C12N 15/09; C12N 5/10; C07K 14/705
[52] U.S. Cl. ............ 435/69.1; 536/24.31; 536/23.1; 536/23.5; 530/300; 530/350; 435/320.1; 435/325; 435/252.3; 435/254.11
[58] Field of Search .................... 536/23.5, 24.31, 536/23.1; 530/350, 300; 435/69.1, 320.1, 325, 254.11, 252.3

[56] References Cited

U.S. PATENT DOCUMENTS

| | | | |
|---|---|---|---|
| 5,556,956 | 9/1996 | Roy et al. | 536/24.1 |
| 5,618,717 | 4/1997 | Wei et al. | 435/325 |

FOREIGN PATENT DOCUMENTS

WO 95/19369  7/1995  WIPO .

OTHER PUBLICATIONS

Pearson et al., Improved tools for biological sequence comparison, Proc. Natl. Acad. Sci. USA, 85: 2444–2448, Apr. 1988.

Adams, M.D. et al., "Sequence identification of 2,375 human brain genes," *Nature* 355:632–634 (1992).

Adams, M.D. et al., "Rapid cDNA sequencing (expressed sequence tags) from a directionally cloned human infant brain cDNA library," *Nat. Genet.* 4(4):373–380 (1993).

Basset, P. et al., "A novel metalloproteinase gene specifically expressed in stromal cells of breast carninomas," *Nature* 348:699–704 (1990).

Borg, A. et al., "ERBB2 amplification in breast cancer with a high rate of proliferation," *Oncogene* 6:137–143 (1991).

Byrne, J.A. et al., "A Screening Method to Identify Genes Commonly Overexpressed in Carcinomas and the Identification of a Novel Complementary DNA Sequence," *Cancer Res.* 55:(13):2896–2903 (Jul. 1995).

Contesso, G. et al., "Tumor Grade as a Prognostic Factor in Primary Breast Cancer," *Eur. J. Clin. Oncol.* 25(3):403–409 (1989).

Dang, C.V. & Lee, W.M.F., "Nuclear and Nucleolar Targeting Seuqences of c–erb–A, c–myb, N–myc, p53, HSP70, and HIV tat Proteins," *J. Biol. Chem.* 264(30):18019–18023 (1989).

(List continued on next page.)

*Primary Examiner*—Lila Feisee
*Assistant Examiner*—Claire M. Kaufman
*Attorney, Agent, or Firm*—Sterne, Kessler, Goldstein & Fox P.L.L.C.

[57] ABSTRACT

The present invention relates to four novel human genes amplified and overexpressed in breast carcinoma and located on the q11-q21.3 region of chromosome 17. The four novel genes are useful in breast cancer prognosis. The present invention also relates to a fifth novel human gene expressed in breast carcinoma and located on chromosome 6q22-q23. A sixth novel gene is also described that is the murine homolog of the human D52 gene. The genes and gene fragments of the present invention are themselves useful as DNA and RNA probes for gene mapping by in situ hybridization with chromosomes and for detecting gene expression in human tissues (including breast and lymph node tissues) by Northern blot analysis.

48 Claims, 45 Drawing Sheets

OTHER PUBLICATIONS

Dingwall, C. & Laskey, R.A., "Nuclear targeting sequnces—a consensus?" *TIBS* 16:478–481 (1991).

Dougall, W.C. et al., "The neu–onocogene: signal transduction pathways, transformation mechanisms and evolving therapies," *Oncogene* 9(8):2109–2123 (1994).

Driscoll, D.M. & Williams, J.G., "Two Divergently Transcribed Genes of *Dictyostelium discoideum* Are Cyclic AMP–Inducible and Coregulated during Development," *Mol. Cell. Biol.* 7(12):4482–4489 (1987).

Elias, J.M. et al., "Paraffin Embedded Breast Carcinomas for the Immunohistochemical Study of Prognostic Factors," *J. Histotechnol.* 15(4):315–320 (1992).

Fidler, I.J. & Ellis, L.M., "The Implications of Angiogenesis for the Biology and Therapy of Cancer Metastasis," *Cell* 79(2):185–188 (1994).

Freemont, P.S., "The RING Finger: A Novel Protein Sequence Motif Related to the Zinc Finger," *Ann. N.Y. Acad. Sci.* 684:174–192 (1993).

Fukushige, S.–I. et al., "Localization of a Novel–v–erb-B–Related Gene, c–erbB–2, on Human Chromosome 17 and Its Amplification in a Gastric Cancer Cell Line," *Mol. Cell. Biol.* 6(3):955–958 (1986).

Futreal, P.A. et al., "BRCA1 Mutations in Primary Breast and Ovarian Carcinomas," *Science* 266:120–122 (1994).

Hall, J.M. et al., "Linkage of Early–Onset Familial Breast Cancer to Chromosome 17q21," *Science* 250:1684–1689 (1990).

Hu, H.M. et al., "A Novel RING Finger Protein Interacts with the Cytoplasmic Domain of CD40," *J. Biol. Chem.* 269(48):30069–30072 (1994).

Kallioniemi, A. et al., "Detection and mapping of amplified DNA squences in breast cancer by comparative genomic hybridization," *Proc. Natl. Acad. Sci. USA* 91:2156–2160 (1994).

Karlseder, J. et al., "Patterns of DNA Amplification at Band q13 of Chromosome 11 in Human Breast Cancer," *Genes Chrom. Cancer* 9:42–48 (1994).

Kirchweger, R. et al., "Patterns of Allele Losses Suggest the Existence of Five Distinct Regions of LOH on Chromosome 17 in Breast Cancer," *Intl. J. Cancer* 56(2):193–199 (1994).

Liebhaber, S.A. et al., "Characterization of a human cDNA encoding a widely expressed and highly conserved cystein-–rich protein with an unusual zinc–finger motif," *Nucl. Acids Res.* 18(13):3871–3879 (1990).

Lönn, U. et al., "Intratumoral Heterogeneity for Amplified Genes in Human Breast Carcinoma," *Intl. J. Cancer* 58:40–45 (1994).

Lyon, M.F. & Kirby, M.C., "Mouse Chromosome Atlas," *Mouse Genome* 93(1):23–66 (Mar. 1995).

McGuire, W.L., "Adjuvant Therapy of Node–Negative Breast Cancer," *New Eng. J. Med.* 320(8):525–527 (1989).

Miki, Y. et al., "A Strong Candidate for the Breast and Ovarian Cancer Susceptibility Gene BRCA1," *Science* 266:66–71 (1994).

Muss, H.B. et al, "c–erbB–2 Expression and Response to Adjuvant Therapy in Women with Node–Positive Early Breast Cancer," *N. Engl. J. Med.* 330(18):1260–1266 (1994).

Okubo, K. et al., "Large Scale cDNA sequencing for analysis of quantitative and qualitative aspects of gene expression," *Nat. Genetics* 2(3):173–179 (1992).

Paterson, M.C. et al., "Correlation between c–erbB–2 Amplification and Risk of Recurrent Disease in Node–negative Breast Cancer," *Cancer Res.* 51(2):556–567 (1991).

Ravdin, P.M. & Chamness, G.C., "The c–erbB–2 proto–oncogene as a prognostic and predictive marker in breast cancer: a paradigm for the development of other macromolecular markers—a review," *Gene* 159(1):19–27 (Jun. 1995).

Razafimahatratra, P. et al., "Nucleotide sequence and expression of a maize H1 histone cNDA," *Nucl. Acids Res.* 19(7):1491–1496 (1991).

Regnier, C.H. et al., "Presence of a New Conserved Domain in CART1, a Novel Member of the Tumor Necrosis Factor Receptor–associated Protein Family, Which Is Expressed in Breast Carcinoma," *J. Biol. Chem.* 270(43):25715–25721 (Oct. 1995).

Reifenberger, G. et al., "Amplification of Multiple Genes from Chromosomal Region 12q13–14 in Human Malignant Gliomas: Preliminary Mapping of the Amplification Shows Preferential Involvement of CDK4, SAS, and MDM2," *Cancer Res.* 54(16):4299–4303 (1994).

Rothe, M. et al., "A Novel Family of Putative Signal Transducers Associated with the Cytoplasmic Domain of the 75 kDa Tumor Necrosis Factor Domain," *Cell* 78:681–692 (1994).

Sillard, R. et al., "Chemical assay for cyst(e)ine–rich peptides detects a novel intestinal peptide ZF–1, homologous to a single zinc–finger motif," *Eur. J. Biochem.* 211(1/2):377–380 (1993).

Takeda, J. et al., "A molecular inventory of human pancreatic islets: sequence analysis of 1000 cDNA clones," *Hum. Mol. Gen.* 2(11):1793–1798 (1993).

Thomasetto, C. et al., "Identification of Four Novel Human Genes Amplified and Overexpressed in Breast Carcinoma and Localized to the q11–q21.3 Region of Chromosome 17," *Genomics* 28(3):367–376 (Aug. 1995).

Waye, M.M.Y. & Li, V.K.C., "Isolation of cDNA Clones From an Osteosarcoma–ROS17/2.8 Library by Differential Hybridization," *J. Cell. Biochem.* 54(3):273–280 (1994).

Weinstock, K.G. et al., "cDNA sequencing: a means of understanding cellular physiology," *Curr. Opin. Biotech.* 5(6):599–603 (1994).

Wilson, R. et al., "2.2. Mb of contiguous nucleotide sequence from chromosome III of *C. elegans*," *Nature* 368:32–38 (1994).

Yang, P. et al., "Molecular cloning and nucleotide sequences of cDNAs for histone H1 and H3B variants from wheat," *Nucl. Acids Res.* 19(18):5077 (1991).

Zou, Z. et al., "Maspin, a Serpin with Tumor–Suppressing Activity in Human Mammary Epithelial Cells," *Science* 263:526–529 (1994).

GenBank Accession No. D11736.
GenBank Accession No. D12116.
GenBank Accession No. D19971.
GenBank Accession No. D73047.
GenBank Accession No. D73326.
GenBank Accession No. D76021.
GenBank Accession No. D76362.
GenBank Accession Number F04305.
GenBank Accession Number F06105.
GenBank Accession Number M85471.
GenBank Accession No. M86141.
GenBank Accession No. N21784.
GenBank Accession No. R02020.
GenBank Accession No. R02021.

GenBank Accession No. R12544.
GenBank Accession No. R17500.
GenBank Accession No. R36697.
GenBank Accession No. R37445.
GenBank Accession No. R37545.
GenBank Accession No. R41043.
GenBank Accession No. R42594.
GenBank Accession No. R48774.
GenBank Accession No. R48877.
GenBank Accession No. R61143.
GenBank Accession No. R61861.
GenBank Accession No. S70803.
GenBank Accession No. T08349.
GenBank Accession No. T08601.
GenBank Accession No. T10815.
GenBank Accession No. T15543.
GenBank Accession No. T24771.
GenBank Accession No. T32123.
GenBank Accession No. T32139.
GenBank Accession No. T32161.
GenBank Accession No. T33692.
GenBank Accession No. T33826.
GenBank Accession No. T34065.
GenBank Accession No. T34158.
GenBank Accession No. T34342.
GenBank Accession No. T41053.
GenBank Accession No. T40174.
GenBank Accession No. T49922.
GenBank Accession No. T51225.
GenBank Accession No. T51339.
GenBank Accession No. T60382.
GenBank Accession No. T61881.
GenBank Accession No. T64889.
GenBank Accession No. T68402.
GenBank Accession No. T85372.
GenBank Accession No. T85470.
GenBank Accession No. T89899.
GenBank Accession No. T93647.
GenBank Accession No. T96972.
GenBank Accession No. T97084.
GenBank Accession No. X80198.
GenBank Accession No. X80199.
GenBank Accession No. X80200.
GenBank Accession No. X82456.
GenBank Accession No. Z25173.
GenBank Accession No. Z45434.
GenBank Accession No. EMBL Z68105.
GenBank Accession No. T93603, Mar. 23, 1995.
Stratagene Cloning Systems 1994 Catalog, Stratagene Cloning Systems: CA. pp. 40, 167, 290, 1994.
GenBank Accession No. R05588, Apr. 3, 1995.
GenBank Accession No. X96702, Mar. 7, 1996.
Adnane, J., et al., "BEK and FLG, two receptors to members of the FGF family, are amplified in subsets of human breast cancers," *Oncogene* 6:659–663 (1991).
Biéche, I., et al., "Two Distinct Amplified Regions at 17q11–q21 Involved in Human Primary Breast Cancer," *Cancer Res.* 56:3886–3890 (Sep. 1996).
Chen, Z., and Sager, R., "Differential Expression of Human Tissue Factor in Normal Mammary Epithelial Cells and in Carcinomas," *Molecular Medicine* 1:153–160 (Jan. 1995).
Lawrence, H.J., et al., "Expression of the HOXA10 homebox gene as a molecular marker or myeloid leukemia," *Proc. Ann. Meet. Am. Assoc. Cancer Res.* 35:217 (Abstract No. 1297) (Mar. 1994).
EMBL Databank Accession No. S60681 (Jul. 19, 1996).
EMBL Databank Accession No. S60682 (Jul. 19, 1996).
Cheng et al., Involvement of CRAF1, a relative of TRAF, in CD40 signaling, Science, 267: 1494–1498, Mar. 1995.

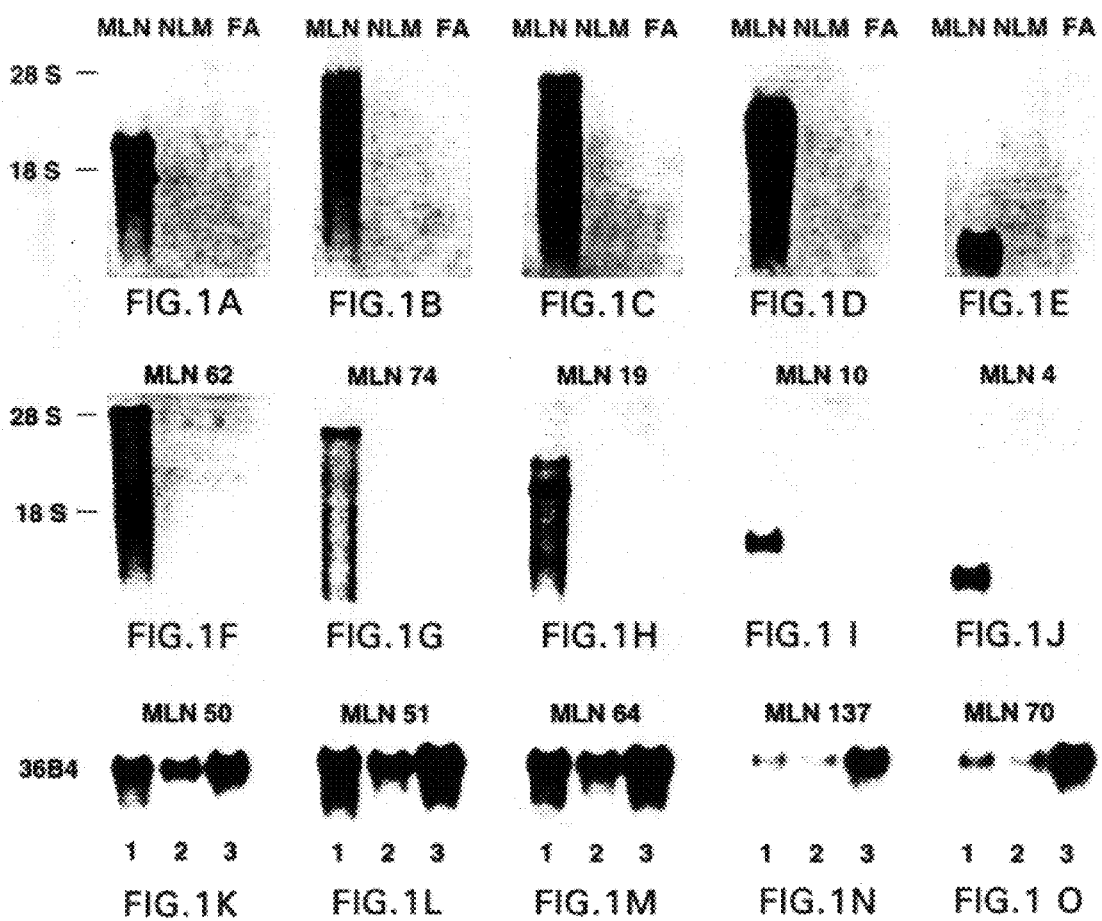

```
CCGGGAGCGCCGCTCCAGCGAGGCGCGGGCTGTGGGGCCGCCGCGTGCCTGGCCCCGCTC      60
GCCCGTGCCGGCCGCTCGCCCGCCATGCCTGGCTTCGACTACAAGTTCCTGGAGAAGCCC     120
                   M  P  G  F  D  Y  K  F  L  E  K  P            12
AAGCGACGGCTGCTGTGCCCACTGTGCGGGAAGCCCATGCGCGAGCCTGTGCAGGTTTCC     180
 K  R  R  L  L  C  P  L  C  G  K  P  M  R  E  P  V  Q  V  S      32
ACCTGCGGCCACCGTTTCTGCGATACCTGCCTGCAGGAGTTCCTCAGTGAAGGAGTCTTC     240
 T  C  G  H  R  F  C  D  T  C  L  Q  E  F  L  S  E  G  V  F      52
AAGTGCCCTGAGGACCAGCTTCCTCTGGACTATGCCAAGATCTACCCAGACCCCGGAGCTG    300
 K  C  P  E  D  Q  L  P  L  D  Y  A  K  I  Y  P  D  P  E  L      72
GAAGTACAAGTATTGGGCCTGCCTATCCGCTGCATCCACAGTGAGGAGGGCTGCCGCTGG     360
 E  V  Q  V  L  G  L  P  R  C  I  H  S  E  E  G  C  R  W         92
AGTGGGCCACTACGTCATCTACAGGGCCACCTGAATACCTGCAGCTTCAATGTCATTCCC     420
 S  G  P  L  R  H  L  Q  G  H  L  N  T  C  S  F  N  V  I  P     112
TGCCCTAATCGCTGCCCCATGAAGCTGAGCCGCCGTGATCTACCTGCACACTTGCAGCAT     480
 C  P  N  R  C  P  M  K  L  S  R  R  D  L  P  A  H  L  Q  H     132
GACTGCCCCAAGCGGCGCCTCAAGTGCGAGTTTTGTGGCTGTGACTTCAGTGGGGAGGCC     540
 D  C  P  K  R  R  L  K  C  E  F  C  G  C  D  F  S  G  E  A     152
TATGAGAGCCATGAGGGTATGTGCCCCCAGGAGAGTGTCTACTGTGAGAATAAGTGTGGT     600
 Y  E  S  H  E  G  M  C  P  Q  E  S  V  Y  C  E  N  K  C  G     172
GCCCGCATGATGCGGGGGCTGCTGGCCCAGCATGCCACCTCTGAGTGCCCCAAGCGCACT    660
 A  R  M  M  R  G  L  L  A  Q  H  A  T  S  E  C  P  K  R  T     192
CAGCCCTGCACCTACTGCACTAAGGAGTTCGTCTTTGACACCATCCAGAGCCACCAGTAC    720
 Q  P  C  T  Y  C  T  K  E  F  V  F  D  T  I  Q  S  H  Q  Y     212
CAGTGCCCAAGGCTGCCTGTTGCCTGCCCCAACCAATGTGGTGTGGGCACTGTGGCTCGG    780
 Q  C  P  R  L  P  V  A  C  P  N  Q  C  G  V  G  T  V  A  R     232
GAGGACCTGCCAGGCCATCTGAAGGACAGCTGTAACACCGCCCTGGTGCTCTGCCCATTC    840
 E  D  L  P  G  H  L  K  D  S  C  N  T  A  L  V  L  C  P  F     252
AAAGACTCCGGCTGCAAGCACAGGTGCCCTAAGCTGGCAATGGCACGGCATGTGGAGGAG    900
 K  D  S  G  C  K  H  R  C  P  K  L  A  M  A  R  H  V  E  E     272
AGTGTGAAGCCACATCTGGCCATGATGTGTGCCCTGGTGAGCCGGCAACGGCAGGAGCTG    960
 S  V  K  P  H  L  A  M  M  C  A  L  V  S  R  Q  R  Q  E  L     292
CAGGAGCTTCGGCGAGAGCTGGAGGAGCTATCAGTGGGCAGTGATGGCGTGCTCATCTGG   1020
 Q  E  L  R  R  E  L  E  E  L  S  V  G  S  D  G  V  L  I  W     312
AAGATTGGCAGCTATGGACGGCGGCTACAGGAGGCCAAGGCCAAGCCCAACCTTGAGTGC   1080
 K  I  G  S  Y  G  R  R  L  Q  E  A  K  A  K  P  N  L  E  C     332
TTCAGCCCAGCCTTCTACACACATAAGTATGGTTACAAGCTGCAGGTGTCTGCATTCCTC   1140
 F  S  P  A  F  Y  T  H  K  Y  G  Y  K  L  Q  V  S  A  F  L     352
AATGGCAATGGCAGTGGTGAGGGCACACACCTCTCACTGTACATTCGTGTGCTGCCTGGT   1200
 N  G  N  G  S  G  E  G  T  H  L  S  L  Y  I  R  V  L  P  G     372
GCCTTTGACAATCTCCTTGAGTGGCCCTTTGCCCGCCGTGTCACCTTCTCCCTGCTGGAT   1260
 A  F  D  N  L  L  E  W  P  F  A  R  R  V  T  F  S  L  L  D     392
CAGAGCGACCCTGGGCTGGCTAAACCACAGCACGTCACTGAGACCTTCCACCCCGACCCA   1320
 Q  S  D  P  G  L  A  K  P  Q  H  V  T  E  T  F  H  P  D  P     412
```

FIG.6A

```
AACTGGAAGAATTTCCAGAAGCCAGGCACGTGGCGGGGCTCCCTGGATGAGAGTTCTCTG   1380
 N  W  K  N  F  Q  K  P  G  T  W  R  G  S  L  D  E  S  S  L    432
GGCTTTGGTTATCCCAAGTTCATCTCCCACCAGGACATTCGAAAGCGAAACTATGTGCGG   1440
 G  F  G  Y  P  K  F  I  S  H  Q  D  I  R  K  R  N  Y  V  R    452
GATGATGCAGTCTTCATCCGTGCTGCTGTTGAACTGCCCCGGAAGATCCTCAGCTGAGTG   1500
 D  D  A  V  F  I  R  A  A  V  E  L  P  R  K  I  L  S  *       470
CAGGTGGGGTTCGAGGGGAAAGGACGATGGGGCATGACCTCAGTCAGGCACTGGCTGAAC   1560
TTGGAGAGGGGGCCGGACCCCCGTCAGCTGCTTCTGCTGCCTAGGTTCTGTTACCCCATC   1620
CTCCCTCCCCCAGCCACCACCCTCAGGTGCCTCCAATTGGTGCTTCAGCCCTGGCCCCTG   1680
TGGGGAACAGGTCTTGGGGTCATGAAGGGCTGGAAACAAGTGACCCCAGGGCCTGTCTCC   1740
CTTCTTGGGTAGGGCAGACATGCCTTGGTGCCGGTCACACTCTACACGGACTGAGGTGCC   1800
TGCTCAGGTGCTATGTCCCAAGAGCCATAAGGGGGTGGGAATTGGGGAGGGAGAAAGGGT   1860
AGTTCAAAGAGTCTGTCTTGAGATCTGATTTTTTCCCCCTTTACCTAGCTGTGCCCCCTC   1920
TGGTTATTTATTTCCTTAGTGCCAGGAGGGCACAGCAGGGGAGCCCTGATTTTTAATAAA   1980
TCCGGAATTGTATTTATTAAAAAA                                       2004
```

FIG.6B

| | | | | | | |
|---|---|---|---|---|---|---|
| CART1 | (101–154) | GHLNT.CSFN | VITPCPNR.CPM | .KLSRRDLPAH | LQHDCPKRRL | KCEF.....CG | CDFSGEAYE |
| CART1 | (155–208) | SHEGM.CPQE | SMYCENK.CGA | .RMMRGLLAQH | ATSECPKRITQ | PCTY.....CT | KEFVFDITIQ |
| CARR1 | (209–267) | SHQYQ.CPRL | PVACPNQ.CGV | GTVAREDLPGH | LKDSCNTALM | LCPFKDSGCK | HRCPKLAMA |
| CD40bp | (134–189) | VHLKNDCHFE | ELPCVRPDCKE | .KVLRKDLRDH | VEKACKYREA | TCSH.....CK | SQVPMIALQ |
| CD40bp | (190–248) | KHEDTDCPCV | VMSCPHK.CSV | QTLLRSELSAH | LSE.CVNAPS | TCSFKRYGCV | FQGTNQQIK |
| TRAF2 | (124–176) | CHEGL.CPFL | LTECP.A.CKG | LVRLSEKEHH | TEQECPKRSL | SCQH.....CR | APCSHVDLE |
| TRAF2 | (177–238) | VHYEV.CPKF | PLTCD.G.CGK | KKIPRETFQDH | VRA.CSKCRV | LCRFHTVGCS | EMVETENLQ |
| DG17 | (193–250) | THYKIT.CPMV | PIDCSQG.CSV | .KIERKSIIDH | IENDCCNTQI | PCKYFEQGCK | VEMKRSELQ |
| consensus | | H C | C C | H | C | C C | C |

FIG.9

```
CART1   (308-387)  GVL IWKI GSY GRRL QEE AKAKPN LECF SPAFYT HKYGYKL QVSAFL NGNGSGE G THLSLYI RVLFGAFDNL LEWPF ARRVT
CD40bp  (415-494)  GVL IWK IRDY KRRKQE AVMGKTL SLYSQPF YTGYF GYKMC ARVYLNGDQMGKG THLSLFF VIMRGEYDALL PWPF KQKVT
TRAF1   (260-339)  GTF LWK ITNVTKRCHE S VCGRT VSL FSPAF YT AKYGYKL CLRL YLNGDSGK KT HLSLF I VIMRGEYDALL PWPF RNKVT
TRAF2   (352-431)  GVF IWK ISDF TRK RQEA VAGRT PAIF SPAFYT SRYGYKM CLRVYLNGDTGRG THLSLFF VVMKGPNDALL QWPF NQKVT consensus          GV  IWKI     Y RR   QEAV GRTL  LFSPAFYT KYGYK  CLRVYLNGDGSKG THLSLF  VIMRG YDALL  WPF  QKVT
                       L        F KK             RF        V LF         T R       Y V K   F            NR CART1   (388-470)  FSL LDQSDPGL AKPQH VTETF HPDPNWKN F QKPG TWRGSL DESSL GFGYPKF . . I SHQD IRK RNYVRDDAVF TRAAVEL PRKILS
CD40bp  (495-567)  LMLM DQGS. . . . . SRRHL GDAFKPDPNS SSF KKP . . . . . . . TGEMN IASGCCPVF VAQTVLENGT . . YIKDDTI LFI KVI VDTT SDL PDP
TRAF1   (340-409)  FML LDQNN. . . . . . REHA I DAFRPD LSSA SFQRP . . . . . . . QSETN VASGCPL FF PLSKLQSPK HAYVKDDT MFLKCI VDT SA
TRAF2   (432-501)  LML DHNN. . . . . . REHV I DAFRPD VTSSS FQRP . . . . . . . VSDMN IASGCPL FC PVSKME . AKNSYVRDDA I TFIKAIVDLT GL consensus          MLLDQ        R HV  DAFRPD   S SFQRP                E NIASGCPLF  PLS    E    K    YVRDD  IFIK  IVD  S L
                                L E K                                 D V   VT        D        IK    V LR       E T
```

FIG.10

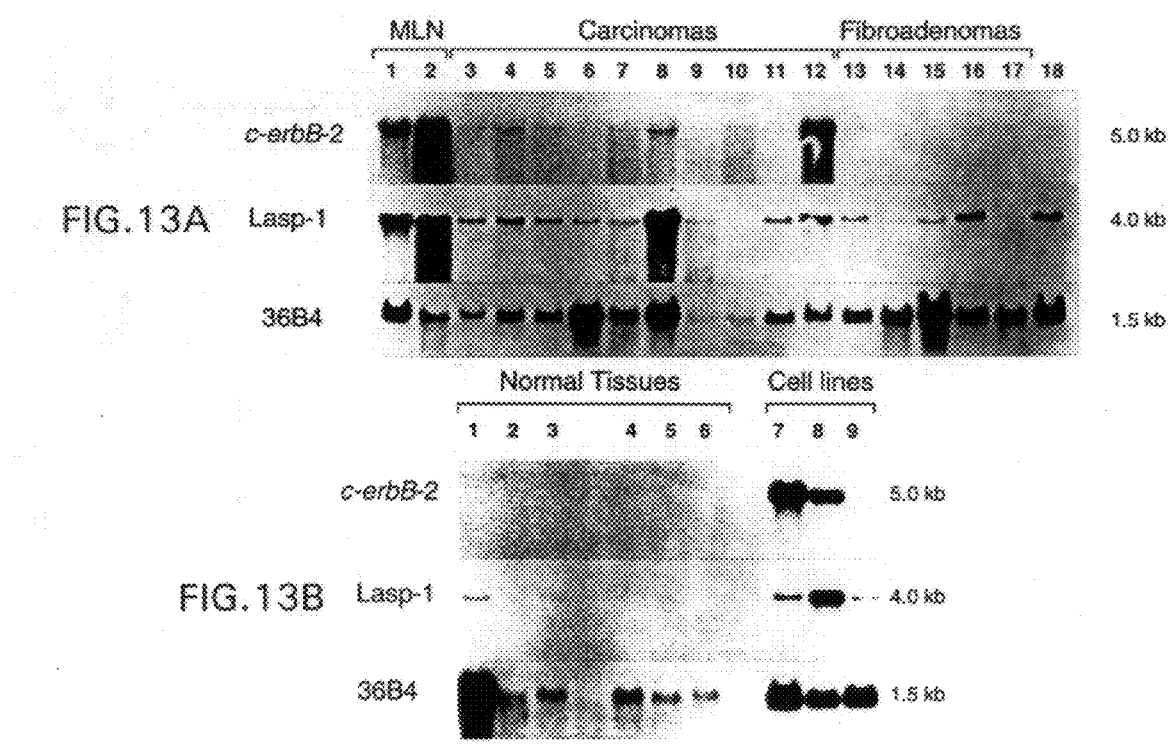

FIG. 14A

```
1801 GAAGATGTCTCAGAGCCTTCCATGACCTCCCCTCCCCAGCCCAATGCCAAGTGGACTTGGAGCTGCACAAAGTCAGCAGGACCACTAAATCTCCAAGAC
1901 CTGGTGTGCGGAGGCAGGAGCATGTATGTCTGCAGGTGTCTGACACGCAAGTGTCTGAGTGTGAGAGATGGGGCGGGGGTGTGTCTGTAGGTGT
2001 CTCTGGGCCTGTGTGTGGGTGGGGTTATGTGAGGGTATGAAGAATTCCTCTGAGAACCCACAGTGAGAGGGGAGGGCTCCTGGG
2101 GCAGAGAAGTTCCTTAGGTTTCTTTGGAATGAAATTCCTCCTTCCCCATCTCGAGTGGAGGAAGCCCACCAATCTGCCCTTTGCAGTGTGTCAGGG
2201 TGGAAGGTAAGAGGTTGGTGTGGAGGCTACAGAATAGGGTGCAGCAGAAGTGTCACCCTGTGTCTCCCTGGGGGCTCTTCCCTAGACCTCCCCTCACTACA
2301 TCCCCATCTCTGTCTGGGGCTACAGAATAGGGTGCAGAAGTGTCACCCTGTGTCTCCCTGGGGGCTGTCTCCCTAGACCTCCCCTCACTACA
2401 TAAAGCTCCCTTGAAGCAAGAAAGAGAGGGTCCCAGGCTGCAAAACTGGAAGCACACGTCCCAGGGATGGGAGGGAAAGACGGTGCTATATCCAGTTCCTG
2501 CTCTCTGCTCATGGGTGGCTGTGACAACCCTGGCTCTCCCTGTCCTTGATTCATCTCTGGTTTTCTTGCCACCTGGGAGTCCCATCCCATTTTCATCCTGAG
2601 CCCAACCAGGCCCTGCCATTGGCCTCTTGTCCCCTGGAGGCTGGAGTGCAGGGCCAGGACCTGAAGGTATTGGCTCTGTTCAACAATCAGTCA
2701 TCATGGGTGTTTTGTCAACTGCTTGTAATTGATTTGGGGATGTGGAGGCAAGTGAAATATCTTATATTGGGGCGATTTGGGGCTCGGGAGGTGGGGGAGGCAGAGAATCTCTTGGGAG
2801 CCATCCCTTTCCTTCTGGCCCCAGCTAGGTGGAGGCAAGAAGCAGCCTGTTTCACTCAGCTTAATTCTCCTTCCCAGATAAGGCAAGCCAGTCATGGAATC
2901 TCTTGGGTGGGCGCTGGTGCATTCTGTTCCTCTTGATCTCAAAGCACAATGGATTTGGGAGCCCAAAGGTCAGGAGCACATCCCCTTAGAGGACCTGAG
3001 TTGGAGAGTGGTGAGTGGAGGCCCTCCTACTCTTCCCGTGTCCTAAAAATAGGGGCCGTTTCTTACACACCCCAGAGAGAGGGCTGGCTGGGCTGAGCCCTGGTC
3101 TTGCTGCAGGCCCTCCTACTCTTCCCGTGTCCTAAAAATAGGGGCCGTTTCTTACACACCCCAGAGAGAGGGCTGGGCTGGGCTGAGCCCCTGGTC
3201 ACGGGGGCTGGGGTCTGGGTCTGTTCTTCAGTCAAAGTGCGTTCTTCAGCTCATTTAATCCCAGCACTGCCTCCTGTTTTCTCCCTCATGTCCCCTGTTTTCTCCCTCATGTCCC
3301 TTCTCTACAGTTCACAGACCCAGTGGTGAGGAAAGTGCGTTCTTCAGCTCATTTAATCCCAGCACTGCCTCCTGTTTTCTCCCTCATGTCCCTGTTTCTCCCTCATGTCCCTCGTTTATAACTTTTGTGGGCCAATACTAAGAAT
3401 AACAAGAAGCCCAGTGGTGAGGAAAGTGCTTCTTCAGGAAAATGCATCCAAAGCTAGAATGTGAATATAACTTTTGTGGGCCAATACTAAGAAT
3501 TCTGCCTTTCCCCCTCACACATGCCTCTGTGAGGAAAGTGCTTCTTCAGGAAAATGCATCCAAAGCTAGAATGTGAATATAACTTTTGTGGGCCAATACTAAGAAT
3601 TGACCAGTGAAATTGCCTCTGTCCAAACATTTCATCCGTGTATGTATGTGTGAGTGTGAGAGCGCCAGTTCATCTTTTATATGGGGTTG
3701 TTGTCTCATTTGGTCTGTTTGGTCCCCTGCCTGTGCTCGGGATCCAAACCTTTCTGGCCTGTTATGATTCTGAACATTTGACTTGAACCA
3801 CAAGTGAATCTTTCCTGGTGACTCAAATAAAGTATAATTTTA
```

FIG. 14B

```
Lasp-1 H. sapiens    (1-51)                  ..MNPNCAR.  .CGKIVPTE  KVNCLDKFWH  KACFHCETCK  MTLNMKNYKG  YEKKPYCNAH  Y......PKQ
                                                                                                                              Identity  Similarity
                                                                                                                                 %          %
rCRP2  R. norvegicus (1-56)                  ..-ASKCPK.  .CD-T-FA-  --SS-G-D-H  -FCLKC-RCN  K--TPGGHAE  HDG--FC-KP  CYATLFG--G    46         55
  -                  (119-180)               TGEPNMCP-.  .CN-R-FA-  --TS-G-D-H  RPCLRC-RCS  K--TPGGHAE  HDGQ--CHKP  CYG.......    44         56
TSF3   H. annus      (5-64)                  TGTTQKCT..  VCE-T-LVD  -LVANQRVYH  --C-RCHHCN  S--KLS-FNS  FDGVV-CRHH  FDQLFKRTGS    35         52
  -                  (104-162)               EGTRDKCN..  ACA-----I- R-KVDGTAYH  R-C-KCCHGG  C-ISPS--IA  H-GRL-CKHH  HIQLFKKKGN    40         54
```

FIG.15A

```
                                                                                                                                       Identity  Similarity
                                                                                                                                          %          %
Lasp-1 H. sapiens    (196-261)  RSAP  GGGGKRYRAV  YDYSAADEDE  VSFQDGDTIV  NVQQIDDGWMYGTVERTGDT  GMLPANYVEA I*                              57         74
YLZ3   C. elegans    (134-200)  I-PT  -KA-FAVK-I  ---A--K---  I--LE--I--  -CEK----T--Q--LQW    ------QP HK                               44         65
EMS1   H. sapiens    (486-550)  DEYE  NDL-YTAV-L  ---Q--GD--  I--DPDDI-T  -IEM----WR-VCK..-RY  -LF-----L RQ*                              33         60
ABP1   S. cerevisiae (526-592)  PEKK  PKENPWAT-E  ---D--EDN-  LT-VEN-K-I  -IEFV--D-WL-EL-KD-SK ----S---SL GN*                             35         56
h/fyn  H. sapiens    (76-141)   -TRG  -T-VTLFV-L  ---E-RT--D  L--HK-EKFQ  ILNSSEGD-WEARSLT--E  ---YI-S---AP VD                            33         55
h/src  H. sapiens    (78-144)   AGPL  A--VTIFV-L  ---ESRT-TD  L--KK-ERLQ  I-NNTEGD-WLAHSLS--Q  ---YI-S---AP SD                            33         52
h/frg  H. sapiens    (71-135)   -GVS  -I-VTLFI-L  ---E-RT--D  LT-TK-EKFH  ILNNTEGD-WEARSLSS-K  ---CI-S---AP VD                            32         52
h/yes  H. sapiens    (85-152)   PAGL  T--VTIFV-L  ---E-RTTED  L--KK-ERFQ  IINNTEGD-WEARSIA--KN ---YI-S---AP AD                            30         50
```

FIG.15B

```
CAGCGGCGGAAGTGGCGCTGCCGGAAGATCTTCTTCCGCTCTGAGGCGCTACTGAGGCCG    60

▼
CGGAGCCGGACTGCGGTTGGGGCGGGAAGAGCCGGGGCCGTGGCTGACATGGAGCAGCCC   120

TGCTGCTGAGGCCGCGCCCTCCCCGCCCTGAGGTGGGGGCCCACCAGGATGAGCAAGCTG   180
                                           M   S   K   L      4

CCCAGGGAGCTGACCCGAGACTTGGAGCGCAGCCTGCCTGCCGTGGCCTCCCTGGGCTCC   240
 P   R   E   L   T   R   D   L   E   R   S   L   P   A   V   A   S   L   G   S     24
              ◊
TCACTGTCCCACAGCCAGAGCCTCTCCTCGCACCTCCTTCCGCCGCCTGAGAAGCGAAGG   300
 S   L   S   H   S   Q   S   L   S   S   H   L   L   P   P   P   E   K   R   R     44

GCCATCTCTGATGTCCGCCGCACCTTCTGTCTCTTCGTCACCTTCGACCTGCTCTTCATC   360
 A   I   S   D   V   R   R   T   F   C   L   F   V   T   F   D   L   L   F   I     64
                                     ▼
TCCCTGCTCTGGATCATCGAACTGAATACCAACACAGGCATCCGTAAGAACTTGGAGCAG   420
 S   L   L   W   I   I   E   L   N   T   N   T   G   I   R   K   N   L   E   Q     84
                                                 ▼
GAGATCATCCAGTACAACTTTAAAACTTCCTTCTTCGACATCTTTGTCCTGGCCTTCTTC   480
 E   I   I   Q   Y   N   F   K   T   S   F   F   D   I   F   V   L   A   F   F    104
                                                           ◊
CGCTTCTCTGGACTGCTCCTAGGCTATGCCGTGCTGCAGCTCCGGCACTGGTGGGTGATT   540
 R   F   S   G   L   L   L   G   Y   A   V   L   Q   L   R   H   W   W   V   I    124
 ▼                                                        ▼
GCGGTCACGACGCTGGTGTCCAGTGCATTCCTCATTGTCAAGGTCATCCTCTCTGAGCTG   600
 A   V   T   T   L   V   S   S   A   F   L   I   V   K   V   I   L   S   E   L    144

CTCAGCAAAGGGGCATTTGGCTACCTGCTCCCCATCGTCTCTTTTGTCCTCGCCTGGTTG   660
 L   S   K   G   A   F   G   Y   L   L   P   I   V   S   F   V   L   A   W   L    164
                                                  ▼
GAGACCTGGTTCCTTGACTTCAAAGTCCTACCCCAGGAAGCTGAAGAGGAGCGATGGTAT   720
                                                  ◆
```

FIG.16A

| | |
|---|---|
| E T W F L D F K V L P Q E A E E E R W Y | 184 |
| CTTGCCGCCCAGGTTGCTGTTGCCCGTGGACCCCTGCTGTTCTCCGGTGCTCTGTCCGAG | 780 |
| L A A Q V A V A R G P L F S G A L S E | 204 |
| GGACAGTTCTATTCACCCCCAGAATCCTTTGCAGGGTCTGACAATGAATCAGATGAAGAA | 840 |
| G Q F Y S P P E S F A G S D N E S D E E | 224 |
| GTTGCTGGGAAGAAAAGTTTCTCTGCTCAGGAGCGGGAGTACATCCGCCAGGGGAAGGAG | 900 |
| V A G K K S F S A Q E R E Y I R Q G K E | 244 |
| GCCACGGCAGTGGTGGACCAGATCTTGGCCCAGGAAGAGAACTGGAAGTTTGAGAAGAAT | 960 |
| A T A V V D Q I L A Q E E N W K F E K N | 264 |
| AATGAATATGGGGACACCGTGTACACCATTGAAGTTCCCTTTCACGGCAAGACGTTTATC | 1020 |
| N E Y G D T V Y T I E V P F H G K T F I | 284 |
| CTGAAGACCTTCCTGCCCTGTCCTGCGGAGCTCGTGTACCAGGAGGTGATCCTGCAGCCC | 1080 |
| L K T F L P C P A E L V Y Q E V I L Q P | 304 |
| GAGAGGATGGTGCTGTGGAACAAGACAGTGACTGCCTGCCAGATCCTGCAGCGAGTGGAA | 1140 |
| E R M V L W N K T V T A C Q I L Q R V E | 324 |
| GACAACACCCTCATCTCCTATGACGTGTCTGCAGGGGCTGCGGGCGGCGTGGTCTCCCCA | 1200 |
| D N T L I S Y D V S A G A A G G V V S P | 344 |
| AGGGACTTCGTGAATGTCCGGCGCATTGAGCGGCGCAGGGACCGATACTTGTCATCAGGG | 1260 |
| R D F V N V R R I E R R R D R Y L S S G | 364 |
| ATCGCCACCTCACACAGTGCCAAGCCCCCGACGCACAAATATGTCCGGGGAGAGAATGGC | 1320 |
| I A T S H S A K P P T H K Y V R G E N G | 384 |

FIG.16B

```
CCTGGGGGCTTCATCGTGCTCAAGTCGGCCAGTAACCCCCGTGTTTGCACCTTTGTCTGG      1380

P   G   G   F   I   V   L   K   S   A   N   P   R   V   C   T   F   V   W      404
                                 ▼
ATTCTTAATACAGATCTCAAGGGCCGCCTGCCCCGGTACCTCATCCACCAGAGCCTCGCG      1440

I   L   N   T   D   L   K   G   R   L   P   R   Y   L   I   H   Q   S   L   A      424

GCCACCATGTTTGAATTTGCCTTTCACCTGCGACAGCGCATCAGCGAGCTGGGGGCCCGG      1500

A   T   M   F   E   F   A   F   H   L   R   Q   R   I   S   E   L   G   A   R      444

GCGTGACTGTGCCCCCTCCCACCCTGCGGGCCAGGGTCCTGTCGCCACCACTTCCAGAGC      1560

A   *                                                                              445

CAGAAAGGGTGCCAGTTGGGCTCGCACTGCCCACATGGGACCTGGCCCCAGGCTGTCACC      1620
CTCCACCGAGCCACGCAGTGCCTGGAGTTGACTGACTGAGCAGGCTGTGGGTGGAGCAC      1680
TGGACTCCGGGGCCCCACTGGCTGGAGGAAGTGGGGTCTGGCCTGTTGATGTTTACATGG      1740
CGCCCTGCCTCCTGGAGGACCAGATTGCTCTGCCCCACCTTGCCAGGGCAGGGTCTGGGC      1800
TGGGCACCTGACTTGGCTGGGGAGGACCAGGGCCCTGGGCAGGGCAGGGCAGCCTGTCAC      1860
CCGTGTGAAGATGAAGGGGCTCTTCATCTGCCTGCGCTCTCGTCGGTTTTTTTAGGATTA      1920
TTGAAAGAGTCTGGGACCCTTGTTGGGGAGTGGGTGGCAGGTGGGGGTGGGCTGCTGGCC      1980
ATGAATCTCTGCCTCTCCCAGGCTGTCCCCTCCTCCCAGGGCCTCCTGGGGGACCTTTG      2040
TATTAAGCCAATTAAAAACATGAATTTAAAAAA                                 2073
```

FIG. 16C

```
GAATTCCGTT GCTGTCGCAC ACACACACAC ACACACACAC ACACCCCAAC ACACACACAC    60

ACACCCCAAC ACACACACAC ACACACACAC ACACACACAC ACACACACAC ACACAGCGGG   120

ATGGCCGAGC GCCGCACGCG TAGCACGCCG GGACTAGCTA TCCAGCCTCC CAGCAGCCTC   180

TGCGACGGGC GCGGTGCGTA NGTACCTCGC CGGTGGTGGC CGTTCTCCGT AAG ATG      236
                                                          Met
                                                           1
GCG GAC CGG CGG CGG CAG CGC GCT TCG CAA GAC ACC GAG GAC GAG GAA     284
Ala Asp Arg Arg Arg Gln Arg Ala Ser Gln Asp Thr Glu Asp Glu Glu
            5                   10                  15
TCT GGT GCT TCG GGC TCC GAC AGC GGC GGC TCC CCG TTG CGG GGA GGC     332
Ser Gly Ala Ser Gly Ser Asp Ser Gly Gly Ser Pro Leu Arg Gly Gly
                20                  25                  30
GGG AGC TGC AGC GGT AGC GCC GGA GGC GGC GGC AGC GGC TCT CTG CCT     380
Gly Ser Cys Ser Gly Ser Ala Gly Gly Gly Gly Ser Gly Ser Leu Pro
        35                  40                  45
TCA CAG CGC GGA GGC CGA ACC GGG GCC CTT CAT CTG CGG CGG GTG GAG     428
Ser Gln Arg Gly Gly Arg Thr Gly Ala Leu His Leu Arg Arg Val Glu
 50                  55                  60                  65
AGC GGG GGC GCC AAG AGT GCT GAG GAG TCG GAG TGT GAG AGT GAA GAT     476
Ser Gly Gly Ala Lys Ser Ala Glu Glu Ser Glu Cys Glu Ser Glu Asp
                70                  75                  80
GGC ATT GAA GGT GAT GCT GTT CTC TCG GAT TAT GAA AGT GCA GAA GAC     524
Gly Ile Glu Gly Asp Ala Val Leu Ser Asp Tyr Glu Ser Ala Glu Asp
            85                  90                  95
TCG GAA GGT GAA GAA GGT GAA TAC AGT GAA GAG GAA AAC TCC AAA GTG     572
Ser Glu Gly Glu Glu Gly Glu Tyr Ser Glu Glu Glu Asn Ser Lys Val
        100                 105                 110
GAG CTG AAA TCA GAA GCT AAT GAT GCT GTT AAT TCT TCA ACA AAA GAA     620
Glu Leu Lys Ser Glu Ala Asn Asp Ala Val Asn Ser Ser Thr Lys Glu
    115                 120                 125
GAG AAG GGA GAA GAA AAG CCT GAC ACC AAA AGC ACT GTG ACT GGA GAG     668
Glu Lys Gly Glu Glu Lys Pro Asp Thr Lys Ser Thr Val Thr Gly Glu
130                 135                 140                 145
AGG CAA AGT GGG GAC GGA CAG GAG AGC ACA GAG CCT GTG GAG AAC AAA     716
Arg Gln Ser Gly Asp Gly Gln Glu Ser Thr Glu Pro Val Glu Asn Lys
                150                 155                 160
GTG GGT AAA AAG GGC CCT AAG CAT TTG GAT GAT GAT GAA GAT CGG AAG     764
Val Gly Lys Lys Gly Pro Lys His Leu Asp Asp Asp Glu Asp Arg Lys
            165                 170                 175
```

FIG.21A

```
AAT CCA GCA TAC ATA CCT CGG AAA GGG CTC TTC TTT GAG CAT GAT CTT    812
Asn Pro Ala Tyr Ile Pro Arg Lys Gly Leu Phe Phe Glu His Asp Leu
        180             185             190
CGA GGG CAA ACT CAG GAG GAG GAA GTC AGA CCC AAG GGG CGT CAG CGA    860
Arg Gly Gln Thr Gln Glu Glu Glu Val Arg Pro Lys Gly Arg Gln Arg
    195             200             205
AAG CTA TGG AAG GAT GAG GGT CGC TGG GAG CAT GAC AAG TTC CGG GAA    908
Lys Leu Trp Lys Asp Glu Gly Arg Trp Glu His Asp Lys Phe Arg Glu
210             215             220             225
GAT GAG CAG GCC CCA AAG TCC CGA CAG GAG CTC ATT GCT CTT TAT GGT    956
Asp Glu Gln Ala Pro Lys Ser Arg Gln Glu Leu Ile Ala Leu Tyr Gly
            230             235             240
TAT GAC ATT CGC TCA GCT CAT AAT CCT GAT GAC ATC AAA CCT CGA AGA   1004
Tyr Asp Ile Arg Ser Ala His Asn Pro Asp Asp Ile Lys Pro Arg Arg
            245             250             255
ATC CGG AAA CCC CGA TAT GGG AGT CCT CCA CAA AGA GAT CCA AAC TGG   1052
Ile Arg Lys Pro Arg Tyr Gly Ser Pro Pro Gln Arg Asp Pro Asn Trp
        260             265             270
AAC GGT GAG CGG CTA AAC AAG TCT CAT CGC CAC CAG GGT CTT GGG GGC   1100
Asn Gly Glu Arg Leu Asn Lys Ser His Arg His Gln Gly Leu Gly Gly
        275             280             285
ACC CTA CCA CCA AGG ACA TTT ATT AAC AGG AAT GCT GCA GGT ACC GGC   1148
Thr Leu Pro Pro Arg Thr Phe Ile Asn Arg Asn Ala Ala Gly Thr Gly
290             295             300             305
CGT ATG TCT GCA CCC AGG AAT TAT TCT CGA TCT GGG GGC TTC AAG GAA   1196
Arg Met Ser Ala Pro Arg Asn Tyr Ser Arg Ser Gly Gly Phe Lys Glu
            310             315             320
GGT CGT GCT GGT TTT AGG CCT GTG GAA GCT GGT GGG CAG CAT GGT GGC   1244
Gly Arg Ala Gly Phe Arg Pro Val Glu Ala Gly Gly Gln His Gly Gly
            325             330             335
CGG TCT GGT GAG ACT GTT AAG CAT GAG ATT AGT TAC CGG TCA CGG CGC   1292
Arg Ser Gly Glu Thr Val Lys His Glu Ile Ser Tyr Arg Ser Arg Arg
        340             345             350
CTA GAG CAG ACT TCT GTG AGG GAT CCA TCT CCA GAA GCA GAT GCT CCA   1340
Leu Glu Gln Thr Ser Val Arg Asp Pro Ser Pro Glu Ala Asp Ala Pro
355             360             365
GTG CTT GGC AGT CCT GAG AAG GAA GAG GCA GCC TCA GAG CCA CCA GCT   1388
Val Leu Gly Ser Pro Glu Lys Glu Glu Ala Ala Ser Glu Pro Pro Ala
370             375             380             385
GCT GCT CCT GAT GCT GCA CCA CCA CCC CCT GAT AGG CCC ATT GAG AAG   1436
Ala Ala Pro Asp Ala Ala Pro Pro Pro Pro Asp Arg Pro Ile Glu Lys
            390             395             400
```

FIG.21B

```
AAA TCC TAT TCC CGG GCA AGA AGA ACT CGA ACC AAA GTT GGA GAT GCA    1484
Lys Ser Tyr Ser Arg Ala Arg Arg Thr Arg Thr Lys Val Gly Asp Ala
            405                 410                 415
GTC AAG CTT GCA GAG GAG GTG CCC CCT CCT CCT GAA GGA CTG ATT CCA    1532
Val Lys Leu Ala Glu Glu Val Pro Pro Pro Pro Glu Gly Leu Ile Pro
            420                 425                 430
GCA CCT CCA GTC CCA GAA ACC ACC CCA ACT CCA CCT ACT AAG ACT GGG    1580
Ala Pro Pro Val Pro Glu Thr Thr Pro Thr Pro Pro Thr Lys Thr Gly
            435                 440                 445
ACC TGG GAA GCT CCG GTG GAT TCT AGT ACA AGT GGA CTT GAG CAA GAT    1628
Thr Trp Glu Ala Pro Val Asp Ser Ser Thr Ser Gly Leu Glu Gln Asp
450                 455                 460                 465
GTG GCA CAA CTA AAT ATA GCA GAA CAG AAT TGG AGT CCG GGG CAG CCT    1676
Val Ala Gln Leu Asn Ile Ala Glu Gln Asn Trp Ser Pro Gly Gln Pro
                470                 475                 480
TCT TTC CTG CAA CCA CGG GAA CTT CGA GGT ATG CCC AAC CAT ATA CAC    1724
Ser Phe Leu Gln Pro Arg Glu Leu Arg Gly Met Pro Asn His Ile His
                485                 490                 495
ATG GGA GCA GGA CCT CCA CCT CAG TTT AAC CGG ATG GAA GAA ATG CTC    1772
Met Gly Ala Gly Pro Pro Pro Gln Phe Asn Arg Met Glu Glu Met Leu
            500                 505                 510
ACT TTG CAA ATA TCC ATT AAA TAC CTG CCA TGT ACC AAG TGT TTT TCA    1820
Thr Leu Gln Ile Ser Ile Lys Tyr Leu Pro Cys Thr Lys Cys Phe Ser
            515                 520                 525
ACA CCT AAA GGA AGG TAG GACTTGATAT GAGAGCCCTC TAGAATTCTT           1868
Thr Pro Lys Gly Arg  *
530                 535

ATTGTTTAGG CCTCTTTCTT TGTCTCAGGG TGTCCAGGGT GTCCAGGGTG GTCGAGCCAA  1928

ACGCTATTCA TCCCAGCGGC AAAGACCTGT GCCAGAGCCC CCCGCCCCTC CAGTGCATAT  1988

CAGTATCATG GAGGGACATT ACTATGATCC ACTGCAGTTC CAGGGACCAA TCTATACCCA  2048

TGGTGACAGC CCTGCCCCGC TGCCTCCACA GGGCATGCTT GTGCAGCCAG GAATGAACCT  2108

TCCCCACCCA GGTTTACATC CCCATCAGAC ACCAGCTCCT CTGCCCAATC CAGGCCTCTA  2168

TCCCCCACCA GTGTCCATGT CTCCAGGACA GCCACCACCT CAGCAGTTGC TTGCTCCTAC  2228

TTACTTTTCT GCTCCAGGCG TCATGAACTT TGGTAATCCC AGTTACCCTT ATGCTCCAGG  2288
```

FIG.21C

```
GGCACTGCCT CCCCCACCAC CGCCTCATCT GTATCCTAAT ACACAGGCCC CATCACAGGT  2348

ATATGGAGGA GTGACCTACT ATAACCCCGC CCAGCAGCAG GTGCAGCCAA AGCCCTCCCC  2408

ACCCCGGAGG ACTCCCCAGC CAGTCACCAT CAAGCCCCCT CCACCTGAGG TTGTAAGCAG  2468

GGGTTCCAGT TAATACAAGT TTCTGAATAT TTTAAATCTT AACATCATAT AAAAAGCAGC  2528

AGAGGTGAGA ACTCAGAAGA GAAATACAGC TGGCTATCTA CTACCAGAAG GGCTTCAAAG  2588

ATATAGGGTG TGGCTCCTAC CAGCAAACAG CTGAAAGAGG AGGACCCCTG CCTTCCTCTG  2648

AGGACAGGCT CTAGAGAGAG GGAGAAACAA GTGGACCTCG TCCCATCTTC ACTCTTCACT  2708

TGAGTTGGCT GTGTTCGGGG GAGCAGAGAG AGCCAGACAG CCCCAAGCTT CTGAGTCTAG  2768

ATACAGAAGC CCATGTCTTC TGCTGTTCTT CACTTCTGGG AAATTGAAGT GTCTTCTGTT  2828

CCCAAGGAAG CTCCTTCCTG TTTGTTTTGT TTTCTAAGAT GTTCATTTTT AAAGCCTGGC  2888

TTCTTATCCT TAATATTATT TTAATTTTTT CTCTTTGTTT CTGTTTCTTG CTCTCTCTCC  2948

CTGCCTTTAA ATGAAACAAG TCTAGTCTTC TGGTTTTCTA GCCCCTCTGG ATTCCCTTTT  3008

GACTCTTCCG TGCATCCCAG ATAATGGAGA ATGTATCAGC CAGCCTTCCC CACCAAGTCT  3068

AAAAAGACCT GGCCTTTCAC TTTTAGTTGG CATTTGTTAT CCTCTTGTAT ACTTGTATTC  3128

CCTTAACTCT AACCCTGTGG AAGCATGGCT GTCTGCACAG AGGGTCCCAT TGTGCAGAAA  3188

AGCTCAGAGT AGGTGGGTAG GAGCCCTTCT CTTTGACTTA GGTTTTTAGG AGTCTGAGCA  3248

TCCATCAATA CCTGTACTAT GATGGGCTTC TGTTCTCTGC TGAGGGCCAA TACCCTACTG  3308

TGGGGAGAGA TGGCACACCA GATGCTTTTG TGAGAAAGGG ATGGTGGAGT GAGAGCCTTT  3368

GCCTTTAGGG GTGTGTATTC ACATAGTCCT CAGGGCTCAG TCTTTTGAGG TAAGTGGAAT  3428

TAGAGGGCCT TGCTTCTCTT CTTTCCATTC TTCTTGCTAC ACCCCTTTTC CAGTTGCTGT  3488

GGACCAATGC ATCTCTTTAA AGGCAAATAT TATCCAGCAA GCAGTCTACC CTGTCCTTTG  3548
```

FIG.21D

```
CAATTGCTCT TCTCCACGTC TTTCCTGCTA CAAGTGTTTT AGATGTTACT ACCTTATTTT   3608

CCCCGAATTC TATTTTTGTC CTTGCAGACA GAATATAAAA ACTCCTGGGC TTAAGGCCTA   3668

AGGAAGCCAG TCACCTTCTG GGCAAGGGCT CCTATCTTTC CTCCCTATCC ATGGCACTAA   3728

ACCACTTCTC TGCTGCCTCT GTGGAAGAGA TTCCTATTAC TGCAGTACAT ACGTCTGCCA   3788

GGGGTAACCT GGCCACTGTC CCTGTCCTTC TACAGAACCT GAGGGCAAAG ATGGTGGCTG   3848

TGTCTCTCCC CGGTAATGTC ACTGTTTTTA TTCCTTCCAT CTAGCAGCTG GCCTAATCAC   3908

TCTGAGTCAC AGGTGTGGGA TGGAGAGTGG GGAGAGGCAC TTAATCTGTA ACCCCCAAGG   3968

AGGAAATAAC TAAGAGATTC TTCTAGGGGT AGCTGGTGGT TGTGCCTTTT GTAGGCTGTT   4028

CCCTTTGCCT TAAACCTGAA GATGTCTCCT CAAGCCTGTG GGCAGCATGC CCAGATTCCC   4088

AGACCTTAAG ACACTGTGAG AGTTGTCTCT GTTGGTCCAC TGTGTTTAGT TGCAAGGATT   4148

TTTCCATGTG TGGTGGTGTT TTTTGTTACT GTTTTAAAGG GTGCCCATTT GTGATCAGCA   4208

TTGTGACTTG GAGATAATAA AATTTAGACT ATAAACTTGA AAAAA                   4253
```

FIG.21E

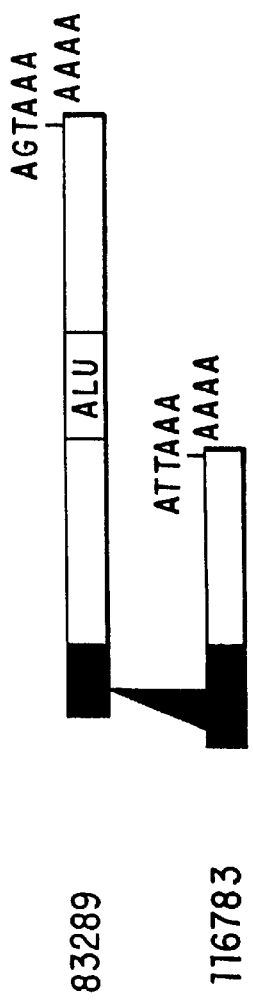
FIG. 23
FIG. 24A

```
   1  CAGAAGCGGCTAGTGGCGGCTGCCTGCGTCCCCAACCCCCTCCGCGCAGCGCTCGCGACA    60
  61  CGCGTGCCAGGAGTGGGAGCGAGCGGCGGGGCCAGCTGCGTTCTGAGCCTGGGCGCAGCT   120
 121  GCCATCTGCTCTGGGAAGCACCAGGGTGTCCCCGCCGCCCTCAGCTCGAAGTCAGCCACC   180
 181  ATGGAGGCGCAGGCACAAGGTTTGTTGGAGACTGAACCGTTGCAAGGAACAGACGAAGAT   240
   1   M  E  A  Q  A  Q  G  L  L  E  T  E  P  L  Q  G  T  D  E  D     20
 241  GCAGTAGCCAGTGCTGACTTCTCTAGCATGCTCTCTGAGGAGGAAAAGGAAGAGTTAAAA   300
  21   A  V  A  S  A  D  F  S  S  M  L  S  E  E  E  K  E  E  L  K     40
 301  GCAGAGTTAGTTCAGCTAGAAGACGAAATTACAACACTACGACAAGTTTTGTCAGCGAAA   360
  41   A  E  L  V  Q  L  E  D  E  I  T  T  L  R  Q  V  L  S  A  K     60
 361  GAAAGGCATCTAGTTGAGATAAAACAAAAACTCGGCATGAACCTGATGAATGAATTAAAA   420
  61   E  R  H  L  V  E  I  K  Q  K  L  G  M  N  L  M  N  E  L  K     80
 421  CAGAACTTCAGCAAAAGCTGGCATGACATGCAGACTACCACTGCCTACAAGAAAACACAT   480
  81   Q  N  F  S  K  S  W  H  D  M  Q  T  T  T  A  Y  K  K  T  H    100
 481  GAAACCCTGAGTCACGCAGGGCAAAAGGCAACTGCAGCTTTCAGCAACGTTGGAACGGCC   540
 101   E  T  L  S  H  A  G  Q  K  A  T  A  A  F  S  N  V  G  T  A    120
 541  ATCAGCAAGAAGTTCGGAGACATGAGTTACTCCATTCGCCATTCCATAAGTATGCCTGCT   600
 121   I  S  K  K  F  G  D  M  S  Y  S  I  R  H  S  I  S  M  P  A    140
 601  ATGAGGAATTCTCCTACTTTCAAATCATTTGAGGAGAGGGTTGAGACAACTGTCACAAGC   660
 141   M  R  N  S  P  T  F  K  S  F  E  E  R  V  E  T  T  V  T  S    160
 661  CTCAAGACGAAAGTAGGCGGTACGAACCCTAATGGAGGCAGTTTTGAGGAGGTCCTCAGC   720
 161   L  K  T  K  V  G  G  T  N  P  N  G  G  S  F  E  E  V  L  S    180
 721  TCCACGGCCCATGCCAGTGCCCAGAGCTTGGCAGGAGGCTCCCGGCGGACCAAGGAGGAG   780
 181   S  T  A  H  A  S  A  Q  S  L  A  G  G  S  R  R  T  K  E  E    200
 781  GAGCTGCAGTGCTAAGTCCAGCCAGCGTGCAGCTGCATCCAGAAACCGGCCACTACCCAG   840
 201   E  L  Q  C  *                                                  204
 841  CCCATCTCTGCCTGTGCTTATCCAGATAAGAAGACCAAAATCCCGCTGGGAAAAACCCAG   900
 901  GCCTTGACATTGTTATTCAAATGGCCCCTCCAGAAAGTTTAATGATTTCCATTTGTATTT   960
 961  GTGTTGATGATGGACCACTTGACCATCACATTTCAGTATTCATAGATGACTGTCACATTT  1020
1021  TAAAATGTTCCCACTTGAGCAGGTACACAACTGGTCATAATTCCTGTCTGTGTAATTCGA  1080
1081  TGTATATTTTTCCAAACATGTAGCTATTGTTTGCTTTGATTTTTGCTTGGCCTCCTTTAT  1140
1141  GATGTGCATGTCCTTGAAGGCTGAATGAACAGTCCCTTTCAGTTCAGCAGATCAACAGGA  1200
1201  TGGAGCTCTTCATGACTGTCTCCAGCAATAGGATGATTTACTATAAATTTCATCCAACTA  1260
1261  CTTGTGATCTCTCTCACCTACATCAATTATGTATGTTAATTTCAGCAATTAAAAGAATTG  1320
1321  ATTTTAAAAAAAAAAAAAAAAAAAAAA                                    1347
```

FIG.24B

```
   1   CGGGAGCGAGGTGGCTCAGACATGGACCGCGGCGAGCAAGGTCTGCTGAAGACAGAGCCG     60
   1                    M  D  R  G  E  Q  G  L  L  K  T  E  P       13
  61   GTGGCCGAGGAAGGAGAGGATGCTGTTACCATGCTCAGTGCTCCAGAGGCGCTGACGGAA    120
  14   V  A  E  E  G  E  D  A  V  T  M  L  S  A  P  E  A  L  T  E   33
 121   GAGGAGCAAGAGGAGCTGAGGCGGGAGCTTACTAAGGTGGAAGAAGAAATCCAGACTCTG    180
  34   E  E  Q  E  E  L  R  R  E  L  T  K  V  E  E  E  I  Q  T  L   53
 181   TCCCAAGTATTGGCCGCAAAAGAGAAGCATCTCGCCGAGCTCAAGCGGAAGCTCGGCATC    240
  54   S  Q  V  L  A  A  K  E  K  H  L  A  E  L  K  R  K  L  G  I   73
 241   TCCTCGCTTCAGGAGTTCAAGCAGAACATTGCCAAAGGGTGGCAAGACGTGACGGCAACC    300
  74   S  S  L  Q  E  F  K  Q  N  I  A  K  G  W  Q  D  V  T  A  T   93
 301   AATGCATACAAGAAGACCTCTGAAACTCTATCGCAAGCTGGGCAGAAGGCCTCCGCTGCA    360
  94   N  A  Y  K  K  T  S  E  T  L  S  Q  A  G  Q  K  A  S  A  A  113
 361   TTTTCATCGGTTGGCTCAGTCATCACCAAAAAGCTGGAAGACGTGAAAAACTCCCCAACT    420
 114   F  S  S  V  G  S  V  I  T  K  K  L  E  D  V  K  N  S  P  T  133
 421   TTCAAGTCATTTGAAGAAAAAGTTGAAAATTTAAAGTCTAAAGTAGGAGGAGCCAAGCCT    480
 134   F  K  S  F  E  E  K  V  E  N  L  K  S  K  V  G  G  A  K  P  153
 481   GCTGGCGGCGATTTTGGAGAAGTCCTGAATTCCACAGCCAACGCTACCAGTACCATGACC    540
 154   A  G  G  D  F  G  E  V  L  N  S  T  A  N  A  T  S  T  M  T  173
 541   ACAGAGCCTCCTCCAGAACAGATGACAGAGAGCCCCTGAGCTGCCGACCTGTGTCCTGCT    600
 174   T  E  P  P  P  E  Q  M  T  E  S  P  *                        185
 601   GCCCACTGCCAGGTGCTGCCGGCGAGAGCCAAGTACATCTTGACAACGCTCATGGCTGCG    660
 661   GATTTCCACCAGATGTGCTTTTATTTAGCTTTACTTATTTCTTTGACCAAATAGTTGATG    720
 721   AATGAAACAAAGTGAAATCACTTGACCTCCACTCCAGGGAAACACTGTTAGCATGCATGG    780
 781   AAGGCCCTTTGTATAGGAAACAGCATCATAGAGCCTCTGGTAGATCCCTGCAGGCAACTA    840
 841   CTGTGTTTCTCCTTAAAATCACTGTACATCTGGATTCTAGTTTGATCTTTCTTTACTATC    900
 901   TACATGAATCATTGTTTTTGGGTCTCTGTACACTTAATCAATTTCTAACAAACTGTCCTT    960
 961   TTCTAAATTCTGGTTATTAAAAGTCTTGGAATTATTTCATTCCTTTCAAAGGAGAAACTA   1020
1021   CCAGCTACATTTTTTTTCTCGGATAAACAGTTCTGTGAGGACCATATCTTGGGTTTCTAA   1080
1081   AGACACCAGACTAAAGTAGACAGGTGTGTATGCAGTTCTATAGTTCTGTAAATTAAAAAC   1140
1141   ATGCAGACACTCAAACTTCCAGTGGGGAGAGTGTGGGTCCTGCTCTTGCCTTGGTAACTG   1200
1201   TCATTTGTAGCTACATCTATTTGAGCTCAAATATGCTTATCAGTTATTTATTATACCATT   1260
1261   CTCACACATTTTTTTACAAGATTAAAATTTAATTTCAGGTAAATTGAGAGAATAACATTG   1320
1321   TGAGTTAAGTATATGATATTACAGTAAGTTGGAATGTTCCCACATTCATCACTGATAATT   1380
1381   CCAAAAGTCTAAACGTCTTTAGGTCTATACAGTTATAAAAATGCTAAAAAAAATTCACCA   1440
1441   TAGGGGAAATTACTGCCTCCATTAAATCCATTTAACACCTTTAGGAAGGACAGAAAGTTC   1500
1501   TATGAGAAATACAACTTGAATATTTTTTATACTAAGGGATTGTTGATAACTCCGAAAGCT   1560
1561   GCGAGGCGTTACTATGACTGAGCTGATCAGGCAGTTTCTGTTCTCAGTGTGTTAGTGCCT   1620
1621   GAGCTGTTCTGTATGTAGAAATCGTTCCCACTCTAAGAACTGTCGGGGCTGTGAGTCAAA   1680
1681   GCTTCCCAGTGGCTCTGCTAAGCCCCTCTGTTAACTGTGGTCACTCCTGACTCACTCCTG   1740
1741   CTTCCTTTGCTGTGTATGTTTATGGCCTATGAGGTTGTATCTGTTACTTCTTTCTCTATT   1800
1801   GTGGTTTTACCAGTGTCCATGCCAAATGTTAACTGCCAAGCTTGGAGTGACCTAAAGCCT   1860
1861   TTTTCAGAGCATGGCTAGATTTAATTGAGGATAAGGTTTCTGCAAACCAGAATTGAAAAG   1920
1921   CCACAGTGTCGGTTGTCACAAAATGACATGCTGCCATTCCTGGTTGCTGCTCGGATGCAA   1980
1981   TGGAAACTATGCTTGATTACATGTGAAAATCTTAATAAAGTCTGTGTCTCAGTAAAAAAA   2040
2041   AAAAAAAAAAA                                                    2051
```

FIG.25B

```
                                              COILED COIL DOMAIN
                      PEST DOMAIN
            10        20        30        40        50        60
mD52  MDRGEQGLLKTEPVAEEGEDAVTMLSAPEALTEEEQEELRRELTKVEEEIQTLSQVLAAK
      ||||||||:|:||  |||||::    :||  |  |:|||||||||||  ||||||||||||||||
hD52  MDRGEQGLLRTDPVPEEGEDVAATISATETLSEEEQEELRRELAKVEEEIQTLSQVLAAK
      |:   ||||  |:|:     ||::|::   :    |||||   |||:   ||:  :|:||  ||  |||  ||
hD53  MEAQAQGLLETEPLQGTDEDAVASADFSSMLSEEEKEELKAELVQLEDEITTLRQVLSAK
            10        20        30        40        50        60

70        80        90        100       110       120
mD52  EKHLAELKRKLGISSLQEFKQNIAKGWQDVTATNAYKKTSETLSQAGQKASAAFSSVGSV
      ||||||:||||||  ||||  ||||||||||||  ||||||||||||||||||||||||||||||||
hD52  EKHLAEIKRKLGINSLQELKQNIAKGWQDVTATSAYKKTSETLSQAGQKASAAFSSVGSV
      |:||:|||  |||:|  ::|||||   |  |  |:   |:|||||  ||||  |||||:||||  ||::
hD53  ERHLVEIKQKLGMNLMNELKQNFSKSWHDMQTTTAYKKTHETLSHAGQKATAAFSNVGTA
            70        80        90        100       110       120

130       140       150       160
mD52  ITKKLED------------VKNSPTFKSFEEKVE----NLKSKVGGAKPAGGDFGEVLN
      |||||||            ||||||||||||||    ||||||||  ||||||||||||
hD52  ITKKLED------------VKNSPTFKSFEEKVE----NLKSKVGGTKPAGGDFGEVLN
      |:|| |              ::|||||||||:||    ||:||||| | || | |||
hD53  ISKKFGDMSYSIRHSISMPAMRNSPTFKSFEERVETTVTSLKTKVGGTNPNGGSFEEVLS
            130       140       150       160       170       180

PEST DOMAIN
            170       180
mD52  STANATSTMTTEPPPEQMTESP*
      | |||: | |||| ||    ||
hD52  SAANASAT-TTEPLPEKTQESL*
      | | |||         | |
hD53  STAHASAQSLAGGSRRTKEEELQC*
            190       200
```

FIG.26A

```
           abcdefgabcdefgabcdefgabcdefgabcdefgabcdefgabcdefga
mD52            EALTEEEQEELRRELTKVEEEIQTLSQVLAAKEKHLAELKRKL
                | |:||||||||||| |||||||||||||||||||||:||||
hD52       AATISATETLSEEEQEELRRELAKVEEEIQTLSQVLAAKEKHLAEIKRKL
            :|:: :   ||||| |||: ||: :|:|| || ||| |||:||:||| ||
hD53       VASADFSSMLSEEEKEELKAELVQLEDEITTLRQVLSAKERHLVEIKQKL
```

FIG.26B

SEQUENCE LISTING (1) GENERAL INFORMATION:

(iii) NUMBER OF SEQUENCES: 124

(2) INFORMATION FOR SEQ ID NO:1:

(i) SEQUENCE CHARACTERISTICS:
      (A) LENGTH: 2004 base pairs
      (B) TYPE: nucleic acid
      (C) STRANDEDNESS: both
      (D) TOPOLOGY: both (ii) MOLECULE TYPE: cDNA (ix) FEATURE:
    (A) NAME/KEY: CDS
    (B) LOCATION: 85..1494

(xi) SEQUENCE DESCRIPTION: SEQ ID NO:1:

| | |
|---|---|
| CCGGGAGCGC CGCTCCAGCG AGGCGCGGGC TGTGGGGCCG CCGCGTGCCT GGCCCCGCTC | 60 |
| GCCCGTGCCG CCGCTCGCC CGCC ATG CCT GGC TTC GAC TAC AAG TTC CTG<br>                                 Met Pro Gly Phe Asp Tyr Lys Phe Leu<br>                                   1                  5 | 111 |
| GAG AAG CCC AAG CGA CGG CTG CTG TGC CCA CTG TGC GGG AAG CCC ATG<br>Glu Lys Pro Lys Arg Arg Leu Leu Cys Pro Leu Cys Gly Lys Pro Met<br> 10                         15                      20                       25 | 159 |
| CGC GAG CCT GTG CAG GTT TCC ACC TGC GGC CAC CGT TTC TGC GAT ACC<br>Arg Glu Pro Val Gln Val Ser Thr Cys Gly His Arg Phe Cys Asp Thr<br>                   30                         35                      40 | 207 |
| TGC CTG CAG GAG TTC CTC AGT GAA GGA GTC TTC AAG TGC CCT GAG GAC<br>Cys Leu Gln Glu Phe Leu Ser Glu Gly Val Phe Lys Cys Pro Glu Asp<br>              45                         50                      55 | 255 |
| CAG CTT CCT CTG GAC TAT GCC AAG ATC TAC CCA GAC CCG GAG CTG GAA<br>Gln Leu Pro Leu Asp Tyr Ala Lys Ile Tyr Pro Asp Pro Glu Leu Glu<br>      60                       65                         70 | 303 |
| GTA CAA GTA TTG GGC CTG CCT ATC CGC TGC ATC CAC AGT GAG GAG GGC<br>Val Gln Val Leu Gly Leu Pro Ile Arg Cys Ile His Ser Glu Glu Gly<br> 75                         80                      85 | 351 |
| TGC CGC TGG AGT GGG CCA CTA CGT CAT CTA CAG GGC CAC CTG AAT ACC<br>Cys Arg Trp Ser Gly Pro Leu Arg His Leu Gln Gly His Leu Asn Thr<br> 90                         95                   100              105 | 399 |
| TGC AGC TTC AAT GTC ATT CCC TGC CCT AAT CGC TGC CCC ATG AAG CTG<br>Cys Ser Phe Asn Val Ile Pro Cys Pro Asn Arg Cys Pro Met Lys Leu<br>                  110                       115                    120 | 447 |
| AGC CGC CGT GAT CTA CCT GCA CAC TTG CAG CAT GAC TGC CCC AAG CGG<br>Ser Arg Arg Asp Leu Pro Ala His Leu Gln His Asp Cys Pro Lys Arg<br>             125                       130                    135 | 495 |
| CGC CTC AAG TGC GAG TTT TGT GGC TGT GAC TTC AGT GGG GAG GCC TAT<br>Arg Leu Lys Cys Glu Phe Cys Gly Cys Asp Phe Ser Gly Glu Ala Tyr<br>      140                       145                       150 | 543 |
| GAG AGC CAT GAG GGT ATG TGC CCC CAG GAG AGT GTC TAC TGT GAG AAT<br>Glu Ser His Glu Gly Met Cys Pro Gln Glu Ser Val Tyr Cys Glu Asn<br>155                     160                       165 | 591 |
| AAG TGT GGT GCC CGC ATG ATG CGG GGG CTG CTG GCC CAG CAT GCC ACC<br>Lys Cys Gly Ala Arg Met Met Arg Gly Leu Leu Ala Gln His Ala Thr<br>170                     175                      180                185 | 639 |
| TCT GAG TGC CCC AAG CGC ACT CAG CCC TGC ACC TAC TGC ACT AAG GAG<br>Ser Glu Cys Pro Lys Arg Thr Gln Pro Cys Thr Tyr Cys Thr Lys Glu<br>                  190                       195                    200 | 687 |
| TTC GTC TTT GAC ACC ATC CAG AGC CAC CAG TAC CAG TGC CCA AGG CTG<br>Phe Val Phe Asp Thr Ile Gln Ser His Gln Tyr Gln Cys Pro Arg Leu<br>             205                       210                    215 | 735 |
| CCT GTT GCC TGC CCC AAC CAA TGT GGT GTG GGC ACT GTG GCT CGG GAG<br>Pro Val Ala Cys Pro Asn Gln Cys Gly Val Gly Thr Val Ala Arg Glu<br>      220                       225                       230 | 783 |
| GAC CTG CCA GGC CAT CTG AAG GAC AGC TGT AAC ACC GCC CTG GTG CTC<br>Asp Leu Pro Gly His Leu Lys Asp Ser Cys Asn Thr Ala Leu Val Leu<br>235                     240                       245 | 831 |
| TGC CCA TTC AAA GAC TCC GGC TGC AAG CAC AGG TGC CCT AAG CTG GCA<br>Cys Pro Phe Lys Asp Ser Gly Cys Lys His Arg Cys Pro Lys Leu Ala<br>250                     255                      260                265 | 879 |
| ATG GCA CGG CAT GTG GAG GAG AGT GTG AAG CCA CAT CTG GCC ATG ATG<br>Met Ala Arg His Val Glu Glu Ser Val Lys Pro His Leu Ala Met Met<br>                  270                       275                    280 | 927 |

-continued

| | |
|---|---|
| TGT GCC CTG GTG AGC CGG CAA CGG CAG GAG CTG CAG GAG CTT CGG CGA<br>Cys Ala Leu Val Ser Arg Gln Arg Gln Glu Leu Gln Glu Leu Arg Arg<br>           285                 290                295 | 975 |
| GAG CTG GAG GAG CTA TCA GTG GGC AGT GAT GGC GTG CTC ATC TGG AAG<br>Glu Leu Glu Glu Leu Ser Val Gly Ser Asp Gly Val Leu Ile Trp Lys<br>       300                 305                310 | 1023 |
| ATT GGC AGC TAT GGA CGG CGG CTA CAG GAG GCC AAG GCC AAG CCC AAC<br>Ile Gly Ser Tyr Gly Arg Arg Leu Gln Glu Ala Lys Ala Lys Pro Asn<br>315                 320                325 | 1071 |
| CTT GAG TGC TTC AGC CCA GCC TTC TAC ACA CAT AAG TAT GGT TAC AAG<br>Leu Glu Cys Phe Ser Pro Ala Phe Tyr Thr His Lys Tyr Gly Tyr Lys<br>330                 335              340                345 | 1119 |
| CTG CAG GTG TCT GCA TTC CTC AAT GGC AAT GGC AGT GGT GAG GGC ACA<br>Leu Gln Val Ser Ala Phe Leu Asn Gly Asn Gly Ser Gly Glu Gly Thr<br>           350                 355                360 | 1167 |
| CAC CTC TCA CTG TAC ATT CGT GTG CTG CCT GGT GCC TTT GAC AAT CTC<br>His Leu Ser Leu Tyr Ile Arg Val Leu Pro Gly Ala Phe Asp Asn Leu<br>               365                370                375 | 1215 |
| CTT GAG TGG CCC TTT GCC CGC CGT GTC ACC TTC TCC CTG CTG GAT CAG<br>Leu Glu Trp Pro Phe Ala Arg Arg Val Thr Phe Ser Leu Leu Asp Gln<br>       380                 385                390 | 1263 |
| AGC GAC CCT GGG CTG GCT AAA CCA CAG CAC GTC ACT GAG ACC TTC CAC<br>Ser Asp Pro Gly Leu Ala Lys Pro Gln His Val Thr Glu Thr Phe His<br>395                 400                405 | 1311 |
| CCC GAC CCA AAC TGG AAG AAT TTC CAG AAG CCA GGC ACG TGG CGG GGC<br>Pro Asp Pro Asn Trp Lys Asn Phe Gln Lys Pro Gly Thr Trp Arg Gly<br>410                 415                420                425 | 1359 |
| TCC CTG GAT GAG AGT TCT CTG GGC TTT GGT TAT CCC AAG TTC ATC TCC<br>Ser Leu Asp Glu Ser Ser Leu Gly Phe Gly Tyr Pro Lys Phe Ile Ser<br>                  430                435                440 | 1407 |
| CAC CAG GAC ATT CGA AAG CGA AAC TAT GTG CGG GAT GAT GCA GTC TTC<br>His Gln Asp Ile Arg Lys Arg Asn Tyr Val Arg Asp Asp Ala Val Phe<br>               445                450                455 | 1455 |
| ATC CGT GCT GCT GTT GAA CTG CCC CGG AAG ATC CTC AGC TGAGTGCAGG<br>Ile Arg Ala Ala Val Glu Leu Pro Arg Lys Ile Leu Ser<br>            460                 465                470 | 1504 |
| TGGGGTTCGA GGGGAAAGGA CGATGGGGCA TGACCTCAGT CAGGCACTGG CTGAACTTGG | 1564 |
| AGAGGGGGCC GGACCCCCGT CAGCTGCTTC TGCTGCCTAG GTTCTGTTAC CCCATCCTCC | 1624 |
| CTCCCCCAGC CACCACCCTC AGGTGCCTCC AATTGGTGCT TCAGCCCTGG CCCCTGTGGG | 1684 |
| GAACAGGTCT TGGGGTCATG AAGGGCTGGA ACAAGTGAC CCCAGGGCCT GTCTCCCTTC | 1744 |
| TTGGGTAGGG CAGACATGCC TTGGTGCCGG TCACACTCTA CACGGACTGA GGTGCCTGCT | 1804 |
| CAGGTGCTAT GTCCCAAGAG CCATAAGGGG GTGGGAATTG GGAGGGAGA AAGGGTAGTT | 1864 |
| CAAAGAGTCT GTCTTGAGAT CTGATTTTTT CCCCCTTTAC CTAGCTGTGC CCCCTCTGGT | 1924 |
| TATTTATTTC CTTAGTGCCA GGAGGGCACA GCAGGGGAGC CCTGATTTTT AATAAATCCG | 1984 |
| GAATTGTATT TATTAAAAAA | 2004 |

(2) INFORMATION FOR SEQ ID NO:2:

(i) SEQUENCE CHARACTERISTICS:
        (A) LENGTH: 470 amino acids
        (B) TYPE: amino acid
        (D) TOPOLOGY: linear (ii) MOLECULE TYPE: protein (xi) SEQUENCE DESCRIPTION: SEQ ID NO:2:

Met Pro Gly Phe Asp Tyr Lys Phe Leu Glu Lys Pro Lys Arg Arg Leu
1                5                  10                15

-continued

```
Leu Cys Pro Leu Cys Gly Lys Pro Met Arg Glu Pro Val Gln Val Ser
             20                  25                  30
Thr Cys Gly His Arg Phe Cys Asp Thr Cys Leu Gln Glu Phe Leu Ser
         35                  40                  45
Glu Gly Val Phe Lys Cys Pro Glu Asp Gln Leu Pro Leu Asp Tyr Ala
     50                  55                  60
Lys Ile Tyr Pro Asp Pro Glu Leu Glu Val Gln Val Leu Gly Leu Pro
 65                  70                  75                  80
Ile Arg Cys Ile His Ser Glu Glu Gly Cys Arg Trp Ser Gly Pro Leu
                 85                  90                  95
Arg His Leu Gln Gly His Leu Asn Thr Cys Ser Phe Asn Val Ile Pro
            100                 105                 110
Cys Pro Asn Arg Cys Pro Met Lys Leu Ser Arg Arg Asp Leu Pro Ala
        115                 120                 125
His Leu Gln His Asp Cys Pro Lys Arg Leu Lys Cys Glu Phe Cys
    130                 135                 140
Gly Cys Asp Phe Ser Gly Glu Ala Tyr Glu Ser His Glu Gly Met Cys
145                 150                 155                 160
Pro Gln Glu Ser Val Tyr Cys Glu Asn Lys Cys Gly Ala Arg Met Met
                165                 170                 175
Arg Gly Leu Leu Ala Gln His Ala Thr Ser Glu Cys Pro Lys Arg Thr
            180                 185                 190
Gln Pro Cys Thr Tyr Cys Thr Lys Glu Phe Val Phe Asp Thr Ile Gln
        195                 200                 205
Ser His Gln Tyr Gln Cys Pro Arg Leu Pro Val Ala Cys Pro Asn Gln
    210                 215                 220
Cys Gly Val Gly Thr Val Ala Arg Glu Asp Leu Pro Gly His Leu Lys
225                 230                 235                 240
Asp Ser Cys Asn Thr Ala Leu Val Leu Cys Pro Phe Lys Asp Ser Gly
                245                 250                 255
Cys Lys His Arg Cys Pro Lys Leu Ala Met Ala Arg His Val Glu Glu
            260                 265                 270
Ser Val Lys Pro His Leu Ala Met Met Cys Ala Leu Val Ser Arg Gln
        275                 280                 285
Arg Gln Glu Leu Gln Glu Leu Arg Arg Glu Leu Glu Glu Leu Ser Val
    290                 295                 300
Gly Ser Asp Gly Val Leu Ile Trp Lys Ile Gly Ser Tyr Gly Arg Arg
305                 310                 315                 320
Leu Gln Glu Ala Lys Ala Lys Pro Asn Leu Glu Cys Phe Ser Pro Ala
                325                 330                 335
Phe Tyr Thr His Lys Tyr Gly Tyr Lys Leu Gln Val Ser Ala Phe Leu
            340                 345                 350
Asn Gly Asn Gly Ser Gly Glu Gly Thr His Leu Ser Leu Tyr Ile Arg
        355                 360                 365
Val Leu Pro Gly Ala Phe Asp Asn Leu Leu Glu Trp Pro Phe Ala Arg
    370                 375                 380
Arg Val Thr Phe Ser Leu Leu Asp Gln Ser Asp Pro Gly Leu Ala Lys
385                 390                 395                 400
Pro Gln His Val Thr Glu Thr Phe His Pro Asp Pro Asn Trp Lys Asn
                405                 410                 415
Phe Gln Lys Pro Gly Thr Trp Arg Gly Ser Leu Asp Glu Ser Ser Leu
            420                 425                 430
Gly Phe Gly Tyr Pro Lys Phe Ile Ser His Gln Asp Ile Arg Lys Arg
```

```
                    435                 440                     445
Asn Tyr Val Arg Asp Asp Ala Val Phe Ile Arg Ala Val Glu Leu
    450                 455                 460

Pro Arg Lys Ile Leu Ser
465                 470

(2) INFORMATION FOR SEQ ID NO:3:

(i) SEQUENCE CHARACTERISTICS:
        (A) LENGTH: 3846 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 76..858

(xi) SEQUENCE DESCRIPTION: SEQ ID NO:3:

GCCTCCCGCC AGCTCGCCTC GGGGAACAGG ACGCGCGTGA GCTCAGGCGT CCCCGCCCCA       60

GCTTTTCTCG GAACC ATG AAC CCC AAC TGC GCC CGG TGC GGC AAG ATC GTG      111
              Met Asn Pro Asn Cys Ala Arg Cys Gly Lys Ile Val
                1              5                  10

TAT CCC ACG GAG AAG GTG AAC TGT CTG GAT AAG TTC TGG CAT AAA GCA        159
Tyr Pro Thr Glu Lys Val Asn Cys Leu Asp Lys Phe Trp His Lys Ala
        15                  20                  25

TGC TTC CAT TGC GAG ACC TGC AAG ATG ACA CTG AAC ATG AAG AAC TAC        207
Cys Phe His Cys Glu Thr Cys Lys Met Thr Leu Asn Met Lys Asn Tyr
    30                  35                  40

AAG GGC TAC GAG AAG AAG CCC TAC TGC AAC GCA CAC TAC CCC AAG CAG        255
Lys Gly Tyr Glu Lys Lys Pro Tyr Cys Asn Ala His Tyr Pro Lys Gln
 45                 50                  55                  60

TCC TTC ACC ATG GTG GCG GAC ACC CCG GAA AAC CTT CGC CTC AAG CAA        303
Ser Phe Thr Met Val Ala Asp Thr Pro Glu Asn Leu Arg Leu Lys Gln
                65                  70                  75

CAG AGT GAG CTC CAG AGT CAG GTG CGC TAC AAG GAG GAG TTT GAG AAG        351
Gln Ser Glu Leu Gln Ser Gln Val Arg Tyr Lys Glu Glu Phe Glu Lys
            80                  85                  90

AAC AAG GGC AAA GGT TTC AGC GTA GTG GCA GAC ACG CCC GAG CTC CAG        399
Asn Lys Gly Lys Gly Phe Ser Val Val Ala Asp Thr Pro Glu Leu Gln
        95                  100                 105

AGA ATC AAG AAG ACC CAG GAC CAG ATC AGT AAT ATA AAA TAC CAT GAG        447
Arg Ile Lys Lys Thr Gln Asp Gln Ile Ser Asn Ile Lys Tyr His Glu
    110                 115                 120

GAG TTT GAG AAG AGC CGC ATG GGC CCT AGC GGG GGC GAG GGC ATG GAG        495
Glu Phe Glu Lys Ser Arg Met Gly Pro Ser Gly Gly Glu Gly Met Glu
125                 130                 135                 140

CCA GAG CGT CGG GAT TCA CAG GAC GGC AGC AGC TAC CGG CGG CCC CTG        543
Pro Glu Arg Arg Asp Ser Gln Asp Gly Ser Ser Tyr Arg Arg Pro Leu
                145                 150                 155

GAG CAG CAG CAG CCT CAC CAC ATC CCG ACC AGT GCC CCG GTT TAC CAG        591
Glu Gln Gln Gln Pro His His Ile Pro Thr Ser Ala Pro Val Tyr Gln
            160                 165                 170

CAG CCC CAG CAG CAG CCG GTG GCC CAG TCC TAT GGT GGC TAC AAG GAG        639
Gln Pro Gln Gln Gln Pro Val Ala Gln Ser Tyr Gly Gly Tyr Lys Glu
        175                 180                 185

CCT GCA GCC CCA GTC TCC ATA CAG CGC AGC GCC CCA GGT GGT GGC GGG        687
Pro Ala Ala Pro Val Ser Ile Gln Arg Ser Ala Pro Gly Gly Gly Gly
    190                 195                 200

AAG CGG TAC CGC GCG GTG TAT GAC TAC AGC GCC GCC GAC GAG GAC GAG        735
```

```
Lys Arg Tyr Arg Ala Val Tyr Asp Tyr Ser Ala Ala Asp Glu Asp Glu
205                 210                 215                 220

GTC TCC TTC CAG GAC GGG GAC ACC ATC GTC AAC GTG CAG CAG ATC GAC        783
Val Ser Phe Gln Asp Gly Asp Thr Ile Val Asn Val Gln Gln Ile Asp
                225                 230                 235

GAC GGC TGG ATG TAC GGG ACG GTG GAG CGC ACC GGC GAC ACG GGG ATG        831
Asp Gly Trp Met Tyr Gly Thr Val Glu Arg Thr Gly Asp Thr Gly Met
                240                 245                 250

CTG CCG GCC AAC TAC GTG GAG GCC ATC TGAACCCGGA GCGCCCCCAT              878
Leu Pro Ala Asn Tyr Val Glu Ala Ile
                255                 260

CTGTCTTCAG CACATTCCAC GGCATCGCAT CCGTCCTGGG CGTGAGCCGT CCATTCTTCA       938
GTGTCTCTGT TTTTTAAAAC CTGCGACAGC TTGTGATTCC TACCCCTCTT CCAGCTTCTT       998
TTGCCAACTG AAGCCTTCTT CTGCCACTTC TGCGGGCTCC CTCCTCTGGC AGGCTTCCCC      1058
CGTGATCGAC TTCTTGGTTT TCTCTCTGGA TGGAACGGGT ATGGGCCTCT CTGGGGGAGG      1118
CAGGGCTGGA ATGGGAGACC TGTTGGCCTG TGGGCCTCAC CTGCCCCTCT GTTCTCTCCC      1178
CTCACATCCT CCTGCCCAGC TCCTCACATA CCCACACATT CCAGGGCTGG GGTGAGCCTG      1238
ACTGCCAGGA CCCCAGGTCA GGGGCTCCCT ACATTCCCCA GAGTGGGATC CACTTCTTGG      1298
TTCCTGGGAT GGCGATGGGG ACTCTGCCGC TGTGTAGGGA CCAGTGGGAT GGGCTCTACC      1358
TCTCTTTCTC AAAGAGGGGG CTCTGCCCAC CTGGGGTCTC TCTCCCTACC TCCCTCCTCA      1418
GGGGCAACAA CAGGAGAATG GGGTTCCTGC TGTGGGGCGA ATTCATCCCC TCCCCGCGCG      1478
TTCCTTCGCA CACTGTGATT TTGCCCTCCT GCCCACGCAG ACCTGCAGCG GGCAAAGAGC      1538
TCCCGAGGAA GCACAGCTTG GGTCAGGTTC TTGCCTTTCT TAATTTTAGG GACAGCTACC      1598
GGAAGGAGGG GAACAAGGAG TTCTCTTCCG CAGCCCCTTT CCCCACGCCC ACCCCCAGTC      1658
TCCAGGGACC CTTGCCTGCC TCCTAGGCTG GAAGCCATGG TCCCGAAGTG TAGGGCAAGG      1718
GTGCCTCAGG ACCTTTTGGT CTTCAGCCTC CCTCAGCCCC CAGGATCTGG GTTAGGTGGC      1778
CGCTCCTCCC TGCTCCTCAT GGGAAGATGT CTCAGAGCCT TCCATGACCT CCCTCCCCA       1838
GCCCAATGCC AAGTGGACTT GGAGCTGCAC AAAGTCAGCA GGGACCACTA AATCTCCAAG      1898
ACCTGGTGTG CGGAGGCAGG AGCATGTATG TCTGCAGGTG TCTGACACGC AAGTGTGTGA      1958
GTGTGAGTGT GAGAGATGGG GCGGGGGTGT GTCTGTAGGT GTCTCTGGGC CTGTGTGTGG      2018
GTGGGGTTAT GTGAGGGTAT GAAGAGCTGT CTTCCCCTGA GAGTTTCCTC AGAACCCACA      2078
GTGAGAGGGG AGGGCTCCTG GGGCAGAGAA GTTCCTTAGG TTTTCTTTGG AATGAAATTC      2138
CTCCTTCCCC CCATCTCTGA GTGGAGGAAG CCCACCAATC TGCCCTTTGC AGTGTGTCAG      2198
GGTGGAAGGT AAGAGGTTGG TGTGGAGTTG GGGCTGCCAT AGGGTCTGCA GCCTGCTGGG      2258
GCTAAGCGGT GGAGGAAGGC TCTGTCACTC CAGGCATATG TTTCCCCATC TCTGTCTGGG      2318
GCTACAGAAT AGGGTGGCAG AAGTGTCACC CTGTGGGTGT CTCCCTCGGG GGCTCTTCCC      2378
CTAGACCTCC CCCTCACTTA CATAAAGCTC CCTTGAAGCA AGAAAGAGGG TCCCAGGGCT      2438
GCAAAACTGG AAGCACAGCC TCGGGGATGG GGAGGGAAAG ACGGTGCTAT ATCCAGTTCC      2498
TGCTCTCTGC TCATGGGTGG CTGTGACAAC CCTGGCCTCA CTTGATTCAT CTCTGGTTTT      2558
CTTGCCACCC TCTGGGAGTC CCCATCCCAT TTTCATCCTG AGCCCAACCA GGCCCTGCCA      2618
TTGGCCTCTT GTCCCTTGGC ACACTTGTAC CCACAGGTGA GGGGCAGGAC CTGAAGGTAT      2678
TGGCCTGTTC AACAATCAGT CATCATGGGT GTTTTTGTCA ACTGCTTGTT AATTGATTTG      2738
GGGATGTTTG CCCCGAATGA GAGGTTGAGG AAAAGACTGT GGGTGGGGAG GCCCTGCCTG      2798
ACCCATCCCT TTTCCTTTCT GGCCCCAGCC TAGGTGGAGG CAAGTGGAAT ATCTTATATT      2858
```

```
GGGCGATTTG GGGGCTCGGG GAGGCAGAGA ATCTCTTGGG AGTCTTGGGT GGCGCTGGTG    2918

CATTCTGTTT CCTCTTGATC TCAAAGCACA ATGTGGATTT GGGGACCAAA GGTCAGGGAC    2978

ACATCCCCTT AGAGGACCTG AGTTTGGGAG AGTGGTGAGT GGAAGGGAGG AGCAGCAAGA    3038

AGCAGCCTGT TTTCACTCAG CTTAATTCTC CTTCCCAGAT AAGGCAAGCC AGTCATGGAA    3098

TCTTGCTGCA GGCCCTCCCT CTACTCTTCC TGTCCTAAAA ATAGGGGCCG TTTTCTTACA    3158

CACCCCCAGA GAGAGGAGGG ACTGTCACAC TGGTGCTGAG TGACCGGGGG CTGCTGGGCG    3218

TCTGTTCTTT ACCAAAACCA TCCATCCCTA GAAGAGCACA GAGCCCTGAG GGGCTGGGCT    3278

GGGCTGGGCT GAGCCCCTGG TCTTCTCTAC AGTTCACAGA GGTCTTTCAG CTCATTTAAT    3338

CCCAGGAAAG AGGCATCAAA GCTAGAATGT GAATATAACT TTTGTGGGCC AATACTAAGA    3398

ATAACAAGAA GCCCAGTGGT GAGGAAAGTG CGTTCTCCCA GCACTGCCTC CTGTTTTCTC    3458

CCTCTCATGT CCCTCCAGGG AAAATGACTT TATTGCTTAA TTTCTGCCTT TCCCCCCTCA    3518

CACATGCACT TTTGGGCCTT TTTTTATAGC TGGAAAAAAC AAAATACCAC CCTACAAACC    3578

TGTATTTAAA AAGAAACAGA AATGACCACG TGAAATTTGC CTCTGTCCAA ACATTTCATC    3638

CGTGTGTATG TGTATGTGTG TGAGTGTGTG AAGCCGCCAG TTCATCTTTT TATATGGGGT    3698

TGTTGTCTCA TTTTGGTCTG TTTTGGTCCC CTCCCTCGTG GGCTTGTGCT CGGGATCAAA    3758

CCTTTCTGGC CTGTTATGAT TCTGAACATT TGACTTGAAC CACAAGTGAA TCTTTCTCCT    3818

GGTGACTCAA ATAAAAGTAT AATTTTTA                                       3846
```

(2) INFORMATION FOR SEQ ID NO:4:

(i) SEQUENCE CHARACTERISTICS:
        (A) LENGTH: 261 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asn Pro Asn Cys Ala Arg Cys Gly Lys Ile Val Tyr Pro Thr Glu
 1               5                  10                  15

Lys Val Asn Cys Leu Asp Lys Phe Trp His Lys Ala Cys Phe His Cys
                20                  25                  30

Glu Thr Cys Lys Met Thr Leu Asn Met Lys Asn Tyr Lys Gly Tyr Glu
            35                  40                  45

Lys Lys Pro Tyr Cys Asn Ala His Tyr Pro Lys Gln Ser Phe Thr Met
        50                  55                  60

Val Ala Asp Thr Pro Glu Asn Leu Arg Leu Lys Gln Gln Ser Glu Leu
 65                  70                  75                  80

Gln Ser Gln Val Arg Tyr Lys Glu Glu Phe Glu Lys Asn Lys Gly Lys
                85                  90                  95

Gly Phe Ser Val Val Ala Asp Thr Pro Glu Leu Gln Arg Ile Lys Lys
                100                 105                 110

Thr Gln Asp Gln Ile Ser Asn Ile Lys Tyr His Glu Glu Phe Glu Lys
            115                 120                 125

Ser Arg Met Gly Pro Ser Gly Gly Glu Gly Met Glu Pro Glu Arg Arg
        130                 135                 140

Asp Ser Gln Asp Gly Ser Ser Tyr Arg Arg Pro Leu Glu Gln Gln Gln
145                 150                 155                 160

Pro His His Ile Pro Thr Ser Ala Pro Val Tyr Gln Gln Pro Gln Gln
                165                 170                 175
```

```
Gln Pro Val Ala Gln Ser Tyr Gly Gly Tyr Lys Glu Pro Ala Ala Pro
            180                 185                 190

Val Ser Ile Gln Arg Ser Ala Pro Gly Gly Gly Lys Arg Tyr Arg
            195                 200                 205

Ala Val Tyr Asp Tyr Ser Ala Asp Glu Asp Val Ser Phe Gln
    210                 215                 220

Asp Gly Asp Thr Ile Val Asn Val Gln Gln Ile Asp Asp Gly Trp Met
225                 230                 235                 240

Tyr Gly Thr Val Glu Arg Thr Gly Asp Thr Gly Met Leu Pro Ala Asn
            245                 250                 255

Tyr Val Glu Ala Ile
            260

(2) INFORMATION FOR SEQ ID NO:5:

(i) SEQUENCE CHARACTERISTICS:
        (A) LENGTH: 2073 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 169..1503

(xi) SEQUENCE DESCRIPTION: SEQ ID NO:5:
```

| | |
|---|---|
| CAGCGGCGGA AGTGGCGCTG CCGGAAGATC TTCTTCCGCT CTGAGGCGCT ACTGAGGCCG | 60 |
| CGGAGCCGGA CTGCGGTTGG GGCGGGAAGA GCCGGGGCCG TGGCTGACAT GGAGCAGCCC | 120 |
| TGCTGCTGAG GCCGCGCCCT CCCCGCCCTG AGGTGGGGGC CCACCAGG ATG AGC AAG | 177 |

```
                                                  Met Ser Lys
                                                   1
```

| | |
|---|---|
| CTG CCC AGG GAG CTG ACC CGA GAC TTG GAG CGC AGC CTG CCT GCC GTG | 225 |
| Leu Pro Arg Glu Leu Thr Arg Asp Leu Glu Arg Ser Leu Pro Ala Val | |
| 5                   10                  15                      | |
| GCC TCC CTG GGC TCC TCA CTG TCC CAC AGC CAG AGC CTC TCC TCG CAC | 273 |
| Ala Ser Leu Gly Ser Ser Leu Ser His Ser Gln Ser Leu Ser Ser His | |
|     20                  25                  30              35 | |
| CTC CTT CCG CCG CCT GAG AAG CGA AGG GCC ATC TCT GAT GTC CGC CGC | 321 |
| Leu Leu Pro Pro Pro Glu Lys Arg Arg Ala Ile Ser Asp Val Arg Arg | |
|                 40                  45                  50     | |
| ACC TTC TGT CTC TTC GTC ACC TTC GAC CTG CTC TTC ATC TCC CTG CTC | 369 |
| Thr Phe Cys Leu Phe Val Thr Phe Asp Leu Leu Phe Ile Ser Leu Leu | |
|             55                  60                  65         | |
| TGG ATC ATC GAA CTG AAT ACC AAC ACA GGC ATC CGT AAG AAC TTG GAG | 417 |
| Trp Ile Ile Glu Leu Asn Thr Asn Thr Gly Ile Arg Lys Asn Leu Glu | |
|         70                  75                  80             | |
| CAG GAG ATC ATC CAG TAC AAC TTT AAA ACT TCC TTC TTC GAC ATC TTT | 465 |
| Gln Glu Ile Ile Gln Tyr Asn Phe Lys Thr Ser Phe Phe Asp Ile Phe | |
|     85                  90                  95                 | |
| GTC CTG GCC TTC TTC CGC TTC TCT GGA CTG CTC TTA GGC TAT GCC GTG | 513 |
| Val Leu Ala Phe Phe Arg Phe Ser Gly Leu Leu Leu Gly Tyr Ala Val | |
| 100                 105                 110                 115 | |
| CTG CAG CTC CGG CAC TGG TGG GTG ATT GCG GTC ACG ACG CTG GTG TCC | 561 |
| Leu Gln Leu Arg His Trp Trp Val Ile Ala Val Thr Thr Leu Val Ser | |
|                 120                 125                 130    | |
| AGT GCA TTC CTC ATT GTC AAG GTC ATC CTC TCT GAG CTG CTC AGC AAA | 609 |
| Ser Ala Phe Leu Ile Val Lys Val Ile Leu Ser Glu Leu Leu Ser Lys | |
|             135                 140                 145        | |
| GGG GCA TTT GGC TAC CTG CTC CCC ATC GTC TCT TTT GTC CTC GCC TGG | 657 |

```
                Gly Ala Phe Gly Tyr Leu Leu Pro Ile Val Ser Phe Val Leu Ala Trp
                            150                 155                 160

TTG GAG ACC TGG TTC CTT GAC TTC AAA GTC CTA CCC CAG GAA GCT GAA           705
Leu Glu Thr Trp Phe Leu Asp Phe Lys Val Leu Pro Gln Glu Ala Glu
        165                 170                 175

GAG GAG CGA TGG TAT CTT GCC GCC CAG GTT GCT GTT GCC CGT GGA CCC           753
Glu Glu Arg Trp Tyr Leu Ala Ala Gln Val Ala Val Ala Arg Gly Pro
180                 185                 190                 195

CTG CTG TTC TCC GGT GCT CTG TCC GAG GGA CAG TTC TAT TCA CCC CCA           801
Leu Leu Phe Ser Gly Ala Leu Ser Glu Gly Gln Phe Tyr Ser Pro Pro
                200                 205                 210

GAA TCC TTT GCA GGG TCT GAC AAT GAA TCA GAT GAA GAA GTT GCT GGG           849
Glu Ser Phe Ala Gly Ser Asp Asn Glu Ser Asp Glu Glu Val Ala Gly
        215                 220                 225

AAG AAA AGT TTC TCT GCT CAG GAG CGG GAG TAC ATC CGC CAG GGG AAG           897
Lys Lys Ser Phe Ser Ala Gln Glu Arg Glu Tyr Ile Arg Gln Gly Lys
                230                 235                 240

GAG GCC ACG GCA GTG GTG GAC CAG ATC TTG GCC CAG GAA GAG AAC TGG           945
Glu Ala Thr Ala Val Val Asp Gln Ile Leu Ala Gln Glu Glu Asn Trp
245                 250                 255

AAG TTT GAG AAG AAT AAT GAA TAT GGG GAC ACC GTG TAC ACC ATT GAA           993
Lys Phe Glu Lys Asn Asn Glu Tyr Gly Asp Thr Val Tyr Thr Ile Glu
260                 265                 270                 275

GTT CCC TTT CAC GGC AAG ACG TTT ATC CTG AAG ACC TTC CTG CCC TGT          1041
Val Pro Phe His Gly Lys Thr Phe Ile Leu Lys Thr Phe Leu Pro Cys
                280                 285                 290

CCT GCG GAG CTC GTG TAC CAG GAG GTG ATC CTG CAG CCC GAG AGG ATG          1089
Pro Ala Glu Leu Val Tyr Gln Glu Val Ile Leu Gln Pro Glu Arg Met
                295                 300                 305

GTG CTG TGG AAC AAG ACA GTG ACT GCC TGC CAG ATC CTG CAG CGA GTG          1137
Val Leu Trp Asn Lys Thr Val Thr Ala Cys Gln Ile Leu Gln Arg Val
                310                 315                 320

GAA GAC AAC ACC CTC ATC TCC TAT GAC GTG TCT GCA GGG GCT GCG GGC          1185
Glu Asp Asn Thr Leu Ile Ser Tyr Asp Val Ser Ala Gly Ala Ala Gly
325                 330                 335

GGC GTG GTC TCC CCA AGG GAC TTC GTG AAT GTC CGG CGC ATT GAG CGG          1233
Gly Val Val Ser Pro Arg Asp Phe Val Asn Val Arg Arg Ile Glu Arg
340                 345                 350                 355

CGC AGG GAC CGA TAC TTG TCA TCA GGG ATC GCC ACC TCA CAC AGT GCC          1281
Arg Arg Asp Arg Tyr Leu Ser Ser Gly Ile Ala Thr Ser His Ser Ala
                360                 365                 370

AAG CCC CCG ACG CAC AAA TAT GTC CGG GGA GAG AAT GGC CCT GGG GGC          1329
Lys Pro Pro Thr His Lys Tyr Val Arg Gly Glu Asn Gly Pro Gly Gly
                375                 380                 385

TTC ATC GTG CTC AAG TCG GCC AGT AAC CCC CGT GTT TGC ACC TTT GTC          1377
Phe Ile Val Leu Lys Ser Ala Ser Asn Pro Arg Val Cys Thr Phe Val
                390                 395                 400

TGG ATT CTT AAT ACA GAT CTC AAG GGC CGC CTG CCC CGG TAC CTC ATC          1425
Trp Ile Leu Asn Thr Asp Leu Lys Gly Arg Leu Pro Arg Tyr Leu Ile
405                 410                 415

CAC CAG AGC CTC GCG GCC ACC ATG TTT GAA TTT GCC TTT CAC CTG CGA          1473
His Gln Ser Leu Ala Ala Thr Met Phe Glu Phe Ala Phe His Leu Arg
420                 425                 430                 435

CAG CGC ATC AGC GAG CTG GGG GCC CGG GCG TGACTGTGCC CCCTCCCACC            1523
Gln Arg Ile Ser Glu Leu Gly Ala Arg Ala
                440                 445

CTGCGGGCCA GGGTCCTGTC GCCACCACTT CCAGAGCCAG AAAGGGTGCC AGTTGGGCTC        1583

GCACTGCCCA CATGGGACCT GGCCCCAGGC TGTCACCCTC CACCGAGCCA CGCAGTGCCT        1643

GGAGTTGACT GACTGAGCAG GCTGTGGGGT GGAGCACTGG ACTCCGGGGC CCCACTGGCT        1703
```

```
GGAGGAAGTG GGGTCTGGCC TGTTGATGTT TACATGGCGC CCTGCCTCCT GGAGGACCAG    1763

ATTGCTCTGC CCCACCTTGC CAGGGCAGGG TCTGGGCTGG GCACCTGACT TGGCTGGGGA    1823

GGACCAGGGC CCTGGGCAGG GCAGGGCAGC CTGTCACCCG TGTGAAGATG AAGGGGCTCT    1883

TCATCTGCCT GCGCTCTCGT CGGTTTTTTT AGGATTATTG AAAGAGTCTG GGACCCTTGT    1943

TGGGGAGTGG GTGGCAGGTG GGGGTGGGCT GCTGGCCATG AATCTCTGCC TCTCCCAGGC    2003

TGTCCCCCTC CTCCCAGGGC CTCCTGGGGG ACCTTTGTAT TAAGCCAATT AAAAACATGA    2063

ATTTAAAAAA                                                           2073
```

(2) INFORMATION FOR SEQ ID NO:6:

(i) SEQUENCE CHARACTERISTICS:
    (A) LENGTH: 445 amino acids
    (B) TYPE: amino acid
    (D) TOPOLOGY: linear (ii) MOLECULE TYPE: protein (xi) SEQUENCE DESCRIPTION: SEQ ID NO:6:

```
Met Ser Lys Leu Pro Arg Glu Leu Thr Arg Asp Leu Glu Arg Ser Leu
 1               5                  10                  15

Pro Ala Val Ala Ser Leu Gly Ser Ser Leu Ser His Ser Gln Ser Leu
            20                  25                  30

Ser Ser His Leu Leu Pro Pro Glu Lys Arg Arg Ala Ile Ser Asp
        35                  40                  45

Val Arg Arg Thr Phe Cys Leu Phe Val Thr Phe Asp Leu Leu Phe Ile
     50                  55                  60

Ser Leu Leu Trp Ile Ile Glu Leu Asn Thr Asn Thr Gly Ile Arg Lys
 65                  70                  75                  80

Asn Leu Glu Gln Glu Ile Ile Gln Tyr Asn Phe Lys Thr Ser Phe Phe
                85                  90                  95

Asp Ile Phe Val Leu Ala Phe Arg Phe Ser Gly Leu Leu Leu Gly
            100                 105                 110

Tyr Ala Val Leu Gln Leu Arg His Trp Trp Val Ile Ala Val Thr Thr
            115                 120                 125

Leu Val Ser Ser Ala Phe Leu Ile Val Lys Val Ile Leu Ser Glu Leu
    130                 135                 140

Leu Ser Lys Gly Ala Phe Gly Tyr Leu Leu Pro Ile Val Ser Phe Val
145                 150                 155                 160

Leu Ala Trp Leu Glu Thr Trp Phe Leu Asp Phe Lys Val Leu Pro Gln
                165                 170                 175

Glu Ala Glu Glu Arg Trp Tyr Leu Ala Ala Gln Val Ala Val Ala
            180                 185                 190

Arg Gly Pro Leu Leu Phe Ser Gly Ala Leu Ser Glu Gly Gln Phe Tyr
        195                 200                 205

Ser Pro Pro Glu Ser Phe Ala Gly Ser Asp Asn Glu Ser Asp Glu Glu
    210                 215                 220

Val Ala Gly Lys Lys Ser Phe Ser Ala Gln Glu Arg Glu Tyr Ile Arg
225                 230                 235                 240

Gln Gly Lys Glu Ala Thr Ala Val Val Asp Gln Ile Leu Ala Gln Glu
                245                 250                 255

Glu Asn Trp Lys Phe Glu Lys Asn Asn Glu Tyr Gly Asp Thr Val Tyr
            260                 265                 270

Thr Ile Glu Val Pro Phe His Gly Lys Thr Phe Ile Leu Lys Thr Phe
    275                 280                 285
```

```
Leu Pro Cys Pro Ala Glu Leu Val Tyr Gln Glu Val Ile Leu Gln Pro
    290                 295                 300

Glu Arg Met Val Leu Trp Asn Lys Thr Val Thr Ala Cys Gln Ile Leu
305                 310                 315                 320

Gln Arg Val Glu Asp Asn Thr Leu Ile Ser Tyr Asp Val Ser Ala Gly
                325                 330                 335

Ala Ala Gly Gly Val Val Ser Pro Arg Asp Phe Val Asn Val Arg Arg
                340                 345                 350

Ile Glu Arg Arg Arg Asp Arg Tyr Leu Ser Ser Gly Ile Ala Thr Ser
                355                 360                 365

His Ser Ala Lys Pro Pro Thr His Lys Tyr Val Arg Gly Glu Asn Gly
    370                 375                 380

Pro Gly Gly Phe Ile Val Leu Lys Ser Ala Ser Asn Pro Arg Val Cys
385                 390                 395                 400

Thr Phe Val Trp Ile Leu Asn Thr Asp Leu Lys Gly Arg Leu Pro Arg
                405                 410                 415

Tyr Leu Ile His Gln Ser Leu Ala Ala Thr Met Phe Glu Phe Ala Phe
                420                 425                 430

His Leu Arg Gln Arg Ile Ser Glu Leu Gly Ala Arg Ala
    435                 440                 445
```

(2) INFORMATION FOR SEQ ID NO:7:

(i) SEQUENCE CHARACTERISTICS:
        (A) LENGTH: 4253 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 234..1835

(xi) SEQUENCE DESCRIPTION: SEQ ID NO:7:

```
GAATTCCGTT GCTGTCGCAC ACACACACAC ACACACACAC ACCCCCAAC ACACACACAC     60

ACCCCCAAC ACACACACAC ACACACACAC ACACACACAC ACACACACAC ACACAGCGGG    120

ATGGCCGAGC GCCGCACGCG TAGCACGCCG GGACTAGCTA TCCAGCCTCC CAGCAGCCTC    180

TGCGACGGGC GCGGTGCGTA NGTACCTCGC CGGTGGTGGC CGTTCTCCGT AAG ATG       236
                                                              Met
                                                               1

GCG GAC CGG CGG CGG CAG CGC GCT TCG CAA GAC ACC GAG GAC GAG GAA     284
Ala Asp Arg Arg Arg Gln Arg Ala Ser Gln Asp Thr Glu Asp Glu Glu
          5                  10                  15

TCT GGT GCT TCG GGC TCC GAC AGC GGC GGC TCC CCG TTG CGG GGA GGC     332
Ser Gly Ala Ser Gly Ser Asp Ser Gly Gly Ser Pro Leu Arg Gly Gly
             20                  25                  30

GGG AGC TGC AGC GGT AGC GCC GGA GGC GGC GGC AGC GGC TCT CTG CCT     380
Gly Ser Cys Ser Gly Ser Ala Gly Gly Gly Ser Gly Ser Leu Pro
         35                  40                  45

TCA CAG CGC GGA GGC CGA ACC GGG GCC CTT CAT CTG CGG CGG GTG GAG     428
Ser Gln Arg Gly Gly Arg Thr Gly Ala Leu His Leu Arg Arg Val Glu
 50                  55                  60                  65

AGC GGG GGC GCC AAG AGT GCT GAG GAG TCG GAG TGT GAG AGT GAA GAT     476
Ser Gly Gly Ala Lys Ser Ala Glu Glu Ser Glu Cys Glu Ser Glu Asp
                 70                  75                  80

GGC ATT GAA GGT GAT GCT GTT CTC TCG GAT TAT GAA AGT GCA GAA GAC     524
Gly Ile Glu Gly Asp Ala Val Leu Ser Asp Tyr Glu Ser Ala Glu Asp
```

-continued

|  |  |  | 85 |  |  |  | 90 |  |  |  | 95 |  |  |  |  |
|---|---|---|---|---|---|---|---|---|---|---|---|---|---|---|---|

```
TCG GAA GGT GAA GAA GGT GAA TAC AGT GAA GAG GAA AAC TCC AAA GTG       572
Ser Glu Gly Glu Glu Gly Glu Tyr Ser Glu Glu Glu Asn Ser Lys Val
        100                 105                 110

GAG CTG AAA TCA GAA GCT AAT GAT GCT GTT AAT TCT TCA ACA AAA GAA       620
Glu Leu Lys Ser Glu Ala Asn Asp Ala Val Asn Ser Ser Thr Lys Glu
    115                 120                 125

GAG AAG GGA GAA GAA AAG CCT GAC ACC AAA AGC ACT GTG ACT GGA GAG       668
Glu Lys Gly Glu Glu Lys Pro Asp Thr Lys Ser Thr Val Thr Gly Glu
130                 135                 140                 145

AGG CAA AGT GGG GAC GGA CAG GAG AGC ACA GAG CCT GTG GAG AAC AAA       716
Arg Gln Ser Gly Asp Gly Gln Glu Ser Thr Glu Pro Val Glu Asn Lys
            150                 155                 160

GTG GGT AAA AAG GGC CCT AAG CAT TTG GAT GAT GAT GAA GAT CGG AAG       764
Val Gly Lys Lys Gly Pro Lys His Leu Asp Asp Asp Glu Asp Arg Lys
        165                 170                 175

AAT CCA GCA TAC ATA CCT CGG AAA GGG CTC TTC TTT GAG CAT GAT CTT       812
Asn Pro Ala Tyr Ile Pro Arg Lys Gly Leu Phe Phe Glu His Asp Leu
    180                 185                 190

CGA GGG CAA ACT CAG GAG GAG GAA GTC AGA CCC AAG GGG CGT CAG CGA       860
Arg Gly Gln Thr Gln Glu Glu Glu Val Arg Pro Lys Gly Arg Gln Arg
195                 200                 205

AAG CTA TGG AAG GAT GAG GGT CGC TGG GAG CAT GAC AAG TTC CGG GAA       908
Lys Leu Trp Lys Asp Glu Gly Arg Trp Glu His Asp Lys Phe Arg Glu
210                 215                 220                 225

GAT GAG CAG GCC CCA AAG TCC CGA CAG GAG CTC ATT GCT CTT TAT GGT       956
Asp Glu Gln Ala Pro Lys Ser Arg Gln Glu Leu Ile Ala Leu Tyr Gly
            230                 235                 240

TAT GAC ATT CGC TCA GCT CAT AAT CCT GAT GAC ATC AAA CCT CGA AGA      1004
Tyr Asp Ile Arg Ser Ala His Asn Pro Asp Asp Ile Lys Pro Arg Arg
        245                 250                 255

ATC CGG AAA CCC CGA TAT GGG AGT CCT CCA CAA AGA GAT CCA AAC TGG      1052
Ile Arg Lys Pro Arg Tyr Gly Ser Pro Pro Gln Arg Asp Pro Asn Trp
    260                 265                 270

AAC GGT GAG CGG CTA AAC AAG TCT CAT CGC CAC CAG GGT CTT GGG GGC      1100
Asn Gly Glu Arg Leu Asn Lys Ser His Arg His Gln Gly Leu Gly Gly
275                 280                 285

ACC CTA CCA CCA AGG ACA TTT ATT AAC AGG AAT GCT GCA GGT ACC GGC      1148
Thr Leu Pro Pro Arg Thr Phe Ile Asn Arg Asn Ala Ala Gly Thr Gly
290                 295                 300                 305

CGT ATG TCT GCA CCC AGG AAT TAT TCT CGA TCT GGG GGC TTC AAG GAA      1196
Arg Met Ser Ala Pro Arg Asn Tyr Ser Arg Ser Gly Gly Phe Lys Glu
            310                 315                 320

GGT CGT GCT GGT TTT AGG CCT GTG GAA GCT GGT GGG CAG CAT GGT GGC      1244
Gly Arg Ala Gly Phe Arg Pro Val Glu Ala Gly Gly Gln His Gly Gly
        325                 330                 335

CGG TCT GGT GAG ACT GTT AAG CAT GAG ATT AGT TAC CGG TCA CGG CGC      1292
Arg Ser Gly Glu Thr Val Lys His Glu Ile Ser Tyr Arg Ser Arg Arg
    340                 345                 350

CTA GAG CAG ACT TCT GTG AGG GAT CCA TCT CCA GAA GCA GAT GCT CCA      1340
Leu Glu Gln Thr Ser Val Arg Asp Pro Ser Pro Glu Ala Asp Ala Pro
355                 360                 365

GTG CTT GGC AGT CCT GAG AAG GAA GAG GCA GCC TCA GAG CCA CCA GCT      1388
Val Leu Gly Ser Pro Glu Lys Glu Glu Ala Ala Ser Glu Pro Pro Ala
370                 375                 380                 385

GCT GCT CCT GAT GCT GCA CCA CCA CCC CCT GAT AGG CCC ATT GAG AAG      1436
Ala Ala Pro Asp Ala Ala Pro Pro Pro Pro Asp Arg Pro Ile Glu Lys
            390                 395                 400

AAA TCC TAT TCC CGG GCA AGA AGA ACT CGA ACC AAA GTT GGA GAT GCA      1484
Lys Ser Tyr Ser Arg Ala Arg Arg Thr Arg Thr Lys Val Gly Asp Ala
```

-continued

```
                    405                 410                 415
GTC AAG CTT GCA GAG GAG GTG CCC CCT CCT CCT GAA GGA CTG ATT CCA           1532
Val Lys Leu Ala Glu Glu Val Pro Pro Pro Pro Glu Gly Leu Ile Pro
            420                 425                 430

GCA CCT CCA GTC CCA GAA ACC ACC CCA ACT CCA CCT ACT AAG ACT GGG           1580
Ala Pro Pro Val Pro Glu Thr Thr Pro Thr Pro Pro Thr Lys Thr Gly
    435                 440                 445

ACC TGG GAA GCT CCG GTG GAT TCT AGT ACA AGT GGA CTT GAG CAA GAT           1628
Thr Trp Glu Ala Pro Val Asp Ser Ser Thr Ser Gly Leu Glu Gln Asp
450                 455                 460                 465

GTG GCA CAA CTA AAT ATA GCA GAA CAG AAT TGG AGT CCG GGG CAG CCT           1676
Val Ala Gln Leu Asn Ile Ala Glu Gln Asn Trp Ser Pro Gly Gln Pro
            470                 475                 480

TCT TTC CTG CAA CCA CGG GAA CTT CGA GGT ATG CCC AAC CAT ATA CAC           1724
Ser Phe Leu Gln Pro Arg Glu Leu Arg Gly Met Pro Asn His Ile His
    485                 490                 495

ATG GGA GCA GGA CCT CCA CCT CAG TTT AAC CGG ATG GAA GAA ATG CTC           1772
Met Gly Ala Gly Pro Pro Pro Gln Phe Asn Arg Met Glu Glu Met Leu
        500                 505                 510

ACT TTG CAA ATA TCC ATT AAA TAC CTG CCA TGT ACC AAG TGT TTT TCA           1820
Thr Leu Gln Ile Ser Ile Lys Tyr Leu Pro Cys Thr Lys Cys Phe Ser
    515                 520                 525

ACA CCT AAA GGA AGG TAGGACTTGA TATGAGAGCC CTCTAGAATT CTTATTGTTT           1875
Thr Pro Lys Gly Arg
530

AGGCCTCTTT CTTTGTCTCA GGGTGTCCAG GGTGTCCAGG GTGGTCGAGC CAAACGCTAT        1935

TCATCCCAGC GGCAAAGACC TGTGCCAGAG CCCCCGCCC CTCCAGTGCA TATCAGTATC         1995

ATGGAGGGAC ATTACTATGA TCCACTGCAG TTCCAGGGAC CAATCTATAC CCATGGTGAC        2055

AGCCCTGCCC CGCTGCCTCC ACAGGGCATG CTTGTGCAGC AGGAATGAA CCTTCCCCAC         2115

CCAGGTTTAC ATCCCCATCA GACACCAGCT CCTCTGCCCA ATCCAGGCCT CTATCCCCCA        2175

CCAGTGTCCA TGTCTCCAGG ACAGCCACCA CCTCAGCAGT TGCTTGCTCC TACTTACTTT       2235

TCTGCTCCAG GCGTCATGAA CTTTGGTAAT CCCAGTTACC CTTATGCTCC AGGGGCACTG       2295

CCTCCCCCAC CACCGCCTCA TCTGTATCCT AATACACAGG CCCCATCACA GGTATATGGA       2355

GGAGTGACCT ACTATAACCC CGCCCAGCAG CAGGTGCAGC CAAAGCCCTC CCCACCCCGG       2415

AGGACTCCCC AGCCAGTCAC CATCAAGCCC CCTCCACCTG AGGTTGTAAG CAGGGGTTCC       2475

AGTTAATACA AGTTTCTGAA TATTTTAAAT CTTAACATCA TATAAAAAGC AGCAGAGGTG       2535

AGAACTCAGA AGAGAAATAC AGCTGGCTAT CTACTACCAG AAGGGCTTCA AGATATAGG        2595

GTGTGGCTCC TACCAGCAAA CAGCTGAAAG AGGAGGACCC CTGCCTTCCT CTGAGGACAG       2655

GCTCTAGAGA GAGGGAGAAA CAAGTGGACC TCGTCCCATC TTCACTCTTC ACTTGAGTTG      2715

GCTGTGTTCG GGGGAGCAGA GAGAGCCAGA CAGCCCCAAG CTTCTGAGTC TAGATACAGA       2775

AGCCCATGTC TTCTGCTGTT CTTCACTTCT GGGAAATTGA AGTGTCTTCT GTTCCCAAGG       2835

AAGCTCCTTC CTGTTTGTTT TGTTTTCTAA GATGTTCATT TTTAAAGCCT GGCTTCTTAT       2895

CCTTAATATT ATTTTAATTT TTTCTCTTTG TTTCTGTTTC TTGCTCTCTC TCCCTGCCTT       2955

TAAATGAAAC AAGTCTAGTC TTCTGGTTTT CTAGCCCCTC TGGATTCCCT TTTGACTCTT       3015

CCGTGCATCC CAGATAATGG AGAATGTATC AGCCAGCCTT CCCCACCAAG TCTAAAAGA       3075

CCTGGCCTTT CACTTTTAGT TGGCATTTGT TATCCTCTTG TATACTTGTA TTCCCTTAAC      3135

TCTAACCCTG TGGAAGCATG GCTGTCTGCA CAGAGGGTCC CATTGTGCAG AAAAGCTCAG      3195

AGTAGGTGGG TAGGAGCCCT TCTCTTTGAC TTAGGTTTTT AGGAGTCTGA GCATCCATCA      3255
```

```
ATACCTGTAC TATGATGGGC TTCTGTTCTC TGCTGAGGGC CAATACCCTA CTGTGGGGAG    3315

AGATGGCACA CCAGATGCTT TTGTGAGAAA GGGATGGTGG AGTGAGAGCC TTTGCCTTTA    3375

GGGGTGTGTA TTCACATAGT CCTCAGGGCT CAGTCTTTTG AGGTAAGTGG AATTAGAGGG    3435

CCTTGCTTCT CTTCTTTCCA TTCTTCTTGC TACACCCCTT TTCCAGTTGC TGTGGACCAA    3495

TGCATCTCTT TAAAGGCAAA TATTATCCAG CAAGCAGTCT ACCCTGTCCT TTGCAATTGC    3555

TCTTCTCCAC GTCTTTCCTG CTACAAGTGT TTTAGATGTT ACTACCTTAT TTTCCCCGAA    3615

TTCTATTTTT GTCCTTGCAG ACAGAATATA AAAACTCCTG GGCTTAAGGC CTAAGGAAGC    3675

CAGTCACCTT CTGGGCAAGG GCTCCTATCT TTCCTCCCTA TCCATGGCAC TAAACCACTT    3735

CTCTGCTGCC TCTGTGGAAG AGATTCCTAT TACTGCAGTA CATACGTCTG CCAGGGGTAA    3795

CCTGGCCACT GTCCCTGTCC TTCTACAGAA CCTGAGGGCA AAGATGGTGG CTGTGTCTCT    3855

CCCCGGTAAT GTCACTGTTT TTATTCCTTC CATCTAGCAG CTGGCCTAAT CACTCTGAGT    3915

CACAGGTGTG GGATGGAGAG TGGGGAGAGG CACTTAATCT GTAACCCCCA AGGAGGAAAT    3975

AACTAAGAGA TTCTTCTAGG GGTAGCTGGT GGTTGTGCCT TTTGTAGGCT GTTCCCTTTG    4035

CCTTAAACCT GAAGATGTCT CCTCAAGCCT GTGGGCAGCA TGCCCAGATT CCCAGACCTT    4095

AAGACACTGT GAGAGTTGTC TCTGTTGGTC CACTGTGTTT AGTTGCAAGG ATTTTTCCAT    4155

GTGTGGTGGT GTTTTTTGTT ACTGTTTTAA AGGGTGCCCA TTTGTGATCA GCATTGTGAC    4215

TTGGAGATAA TAAAATTTAG ACTATAAACT TGAAAAAA                            4253
```

(2) INFORMATION FOR SEQ ID NO:8:

(i) SEQUENCE CHARACTERISTICS:
        (A) LENGTH: 534 amino acids
        (B) TYPE: amino acid
        (D) TOPOLOGY: linear (ii) MOLECULE TYPE: protein (xi) SEQUENCE DESCRIPTION: SEQ ID NO:8:

```
Met Ala Asp Arg Arg Arg Gln Arg Ala Ser Gln Asp Thr Glu Asp Glu
 1               5                  10                  15

Glu Ser Gly Ala Ser Gly Ser Asp Ser Gly Gly Ser Pro Leu Arg Gly
                20                  25                  30

Gly Gly Ser Cys Ser Gly Ser Ala Gly Gly Gly Ser Gly Ser Leu
            35                  40                  45

Pro Ser Gln Arg Gly Gly Arg Thr Gly Ala Leu His Leu Arg Arg Val
    50                  55                  60

Glu Ser Gly Gly Ala Lys Ser Ala Glu Ser Glu Cys Glu Ser Glu
 65                  70                  75                  80

Asp Gly Ile Glu Gly Asp Ala Val Leu Ser Asp Tyr Glu Ser Ala Glu
                85                  90                  95

Asp Ser Glu Gly Glu Glu Gly Glu Tyr Ser Glu Glu Asn Ser Lys
            100                 105                 110

Val Glu Leu Lys Ser Glu Ala Asn Asp Ala Val Asn Ser Ser Thr Lys
        115                 120                 125

Glu Glu Lys Gly Glu Glu Lys Pro Asp Thr Lys Ser Thr Val Thr Gly
    130                 135                 140

Glu Arg Gln Ser Gly Asp Gly Gln Glu Ser Thr Glu Pro Val Glu Asn
145                 150                 155                 160

Lys Val Gly Lys Lys Gly Pro Lys His Leu Asp Asp Glu Asp Arg
                165                 170                 175

Lys Asn Pro Ala Tyr Ile Pro Arg Lys Gly Leu Phe Phe Glu His Asp
```

```
                    180                 185                 190
Leu Arg Gly Gln Thr Gln Glu Glu Val Arg Pro Lys Gly Arg Gln
                195                 200                 205

Arg Lys Leu Trp Lys Asp Glu Gly Arg Trp Glu His Asp Lys Phe Arg
210                 215                 220

Glu Asp Glu Gln Ala Pro Lys Ser Arg Gln Glu Leu Ile Ala Leu Tyr
225                 230                 235                 240

Gly Tyr Asp Ile Arg Ser Ala His Asn Pro Asp Ile Lys Pro Arg
                245                 250                 255

Arg Ile Arg Lys Pro Arg Tyr Gly Ser Pro Pro Gln Arg Asp Pro Asn
                260                 265                 270

Trp Asn Gly Glu Arg Leu Asn Lys Ser His Arg His Gln Leu Gly
                275                 280                 285

Gly Thr Leu Pro Pro Arg Thr Phe Ile Asn Arg Asn Ala Ala Gly Thr
                290                 295                 300

Gly Arg Met Ser Ala Pro Arg Asn Tyr Ser Arg Ser Gly Gly Phe Lys
305                 310                 315                 320

Glu Gly Arg Ala Gly Phe Arg Pro Val Glu Ala Gly Gly Gln His Gly
                325                 330                 335

Gly Arg Ser Gly Glu Thr Val Lys His Glu Ile Ser Tyr Arg Ser Arg
                340                 345                 350

Arg Leu Glu Gln Thr Ser Val Arg Asp Pro Ser Pro Glu Ala Asp Ala
                355                 360                 365

Pro Val Leu Gly Ser Pro Glu Lys Glu Val Ala Ala Ser Glu Pro Pro
                370                 375                 380

Ala Ala Ala Pro Asp Ala Ala Pro Pro Pro Asp Arg Pro Ile Glu
385                 390                 395                 400

Lys Lys Ser Tyr Ser Arg Ala Arg Arg Thr Arg Thr Lys Val Gly Asp
                405                 410                 415

Ala Val Lys Leu Ala Glu Val Pro Pro Pro Glu Gly Leu Ile
                420                 425                 430

Pro Ala Pro Pro Val Pro Glu Thr Thr Pro Thr Pro Thr Lys Thr
                435                 440                 445

Gly Thr Trp Glu Ala Pro Val Asp Ser Ser Thr Ser Gly Leu Glu Gln
450                 455                 460

Asp Val Ala Gln Leu Asn Ile Ala Glu Gln Asn Trp Ser Pro Gly Gln
465                 470                 475                 480

Pro Ser Phe Leu Gln Pro Arg Glu Leu Arg Gly Met Pro Asn His Ile
                485                 490                 495

His Met Gly Ala Gly Pro Pro Pro Gln Phe Asn Arg Met Glu Glu Met
                500                 505                 510

Leu Thr Leu Gln Ile Ser Ile Lys Tyr Leu Pro Cys Thr Lys Cys Phe
                515                 520                 525

Ser Thr Pro Lys Gly Arg
    530

(2) INFORMATION FOR SEQ ID NO:9:

(i) SEQUENCE CHARACTERISTICS:
        (A) LENGTH: 1347 base pairs
        (B) TYPE: nucleic acid
        (C) STRANDEDNESS: both
        (D) TOPOLOGY: both (ii) MOLECULE TYPE: cDNA (ix) FEATURE:
```

(A) NAME/KEY: CDS
(B) LOCATION: 181..792

(xi) SEQUENCE DESCRIPTION: SEQ ID NO:9:

```
CAGAAGCGGC TAGTGGCGGC TGCCTGCGTC CCCAACCCCC TCCGCGCAGC GCTCGCGACA      60

CGCGTGCCAG GAGTGGGAGC GAGCGGCGGG GCCAGCTGCG TTCTGAGCCT GGGCGCAGCT     120

GCCATCTGCT CTGGGAAGCA CCAGGGTGTC CCCGCCGCCC TCAGCTCGAA GTCAGCCACC     180

ATG GAG GCG CAG GCA CAA GGT TTG TTG GAG ACT GAA CCG TTG CAA GGA       228
Met Glu Ala Gln Ala Gln Gly Leu Leu Glu Thr Glu Pro Leu Gln Gly
 1               5                  10                  15

ACA GAC GAA GAT GCA GTA GCC AGT GCT GAC TTC TCT AGC ATG CTC TCT       276
Thr Asp Glu Asp Ala Val Ala Ser Ala Asp Phe Ser Ser Met Leu Ser
             20                  25                  30

GAG GAG GAA AAG GAA GAG TTA AAA GCA GAG TTA GTT CAG CTA GAA GAC       324
Glu Glu Glu Lys Glu Glu Leu Lys Ala Glu Leu Val Gln Leu Glu Asp
         35                  40                  45

GAA ATT ACA ACA CTA CGA CAA GTT TTG TCA GCG AAA GAA AGG CAT CTA       372
Glu Ile Thr Thr Leu Arg Gln Val Leu Ser Ala Lys Glu Arg His Leu
     50                  55                  60

GTT GAG ATA AAA CAA AAA CTC GGC ATG AAC CTG ATG AAT GAA TTA AAA       420
Val Glu Ile Lys Gln Lys Leu Gly Met Asn Leu Met Asn Glu Leu Lys
 65                  70                  75                  80

CAG AAC TTC AGC AAA AGC TGG CAT GAC ATG CAG ACT ACC ACT GCC TAC       468
Gln Asn Phe Ser Lys Ser Trp His Asp Met Gln Thr Thr Thr Ala Tyr
                 85                  90                  95

AAG AAA ACA CAT GAA ACC CTG AGT CAC GCA GGG CAA AAG GCA ACT GCA       516
Lys Lys Thr His Glu Thr Leu Ser His Ala Gly Gln Lys Ala Thr Ala
            100                 105                 110

GCT TTC AGC AAC GTT GGA ACG GCC ATC AGC AAG AAG TTC GGA GAC ATG       564
Ala Phe Ser Asn Val Gly Thr Ala Ile Ser Lys Lys Phe Gly Asp Met
        115                 120                 125

AGT TAC TCC ATT CGC CAT TCC ATA AGT ATG CCT GCT ATG AGG AAT TCT       612
Ser Tyr Ser Ile Arg His Ser Ile Ser Met Pro Ala Met Arg Asn Ser
    130                 135                 140

CCT ACT TTC AAA TCA TTT GAG GAG AGG GTT GAG ACA ACT GTC ACA AGC       660
Pro Thr Phe Lys Ser Phe Glu Glu Arg Val Glu Thr Thr Val Thr Ser
145                 150                 155                 160

CTC AAG ACG AAA GTA GGC GGT ACG AAC CCT AAT GGA GGC AGT TTT GAG       708
Leu Lys Thr Lys Val Gly Gly Thr Asn Pro Asn Gly Gly Ser Phe Glu
                165                 170                 175

GAG GTC CTC AGC TCC ACG GCC CAT GCC AGT GCC CAG AGC TTG GCA GGA       756
Glu Val Leu Ser Ser Thr Ala His Ala Ser Ala Gln Ser Leu Ala Gly
            180                 185                 190

GGC TCC CGG CGG ACC AAG GAG GAG GAG CTG CAG TGC TAAGTCCAGC            802
Gly Ser Arg Arg Thr Lys Glu Glu Glu Leu Gln Cys
        195                 200

CAGCGTGCAG CTGCATCCAG AAACCGGCCA CTACCCAGCC CATCTCTGCC TGTGCTTATC     862

CAGATAAGAA GACCAAAATC CCGCTGGGAA AAACCCAGGC CTTGACATTG TTATTCAAAT     922

GGCCCCTCCA GAAAGTTTAA TGATTTCCAT TTGTATTTGT GTTGATGATG GACCACTTGA     982

CCATCACATT TCAGTATTCA TAGATGACTG TCACATTTTA AAATGTTCCC ACTTGAGCAG    1042

GTACACAACT GGTCATAATT CCTGTCTGTG TAATTCGATG TATATTTTTC CAAACATGTA    1102

GCTATTGTTT GCTTTGATTT TTGCTTGGCC TCCTTTATGA TGTGCATGTC CTTGAAGGCT    1162

GAATGAACAG TCCCTTTCAG TTCAGCAGAT CAACAGGATG GAGCTCTTCA TGACTGTCTC    1222

CAGCAATAGG ATGATTTACT ATAAATTTCA TCCAACTACT TGTGATCTCT CTCACCTACA    1282

TCAATTATGT ATGTTAATTT CAGCAATTAA AAGAATTGAT TTTAAAAAAA AAAAAAAAA     1342
```

AAAAA                                                                1347

(2) INFORMATION FOR SEQ ID NO:10:

(i) SEQUENCE CHARACTERISTICS:
        (A) LENGTH: 204 amino acids
        (B) TYPE: amino acid
        (D) TOPOLOGY: linear (ii) MOLECULE TYPE: protein (xi) SEQUENCE DESCRIPTION: SEQ ID NO:10:

Met Glu Ala Gln Ala Gln Gly Leu Leu Glu Thr Glu Pro Leu Gln Gly
 1               5                  10                  15

Thr Asp Glu Asp Ala Val Ala Ser Ala Asp Phe Ser Ser Met Leu Ser
            20                  25                  30

Glu Glu Glu Lys Glu Glu Leu Lys Ala Glu Leu Val Gln Leu Glu Asp
        35                  40                  45

Glu Ile Thr Thr Leu Arg Gln Val Leu Ser Ala Lys Glu Arg His Leu
    50                  55                  60

Val Glu Ile Lys Gln Lys Leu Gly Met Asn Leu Met Asn Glu Leu Lys
65                  70                  75                  80

Gln Asn Phe Ser Lys Ser Trp His Asp Met Gln Thr Thr Thr Ala Tyr
                85                  90                  95

Lys Lys Thr His Glu Thr Leu Ser His Ala Gly Gln Lys Ala Thr Ala
            100                 105                 110

Ala Phe Ser Asn Val Gly Thr Ala Ile Ser Lys Lys Phe Gly Asp Met
        115                 120                 125

Ser Tyr Ser Ile Arg His Ser Ile Ser Met Pro Ala Met Arg Asn Ser
    130                 135                 140

Pro Thr Phe Lys Ser Phe Glu Glu Arg Val Glu Thr Thr Val Thr Ser
145                 150                 155                 160

Leu Lys Thr Lys Val Gly Gly Thr Asn Pro Asn Gly Ser Phe Glu
                165                 170                 175

Glu Val Leu Ser Ser Thr Ala His Ala Ser Ala Gln Ser Leu Ala Gly
            180                 185                 190

Gly Ser Arg Arg Thr Lys Glu Glu Glu Leu Gln Cys
        195                 200

(2) INFORMATION FOR SEQ ID NO:11:

(i) SEQUENCE CHARACTERISTICS:
        (A) LENGTH: 2051 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 22..576

(xi) SEQUENCE DESCRIPTION: SEQ ID NO:11:

CGGGAGCGAG GTGGCTCAGA C ATG GAC CGC GGC GAG CAA GGT CTG CTG AAG      51
                        Met Asp Arg Gly Glu Gln Gly Leu Leu Lys
                         1               5                  10

ACA GAG CCG GTG GCC GAG GAA GGA GAG GAT GCT GTT ACC ATG CTC AGT      99
Thr Glu Pro Val Ala Glu Glu Gly Glu Asp Ala Val Thr Met Leu Ser
            15                  20                  25

GCT CCA GAG GCG CTG ACG GAA GAG GAG CAA GAG GAG CTG AGG CGG GAG     147

```
        Ala Pro Glu Ala Leu Thr Glu Glu Gln Glu Glu Leu Arg Arg Glu
                     30                  35                  40

CTT ACT AAG GTG GAA GAA GAA ATC CAG ACT CTG TCC CAA GTA TTG GCC         195
Leu Thr Lys Val Glu Glu Glu Ile Gln Thr Leu Ser Gln Val Leu Ala
             45                  50                  55

GCA AAA GAG AAG CAT CTC GCC GAG CTC AAG CGG AAG CTC GGC ATC TCC         243
Ala Lys Glu Lys His Leu Ala Glu Leu Lys Arg Lys Leu Gly Ile Ser
     60                  65                  70

TCG CTT CAG GAG TTC AAG CAG AAC ATT GCC AAA GGG TGG CAA GAC GTG         291
Ser Leu Gln Glu Phe Lys Gln Asn Ile Ala Lys Gly Trp Gln Asp Val
 75                  80                  85                  90

ACG GCA ACC AAT GCA TAC AAG AAG ACC TCT GAA ACT CTA TCG CAA GCT         339
Thr Ala Thr Asn Ala Tyr Lys Lys Thr Ser Glu Thr Leu Ser Gln Ala
                 95                 100                 105

GGG CAG AAG GCC TCC GCT GCA TTT TCA TCG GTT GGC TCA GTC ATC ACC         387
Gly Gln Lys Ala Ser Ala Ala Phe Ser Ser Val Gly Ser Val Ile Thr
             110                 115                 120

AAA AAG CTG GAA GAC GTG AAA AAC TCC CCA ACT TTC AAG TCA TTT GAA         435
Lys Lys Leu Glu Asp Val Lys Asn Ser Pro Thr Phe Lys Ser Phe Glu
         125                 130                 135

GAA AAA GTT GAA AAT TTA AAG TCT AAA GTA GGA GGA GCC AAG CCT GCT         483
Glu Lys Val Glu Asn Leu Lys Ser Lys Val Gly Gly Ala Lys Pro Ala
     140                 145                 150

GGC GGC GAT TTT GGA GAA GTC CTG AAT TCC ACA GCC AAC GCT ACC AGT         531
Gly Gly Asp Phe Gly Glu Val Leu Asn Ser Thr Ala Asn Ala Thr Ser
155                 160                 165                 170

ACC ATG ACC ACA GAG CCT CCT CCA GAA CAG ATG ACA GAG AGC CCC             576
Thr Met Thr Thr Glu Pro Pro Pro Glu Gln Met Thr Glu Ser Pro
                 175                 180                 185

TGAGCTGCCG ACCTGTGTCC TGCTGCCCAC TGCCAGGTGC TGCCGGCGAG AGCCAAGTAC       636

ATCTTGACAA CGCTCATGGC TGCGGATTTC CACCAGATGT GCTTTTATTT AGCTTTACTT       696

ATTTCTTTGA CCAAATAGTT GATGAATGAA ACAAAGTGAA ATCACTTGAC CTCCACTCCA       756

GGGAAACACT GTTAGCATGC ATGGAAGGCC CTTTGTATAG GAAACAGCAT CATAGAGCCT       816

CTGGTAGATC CCTGCAGGCA ACTACTGTGT TTCTCCTTAA AATCACTGTA CATCTGGATT       876

CTAGTTTGAT CTTTCTTTAC TATCTACATG AATCATTGTT TTTGGGTCTC TGTACACTTA       936

ATCAATTTCT AACAAACTGT CCTTTTCTAA ATTCTGGTTA TTAAAAGTCT TGGAATTATT       996

TCATTCCTTT CAAAGGAGAA ACTACCAGCT ACATTTTTTT TCTCGGATAA ACAGTTCTGT      1056

GAGGACCATA TCTTGGGTTT CTAAAGACAC CAGACTAAAG TAGACAGGTG TGTATGCAGT      1116

TCTATAGTTC TGTAAATTAA AAACATGCAG ACACTCAAAC TTCCAGTGGG GAGAGTGTGG      1176

GTCCTGCTCT TGCCTTGGTA ACTGTCATTT GTAGCTACAT CTATTTGAGC TCAAATATGC      1236

TTATCAGTTA TTTATTATAC CATTCTCACA CATTTTTTTA CAAGATTAAA ATTTAATTTC      1296

AGGTAAATTG AGAGAATAAC ATTGTGAGTT AAGTATATGA TATTACAGTA AGTTGGAATG      1356

TTCCCACATT CATCACTGAT AATTCCAAAA GTCTAAACGT CTTTAGGTCT ATACAGTTAT      1416

AAAAATGCTA AAAAAAATTC ACCATAGGGG AAATTACTGC CTCCATTAAA TCCATTTAAC      1476

ACCTTTAGGA AGGACAGAAA GTTCTATGAG AAATACAACT TGAATATTTT TTATACTAAG      1536

GGATTGTTGA TAACTCCGAA AGCTGCGAGG CGTTACTATG ACTGAGCTGA TCAGGCAGTT      1596

TCTGTTCTCA GTGTGTTAGT GCCTGAGCTG TTCTGTATGT AGAAATCGTT CCCACTCTAA      1656

GAACTGTCGG GGCTGTGAGT CAAAGCTTCC CAGTGGCTCT GCTAAGCCCC TCTGTTAACT      1716

GTGGTCACTC CTGACTCACT CCTGCTTCCT TTGCTGTGTA TGTTTATGGC CTATGAGGTT      1776

GTATCTGTTA CTTCTTTCTC TATTGTGGTT TTACCAGTGT CCATGCCAAA TGTTAACTGC      1836
```

```
CAAGCTTGGA GTGACCTAAA GCCTTTTTCA GAGCATGGCT AGATTTAATT GAGGATAAGG      1896

TTTCTGCAAA CCAGAATTGA AAAGCCACAG TGTCGGTTGT CACAAAATGA CATGCTGCCA      1956

TTCCTGGTTG CTGCTCGGAT GCAATGGAAA CTATGCTTGA TTACATGTGA AAATCTTAAT      2016

AAAGTCTGTG TCTCAGTAAA AAAAAAAAAA AAAAA                                 2051
```

(2) INFORMATION FOR SEQ ID NO:12:

(i) SEQUENCE CHARACTERISTICS:
        (A) LENGTH: 185 amino acids
        (B) TYPE: amino acid
        (D) TOPOLOGY: linear (ii) MOLECULE TYPE: protein (xi) SEQUENCE DESCRIPTION: SEQ ID NO:12:

```
Met Asp Arg Gly Glu Gln Gly Leu Leu Lys Thr Glu Pro Val Ala Glu
 1               5                  10                  15

Glu Gly Glu Asp Ala Val Thr Met Leu Ser Ala Pro Glu Ala Leu Thr
                20                  25                  30

Glu Glu Glu Gln Glu Glu Leu Arg Arg Glu Leu Thr Lys Val Glu Glu
            35                  40                  45

Glu Ile Gln Thr Leu Ser Gln Val Leu Ala Ala Lys Glu Lys His Leu
        50                  55                  60

Ala Glu Leu Lys Arg Lys Leu Gly Ile Ser Ser Leu Gln Glu Phe Lys
65                  70                  75                  80

Gln Asn Ile Ala Lys Gly Trp Gln Asp Val Thr Ala Thr Asn Ala Tyr
                85                  90                  95

Lys Lys Thr Ser Glu Thr Leu Ser Gln Ala Gly Gln Lys Ala Ser Ala
            100                 105                 110

Ala Phe Ser Ser Val Gly Ser Val Ile Thr Lys Lys Leu Glu Asp Val
        115                 120                 125

Lys Asn Ser Pro Thr Phe Lys Ser Phe Glu Glu Lys Val Glu Asn Leu
    130                 135                 140

Lys Ser Lys Val Gly Gly Ala Lys Pro Ala Gly Gly Asp Phe Gly Glu
145                 150                 155                 160

Val Leu Asn Ser Thr Ala Asn Ala Thr Ser Thr Met Thr Thr Glu Pro
                165                 170                 175

Pro Pro Glu Gln Met Thr Glu Ser Pro
            180                 185
```

(2) INFORMATION FOR SEQ ID NO:13:

(i) SEQUENCE CHARACTERISTICS:
        (A) LENGTH: 47 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:13:

```
Glu Leu Met Cys Pro Ile Cys Leu Asp Met Leu Lys Asn Thr Met Thr
 1               5                  10                  15

Thr Lys Glu Cys Leu His Arg Phe Cys Ser Asp Cys Ile Val Thr Ala
                20                  25                  30

Leu Arg Ser Gly Asn Lys Glu Cys Pro Thr Cys Arg Lys Lys Leu
        35                  40                  45
```

(2) INFORMATION FOR SEQ ID NO:14:

(i) SEQUENCE CHARACTERISTICS:
        (A) LENGTH: 48 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:14:

```
Ile Leu Glu Cys Pro Ile Cys Leu Glu Leu Ile Lys Glu Pro Val Ser
 1               5                  10                  15

Thr Lys Cys Asp His Ile Phe Cys Lys Phe Cys Met Leu Lys Leu Leu
            20                  25                  30

Asn Gln Lys Lys Gly Pro Ser Gln Cys Pro Leu Cys Lys Asn Asp Ile
        35                  40                  45
```

(2) INFORMATION FOR SEQ ID NO:15:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:15:

```
Lys Tyr Lys Cys Glu Lys Cys His Leu Val Leu Cys Ser Pro Lys Gln
 1               5                  10                  15

Thr Glu Cys Gly His Arg Phe Cys Glu Ser Cys Met Ala Ala Leu Leu
            20                  25                  30

Ser Ser Ser Ser Pro Lys Cys Thr Ala Cys Gln Glu Ser Ile
        35                  40                  45
```

(2) INFORMATION FOR SEQ ID NO:16:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:16:

```
Glu Val Thr Cys Pro Ile Cys Leu Asp Pro Phe Val Glu Pro Val Ser
 1               5                  10                  15

Ile Glu Cys Gly His Ser Phe Cys Gln Glu Cys Ile Ser Gln Val Gly
            20                  25                  30

Lys Gly Gly Gly Ser Val Cys Pro Val Cys Arg Gln Arg Phe
        35                  40                  45
```

(2) INFORMATION FOR SEQ ID NO:17:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:17:

```
His Leu Met Cys Ala Leu Cys Gly Gly Tyr Phe Ile Asp Ala Thr Thr
 1               5                  10                  15
```

-continued

```
Ile Val Glu Cys Leu His Ser Phe Cys Lys Thr Cys Ile Val Arg Tyr
            20                  25                  30

Leu Glu Thr Asn Lys Tyr Cys Pro Met Cys Asp Val Gln Val
            35                  40                  45
```

(2) INFORMATION FOR SEQ ID NO:18:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:18:

```
Lys Tyr Leu Cys Ser Ala Cys Lys Asn Ile Leu Arg Arg Pro Phe Gln
 1               5                  10                  15

Ala Gln Cys Gly His Arg Tyr Cys Ser Phe Cys Leu Thr Ser Ile Leu
            20                  25                  30

Ser Ser Gly Pro Gln Asn Cys Ala Ala Cys Val Tyr Glu Gly
            35                  40                  45
```

(2) INFORMATION FOR SEQ ID NO:19:

(i) SEQUENCE CHARACTERISTICS:
        (A) LENGTH: 51 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:19:

```
Glu Val Thr Cys Pro Ile Cys Leu Glu Leu Leu Lys Glu Pro Val Ser
 1               5                  10                  15

Ala Asp Cys Asn His Ser Phe Cys Arg Ala Cys Ile Thr Leu Asn Tyr
            20                  25                  30

Glu Ser Asn Arg Asn Thr Asp Gly Lys Gly Asn Cys Pro Val Cys Arg
            35                  40                  45

Val Pro Tyr
    50
```

(2) INFORMATION FOR SEQ ID NO:20:

(i) SEQUENCE CHARACTERISTICS:
        (A) LENGTH: 47 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:20:

```
Glu Leu Thr Cys Pro Leu Cys Val Glu Leu Phe Lys Asp Pro Val Met
 1               5                  10                  15

Val Ala Cys Gly His Asn Phe Cys Arg Ser Cys Ile Asp Lys Ala Trp
            20                  25                  30

Glu Gly Asn Ser Ser Phe Ala Cys Pro Glu Cys Arg Arg Glu Ser
            35                  40                  45
```

(2) INFORMATION FOR SEQ ID NO:21:

(i) SEQUENCE CHARACTERISTICS:

(A) LENGTH: 46 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:21:

```
Leu Ile Thr Cys Arg Leu Cys Arg Gly Tyr Asn Ile Asp Pro Thr Thr
1               5                   10                  15

Val Asp Tyr Cys Tyr His Thr Tyr Cys Arg Ser Cys Ile Leu Lys His
            20                  25                  30

Leu Leu Arg Ala Val Tyr Cys Pro Glu Cys Lys Ala Ser Gly
        35                  40                  45
```

(2) INFORMATION FOR SEQ ID NO:22:

(i) SEQUENCE CHARACTERISTICS:
        (A) LENGTH: 45 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:22:

```
Leu Leu Arg Cys His Ile Cys Lys Asp Phe Leu Lys Val Pro Val Leu
1               5                   10                  15

Thr Pro Cys Gly His Thr Phe Cys Ser Leu Cys Ile Arg Thr His Leu
            20                  25                  30

Asn Asn Gln Pro Asn Cys Pro Leu Cys Leu Phe Glu Phe
        35                  40                  45
```

(2) INFORMATION FOR SEQ ID NO:23:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:23:

```
Lys Tyr Thr Cys Pro Ile Cys Phe Glu Phe Ile Tyr Lys Lys Gln Ile
1               5                   10                  15

Tyr Gln Cys Lys Ser Gly His His Ala Cys Lys Glu Cys Trp Glu Lys
            20                  25                  30

Ser Leu Glu Thr Lys Glu Cys Met Thr Cys Lys Ser Val Val
        35                  40                  45
```

(2) INFORMATION FOR SEQ ID NO:24:

(i) SEQUENCE CHARACTERISTICS:
        (A) LENGTH: 56 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:24:

```
Val His Leu Lys Asn Asp Cys His Phe Glu Glu Leu Pro Cys Val Arg
1               5                   10                  15

Pro Asp Cys Lys Glu Lys Val Leu Arg Lys Asp Leu Arg Asp His Val
            20                  25                  30
```

```
Glu Lys Ala Cys Lys Tyr Arg Glu Ala Thr Cys Ser His Cys Lys Ser
        35                  40                  45

Gln Val Pro Met Ile Ala Leu Gln
    50                  55

(2) INFORMATION FOR SEQ ID NO:25:

(i) SEQUENCE CHARACTERISTICS:
        (A) LENGTH: 59 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:25:

Lys His Glu Asp Thr Asp Cys Pro Cys Val Val Ser Cys Pro His
1               5                   10                  15

Lys Cys Ser Val Gln Thr Leu Leu Arg Ser Glu Leu Ser Ala His Leu
        20                  25                  30

Ser Glu Cys Val Asn Ala Pro Ser Thr Cys Ser Phe Lys Arg Tyr Gly
        35                  40                  45

Cys Val Phe Gln Gly Thr Asn Gln Gln Ile Lys
        50                  55

(2) INFORMATION FOR SEQ ID NO:26:

(i) SEQUENCE CHARACTERISTICS:
        (A) LENGTH: 53 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:26:

Cys His Glu Gly Leu Cys Pro Phe Leu Leu Thr Glu Cys Pro Ala Cys
1               5                   10                  15

Lys Gly Leu Val Arg Leu Ser Glu Lys Glu His His Thr Glu Gln Glu
        20                  25                  30

Cys Pro Lys Arg Ser Leu Ser Cys Gln His Cys Arg Ala Pro Cys Ser
        35                  40                  45

His Val Asp Leu Glu
    50

(2) INFORMATION FOR SEQ ID NO:27:

(i) SEQUENCE CHARACTERISTICS:
        (A) LENGTH: 57 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:27:

Val His Tyr Glu Val Cys Pro Lys Phe Pro Leu Thr Cys Asp Gly Cys
1               5                   10                  15

Gly Lys Lys Lys Ile Pro Arg Glu Thr Phe Gln Asp His Val Arg Ala
        20                  25                  30

Cys Ser Lys Cys Arg Val Leu Cys Arg Phe His Thr Val Gly Cys Ser
        35                  40                  45

Glu Met Val Glu Thr Glu Asn Leu Gln
```

```
                 50                  55

(2) INFORMATION FOR SEQ ID NO:28:

(i) SEQUENCE CHARACTERISTICS:
        (A) LENGTH: 58 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:28:

Thr His Tyr Lys Thr Cys Pro Met Val Pro Ile Asp Cys Ser Gln Gly
1               5                  10                  15

Cys Ser Val Lys Ile Glu Arg Lys Ser Ile Ile Asp His Ile Glu Asn
                20                  25                  30

Asp Cys Cys Asn Thr Gln Ile Pro Cys Lys Tyr Phe Glu Gln Gly Cys
            35                  40                  45

Lys Val Glu Met Lys Arg Ser Glu Leu Gln
        50                  55

(2) INFORMATION FOR SEQ ID NO:29:

(i) SEQUENCE CHARACTERISTICS:
        (A) LENGTH: 80 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:29:

Gly Val Leu Ile Trp Lys Ile Arg Asp Tyr Lys Arg Arg Lys Gln Glu
1               5                  10                  15

Ala Val Met Gly Lys Thr Leu Ser Leu Tyr Ser Gln Pro Phe Tyr Thr
                20                  25                  30

Gly Tyr Phe Gly Tyr Lys Met Cys Ala Arg Val Tyr Leu Asn Gly Asp
            35                  40                  45

Gly Met Gly Lys Gly Thr His Leu Ser Leu Phe Phe Val Ile Met Arg
        50                  55                  60

Gly Glu Tyr Asp Ala Leu Leu Pro Trp Pro Phe Lys Gln Lys Val Thr
65                  70                  75                  80

(2) INFORMATION FOR SEQ ID NO:30:

(i) SEQUENCE CHARACTERISTICS:
        (A) LENGTH: 80 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:30:

Gly Thr Phe Leu Trp Lys Ile Thr Asn Val Thr Lys Arg Cys His Glu
1               5                  10                  15

Ser Val Cys Gly Arg Thr Val Ser Leu Phe Ser Pro Ala Phe Tyr Thr
                20                  25                  30

Ala Lys Tyr Gly Tyr Lys Leu Cys Leu Arg Leu Tyr Leu Asn Gly Asp
            35                  40                  45

Gly Ser Gly Lys Lys Thr His Leu Ser Leu Phe Ile Val Ile Met Arg
        50                  55                  60
```

Gly Glu Tyr Asp Ala Leu Leu Pro Trp Pro Phe Arg Asn Lys Val Thr
65                  70                  75                  80

(2) INFORMATION FOR SEQ ID NO:31:

(i) SEQUENCE CHARACTERISTICS:
        (A) LENGTH: 80 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:31:

Gly Val Phe Ile Trp Lys Ile Ser Asp Phe Thr Arg Lys Arg Gln Glu
1               5                   10                  15

Ala Val Ala Gly Arg Thr Pro Ala Ile Phe Ser Pro Ala Phe Tyr Thr
                20                  25                  30

Ser Arg Tyr Gly Tyr Lys Met Cys Leu Arg Val Tyr Leu Asn Gly Asp
            35                  40                  45

Gly Thr Gly Arg Gly Thr His Leu Ser Leu Phe Phe Val Val Met Lys
        50                  55                  60

Gly Pro Asn Asp Ala Leu Leu Gln Trp Pro Asn Gln Lys Val Thr
65                  70                  75                  80

(2) INFORMATION FOR SEQ ID NO:32:

(i) SEQUENCE CHARACTERISTICS:
        (A) LENGTH: 67 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:32:

Gly Val Ile Trp Lys Ile Tyr Arg Arg Gln Glu Ala Val Gly Arg Thr
1               5                   10                  15

Leu Leu Phe Ser Pro Ala Phe Tyr Thr Lys Tyr Gly Tyr Lys Cys Leu
                20                  25                  30

Arg Val Tyr Leu Asn Gly Asp Gly Ser Gly Lys Gly Thr His Leu Ser
            35                  40                  45

Leu Phe Val Ile Met Arg Gly Tyr Asp Ala Leu Leu Trp Pro Phe Gln
        50                  55                  60

Lys Val Thr
65

(2) INFORMATION FOR SEQ ID NO:33:

(i) SEQUENCE CHARACTERISTICS:
        (A) LENGTH: 73 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:33:

Leu Met Leu Met Asp Gln Gly Ser Ser Arg Arg His Leu Gly Asp Ala
1               5                   10                  15

Phe Lys Pro Asp Pro Asn Ser Ser Ser Phe Lys Lys Pro Thr Gly Glu
                20                  25                  30

Met Asn Ile Ala Ser Gly Cys Pro Val Phe Val Ala Gln Thr Val Leu
            35                  40                  45

Glu Asn Gly Thr Tyr Ile Lys Asp Asp Thr Ile Phe Ile Lys Val Ile
                50                  55                  60

Val Asp Thr Ser Asp Leu Pro Asp Pro
 65                  70

(2) INFORMATION FOR SEQ ID NO:34:

(i) SEQUENCE CHARACTERISTICS:
        (A) LENGTH: 70 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:34:

Phe Met Leu Leu Asp Gln Asn Asn Arg Glu His Ala Ile Asp Ala Phe
 1               5                  10                  15

Arg Pro Asp Leu Ser Ser Ala Ser Phe Gln Arg Pro Gln Ser Glu Thr
                20                  25                  30

Asn Val Ala Ser Gly Cys Pro Leu Phe Pro Leu Ser Lys Leu Gln
                35                  40                  45

Ser Pro Lys His Ala Tyr Val Lys Asp Asp Thr Met Phe Leu Lys Cys
                50                  55                  60

Ile Val Asp Thr Ser Ala
 65                  70

(2) INFORMATION FOR SEQ ID NO:35:

(i) SEQUENCE CHARACTERISTICS:
        (A) LENGTH: 70 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:35:

Leu Met Leu Leu Asp His Asn Asn Arg Glu His Val Ile Asp Ala Phe
 1               5                  10                  15

Arg Pro Asp Val Thr Ser Ser Ser Phe Gln Arg Pro Val Ser Asp Met
                20                  25                  30

Asn Ile Ala Ser Gly Cys Pro Leu Phe Cys Pro Val Ser Lys Met Glu
                35                  40                  45

Ala Lys Asn Ser Tyr Val Arg Asp Asp Ala Ile Phe Ile Lys Ala Ile
                50                  55                  60

Val Asp Leu Thr Gly Leu
 65                  70

(2) INFORMATION FOR SEQ ID NO:36:

(i) SEQUENCE CHARACTERISTICS:
        (A) LENGTH: 49 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:36:

Met Leu Leu Asp Gln Arg His Val Asp Ala Phe Arg Pro Asp Ser Ser
 1               5                  10                  15

Phe Gln Arg Pro Glu Asn Ile Ala Ser Gly Cys Pro Leu Phe Pro Leu

```
            20                  25                  30
Ser Glu Lys Tyr Val Arg Asp Asp Ile Phe Ile Lys Ile Val Asp Ser
            35                  40                  45

Leu
```

(2) INFORMATION FOR SEQ ID NO:37:

(i) SEQUENCE CHARACTERISTICS:
        (A) LENGTH: 29 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:37:

```
Ser Lys Lys Cys Glu Asp Cys Thr Val Glu Leu Lys Val His Gln Cys
1               5                  10                  15

Lys Cys Thr Val Cys Gly Asp Arg Cys Asp Pro His Thr
            20                  25
```

(2) INFORMATION FOR SEQ ID NO:38:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:38:

```
Met Lys Cys Pro Lys Cys Asn Glu Phe Ala Arg Thr Ser Gly Asp His
1               5                  10                  15

Arg Pro Cys Leu Lys Cys Lys Cys Gly Lys Thr Ser Gly Gly His Ala
            20                  25                  30

Glu His Gly Cys His Pro Cys Tyr Val Ala Met Phe Gly Gly
            35                  40                  45
```

(2) INFORMATION FOR SEQ ID NO:39:

(i) SEQUENCE CHARACTERISTICS:
        (A) LENGTH: 47 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:39:

```
Ala Ser Lys Cys Pro Lys Cys Asp Thr Phe Ala Ser Ser Gly Asp His
1               5                  10                  15

Phe Cys Leu Lys Cys Arg Cys Asn Lys Thr Pro Gly Gly His Ala Glu
            20                  25                  30

His Asp Gly Phe Cys Lys Pro Cys Tyr Ala Thr Leu Phe Gly Gly
            35                  40                  45
```

(2) INFORMATION FOR SEQ ID NO:40:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:40:

Thr Gly Glu Pro Asn Met Cys Pro Cys Asn Arg Phe Ala Thr Ser Gly
1               5                   10                  15

Asp His Arg Pro Cys Leu Arg Cys Arg Cys Ser Lys Thr Pro Gly Gly
                20                  25                  30

His Ala Glu His Asp Gly Gln Cys His Lys Pro Cys Tyr Gly
                35                  40                  45

(2) INFORMATION FOR SEQ ID NO:41:

(i) SEQUENCE CHARACTERISTICS:
        (A) LENGTH: 57 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:41:

Thr Gly Thr Thr Gln Lys Cys Thr Val Cys Glu Thr Leu Val Asp Leu
1               5                   10                  15

Val Ala Asn Gln Arg Val Tyr His Cys Arg Cys His His Cys Asn Ser
                20                  25                  30

Lys Leu Ser Phe Asn Ser Phe Asp Gly Val Val Cys Arg His His Phe
                35                  40                  45

Asp Gln Leu Phe Lys Arg Thr Gly Ser
50                  55

(2) INFORMATION FOR SEQ ID NO:42:

(i) SEQUENCE CHARACTERISTICS:
        (A) LENGTH: 54 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:42:

Glu Gly Thr Arg Asp Lys Cys Asn Ala Cys Ala Ile Arg Lys Val Asp
1               5                   10                  15

Gly Thr Ala Tyr His Arg Cys Lys Cys Cys His Gly Gly Cys Ile Ser
                20                  25                  30

Pro Ser Ile Ala His Gly Arg Leu Cys Lys His His Ile Gln Leu
                35                  40                  45

Phe Lys Lys Lys Gly Asn
50

(2) INFORMATION FOR SEQ ID NO:43:

(i) SEQUENCE CHARACTERISTICS:
        (A) LENGTH: 28 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:43:

Ile Pro Thr Lys Ala Phe Ala Val Lys Ile Ala Lys Ile Leu Glu Ile
1               5                   10                  15

Cys Glu Lys Thr Gln Leu Gln Trp Gln Pro His Lys
                20                  25

(2) INFORMATION FOR SEQ ID NO:44:

(i) SEQUENCE CHARACTERISTICS:
        (A) LENGTH: 37 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:44:

```
Asp Glu Tyr Glu Asn Asp Leu Tyr Thr Ala Val Leu Gln Gly Asp Ile
1               5                   10                  15

Asp Pro Asp Asp Ile Thr Ile Glu Met Trp Arg Val Cys Lys Arg Tyr
            20                  25                  30

Leu Phe Leu Arg Gln
        35
```

(2) INFORMATION FOR SEQ ID NO:45:

(i) SEQUENCE CHARACTERISTICS:
        (A) LENGTH: 42 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:45:

```
Pro Glu Lys Lys Pro Lys Glu Asn Pro Trp Ala Thr Glu Asp Glu Asp
1               5                   10                  15

Asn Leu Thr Val Glu Asn Lys Ile Ile Glu Phe Val Asp Trp Leu Glu
            20                  25                  30

Leu Lys Asp Ser Lys Ser Ser Leu Gly Asn
        35                  40
```

(2) INFORMATION FOR SEQ ID NO:46:

(i) SEQUENCE CHARACTERISTICS:
        (A) LENGTH: 44 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:46:

```
Thr Arg Gly Thr Val Thr Leu Phe Val Leu Glu Arg Thr Asp Leu His
1               5                   10                  15

Lys Glu Lys Phe Gln Ile Leu Asn Ser Ser Glu Gly Asp Trp Glu Ala
            20                  25                  30

Arg Ser Leu Thr Glu Tyr Ile Ser Ala Pro Val Asp
        35                  40
```

(2) INFORMATION FOR SEQ ID NO:47:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:47:

Ala Gly Pro Leu Ala Val Thr Thr Phe Val Leu Glu Ser Arg Thr Thr
1               5                   10                  15

Asp Leu Lys Lys Glu Arg Leu Gln Ile Asn Asn Thr Glu Gly Asp Trp
            20                  25                  30

Leu Ala His Ser Leu Ser Gln Tyr Ile Ser Ala Pro Ser Asp
        35                  40                  45

(2) INFORMATION FOR SEQ ID NO:48:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:48:

Gly Val Ser Ile Val Thr Leu Phe Ile Leu Glu Arg Thr Asp Leu Thr
1               5                   10                  15

Thr Lys Glu Lys Phe His Ile Leu Asn Asn Thr Glu Gly Asp Trp Glu
            20                  25                  30

Ala Arg Ser Leu Ser Ser Lys Cys Ile Ser Ala Pro Val Asp
        35                  40                  45

(2) INFORMATION FOR SEQ ID NO:49:

(i) SEQUENCE CHARACTERISTICS:
        (A) LENGTH: 48 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:49:

Pro Ala Gly Leu Thr Val Thr Ile Phe Val Leu Glu Arg Thr Thr Glu
1               5                   10                  15

Asp Leu Lys Lys Glu Arg Phe Gln Ile Ile Asn Asn Thr Glu Gly Asp
            20                  25                  30

Trp Glu Ala Arg Ser Ile Ala Lys Asn Tyr Ile Ser Ala Pro Ala Asp
        35                  40                  45

(2) INFORMATION FOR SEQ ID NO:50:

(i) SEQUENCE CHARACTERISTICS:
        (A) LENGTH: 184 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:50:

Met Asp Arg Gly Glu Gln Gly Leu Leu Arg Thr Asp Pro Val Pro Glu
1               5                   10                  15

Glu Gly Glu Asp Val Ala Ala Thr Ile Ser Ala Thr Glu Thr Leu Ser
            20                  25                  30

Glu Glu Glu Gln Glu Glu Leu Arg Arg Glu Leu Ala Lys Val Glu Glu
        35                  40                  45

Glu Ile Gln Thr Leu Ser Gln Val Leu Ala Ala Lys Glu Lys His Leu
    50                  55                  60

Ala Glu Ile Lys Arg Lys Leu Gly Ile Asn Ser Leu Gln Glu Leu Lys
65                  70                  75                  80

```
Gln Asn Ile Ala Lys Gly Trp Gln Asp Val Thr Ala Thr Ser Ala Tyr
                85                  90                  95
Lys Lys Thr Ser Glu Thr Leu Ser Gln Ala Gly Gln Lys Ala Ser Ala
                100                 105                 110
Ala Phe Ser Ser Val Gly Ser Val Ile Thr Lys Lys Leu Glu Asp Val
                115                 120                 125
Lys Asn Ser Pro Thr Phe Lys Ser Phe Glu Glu Lys Val Glu Asn Leu
                130                 135                 140
Lys Ser Lys Val Gly Gly Thr Lys Pro Ala Gly Gly Asp Phe Gly Glu
145                 150                 155                 160
Val Leu Asn Ser Ala Ala Asn Ala Ser Ala Thr Thr Thr Glu Pro Leu
                165                 170                 175
Pro Glu Lys Thr Gln Glu Ser Leu
                180
```

(2) INFORMATION FOR SEQ ID NO:51:

(i) SEQUENCE CHARACTERISTICS:
        (A) LENGTH: 50 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:51:

```
Ala Ala Thr Ile Ser Ala Thr Glu Thr Leu Ser Glu Glu Glu Gln Glu
1               5                   10                  15
Glu Leu Arg Arg Glu Leu Ala Lys Val Glu Glu Ile Gln Thr Leu
                20                  25                  30
Ser Gln Val Leu Ala Ala Lys Glu Lys His Leu Ala Glu Ile Lys Arg
            35                  40                  45
Lys Leu
    50
```

(2) INFORMATION FOR SEQ ID NO:52:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:52:

CCTCAGGTGC TGTATCAGTG AAGG                                      24

(2) INFORMATION FOR SEQ ID NO:53:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:53:

GCCAAGGTGC AGCCCCAGAT CTAC                                      24

(2) INFORMATION FOR SEQ ID NO:54:

(i) SEQUENCE CHARACTERISTICS:
    (A) LENGTH: 24 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:54:

CTACAGGTGA GGCACCAGGG CCAC                                               24

(2) INFORMATION FOR SEQ ID NO:55:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:55:

TATGAGGTGG GTTTCCAGAG CCAT                                               24

(2) INFORMATION FOR SEQ ID NO:56:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:56:

ATCCAGGTGA GGCCCCAGAG CCAC                                               24

(2) INFORMATION FOR SEQ ID NO:57:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:57:

CACAGGGTGA GACAACAGTG CCCT                                               24

(2) INFORMATION FOR SEQ ID NO:58:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:58:

ATGGAGCGCC CCCAGCCC                                                      18

(2) INFORMATION FOR SEQ ID NO:59:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:59:

CTGAATGTGA GTTCACAGAC CACC                                              24

(2) INFORMATION FOR SEQ ID NO:60:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:60:

ATCTTTGTGA GTCACCAGGT CCTG                                              24

(2) INFORMATION FOR SEQ ID NO:61:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:61:

ATTGCGGTAA GAGGGCAGGT CACG                                              24

(2) INFORMATION FOR SEQ ID NO:62:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:62:

TCTGAGGTCA GTTCACAGCT GCTC                                              24

(2) INFORMATION FOR SEQ ID NO:63:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:63:

AGCGATGTGA GTCTCCAGGG TATC                                              24

(2) INFORMATION FOR SEQ ID NO:64:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:64:

```
TTGCAGGTGA GGCTGCAGGG TCTG                                        24

(2) INFORMATION FOR SEQ ID NO:65:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:65:

GCTCAGGTAT TTGTCCAGGA GCGG                                        24

(2) INFORMATION FOR SEQ ID NO:66:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:66:

AATAATGTAA GACCATAGGA ATAT                                        24

(2) INFORMATION FOR SEQ ID NO:67:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:67:

CTGAAGGTGA GTTCCCAGAC CTTC                                        24

(2) INFORMATION FOR SEQ ID NO:68:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:68:

TGCCAGGTGA GCCCTCAGAT CCTG                                        24

(2) INFORMATION FOR SEQ ID NO:69:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:69:

CCCAAGGTGA GTCCGCAGGG ACTT                                        24

(2) INFORMATION FOR SEQ ID NO:70:
```

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:70:

TGTCCGGTGA GCCCATAGGG GAGA                                            24

(2) INFORMATION FOR SEQ ID NO:71:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:71:

CTCAAGGTGG GGCCCCAGGG CCGC                                            24

(2) INFORMATION FOR SEQ ID NO:72:

(i) SEQUENCE CHARACTERISTICS:
        (A) LENGTH: 31 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:72:

Arg Thr Asp Pro Val Pro Glu Glu Gly Glu Asp Val Ala Ala Thr Ile
1               5                   10                  15

Ser Ala Thr Glu Thr Leu Ser Glu Glu Gln Glu Glu Leu Arg
            20                  25                  30

(2) INFORMATION FOR SEQ ID NO:73:

(i) SEQUENCE CHARACTERISTICS:
        (A) LENGTH: 28 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:73:

Lys Pro Ala Gly Gly Asp Phe Gly Glu Val Leu Asn Ser Ala Ala Asn
1               5                   10                  15

Ala Ser Ala Thr Thr Thr Glu Pro Leu Pro Glu Lys
            20                  25

(2) INFORMATION FOR SEQ ID NO:74:

(i) SEQUENCE CHARACTERISTICS:
        (A) LENGTH: 383 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:74:

AAAAATTATA CTTTTATTTG AGTCACCAGG AGAAAGATTC ACTTGTGGTT CAAGTCAAAT     60

```
GTTCAGAATC ATAACAGGCC AGAAAGGTTT GATCCCGAGC ACAAGCCCAC GAGGGAGGGG      120

ACCAAAACAG ACCAAAATGA GACAACAACC CCATATAAAA AGATGANCTG NCGGCTTCAC      180

ACACTCACAC ACATACACAT ACACACGGAT GAAATGTTTG ACAGGGGCA AATTTCACGT       240

GGTCATTTCT GTTTCTTTTT AAATACAGGT TTNTAGGGTG GTATTTTGTT TTTTCCAGCT     300

TTAAAAAAAG GCCCAAAAGT GCATGTNTGA GGGGGGAAAG GCAGAAATTA AGCAATAAAG     360

GTCATTTTCC CTGGGGGGCC ATG                                             383
```

(2) INFORMATION FOR SEQ ID NO:75:

(i) SEQUENCE CHARACTERISTICS:
        (A) LENGTH: 300 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:75:

```
CCGCAGNAAA AATTATACTT TTATTTGAGT CACCAGGAGA AAGATTCACT TGTGGTTCAA      60

GTCAAATGTT CAGAATCATA ACAGGNCAGA AAGGTTTGAT CCCGAGCACA AGCCCACGAG     120

GGAGGGGACC AAAACAGACC AAAATGAGAC AACAACCCCA TATAAAANGA TGANCTGGCG     180

GNTTCACACA CTCACACACA TACACATACA CACGGATGAA ATGTTTGGAC AGAGGCAAAT    240

TTCACGTGGT CATTTCTGTT TCTTTTTAAA TACAGGTTTN TAGGGTGGTA TTTTGTTTTT    300
```

(2) INFORMATION FOR SEQ ID NO:76:

(i) SEQUENCE CHARACTERISTICS:
        (A) LENGTH: 245 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:76:

```
CGCAGGTAAA ANTTATACTT TTNTTTGAGT CACCAGGAGA AAGATTCANT TGTGGTTCAA      60

GTCAAATGTT CAGAATCATA ACAGGCCAGA AAGGTTTGNT CCCGAGCACA AGCCCACGAG    120

GGAGGGGACC AAAACAGACC AAAATGAGAC AACAACCCCA TATAAAAGA TGAACTGGCG     180

GCTTCACACA CTCACACACA TACACATACA CACGGTTGAA ATGTTTGGAC AGAGGCAAAT    240

TTCAC                                                                 245
```

(2) INFORMATION FOR SEQ ID NO:77:

(i) SEQUENCE CHARACTERISTICS:
        (A) LENGTH: 251 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:77:

```
CAGAAATGAC CACGTGAAAT TTGCCTCTTT CCAAACATTT CATCCGTGTG TATGTGTATG      60

TTTGTNAGTN TGTGAAGCCG CCAGTTCATC TTTTTATATG GGGTTGTTGT CTCATTTTGG    120

TCTGTTTTGG TCCCTCCCT CGTGGGCTTG TGCTCGGGAT CAAACCTTTN TGGCCTGTTA     180

TGATTCTNAA CATTTGACTT GAACCACAAG TGAATCTTTN TCCTGGTGAC TCAAATAAAA   240

GTATAATTTT T                                                         251
```

(2) INFORMATION FOR SEQ ID NO:78:

(i) SEQUENCE CHARACTERISTICS:
        (A) LENGTH: 276 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:78:

```
GCAGGTAAAA ATTATACTTT NATTTGAGTC ACCAGGAGAA AGATTCACTT GTGGTTCAAG        60
TCAAATGTTC AGAATCATAA CAGGCCAGAA AGNTTTGNNC CCGAGCACAA GCCCACGAGG       120
GAGGGGACCA AAACAGACCA AAATGAGACA ACAACCCCNT ATAAAAAGAT GAACTGCCGG       180
CTTCACACAC TCACACACAT ACACATACAC ACGGATGAAN TNTTTGGNCA GCGGCAAATT       240
TCACGTGGTC ATTTCTGTTT CTTTTTAAAT ACAGGT                                 276
```

(2) INFORMATION FOR SEQ ID NO:79:

(i) SEQUENCE CHARACTERISTICS:
        (A) LENGTH: 275 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:79:

```
TTTTATTTGA GTCACCAGGA GAAAGATTCA NTTGTGGTTC AAGTCAAATG TTCAGAATCA        60
TAACAGGCCA GAAAGGTTTG NNCCCGAGCA CAAGCCCACG AGGGAGGGGA CCAAAACAGA       120
CCAAAATGAG ACAACAACCC CATATAAAAN GNTGAACTGG CGGCTTCACA CACTCACACA       180
CATACACATA CACACGGATG AAATGTTTGG ACAGAGGCAA ATTTCACGTG GTCATTTCTG       240
TTTCTTTTTA AATACAGGTT TGTAGGGTGG TATTT                                  275
```

(2) INFORMATION FOR SEQ ID NO:80:

(i) SEQUENCE CHARACTERISTICS:
        (A) LENGTH: 290 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:80:

```
GCAGGTAAAA ATTATACTTT TATTTGAGTC ACCAGGAGAA AGATTCACTT GTGGTTCAAG        60
TCAAATGTTC AGAATCATAA CAGGCCAGAA AGGTTTGNTC CCGAGCACAA GCCCACGAGG       120
GAGGGGACCA AAACAGACCA AAATGAGACA ACAACCCCAT ATAAAAAGAT GAACTGGCGG       180
NTTCACACAC TCACACACAT ACACATACAC ACGGNTGAAA TGTTTGGACA GAGGCAAATT       240
TCACGTGGTC ATTTCTGTTT CTTTTTAAAT ACAGGTTTNT AGGGTGGTAT                  290
```

(2) INFORMATION FOR SEQ ID NO:81:

(i) SEQUENCE CHARACTERISTICS:
        (A) LENGTH: 543 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:81:

```
AAAATTATAC TTTTATTTGA GTCACCAGGA GAAAGATTCA CTTGTGGTTC AAGTCAAATG        60

TTCAGAATCA TAACAGGCCA GAAAGGTTTG ATCCCGAGCA CAAGCCCACG AGGGAGGGGA       120

CCAAAACAGA CCAAAATGAG ACAACAACCC CATATAAAAA GATGAACTGG CGGCTTCACA       180

CACTCACACA CATACACATA CACACGGATG AAATGTTTGG ACAGAGGCAA ATTTCACGTG       240

GTCATTTCTG TTTCTTTTTA AATACAGGTT TGTAGGGGTG GGTATTTTGT TTTTTCCAGC       300

TATTAAAAAA AGGCCCAAAA GTGCATGTGT GAGGGGGGGA AAGGCAGGAA ATTTAGGCAA       360

TTAAAGTCAT TTTCCCTGGG GNGGGGACNT TGAGGAGGGG GAGGAAAACA GGGGGGCAGT       420

TCTTGGGGAG GACCGCCTTT TCCTNCCTTC GTGCCCGATT TCCTTGCCAG CCCCGGGGGA       480

TCCCNCTAGG TTCTTGGGGC CGNCCGCCAC CGGGTTGGGA GCTTCCNCTT TTTGNTTCCC       540

TTT                                                                    543
```

(2) INFORMATION FOR SEQ ID NO:82:

(i) SEQUENCE CHARACTERISTICS:
        (A) LENGTH: 101 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:82:

```
GATCAAACCT TTCTGGCCTG TNATNATTCT NAACATTTGA CTTGAACCAC AAGTGAATCT        60

TTCTCCTTGG TGACTCAAAT AAAAGTATAA TTTTNACCTG C                          101
```

(2) INFORMATION FOR SEQ ID NO:83:

(i) SEQUENCE CHARACTERISTICS:
        (A) LENGTH: 146 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:83:

```
GGAGAAAGAT TCACTTGTGG TTCAAGTCAA ATGTTCAGAA TCATAACAGG CCAGAAAGGT        60

TTGATCCCGA GCACAAGCCC ACGAGGGAGG GGACCAAAAC AGACCAAAAT GAGACAACAA       120

CCCCATATAA AANGATGAAC TGGCGG                                           146
```

(2) INFORMATION FOR SEQ ID NO:84:

(i) SEQUENCE CHARACTERISTICS:
        (A) LENGTH: 431 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:84:

```
AGGAAAGTGC GTTCTCCCAG CACTGCCTCC TGTTTTCTCC CTCTCATGTC CCTCCAGGGA        60

AAATGACTTT ATTGCTTAAT TTCTGCCTTT CCCCCCTCAC ACATGCACTT TTGGGCCTTT       120

TTTTATAGCT GGAAAAAACA AAATACCACC CTACAAACCT GTATTTAAAA AGAAACAGAA       180

ATGACCACGT GAAATTTGCC TCTGTCCAAA CATTTCATCC GTGTGTATGT GTATGTGTGT       240
```

| | |
|---|---|
| GAGTGTGTGA AGCCGCCAGT TCATCTTTTT ATATGGGGGT TGTTGTCTTC ATTTTGGGTC | 300 |
| TGTTTTGGGT CCCCTCCCTC GTGGGGCTTG TGCTCGGGGA TCCAAACCTT TCTGGGCCTG | 360 |
| TTANGGATTC TGGAACATTT GGANTTGAAC CACAAGTGAA TCTTTCTCCN GGGTGACTCA | 420 |
| AATAAAGTAT N | 431 |

(2) INFORMATION FOR SEQ ID NO:85:

(i) SEQUENCE CHARACTERISTICS:
        (A) LENGTH: 215 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:85:

| | |
|---|---|
| CAGCTCATTT AATCCCAGGA AAGAGGCATC AAAGCTACAA TGTGAATATA ACTTTTGTGG | 60 |
| ACCAATACTA AGAATAACAA GAAGCCCACT GGTGAGGAAA GTGCGTTCTC CCAGCACTGC | 120 |
| CTCCTGTTTT CTCCCTCTCA TGTCCCTCCA GGGAAAATGA CTTTATTGCT TAATTTCTGC | 180 |
| CTTTCCCCCN TCACACATGC ACTTTTGGGC CTTTT | 215 |

(2) INFORMATION FOR SEQ ID NO:86:

(i) SEQUENCE CHARACTERISTICS:
        (A) LENGTH: 153 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:86:

| | |
|---|---|
| GGGACCAAAG GTAGGGACAC ATCCCCTTAG AGGACCTGAG TTTGGGAGAG TGGTGAGTGG | 60 |
| AACGGAGGAG CAGCAAGAAG CAGCCTGTTT TCACTCAGCT TAATTCTCCT TCCCAGATAA | 120 |
| GGCAAGCCAG TCATGGAATC TTGCTGCAGG CCC | 153 |

(2) INFORMATION FOR SEQ ID NO:87:

(i) SEQUENCE CHARACTERISTICS:
        (A) LENGTH: 454 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:87:

| | |
|---|---|
| TCGTCATTAC NTCCTTGGGA GTCTTGGGTN GCGCTGGTGC ATTCTGTTTC CTCTTGATCT | 60 |
| CAAAGCACAA TGTGGATTTG GGGACCAAAG GNAGGGGACA CATCCCCTTA GAGGACCTGA | 120 |
| GTTTTGGAGA GTTGTGAGTT GAAGGGANGA GCAGCAAGAA GCAGCCTGTT TTCACTCAGC | 180 |
| TTAATTCTCC TTCCCAGATA AGGCAAGCCA GTCATGGAAT CTTGCTGCAG GCCCTNCCTC | 240 |
| TACTCTTCCT GTCCTAAAAA TAGGGCCGT TTTCTTACAC ACCCCCAGAG AGAGGAGGGA | 300 |
| CTTTCACACT GGTGCTTGAG TTGACCGGGN GCTGCTTGGC GTCTATTCTT TNACCAAAAC | 360 |
| CATCCATCCC TAGGAAGAGC ACAGAGNCCT GAGGGTTGGG GCTTGGGTTN GGTTGAGCCT | 420 |
| AGGTCTTCTT NTACAATTTC ACAGAGGTCT TTTT | 454 |

(2) INFORMATION FOR SEQ ID NO:88:

(i) SEQUENCE CHARACTERISTICS:
    (A) LENGTH: 283 base pairs
    (B) TYPE: nucleic acid
    (C) STRANDEDNESS: both
    (D) TOPOLOGY: both (ii) MOLECULE TYPE: cDNA (xi) SEQUENCE DESCRIPTION: SEQ ID NO:88:

```
GATTTGGGGG CTCGGGGAGG CAGAGAATCT CTTGGGAGTC TTGGGTGGCG CTGGTGCATT      60

CTGTTTCCTC TTGATCTCAA AGGACAATGT GGATTTNGGG ACCAAAGGTC AGGGACACAT     120

CCCCTTAGAG GACCTGAGTT TNGGAGAGTG GTGAGTGGAA GGGAGGAGCA GCAAGAAGCA     180

GCCTGTTTTC ACTCAGCTTA ATTCTCCTTC CCAGATAAGG CAAGCCAGTC ATGGAATCTT     240

GCTGCAGGAC CTCCCTCTAC TACTTCCTGT CCTAAAAATA GGG                      283
```

(2) INFORMATION FOR SEQ ID NO:89:

(i) SEQUENCE CHARACTERISTICS:
        (A) LENGTH: 325 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:89:

```
GTCTTGGGTG GCGCTGGTGC ATTCTGTTTC CTCTTGATCT CAAAGCACAA TGTGGATTTG      60

GGGACCAAAG GTCAGGGACA CATCCCCTTA GAGGACCTGA GTTTGGGAGA GTGGTGAGTG     120

GAAGGGAGGA GCAGCAAGAA GCAGCCTGTT TCACTCAGC TTAATTCTCC TTCCCAGATA     180

AGGCAAGCCA GTCATGGAAT CTTGCTGCAG GCCCTCCCTC TACTCTTCCT GTCCTAAAAA     240

TAGGGGCCGT TTTCTTACAC ACCCCCAGAG AGAGGAGGGA CTNTCACACT GGTGCTGAGT     300

GACCGGGGGC TGCTGGGCGT CTGTT                                         325
```

(2) INFORMATION FOR SEQ ID NO:90:

(i) SEQUENCE CHARACTERISTICS:
        (A) LENGTH: 303 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:90:

```
AAAAGACTGT GGGTGGGGAG GCCCTGCCTG ACCCATCCCT NTNCCTTTCT GGCCCCAGCC      60

TAGGTGGAGG CAAGTGGAAT ATCTNATATT GGGCGATTTG GGGGCTCGGG GAGGCAGAGA     120

ATCTCTTGGG AGTCTTGGGT GGCGCTGGTG CATTCTGTTT CCTCTTGATC TCAAAGCACA     180

ATGTGGATTT GGGGACCAAA GGTCAGGGAC ACATCCCCTT AGAGGACCTG AGTTTGGGAG     240

AGTGGTGAGT GGAAGGGAGG AGCAGCAAGA AGCAGCCTNT TTTNACTCAG CTTAATTCTC     300

CTT                                                                 303
```

(2) INFORMATION FOR SEQ ID NO:91:

(i) SEQUENCE CHARACTERISTICS:
        (A) LENGTH: 284 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:91:

ACAATCAGTC ATCATGGGTG TTTTTGTCAA CTGCTTGTTA ATTGATTTGG GGATGTTTGC      60

CCCGAATGAG AGGTTAGGA AAAGACTGTG GGTGGGGAGG CCCTGCCTGA CCCATCCCTT      120

TTCCTTTCTG GCCCCAGCCT AGGTGGAGGC AAGTGGAATA TCTTATATTG GGCGATTTNG      180

GGGCTCGGGG AGGCAGAGAA TCTCTTNGGA GTCTTGGGTG GCGCTGGTGC ATTCTGTTTC      240

CTCTTGATCT CAAAGCACAA TGTGGATTTG GGACCAAAG GTCA      284

(2) INFORMATION FOR SEQ ID NO:92:

(i) SEQUENCE CHARACTERISTICS:
        (A) LENGTH: 370 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:92:

GTTTTCTTTG GAATGAAATT CCTCCTTCCC CCCATCTCTG AGTAGAGGAA GCCCACCAAT      60

CTGCCCTTTG CAGTGTGCAG GGTGGAAGGT AAGAGGTTGG TGTGGAGTTG GGGCTGCCAT      120

AGGGTCTGCA GCCTGCTGGG GCTAAGCGGT GGAGGAAGGC TCTGTCACTC CAGGCATATG      180

TTTCCCCATC TCTGTCTGGG GCTACAGAAT AGGGTGGCAG AAGTNCACC CTGTGGGTGT      240

CTCCCTCGGG GGCTCTTCCC CTAGACCTCC CCCTCACTTA CATAAAGCTC CCTTGAAGCA      300

AGAAAGAGGG TCCCAGGGCT GCAAAACTGG AAGCACAGNC TCGGGGATNG GGAGGGAAAG      360

ACGGTGCTAT      370

(2) INFORMATION FOR SEQ ID NO:93:

(i) SEQUENCE CHARACTERISTICS:
        (A) LENGTH: 330 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:93:

AGTTGGGGCT GCCATAGGGT CTGCAGCCTG CTGGGGCTAA GCGGTGGAGG AAGGCTCTGT      60

CACTCCAGGC ATATGTTTCC CCATCTCTGT CTGGGGCTAC AGAATAGGGT GGNAGAAGTG      120

TCACCCTGTG GGTGTCTCCC TCGGGGCTC TTCCCCTAGA CCTCCCCCTC ACTTACATAA      180

AGCTCCCTTG AAGCAAAAAA GAGGGTCCCA GGGCTGCAAA ACTGGAAGCA CAGCCTCGGG      240

GATGGGAGG GAAAGACGGT GCTATATCCA GTTCCTGCTC TCTGCTCATG GGTGGCTGTG      300

ACAACCCTGG CCTCACTTGA TTCATCTCTG      330

(2) INFORMATION FOR SEQ ID NO:94:

(i) SEQUENCE CHARACTERISTICS:
        (A) LENGTH: 342 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:94:

TTATGTGAGG GTATGAAGAG CTGTCTTCCC CTGAGAGTTT CCTCAGAACC CACAGTGAGA      60

```
GGGGAGGGCT GNTGGGGCAG AGAAGTTCCT TAGGTTTTCT TTGGAATGAA ATTCCTNCTT        120

NCCCCCATCT CTGAGTAGAG GAAGCCCACC AATCTGNCCT TTGCAGTGTG CAGGGTGGAA        180

GGTAAGAGGT TGGTGTGGAG TTGGGGCTGC CATAGGGTCT GCAGNCTGCT GGGGCTAAGC        240

GGTGGAGGAA GGCTCTNTCA CTCCAGGCAT ATGTTTCCCC ATNTCTGTCT GGGGCTACAG        300

AATAGGGTGG CAGAAGTTTC ACCCTGTGGG TGTCATCCCT CG                          342
```

(2) INFORMATION FOR SEQ ID NO:95:

(i) SEQUENCE CHARACTERISTICS:
        (A) LENGTH: 298 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:95:

```
CAGCGCCCAG GTGGTGGCGG GAAGCGGTAC CGGCGGTGTA TGACTACAGC GCCGCCGACG         60

AGGACGAGGT CTCCTTCCAG GACGGGGACA CCATTGTCAA CGTGCAGCAG ATCGACGACG        120

GCTGGATGTA CGGGACGNTG GAGCGCACCG GCGACACGGG GATGCTGCCG GCCAACTACG        180

TGGAGGCCAT CTNAACCCGC AGCGNCCCCA TCTGTCTTNA GCACATTCCA CGGCATCGCA        240

TCCGTCCTGG GCGTGACCCG TCCATTCTTC AGTGTCTCTG TTTTTTAAAA CCTGCGAC         298
```

(2) INFORMATION FOR SEQ ID NO:96:

(i) SEQUENCE CHARACTERISTICS:
        (A) LENGTH: 336 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:96:

```
CAACACAGTG GACCAACAGA GACAACTCTC ACAGTGTCTT AAGGTCTGGG AATCTGGGCA         60

TGCTGCCCAC AGGCTTGAGG AGACATCTTC AGGTTTAAGG CAAAGGGAAC AGCCTACAAA        120

AGGCACAACC ACCAGCTACC CCTAGAAGAN TCTNTTAGTT ATTTCCTCCT TGGGGGTTAC        180

AGATTAAGTG CCTCTCCCCA CTCTCCATCC CACAACTGTG ACTCAGAGTG ATTAGGCCAG        240

CTGCTAGATG GAAGGAATAA AAACAGTGAC ATTACCGGGG AGAGNCACAG CCACCATCTT        300

TGCCCTCAGG TTCTTTAGGA GGACAGGGNC AATGGC                                 336
```

(2) INFORMATION FOR SEQ ID NO:97:

(i) SEQUENCE CHARACTERISTICS:
        (A) LENGTH: 51 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:97:

```
GATCAGCATT GTGACTTGGA GATAATAAAA TTTAGACTAT AAACTTGGAA A                 51
```

(2) INFORMATION FOR SEQ ID NO:98:

(i) SEQUENCE CHARACTERISTICS:
        (A) LENGTH: 174 base pairs
        (B) TYPE: nucleic acid
        (C) STRANDEDNESS: both (D) TOPOLOGY: both (ii) MOLECULE TYPE: cDNA (xi) SEQUENCE DESCRIPTION: SEQ ID NO:98:

CGGTTCGGCC TCCGCNCTGT GAAGGCAGAG AGCCGCTGCC GCCGNCTCCT GTTTAGCAGG       60

AAGGCAACAC ATTCCTACAC TTTTAATGTA TATGTTTGTN ATAATGTCCA TGTAAACATG      120

CCCTATGTTT GTCCCTTTNA ATTAGTTTGT CTCAATAAAC AAAATGTAGA GAAA           174

(2) INFORMATION FOR SEQ ID NO:99:

(i) SEQUENCE CHARACTERISTICS:
        (A) LENGTH: 417 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:99:

GCAGGGCAAA AGGCAACTGA NGCTTTCAGA ACGTTGGAAC GGCCATCAGC AAGAAGTTCG       60

GAGACATGAG TTACTCCATT CGCCATTCCA TAAGTATGCC TGCTATGAGG AATTCTCCTA      120

CTTTCAAATC ATTTGAGGAG AGGGTTGAGA CAACTGTCAC AAGCCTCAAG ACGAAAGTAG      180

GGCGGTACGA ACCCTAATGG AGGCAGTTTT GAGGAGGTCC TCAGCTCCAC GGCCCATGCC      240

AGTGCCCAGA GCTTGGCAGG AGGCTCCCGG CGGACCAAGG AGGGAGGAGC TGCAGTGTTA      300

AGTCCAGCCA GCNTGCAGTT CATTCCAGGA AACCGGGCCA TTACCCCAGC CCNTTTTTGC      360

CTGTGGTTTA TTCCTTTTAA GGAAGGACCA AATTCCCGTT GGGGNAAAAA CCCAGGG        417

(2) INFORMATION FOR SEQ ID NO:100:

(i) SEQUENCE CHARACTERISTICS:
        (A) LENGTH: 323 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:100:

TCGGCACGAG CNTGCAGCTT TCAGCAACGT TGGAACGGCC ATCAGCAAGA AGTTCGGAGA       60

CATGAGACGA AAGTAGGCGG TACGAACCCT AATGGAGGCA GTTTTGAGGA GGTCCTCAGC      120

TCCACGGCCC ATGCCAGTGC CCAGAGCTTG GCAGGAGGCT CCCGGCGGAC CAAGGAGGAG      180

GAGCTGCAGT GCTTAAGTCC AGCCAGCGTG CAGTGCATTC CAGAAACCGG CCATTACCCA      240

GCCCATTTTT GCCTGTGNTT ATTCCAGATA AGGAAGGACC AAANTCCCGT TNGGGAAAAA      300

ACCCAGGGNT TTGACATTGT TTA                                             323

(2) INFORMATION FOR SEQ ID NO:101:

(i) SEQUENCE CHARACTERISTICS:
        (A) LENGTH: 171 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:101:

TACTCCATTC GCCATTCCAT AAGTATGCCT GCTATGAGGA NTTCTCCTAC TTTCAAATCA       60

TTTGAGGAGA GGGTTGAGAC ANCTGTCACA AGCCTCAAGA CGAAANTAGG CGGTACGACC      120

```
CCTANTGGAG GCAGTTTTTA GGGAGGTCCT CAGNTTCCAC GGGCCCNTTC C          171

(2) INFORMATION FOR SEQ ID NO:102:

(i) SEQUENCE CHARACTERISTICS:
        (A) LENGTH: 520 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:102:

TTTTAGNTAA ATACAATTCC GGATTTATTA AAAATCAGGG TCCCCTGCTG TNCCTCCTGG    60

ANTAAGGAAA TAAATAACCA GAGGGGGCAC AGCTAGGTAA ANGGGGAAAA ATCAGATCTC   120

AAGACAGACT CTTTGAACTA CCCTTTCTCC CTCCCCAATT CCCACCCCCT TATGGCTCTT   180

GGGACATAGC ACCTGAGCAG GCACCTCAGT CCGTGTAGAG TGTGACCGGC ACCAAGGCAT   240

GTCTGCCCTA CCCAAGAAGG GAGACAGGCC CTGGGGTCAC TTNTTTCCAG CCCTTCATGA   300

CCCCAAGACC TGTTCCCCAC AGGCNCAGGG CTGAAGCACC ANTTGGAGGC ACCTGAGGGT   360

NGTGGCTGGG GGAGGGAGGA TGGGGTAACA GAACCTAGGC AGCAGAAGCA GCTGACGGGG   420

GTCCGGCCCC TTCTCCAAGT TCAGCCAGTG CCTGACTNAG GTCATGCCCC ATCGTCCTTT   480

CCCTCGACCC CANCTGCATT CAGCTGAGGA TCTTCNGGGC                        520

(2) INFORMATION FOR SEQ ID NO:103:

(i) SEQUENCE CHARACTERISTICS:
        (A) LENGTH: 397 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:103:

CCTTTGACAA TCTCCTTGAG TGGCCCTTTG CCCGCCGTGT CACCTTCTCC CTGCTGGATC    60

AGAGCGACCC TGGGCTGGCT AAACCACAGC ACGTCACTGA GACCTTCCAC CCCGACCCAA   120

ACTGGAAGAA TTTCCAGAAG CCAGGCACGT GGCGNGGCTC CCTGGGATGA GAGTTCTCTG   180

GGCTTTGGTT ATCCCAAGTT CATCTCCCAC CAGGGACATT CGAAAGCGAA ACTATGTGCG   240

GGATGATGCA GTCTTCATCC GTGCTGCTGT TGAACTGCCC CGGAAGATCC TCAGCTGAGT   300

GCAGGTGGGG TTTCGAGGGG GAAAGGGACG ATGGGGGCAT GACCTTCAGT TCAGGGCACT   360

TGGCTTGAAA CTTTNGGAGA GGGGGNCCC GNACCCC                            397

(2) INFORMATION FOR SEQ ID NO:104:

(i) SEQUENCE CHARACTERISTICS:
        (A) LENGTH: 385 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:104:

TTTTTTTTTT TAATAAATAC AATTCCCGGA TTTATTAAAA ATCAGGGCTC CCCTGCTGTG    60

NCCTCCTGGA CTAAGGAAAT AAATAACCAG AGGGGGCACA GCTAGGTAAA GGGGGAAAAA   120

ATCAGATCTC AAGACAGACT CTTTGAACTA CCCTTTCTCC CTCCCCAATT CCCACCCCCT   180
```

```
TATGGCTCTT GGGACATAGC ACCTGAGCAG GCACCTCAGT CCGTGTAGAG TGTGACCGGC       240

ACCAAGGCAT GTCTGCCCTA CCCAAGAAGG GAGACAGGCC CTGGGGTCAC TTGTTTCCAG       300

CCCTTCATGA CCCCAAGACC TGTTCCCCAC AGGGCNCAGG GGCTTGAAGC ACCAATTGGG       360

AGGCACCTNA GGGTGGNTGG CTTGG                                            385
```

(2) INFORMATION FOR SEQ ID NO:105:

(i) SEQUENCE CHARACTERISTICS:
        (A) LENGTH: 418 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:105:

```
GGAGAGTGTG ANGNCACATC TGGCCNTGAT GTGTGCCCTG GTGAGCCGGC AACNCNGNAG        60

CTGCAGGAGC TTCGGCNAGA NTGGAGGAGC TATCAGTGGG CAGGGATGGC GTGCTCATCT       120

GGAAGATTNG CAGCTATGGA CGGCGGCTAC AGGAGGCCAA GGCAAGCCCA ACCTTNAGTG       180

CTTCAGCCCA GCCTTCTACA CACATAAGTA TGGTTACAAG CTGCAGGTAT CTGCATTCCT       240

CAATGGCAAT NGCAGTGGTG AGGGCACACA CCTCTTCACT GTACATTNCG TGTGCTGCCT       300

GGGTNCCTTT GACAATCTCC TTNAGTGGCC CTTTGCCCGC CGTGTNACCT TCTTCCCTGC       360

TGGATTCAGA GCNACCCTGG GGCTNGGTTA AACCACAGGA CGTTNAATGN AGACCTTT        418
```

(2) INFORMATION FOR SEQ ID NO:106:

(i) SEQUENCE CHARACTERISTICS:
        (A) LENGTH: 375 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:106:

```
TTTAAANTAT AAATACAATT CCGGATTTAT TAAAAATCAG GGCTCCCCTG CTGTGCCCTC        60

CTGGCCTAAG GAAATAAATA ACCAGAGGGG GCACAGCTAG GTAAAGGGGG AAAAAATCAG       120

ATCTCAAGAC AGACTCTTTG AACTACCCTT TCTCCCTCCC CAATTCCCAC CCCCTTATGG       180

CTCTTGGGAC ATAGCACCTG AGCAGGCACC TCAGTCCGTG TAGAGTNTGA CCGGCACCAA       240

GGCATGTCTG CCCTACCCAA GAAGGGAGAC AGGCCCTGGG GTCACTTGTT TCCAGCCCTT       300

CATGACCCCA AGNCCTGTTC CCCANAGGGC CCAGGGCTTA AGNACCANTT GGGAGGGNAC       360

CTTAGGGTGG TTGCT                                                       375
```

(2) INFORMATION FOR SEQ ID NO:107:

(i) SEQUENCE CHARACTERISTICS:
        (A) LENGTH: 307 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:107:

```
TNCGACTACA AGTTCCTGGG AGAAGCCCAA GCNNCGGCTG CTGTGCCCAC TGTGCGGGAA        60

GCCCATGCGC GANCTGTTGC AGGTTTCCAC CTGCGGCCAC CGTTTCTGCG ATACCTGCCT       120

GCAGAGTTCC TCAGTGAAGG AGTCTTCAAG TGCCCTGAGG ACCAGCTTCC TCTGGACTAT       180
```

```
GCCAAGATCT ACCCAGACCC GGAGCTGGAA GTACAAGTAT TGGGGCCTGC CTATTCACTG       240

CATCCACAGT GAGGAGGGCT GCCGCTGGAG TNGGGCCATT ACGTCATCTA CAGGGGNCAC       300

TTGAATT                                                                 307
```

(2) INFORMATION FOR SEQ ID NO:108:

(i) SEQUENCE CHARACTERISTICS:
        (A) LENGTH: 243 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:108:

```
TGCATTCCTC AATGGCAATG GCAGTGGTGA GGGCCACACC TCTCACTGTA CATTCGTGTG        60

CTGCCTGGTG CCTTTGACAA TCTCCTTGAG TGGCCCTTTG CCCGCCGTGT CACCTTCTCC       120

CTGCTGGATC AGAGCGACCC TGGGCTGGCT AAACCACAGC ACGTCACTGA GACCTTCCAC       180

CCCGACCCAA ACTGGAAGAA TTTCCAGAAG CCAGGCACGT GGCGGGCTC CCTGGATGAG        240

AGT                                                                     243
```

(2) INFORMATION FOR SEQ ID NO:109:

(i) SEQUENCE CHARACTERISTICS:
        (A) LENGTH: 396 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:109:

```
TTTTTTTTTT AATAAATACA ATTCCGGATT TATTAAAAAT CAGGGCTNCC CTGCTGTGCC        60

CTCCTGGCAC TAAGGAAATA ANTAACCAGA GGGGCACAG CTAGGTAAAG GGGGAAAAAA       120

TCAGATCTCA AGACAGACTC TTTGAACTAC CCTTTCTCCC TCCCGAATTC CCACCCCCTT       180

ATGGCTCTTG GGACATAGGC ACCTGAGGCA GGCACCTCAG TCCGTGTAGN AGTGTGACCG       240

GGNACCAAGG GCATNTATGC CCTACCCAAG ANGGGAGACA GGCCCTGGGG TTCACTTGTT       300

TCCAGNCCTT NCATGTACCC CAAGGACCTG TTNCCCCANA GGGGAACAGG GGCTGGAAGG       360

CACCAATTGG GAGGGCANCT TTAGGNGTGG TTGGGC                                  396
```

(2) INFORMATION FOR SEQ ID NO:110:

(i) SEQUENCE CHARACTERISTICS:
        (A) LENGTH: 239 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:110:

```
TAAATACAAT TCCGGATTTA TTAAAAATCA GGGCTCCCCT GNCTGTCCCT CCTGGCACTA        60

AGGAAATAAA TAACCAGAGG GGGCACAGCT AGGTAAAGGG GGAAAAAATC AGATCTCAAG       120

ACAGACTCTT TGAACTACCC TTTCTCCCTC CCAATTCCC ACCCCCTTAT GGCTCTTGGG        180

ACATAGCACC TGAGCAGGCA CCTCAGTCCG TGTAGAGTTT GACCGGCACC AGGGCATGT        239
```

(2) INFORMATION FOR SEQ ID NO:111:

(i) SEQUENCE CHARACTERISTICS:
    (A) LENGTH: 401 base pairs
    (B) TYPE: nucleic acid
    (C) STRANDEDNESS: both
    (D) TOPOLOGY: both (ii) MOLECULE TYPE: cDNA (xi) SEQUENCE DESCRIPTION: SEQ ID NO:111:

| | | | | | |
|---|---|---|---|---|---|
| TTCTCAAACT | TCCAGTTCTC | TTCCTGGGCC | AAGATCTGGT | CCACCACTGC | CGTGGCCTCC | 60 |
| TTCCCCTGGC | GGATGTACTC | CCGCTCCTGA | GCAGAGAAAC | TTTTCTTCCC | AGCAACTTCT | 120 |
| TCATCTGATG | GGAGGAGGGA | ACTGAATAGC | TTTCCAAGGA | GGGAGATAAG | AAAGAAGAGT | 180 |
| GTGGTGTGAA | CAGGGAGCTT | TGAGCTGTGG | AGTTGGGCTG | GGCATGGAAA | ATNCGGTGGA | 240 |
| GAGTAGCAAG | GAATGAGGGG | CTTCAGAGAA | CTCTNGGATC | AGCCCTCCCA | CACTCACTGC | 300 |
| CCTTTAAGGT | ATCTTTGGGG | AAAAAAAGGG | GCTTCTATGA | TGAGTCTGGC | AGCTNCCCAC | 360 |
| ACTGCATTCT | CCTCCTGCAT | TTTTTTACCA | TGCACCAGGG | C | | 401 |

(2) INFORMATION FOR SEQ ID NO:112:

(i) SEQUENCE CHARACTERISTICS:
    (A) LENGTH: 322 base pairs
    (B) TYPE: nucleic acid
    (C) STRANDEDNESS: both
    (D) TOPOLOGY: both (ii) MOLECULE TYPE: cDNA (xi) SEQUENCE DESCRIPTION: SEQ ID NO:112:

| | | | | | |
|---|---|---|---|---|---|
| GGCACGAGAA | GAAGTTGCTG | GGAAGAAAAG | TTTCTCTGCT | CAGGAGCGGG | AGTACATCCG | 60 |
| CCAGGGAAGG | AGGCCACGGC | AGNTAAGNAC | CAGATCTTGG | CCCAGGAAGA | GAACTNGAAG | 120 |
| TTTGAGAAGA | ATAATGNATA | TNGGGACACC | GTGTACACCA | TTGAGGTTCC | CTTTCACGGC | 180 |
| AAGACGTTTA | TCCTGAAGAC | CTTCCTGCCC | TGTCCTGCGG | ACTCAGTGGT | ACCAGGAGGT | 240 |
| GATCCTGCAG | CCCGAGAGAT | GGTGCTGTGG | GACAGGNCAG | TGACTGCCTG | CCAGNTCCTG | 300 |
| GCAGCGGAGT | NGAAAGACAA | CA | | | | 322 |

(2) INFORMATION FOR SEQ ID NO:113:

(i) SEQUENCE CHARACTERISTICS:
    (A) LENGTH: 356 base pairs
    (B) TYPE: nucleic acid
    (C) STRANDEDNESS: both
    (D) TOPOLOGY: both (ii) MOLECULE TYPE: cDNA (xi) SEQUENCE DESCRIPTION: SEQ ID NO:113:

| | | | | | |
|---|---|---|---|---|---|
| GCCCTGGGCT | TACATCGTGC | TCAAGTCGGC | CAGTAACCCC | CGTGTTTGCA | CCNTTGTCTG | 60 |
| GATTCTTAAT | ACAGATCTCA | AGGGCCGNCT | GCCCCGGTAC | CTCATCCACC | AGAGCCTCGC | 120 |
| GNCCACCATG | TTTGAATTTG | CCTTTCACCT | GCGACAGGCA | NTCAGNAGCT | GGGGGCCCGG | 180 |
| GCGTGACTGT | GCCCCCTCCC | ACCCTGCGGG | CCAGGGTCCT | GTCGCCACCA | CTTCCAGAGC | 240 |
| CAGAAAGGGT | GCCAGTTGGG | CTTCGCACTG | CCCACATNGG | GACCTGGGNC | CAGGGTGTT | 300 |
| CAACCCTTNC | ACCGAGGCCA | NGGAGTTCCT | GGGGAGTTTG | ACTTGACTTG | AGGCAG | 356 |

(2) INFORMATION FOR SEQ ID NO:114:

(i) SEQUENCE CHARACTERISTICS:
    (A) LENGTH: 440 base pairs (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:114:

```
TTTTTTAAAT TCATGTTTTT AATTGGCTTA ATACAAAGGT CCCCCAGGAG GCCCTGGGAG      60

GAGGGGGACA GCCTGGGAGA GGCAGAGATT CATGGCCAGC AGCCACCCCC ACCTGCCACC     120

CANTCCCCAA CAAGGGTCCC AGACTCTTTC AATAATCCTA AAAAAACCGA CGAGAGCGCA     180

GGCAGATGAA GAGCCCCTTC ATCTTCACAC GGGTGACAGG NTGCCCTGCC CTGCCCAGGG     240

GCCTGGGTCC TCCCCAGCCA AGTCAGGTTG CCCAGCCCAG ACCCTTGCCC TGGGNAAGGG     300

TGGGGGCAGA GAATNTTGGG TCCTCCAGGG GAGGGCAGGG CGCCATTNTT AAACATTTCA     360

ACAGGGCCAA GACCCCANTT TTTCTTNCAG CCANTTGGGG CCCCGGAGTT NCAGTTGTTT     420

TCAACCCACA GGCTTNTTTC                                                 440
```

(2) INFORMATION FOR SEQ ID NO:115:

(i) SEQUENCE CHARACTERISTICS:
        (A) LENGTH: 289 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:115:

```
AGACCCTGCT GAGGGCAGGC CATCAAGTGT GACTTCTGCC TGCCTTCCCC CAGGNCCGCC      60

TGCCNCGGTA CCTCATCCAC CAGAGCCTCG CGCCACCATG TTTGAATTTG CCTTTCACCT     120

GCGACAGGCA CTGCAGCAGC TGGGGGCCCG GGCGTGACTG TGCCCCCTCC CACCCTGCGG     180

GCCAGGGGTC CTGTTCGCCA CCACTTCCAG AGGCCAGAAA GGGTGCCAGT TGGGGTTCGC     240

ACTTGCCCAC ATGGGGACTG GGGCCCAGGG TTGTTCACCC TTCCACCGA                 289
```

(2) INFORMATION FOR SEQ ID NO:116:

(i) SEQUENCE CHARACTERISTICS:
        (A) LENGTH: 737 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:116:

```
CGTCAGCCAG CAACCCCCGG GTCTGCACCT TCGTCTGGAT TCTTAACACA GACCTCAAGG      60

GCCGCCTGCC TCGGTACCCC ATCCACCAGA GCCTTGGGCC ACCATGTTTG AATTTGCCTT     120

TTACCTGCGG CACGTGTTGG AGAGCCTGGG CGCCCGAGCT GACCATGTTC CCTCGCCACC     180

CTGCGGCCAG GGTCCTGTCC ACAGCCTCTG GAGCCAGAAA GTGGAAATGT TTGGGTTTCT     240

GCTGCCCATG AAGGACTTTG TGCTAAGCAG GCCCGTGCGA CCTCCTTCCA TGGCTGTAGC     300

TTCCACTAAG CCACACTGCT CGGAACAGGG CCCTGAGCGG TTGTGGGGTT GAGTACCTGG     360

ACTCGGGGTT CCATACTGGA GGAGCCGGGA CTGTCTTGCC TATGCTGACC TACAGCTCCT     420

GCCTTCTGGA GAGGAGACCC CCGCCATGCC TCACTGGGCA CCTTAGACTT GGTCACAGAG     480

GACTGGGCCT GGGTAGGGCA GGAGACCATC CCGTTGCAAC GTGAAGGTGA GGAAGCCCTC     540

TAGTCCAGGT TTTGTACCAT TAGGGAAGGG GTCTGGGACT GTTCCATACA CACTGTGGGG     600
```

```
ATGTAAGGCA GGGGGACAGC ATTGCCTTCC TGCCTCTCCT CGCCTTCTCG GGAACCTTTG    660

TAATAAATTG AGCCAATTAA AAACACAAAA TAAAGAATCA AAATGCAAAA AAAAAAACAA    720

AAAAAAAAAA AAAAAA                                                    737
```

(2) INFORMATION FOR SEQ ID NO:117:

(i) SEQUENCE CHARACTERISTICS:
        (A) LENGTH: 464 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:117:

```
GTTTTTAATT GGCTTAATAC AAAGGTCCCC CAGGAGGCCC TGGGAGGAGG GGGACAGCCT     60

GGGAGAGGCA GAGATTCATG GCCAGCAGCC CACCCCCACC TGCCACCCAC TCCCCAACAA    120

GGGTCCCAGA CTCTTTCAAT AATCCTAAAA AAACCGACGA GAGCGCAGGC AGATGAAGAG    180

CCCCTTCATC TTCACACGGG TGACAGGCTG CCCTGCCCTG CCCAGGGGCC TGGGGTCCTC    240

CCCAGCCAAG TCAGGGTGCC CAGCCCAGAC CCTGCCTGGG GGAAGGTTGG GGGCAGAGCA    300

ATCTTGGTCN TCAGGGGAGG GCAAGGGCGC CATTGTTAAA CATTCAACAA GGGNCAAGAC    360

CCCAATTTTC TTCCAAGCCA NTTGGGGGCC CCNGAGTTCA AGTTGTTTCC AACCCAAAGC    420

TTTNTTTAGT TAANTCAAAT TCANGGGGAT TTNGTTGGTT TTTT                     464
```

(2) INFORMATION FOR SEQ ID NO:118:

(i) SEQUENCE CHARACTERISTICS:
        (A) LENGTH: 465 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:118:

```
GGGAAGAGCC GNGGCCGTGG TGACATGGAG CAGCCCTGCN TNGNAGGCCG CGCCTCCCCG     60

CCCTGAGGTG GGGGCCCACC AGGATGAGCA AGCTGCCCAG GGAGCTGACC CGAGACTTGG    120

AGCGCAGCTG GCCTGCCGTG GCCTCCCTGG GCTCCTCACT GTCCCACAGC CAGAGCCTCT    180

CCTCGCACCT CCTTCCGCCG CCTGAGAAGC GAAGGGCCAT CTCTGATGTC CGCCGCACCT    240

TCTGTCTCTT CGTCACCTTC GACCTGCTCT TCATCTCCCT GCTCTGGATC ATCGAACTGA    300

ATACCAACAC AGGGCATCCG TAAGAACTTG GGAGGCAGGA GATCATCCAG TACAACTTTT    360

AAAATTTCCT TCTTTCGACA TCTTTTGTNC TGGGNTTTTT TCCGTTTTTC TGGGATTGTT    420

CCNAGGGTTA TGNCTTGTTG GCAGNTTCCG GCATTGGTNG GGTGA                    465
```

(2) INFORMATION FOR SEQ ID NO:119:

(i) SEQUENCE CHARACTERISTICS:
        (A) LENGTH: 240 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:119:

```
CGCAGCTTGC CTGCCGTGGC CTCCCTGGGC TCCTCACTGT CCCACAGCCA GAGCCTCTGC     60

TCGCACCTTC TTCCGCCGCC TGAAGAAAGC GAAAGGTGCC CAATCTTCTG AATGGTTCCG    120
```

```
GCCGGCAACC CTTTCTTGGT GTTCTATCGG TAAACCTTTC GAACCTGGCT TCTTTAAATC        180

CTTCCCTTGG CTTCTGGGAA TCAATCGAAA CTTGAAATAA CCAAACAAAA GGGAATTCCG        240
```

(2) INFORMATION FOR SEQ ID NO:120:

(i) SEQUENCE CHARACTERISTICS:
        (A) LENGTH: 482 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:120:

```
TAAATTCATG TTTTTAATTG GCTTAATACA AAGGTCCCAC AGGAGGCCCT GGGAGGAGGG         60

GGACAGCCTG GGAGAGGCAG AGATTCATGG CCAGCAGCCC ACCCCCACCT GCCACCCACT        120

CCCCAACAAG GGTCCCAGAC TCTTTCAATA ATCCTAAAAA AACCGACGAG AGCGCAGGCA        180

GGATGAAGAG CCCCTTCATN TTCACACGGG GTGACAGGCT GCCCTGCCCT GCCCGGGGGC        240

CTGGGGTCCT CCCCAGCCAA GTCAGGGTNC CCAGCCCAGA CCCTGCCTGG GGAAGGTNGG        300

GGGAGAGCAA TTTNGGTCCT TCAGGGNGGC AGGGGCGCCA TNTTTAAACA TTTAAACAGG        360

GNCAGACCCC ATTTTTTCTT TCAGCCATTG GGGGGCCCCG GAGTTNCAGT TGTTTTTCAA        420

CCCAAAGNTT TTTTTAATTT NAGTTNAATT TTNGGGGGAT TTNGTTGGGT TTNGGTTGGG        480

AN                                                                      482
```

(2) INFORMATION FOR SEQ ID NO:121:

(i) SEQUENCE CHARACTERISTICS:
        (A) LENGTH: 352 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:121:

```
CCCCAAGGGA CTTCGTGAAT GTCCGGCGCA TTGAGCGGCG CAGGGACCGA TACTTGTCAT         60

CAGGGATCGC CACCTCACAC AGTGCCAAGC CCCCGACGCA CAAATATGTC CGGGGAGAGA        120

ATGGCCCTGG GGNTTTCATC GTGCTCAAGT CGGCCAGTAA CCCCCGTGTT TGCACCTTTG        180

TCTGGATTCT TAATACAGAT CTCAAGGGCC GCCTGCCCCG GTACCTCATC CACCAGAGCC        240

TCGCGGCCAC CATGTTTTGA ATTTGCCTTT CACCTGCGAC ANGCATTCAG CGAGCTGGGG        300

GGCCCGGGCG TTGATTGTGG CCCCTTCCCA CCNTGCGGGG CCAGGGGTCC TG               352
```

(2) INFORMATION FOR SEQ ID NO:122:

(i) SEQUENCE CHARACTERISTICS:
        (A) LENGTH: 498 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:122:

```
TTTTTTTTTT AAATTCATGT TTTTAATTGG ACTTAATACA AAGGTCCCCC AGGAGGCCCT         60

GGGAGGAGGG GGACAGCCTG GGAGAGGCAG AGATTCATGG CCAGCAGCCC ACCCCCACCT        120

GCCACCCACT CCCCAACAAG GGTCCCAGAC TCTTTCAATA ATCCTAAAAA AACCGACGAG        180
```

```
AGCGCAGGCA GATGAAGAGC CCCTTCATCT TCACACGGGT GACAGGCTGC CCTGCCCTGC    240

CCAGGGCCCT GGTTCCTCCC CAGCCAAGTC AGGTGCCCAG CCCAGACCCT GCCCTGGCAA    300

GGTGGGGCAG AGCAATCTGG TCCTCCAGGG AGGNCAGGGC GCCATGTTAA ACATTCAACA    360

GGGCCAGACC CCATTTCCTT CCAGCCAGTG GGGGCCCCGG AGTTCCAGTT GTTNCACCCC    420

ACAGCTTGTT TCAGTTCAGT TCAATTTCCA GGGCATTNCT TGGTTTCGGT TGGANGGTTG    480

ACAGNTTGGG GGCAGGTT                                                  498

(2) INFORMATION FOR SEQ ID NO:123:

(i) SEQUENCE CHARACTERISTICS:
        (A) LENGTH: 394 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:123:

TAAANTCATG TTTTTAATTG GCTTAATACA AAGGTCCCCC AGGAGGCCCT GGGAGGAGGG     60

GGACANCCTG GGAGAGGCAG AGATTCATGG CCAGCAGCCC ACCCCACCT GCCACCCACT    120

CCCCAACAAG GGTCCCAGAC TNTTTCAATA ATCCTAAAAA AACCGACGAG AGCGCAGGCA    180

GATGAAGAGC CCCTTCATCT TCACACGGGT GACAGGCTGC CCTGCCCTGC CCAGGGCCCT    240

GGGTCCTCCC CAGCCAAGTC AGGTGCCCAG CCCAGACCCT GCCCTGGNAA GGTGGGGCAG    300

AGCAATNTGG TCCTCCAGGG AGGCAGGGCG CCATGTAAAC ATCAACAGGC CAGACCCCAC    360

TTCCTTCAAG CCAGTGGGGG CCCCGGAGTT CCAG                                394

(2) INFORMATION FOR SEQ ID NO:124:

(i) SEQUENCE CHARACTERISTICS:
        (A) LENGTH: 445 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:124:

GGAGAACTGG AAGTTTGAGA AGAATAATGA ATATGGGGAC ACCGTGTACA CCATTGAAGT     60

TCCCTTTCAC GGCAAGACGT TTATCCTGAA GACCTTCCTG CCCTGTCCTG CGGANTCGTG    120

TACCAGGAGG TGATCCTGCA GCCCGAGAGG ATGGTGCTGT GGAACAAGAC AGTGACTGCC    180

TGCCAGATCC TGCAGCGAGT GGAAGACAAC ACCCTCATCT CCTATGACGT GTCTGCAGGG    240

GCTGCGGGCG GCGTGGTCTC CCCAAGGGAC TTCGTGAATG TCCGGCGCAT TGAGCGGCGC    300

AGGGACCGAT ACTTGTTCAT CAGGGATCGC CACCTTCACA CAGTGCCAAG CCCCCGACGC    360

ACAAATATGT TCCGGGGAGA GAATGGCCTG GGGGTTTCAT CGTGGTTCAA NTCGGCCATT    420

AACCCCCTGT TTTGCACNTT GTNTG                                          445
```

ISOLATED NUCLEIC ACID MOLECULES USEFUL AS LEUKEMIA MARKERS AND IN BREAST CANCER PROGNOSIS AND ENCODED POLYPEPTIDES

The present application claims benefit of the filing date of United States provisional application no. 60/002,183, filed Aug. 9, 1995, which is herein incorporated by reference.

FIELD OF THE INVENTION

The invention relates to four novel human genes amplified and overexpressed in breast carcinoma. The four genes are located at chromosome 17q11-q21.3. The invention also relates to a fifth novel human gene expressed in breast carcinoma and located at chromosome 6q22-q23. A sixth novel gene is also described that is the murine homolog of the human D52 gene.

BACKGROUND OF THE INVENTION

Despite earlier detection and a lower size of the primary tumors at the time of diagnosis (Nyström, L. et al., *Lancet* 341:973–978 (1993); Fletcher, S. W. et al., *J. Natl. Cancer Inst.* 85:1644–1656 (1993)), associated metastases remain the major cause of breast cancer mortality (Frost, P. & Levin, R., *Lancet* 339:1458–1461 (1992)). The initial steps of transformation characterized by the malignant cell escape from normal cell cycle controls are driven by the expression of dominant oncogenes and/or the loss of tumor suppressor genes (Hunter, T. & Pines, J., *Cell* 79:573–582 (1994)).

Tumor progression can be considered as the ability of the malignant cells to leave the primary tumoral site and, after migration through lymphatic or blood vessels, to grow at a distance in host tissue and form a secondary tumor (Fidler, I. J., *Cancer Res.* 50:6130–6138 (1990); Liotta, L. et al., *Cell* 64:327–336 (1991)). Progression to metastasis is dependent not only upon transformation but also upon the outcome of a cascade of interactions between the malignant cells and the host cells/tissues. These interactions may reflect molecular modification of synthesis and/or of activity of different gene products both in malignant and host cells. Several genes involved in the control of tumoral progression have been identified and shown to be implicated in cell adhesion, extracellular matrix degradation, immune surveillance, growth factor synthesis and/or angiogenesis (reviewed in Hart, I. R. & Saini, A., *Lancet* 339:1453–1461 (1992); Ponta, H. et al., *B.B.A.* 1198:1–10(1994); Bernstein, L. R. & Liotta, L. A., *Curr. Opin. Oncol.* 6:106–113 (1994); Brattain, M. G. et al., *Curr. Opin. Oncol.* 6:77–81 (1994); and Fidler, I. J. & Ellis, L. M., *Cell* 79:185–188 (1994)).

However, defining the mechanisms involved in the formation and growth of metastases is still a major challenge in breast cancer research (Rusciano, D. & Burger, M. M., *BioEssays* 14:185–194 (1992); Hoskins, K. & Weber, B. L., *Current Opinion in Oncology* 6:554–559 (1994)). The processes leading to the formation of metastases are complex (Fidler, I. J., *Cancer Res.* 50:6130–6138 (1990); Liotta, L. et al., *Cell* 64:327–336 (1991)), and identifying the related molecular events is thus critical for the selection of optimal treatments.

SUMMARY OF THE INVENTION

By differential screening of a cDNA library from breast cancer derived metastatic axillary lymph nodes, four clones (MLN 50, 51, 62 and 64) were isolated by the present inventors and determined to be co-localized at the q11-q21.3 region of the chromosome 17 long arm. Several genes implicated in breast cancer progression have been assigned to the same portion of chromosome 17, most notably the oncogene c-erbB-2 in q12 and the recently cloned tumor suppressor gene BRCA1 in q21. Additionally, the D53 gene was cloned by the present inventors from a cDNA library of primary infiltrating ductal breast carcinoma using a expressed sequence tag that was identified to be homologous to the previously identified D52 gene, and the D53 gene was localized to chromosome 6q22-q23.

The four MLN genes of the present invention are useful as prognostic markers for breast cancer. Although no group of the art-known prognosticators completely fulfills the objective to fully distinguish high- and low-risk patients, combinations of the prognostic factors can improve the prediction of a patient's prognosis. Thus, by the invention, further prognostic markers are provided which can be added to the population of art-known prognosticators to more particularly distinguish between high- and low-risk breast cancer patients. By the invention, when compared to MLN 50, 51, 62, or 64 gene expression level or gene copy number in non-tumorigenic breast tissue, enhanced MLN 50, 51, 62, or 64 gene expression level or gene copy number in breast cancer tissue is indicative of a high-risk breast cancer patient.

The invention further provides a method for distinguishing between different types of acute myeloid leukemia, which involves assaying leukemia cells for D52 or D53 gene expression; whereby, the presence of D52 transcripts (mRNA) or protein or the lack of D53 mRNA or protein indicates that the leukemia cells have myelocytic characteristics (such as HL-60 cells) and the presence of D53 mRNA or protein or the lack of D52 mRNA or protein indicates that the leukemia cells have erythroid characteristics (such as K-562 cells).

Also provided are isolated nucleic acid molecules encoding MLN 50, 51, 62, 64, D53, or murine (m) D52 polypeptides whose amino acid sequences are shown in FIGS. 14(A–B), 21(A–E), 6(A–B), 16(A–C), 24(B) and 25(B), respectively (SEQ ID NOs:4, 8, 2, 6, 10 and 12, respectively). In another aspect, the invention provides isolated nucleic acid molecules encoding MLN 50, 51, 62, 64, or D53 polypeptides having an amino acid sequence as encoded by the cDNAs deposited as ATCC Deposit Nos. 97608, 97611, 97610, 97609 and 97607, respectively. The deposits were made Jun. 14, 1996, under the Budapest Treaty on the International Recognition of the Deposit of Microorganisms for the Purposes of Patent Procedure at the American Type Culture Collection, at the address of 12301 Parklawn Drive, Rockville, Md., U.S.A. MLN50 (ATCC No. 97608) was deposited as pBS-MLN50, which contains the MLN50 cDNA inserted into the EcoRI site of pBluescript SK⁻ (Stratagene, Calif.). MLN64 (ATCC No. 97609) was deposited as pBS-MLN64, which contains the MLN64 cDNA inserted into the EcoRI/XhoI sites of pBluescript SK⁻ (Stratagene, Calif.). MLN62 (ATCC No. 97610) was deposited as pBS-MLN62, which contains the MLN62 cDNA inserted into the EcoRI site of pBluescript SK⁻ (Stratagene, Calif.). MLN51 (ATCC No. 97611) was deposited as pBS-MLN51, which contains the MLN51 cDNA inserted into the EcoRI/XhoI sites of pBluescript SK⁻ (Stratagene, Calif.). hD53 was deposited as pBS-hD53, which contains the hD53 cDNA inserted into the EcoRI site of pBluescript SK⁻ (Stratagene, Calif.). Further embodiments of the invention include isolated nucleic acid molecules that are at least 90% and preferably at least 95%, 97%, 98% or 99% identical the above-described isolated nucleic acid molecules of the present invention.

The present invention also relates to vectors which contain the above-described isolated nucleic acid molecules, host cells transformed with the vectors and the production of MLN 50, 51, 62, 64, mD52 or D53 polypeptides or fragments thereof by recombinant techniques.

The present invention further provides an isolated MLN 50, 51, 62, 64, D53 or mD52 polypeptide having the amino acid sequence as shown in FIG. 14(A–B), 21(A–E), 6(A–B), 16(A–C), 24(B) or 25(B), respectively (SEQ ID NOs:4, 8, 2, 6, 10 and 12, respectively). In a further aspect, an isolated MLN 50, 51, 62, 64 or D53 polypeptide is provided having an amino acid sequence as encoded by the cDNAs deposited as ATCC Deposit Nos. 97608, 97611, 97610, 97609 and 97607, respectively.

BRIEF DESCRIPTION OF THE FIGURES

FIG. 1. Expression Analysis of the 10 MLN Genes. (A–O) Northern blots contained 10 μg of total RNA isolated from MLN (lanes 1), NLN (lanes 2) and FA (lanes 3). Five filters have been prepared and each of them was successively hybridized using two MLN cDNA probes (MLN 62 and 50; MLN 74 and 51; MLN 19 and 64; MLN 10 and 137; MLN 4 and 70) and the internal loading control 36B4. rRNA size markers (S values) are indicated (left).

FIG. 6. Nucleotide and Amino Acid Sequences of Human CART1. (A–C) Nucleotide sequence (SEQ ID NO:1) is numbered in the 5' to 3' direction and amino acid sequence (SEQ ID NO:2) in the open reading frame is designated by the one letter code. The underlined nucleotide sequences correspond to the Kozak and poly(A) addition signal sequences. Putative NLS sequences are bold-typed and broken underlined. The two C-rich regions are boxed and H and C residues are bold-typed. Restricted TRAF domain is grey-boxed. Arrow-heads indicate the splicing sites and asterisk the stop codon.

FIG. 9. Primary Structure of the Three Original HC3HC3 C-rich Motifs Present in CART1 and Comparison with Those of CD40-bp, TRAF2 and DG17. Alignment and conventional symbols are as described in the FIG. 7 legend above: CART1 (101–154) (SEQ ID NO:2); CART1 (155–208) (SEQ ID NO:2); CART1 (209–267) (SEQ ID NO:2); CD40bp (134–189) (SEQ ID NO:24); CD40bp (190–248) (SEQ ID NO:25); TRAF2 (124–176) (SEQ ID NO:26); TRAF2 (177–238) (SEQ ID NO:27); DG17 (193–250) (SEQ ID NO:28).

FIG. 10. Primary Structure of the Restricted TRAF Motif and Comparison with Those of CD40-bp, TRAF1 and TRAF2. Alignment and conventional symbols are as described in the FIG. 7 legend above. Consensus sequence (SEQ ID NO:32) is indicated for CART1 (308–387) (SEQ ID NO:2), CD40bp (415–494) (SEQ ID NO:29), TRAF1 (260–339) (SEQ ID NO:30), and TRAF2 (352–431) (SEQ ID NO:31). Consensus sequence (SEQ ID NO:36) is indicated for CART1 (388–470) (SEQ ID NO:2), CD40bp (495–567) (SEQ ID NO:33), TRAF1 (340–409) (SEQ ID NO:34), and TRAF2 (432–501) (SEQ ID NO:35).

FIG. 13. Northern Blot Analysis of Lasp-1 mRNA Expression in Human Tissues. (A) Total RNA (10 μg) extracted from breast-derived metastatic lymph node (lanes 1 and 2), breast carcinomas (lanes 3–12), fibroadenomas (lanes 13–17) and breast hyperplasia (lane 18) were loaded, transferred, and hybridized with $^{32}$P-labeled probes specific for c-erbB-2, Lasp-1 and to the RNA loading control 36B4. Approximate transcript sizes are indicated (right). (B) Total RNA extracted from normal lymph node (lane 1), normal skin (lane 2), normal lung (lane 3), normal stomach (lane 4), normal colon (lane 5), normal liver (lane 6), SK-Br-3 (lane 7), BT474 (lane 8) and MCF-7 (lane 9) were loaded, transferred, and hybridized with $^{32}$P-labeled probes specific for c-erbB-2, Lasp-1 and to the RNA loading control 36B4. Approximate transcript sizes are indicated (right).

FIG. 15. Comparison of the Lasp1 LIM and SH3 Domains with Other Proteins. (A) Comparison of Lasp-1 LIM domain (residues 1–51 of SEQ ID NO:4) with other LIM proteins: YLZ4 (1–51) (SEQ ID NO:37); hCRIP (1–55) (SEQ ID NO:38); rCRP2 (1–56) (SEQ ID NO:39); rCRP2 (119–180) (SEQ ID NO:40); TSF3 (5–64) (SEQ ID NO:41); TSF3 (104–162) (SEQ ID NO:42)). The consensus LIM domain residues are bolded, identical residues are dashed, (.) indicates gaps in the alignment. (B) Comparison of Lasp-1 SH3 domain (residues 196–261 of SEQ ID NO:4) with other proteins: YLZ3 (134–200) (SEQ ID NO:43); EMS1 (486–550) (SEQ ID NO:44); ABP1 (526–592) (SEQ ID NO:45); h/fyn (76–141) (SEQ ID NO:46); h/src (78–144) (SEQ ID NO:47); h/frg (71–135) (SEQ ID NO:48); h/yes (85–152) (SEQ ID NO:49). The identical residues are dashed, conserved or semiconserved residues in more then half or the aligned sequences are bolded, (.) indicates gaps in the alignment.

FIG. 16. Nucleotide and Amino Acid Sequences of Human MLN 64. (A–C) Nucleotide sequence (SEQ ID NO:5) is numbered in the 5' to 3' direction and amino acid sequence (SEQ ID NO:6) in the open reading frame is designated by the one letter code. The underlined nucleotide sequences correspond to the Kozak and poly(A) addition signal sequences. The dashed underlined nucleotide sequences correspond to the sequences which could be deleted; ◊ new splicing site after deletion; ♦ sites of insertions. Synthetic peptide sequence is bold-typed. Arrowheads indicate the splicing sites and asterisk the stop codon.

FIG. 21 (A–E). Nucleotide and Amino Acid Sequences of Human MLN 51. Nucleotide sequence (SEQ ID NO:7) is numbered in the 5' to 3' direction. The length of the sequence is 4253 bases and includes an additional untranslated 233 nucleotides on the 5' end. Amino acid sequence (SEQ ID NO:8) is numbered in the 5' to 3' direction (underneath). The length of the sequence is 534 amino acids.

FIG. 23. Alignment of Expressed Sequence Tags (ESTs) with Homology to the MLN 51 cDNA Sequence. Three ESTs with homology to part of the MLN 51 nucleotide sequence were identified in GenBank. The accession number and alignment relative to the MLN 51 gene are indicated.

FIG. 24 (A)–(B). Diagrammatic Representation of 3 hD53 cDNAs. (A) Diagrammatic representation of 3 hD53 cDNAs, with clones 83289 and 116783 representing cDNAs isolated by the Washington University-Merck EST project, and clone U1 representing a cDNA isolated from the human breast carcinoma cDNA library during this study. Shaded regions indicate 5'-UTR sequence, solid regions indicate coding sequence and open regions indicate 3'-UTR sequence. The polyadenylation signals associated with polyA sequences are indicated, as is a clone 83289 deletion, and an Alu sequence in the 3'-UTR of clone 83289. (B) Nucleotide sequence (SEQ ID NO:9) and amino acid sequence (SEQ ID NO:10) determined for the hD53 U1 cDNA. The predicted coding sequence is translated using the one letter code (in bold), with numbering in italics referring to the translated product, and all other numbering referring to the nucleotide sequence. Within the 3'-UTR, the polyadenylation signal (ATTAAA, nucleotides 1308–1313 of SEQ ID NO:9) is shown underlined and in bold, as is the corresponding site of polyA addition (nucleotide 1325).

FIG. 26 (A)–(B). Alignment of mD52, hD52 and hD53. (A) Alignment of mD52 (SEQ ID NO:12), hD52 (SEQ ID NO:50) and hD53 (SEQ ID NO:10) amino acid sequences, shown using the one-letter code, as produced by the program PileUp. Numbers above and below the sequences refer to amino acid positions in mD52 and hD53, respectively, with numbering being identical for the 3 sequences up to residue 127, and for hD52 and mD52 up to residue 171. Vertical lines and colons indicate residues identical or conserved, respectively, in mD52 and hD52, and/or in hD52 and hD53 sequences. The following substitutions were allowed: MILVA, GA, DE, TS, QN, YFW, RKH. The combined limits of the N-terminal PEST domains ($Lys^{10}$-$Arg^{40}$ in mD52, $Arg^{10}$-$Arg^{40}$ in hD52, and $Met^{1}$-$Lys^{37}$ in hD53), coiled-coil domains ($Glu^{29}$-$Leu^{71}$ mD52, $Ala^{22}$-$Leu^{71}$ in hD52 and $Val^{22}Leu^{71}$ in hD53), and C-terminal PEST domains ($Lys^{152}$-$Pro^{185}$ in mD52, $Lys^{152}$-$Lys^{179}$ in hD52 and $Lys^{164}$-$His^{184}$ in hD53) are indicated above the sequences. In addition, potential sites of N-glycosylation ($Asn^{163}$ and $Asn^{167}$ in mD52, $Asn^{167}$ in hD52, and $Asn^{82}$ in hD53) are shown underlined and in bold. Potential sites of phosphorylation by casein II kinase ($Ser^{26}$, $Thr^{32}$, $Thr^{44}$, $Ser^{75}$, $Ser^{136}$ in mD52; $Ser^{26}$, $Thr^{30}$, $Ser^{32}$, $Ser^{75}$ $Ser^{136}$, $Thr^{171}$ in hD52; $Thr^{17}$, $Ser^{32}$, $Ser^{58}$, $Ser^{86}$, $Ser^{149}$, $Ser^{174}$, $Thr^{197}$ in hD53), protein kinase C ($Thr^{122}$, $Thr^{133}$ in mD52 and hD52; $Thr^{52}$, $Ser^{58}$, $Ser^{122}$, $Ser^{131}$, $Thr^{146}$, $Ser^{160}$, $Ser^{194}$ in hD53), cAMP- and cGMP-dependent kinase ($Ser^{100}$ in mD52 and hD52), and tyrosine kinase ($Tyr^{130}$ in hD53) are all shown in bold. (B) The aligned coiled-coil domains identified in mD52 (SEQ ID NO:12), hD52 (SEQ ID NO:51) and hD53 (SEQ ID NO:10) sequences, shown using the one-letter code. Numbers below the sequences refer to amino acid positions in the 3 sequences. The abcdefg heptad repeat pattern is indicated above the sequences, with positions a and d (frequently occupied by hydrophobic amino acids in coiled-coil domains) shown in bold, and positions e and g (frequently occupied by negatively and positively charged amino acids, respectively) are underlined. Where mD52, hD52 and hD53 sequences are in accordance with this consensus, the relevant residues are correspondingly shown in bold or underlined.

DETAILED DESCRIPTION OF THE INVENTION

Figure 2A:
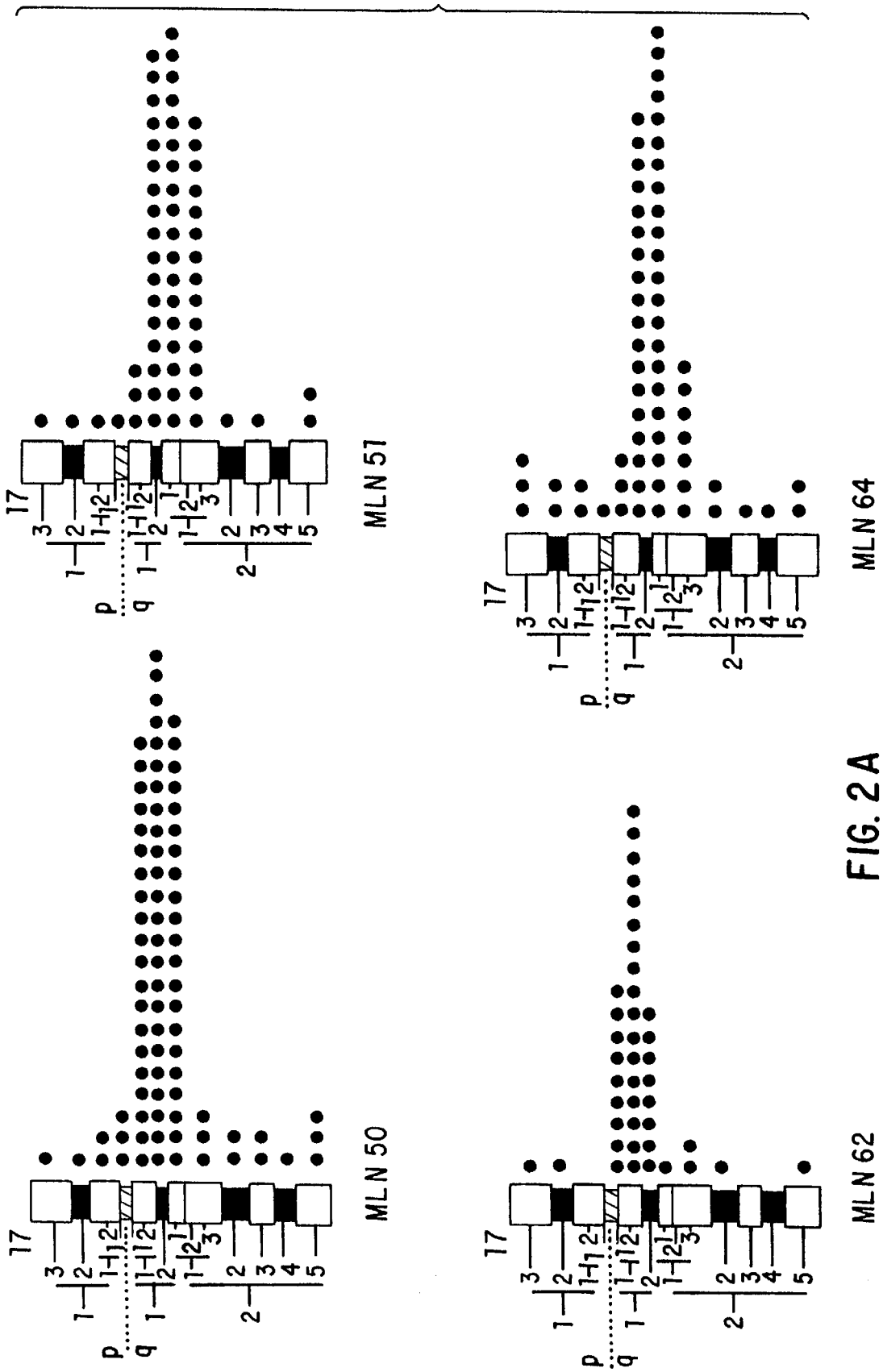
FIG. 2. Chromosomal Assignment of MLN 50, 51, 62 and 64 Genes by in Situ Hybridization. (A) Idiogram of the human G-banded chromosome 17 illustrating the distribution of labeled sites for MLN 50, 51, 62 and 64 cDNA probes. (B) Putative relative assignment of the MLN genes within the q11-q21.3 region of the long arm of the chromosome 17.

Isolation and Localization of Six Novel Genes, MLN 50, 51, 62, 64, D53 and mD52

The present inventors have identified four genes, co-localized on the long arm of chromosome 17, which are amplified and overexpressed in malignant breast tissues. In order to identify and clone these genes involved in tumor progression, differential screening of a cDNA library from breast cancer derived metastatic axillary lymph nodes was performed. The method involved screening the MLN cDNA library using two probes representative of malignant (MLN) and nonmalignant (fibroadenomas; FA) breast tissues. FAs were selected as control tissues since, although nonmalignant, they are proliferating tissues, thereby minimizing the probability to identify mRNAs characteristic of cellular growth, but unrelated to the malignant process. The differential screening method is explained in detail in Example 1, below, and in Basset, P. et al., *Nature* 348:699–704 (1990), where it is described as allowing identification of the stromelysin-3 gene (see also, U.S. Pat. No. 5,236,844).

Four differential clones (MLN 50, 51, 62 and 64) were isolated which correspond to cDNAs whose sequences do not belong to any previously characterized gene or protein family as determined by comparison to the combined GenBank/EMBL databanks. By in situ hybridization of metaphase cells, the four new genes of the present invention were determined to be co-located to the q11-q21.3 region of the chromosome 17 long arm. Several genes implicated in breast cancer progression have been assigned to the same portion of chromosome 17, most notably the oncogene c-erbB-2 in q12 (Fukushige, S. I. et al., *Mol. Cell. Biol.* 6:955–958 (1986)) and the recently cloned tumor suppressor gene BRCA1 in q21 (Hall, J. M. et al., *Science* 250:1684–1689 (1990); and Miki, Y. et al., *Science* 266:66–71 (1994)). According to their chromosomal assignments, the present inventors mapped the four novel genes proximal (MLN 62 and 50) and distal (MLN 64 and 51) to the c-erbB-2 gene, and proximal to the BRCA1 gene.

It has been shown previously that multiple chromosome segments on the chromosome 17 long arm are targets for amplification in breast tumorigenesis (Muleris, M. et al., *Genes Chrom. Cancer* 10:160–170 (1994); Kallioniemi, A. et al., *Proc. Natl. Acad. Sci. USA* 91:2156–2160 (1994)), and 17q12 was found to be the most commonly amplified chromosomal band-region (Guan, X. Y. et al., *Nat. Genet.* 8:155–161 (1994)). Consistently, in breast cancers, c-erbB-2 overexpression is most often correlated to gene amplification (Slamon, D. J. et al., *Science* 235:177–182 (1987); van de Vijver, M. et al., *Mol. Cell. Biol.* 7:2019–2023 (1987)).

It is assumed in the art that DNA amplification plays a crucial role in tumor progression by allowing cancer cells to upregulate numerous genes (Kallioniemi, A. et al., *Proc. Natl. Acad. Sci. USA* 91:2156–2160 (1994); Lönn, U. et al., *Intl. J. Cancer* 58:40–45 (1994)). Amplification is known to target oncogenes and genes involved in drug resistance. Frequency of gene amplification as well as gene copy number increase during breast cancer progression, notably in patients who do not respond to treatment, suggesting that overexpression of the amplified target genes confers a selective advantage to malignant cells (Lönn, U. et al., *Intl. J. Cancer* 58:40–45 (1994); Guan, X. Y. et al., *Nat. Genet.* 8:155–161 (1994)). In vivo, the four MLN genes showed amplification in 10–20% of breast carcinomas tested.

The D52 gene has been isolated by differential screening of a cDNA library from primary infiltrating ductal breast carcinoma (Byrne, J. A. et al., *Cancer Res.* 55:2896–2903 (1995)) and found to be overexpressed and localized exclusively to cancer cells, and not to other cell types such as fibroblastic cells. By in situ hybridization of metaphase cells, D52 was localized to chromosome 8q21. This region of the human genome has been noted to be amplified in breast cancer cell lines, and it was suggested that the frequent gain of the entire chromosome 8q arm in breast carcinomas may indicate the existence of several important loci within this region (Kallioniemi, A. et al., *Proc. Natl. Acad. Sci. USA* 91:2156–2160 (1994)).

The present inventors have isolated a homolog of D52 by screening a cDNA library from primary infiltrating ductal breast carcinoma with an expressed sequence tag (EST) that was identified to be homologous to the hD52 gene, followed by a secondary screening of the resulting positive clones. The method for cloning the D52 homolog is explained in detail in Example 5 below. One clone (D53) was isolated by the present inventors that encodes a protein sharing 52% identity to the D52 protein. By in situ hybridization of metaphase cells, the new gene of the present invention was determined to be localized to the q22-q23 region of chromosome 6.

The present inventors have also isolated a murine homolog of the hD52 gene from an apoptotic mouse mammary gland cDNA library by screening with a fragment (containing 91 bp of 5'UTR and 491 bp of coding sequence) of the hD52 gene. The method for cloning the murine (m) D52 is explained in detail in Example 5 below. The mD52 clone encodes a 185 amino acids protein sharing 82% homology with hD52. By in situ hybridization of murine metaphase cells, the mD52 gene of the present invention was determined to be localized to chromosome 3A1 -3A2, as well as chromosome 8C.

MLN 50, 51, 62 and 64 as Breast Cancer Prognosticators

The four MLN genes of the present invention encode polypeptides which are useful as prognostic markers for breast cancer. It is known in the art that prognostic markers provide important information in the management of breast cancer patients (Elias et al., *J. Histotechnol.* 15(4):315–320 (1992)). For example, for application of systemic adjuvant therapy in primary breast cancer, identification of high- and low-risk patients is a major issue (McGuire, W. L., *N. Engl. J. Med* 320:525–527 (1989)). Several classical (tumor size, lymph node status, histopathology, steroid receptor status) and second-generation prognostic factors (proliferation rate, DNA ploidy, oncogenes, growth factor receptors and some glycoproteins) are currently available for making therapeutic decisions (McGuire, W. L., *Prognostic Factors for Recurrence and Survival*, in EDUCATIONAL BOOKLET AMERICAN SOCIETY OF CLINICAL ONCOLOGY, 25th Annual Meeting, 89–92 (1989); Contesso et al., *Eur. J. Clin. Oncol.* 25:403–409 (1989)). Although no group of the art-known prognosticators completely fulfills the objective to fully distinguish high- and low-risk patients, combinations of the prognostic factors can improve the prediction of a patient's prognosis (McGuire, W. L., *N. Engl. J. Med.* 320:525–527 (1989)). Thus, by the invention, further prognostic markers are provided which can be added to the population of art-known prognosticators to more particularly distinguish between high- and low-risk breast cancer patients.

The present inventors have discovered that, in many instances, cells obtained from breast tumors contain significantly greater copy number of at least one of the four MLN genes and express significantly enhanced levels of MLN 50, 51, 62 or 64 mRNA and/or protein when compared to cells obtained from "normal" breast tissue, i.e., non-tumorigenic breast tissue. Thus, the invention provides a method useful during breast cancer prognosis, which involves assaying a first MLN 50, 51, 62 or 64 gene expression level or gene copy number in breast tissue and comparing the gene expression level or gene copy number with a second MLN 50, 51, 62 or 64 gene expression level or gene copy number, whereby the relative levels of said first gene expression level or gene copy number over said second is a prognostic marker for breast cancer.

The present inventors have not observed any unamplified tumor overexpression of the MLN 50, 51, 62 or 64 genes. Thus, while the inventors do not intend to be bound by theory, it appears that the four MLN genes could not be activated by mechanisms other than gene amplification in breast carcinoma such as, for example, by alteration of regulatory sequences of the genes. Accordingly, by the invention, gene amplification and enhanced gene expression over the standard is clinically relevant for breast cancer prognosis as independent studies have shown an association between the presence of amplification and an increased risk of relapse (Slamon et al., *Science* 235:177 (1987); Ravdin & Chamness, *Gene* 159:19 (1995)).

The methods of the invention can be used alone or together with other markers known in the art for breast cancer prognosis, including those discussed above. By "assaying MLN 50, 51, 62 or 64 gene expression level" is intended qualitatively or quantitatively measuring or estimating the MLN 50, 51, 62 or 64 protein level or MLN 50, 51, 62 or 64 mRNA level in a first biological sample either directly or relatively by comparing to the MLN 50, 51, 62 or 64 protein level or mRNA level in a second biological sample. By "assaying MLN 50, 51, 62 or 64 gene copy number" is intended qualitatively or quantitatively measuring or estimating MLN 50, 51, 62 or 64 gene copy number in a first biological sample either directly or relatively by comparing to the MLN 50, 51, 62 or 64 gene copy number in a second biological sample.

Preferably, the MLN 50, 51, 62 or 64 protein level, mRNA level, or gene copy number in the first biological sample is measured or estimated and compared to a second standard MLN 50, 51, 62 or 64 protein level, mRNA level, or gene copy number, the standard being taken from a second biological sample obtained from an individual not having breast cancer. As will be appreciated in the art, once a standard MLN 50, 51, 62 or 64 protein level, mRNA level, or gene copy number is known, it can be used repeatedly as a standard for comparison. It will also be appreciated in the art, however, that the first and second biological samples can both be obtained from individuals having breast cancer. In such a scenario, the relative MLN 50, 51, 62 or 64 protein levels, mRNA levels or gene copy numbers will provide a relative prognosis between the individuals.

By "biological sample" is intended any biological sample obtained from an individual cell line, tissue culture, or other source which contains MLN 50, 51, 62 or 64 protein; MLN 50, 51, 62 or 64 mRNA; or the MLN 50, 51, 62 or 64 gene. Preferably, the biological sample includes tumorigenic or non-tumorigenic breast tissue. Methods for obtaining tissue biopsies are well known in the art.

The present invention is useful as a prognostic indicator for breast cancer in mammals. Preferred mammals include monkeys, apes, cats, dogs, cows, pigs, horses, rabbits and humans. Particularly preferred are humans.

Assaying MLN 50, 51, 62 or 64 gene copy number can occur according to any known technique such as, for example, by visualizing extrachromosomal double minutes (dmin) or integrated homogeneously staining regions (hsrs) (Gebhart et al., *Breast Cancer Res. Treat.* 8:125 (1986); Dutrillaux et al., *Cancer Genet. Cytogenet.* 49:203 (1990)). Other techniques such as comparative genomic hybridization (CGH) and a strategy based on chromosome microdissection and fluorescence in situ hybridization can also be used to search for regions of increased DNA copy number in tumor cells (Guan et al., *Nature Genet.* 8:155 (1994); Muleris et al., *Genes Chrom. Cancer* 10:160 (1994)). DNA probes that hybridize to the four MLN genes can be prepared as described below.

Total cellular RNA can be isolated from normal and tumorigenic breast tissue using any suitable technique such as the single-step guanidinium-thiocyanate-phenol-chloroform method described in Chomczynski and Sacchi, *Anal. Biochem.* 162:156–159 (1987). The LiCL/urea method described in Auffray and Rougeon, *Eur. J. Biochem.* 107:303 (1980) can also be used. MLN 50, 51, 62 or 64 mRNA levels are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., *Cell* 63:303–312 (1990). Briefly, total RNA is prepared from a biological sample as described above. For the Northern blot, the RNA is denatured in an appropriate buffer (such as glyoxal/dimethyl, sulfoxide/sodium phosphate buffer), subjected to agarose gel electrophoresis, and transferred onto a nitrocellulose or nylon filter. MLN 50, 51, 62 or 64 DNA labeled according to any appropriate method (such as the $^{32}$P-multiprimed DNA labeling system (Amersham)) is used as probe. After hybridization, the filter is washed and exposed to x-ray film.

MLN 50, 51, 62 or 64 DNA for use as probes according to the present invention are described below. Where a fragment is used, the DNA probe will be at least about 15–30 nucleotides in length, and preferably, at least about 50 nucleotides in length.

S1 mapping can be performed as described in Fujita et al., *Cell* 49:357–367 (1987). To prepare probe DNA for use in S1 mapping, the sense strand of MLN 50, 51, 62 or 64 cDNA is used as a template to synthesize labeled antisense DNA. The antisense DNA can then be digested using an appropriate restriction endonuclease to generate further DNA probes of a desired length. Such antisense probes are useful for visualizing protected bands corresponding to MLN 50, 51, 62 or 64 mRNA. Northern blot analysis can be performed as described above.

Alternatively, MLN 50, 51, 62 or 64 mRNA levels are assayed using the RT-PCR method described in Makino et al., *Technique* 2:295–301 (1990). By this method, the radioactivities of the amplification products in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the MLN 50, 51, 62 or 64 mRNA) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed MLN 50, 51, 62 or 64 mRNA can be used and can be designed by reference to the MLN 50, 51, 62 or 64 DNA sequence provided below.

Assaying MLN 50, 51, 62 or 64 protein levels in a biological sample can occur using any art-known method. Preferred are antibody-based techniques. For example, MLN 50, 51, 62 or 64 protein expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of MLN 50, 51, 62 or 64 protein for Western-blot or dot/slot assay (Jalkanen, M., et al., *J. Cell. Biol.* 101:976–985 (1985); Jalkanen, M., et al., *J. Cell. Biol.* 105:3087–3096 (1987)). In this technique, which is based on the use of cationic solid phases, quantitation of MLN 50, 51, 62 or 64 protein can be accomplished using isolated MLN 50, 51, 62 or 64 as a standard. This technique can also be applied to body fluids. With these samples, a molar concentration of MLN 50, 51, 62 or 64 protein will aid to set standard values of MLN 50, 51, 62 or 64 protein content for different body fluids, like serum, plasma, urine, spinal fluid, etc. The normal appearance of MLN 50, 51, 62 or 64 amounts can then be set using values from healthy individuals, which can be compared to those obtained from a test subject.

Other antibody-based methods useful for detecting MLN 50, 51, 62 or 64 gene expression include immunoassays, such as the enzyme linked immunosorbent assay (ELISA) and the radioimmunoassay (RIA). For example, a monoclonal antibody can be used both as an immunoabsorbent and as an enzyme-labeled probe to detect and quantify the MLN 50, 51, 62 or 64 protein. The amount of MLN 50, 51, 62 or 64 protein present in the sample can be calculated by reference to the amount present in a standard preparation using a linear regression computer algorithm. Such an ELISA for detecting a tumor antigen is described in Iacobelli et al., *Breast Cancer Research and Treatment* 11:19–30 (1988). In another ELISA assay, two distinct monoclonal antibodies can be used to detect MLN 50, 51, 62 or 64 protein in a body fluid. In this assay, one of the antibodies is used as the immunoabsorbent and the other as the enzyme-labeled probe.

The above techniques may be conducted essentially as a "one-step" or "two-step" assay. The "one-step" assay involves contacting MLN 50, 51, 62 or 64 protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}I$, $^{121}I$), carbon ($^{14}C$), salphee ($^{35}S$), tritium ($^{3}H$), indium ($^{112}In$), and technetium ($^{99m}Tc$), and fluorescent labels, such as fluorescein and rhodamine, and biotin.

In addition to assaying MLN 50, 51, 62 or 64 protein levels in a biological sample obtained from an individual, MLN 50, 51, 62 or 64 protein can also be detected in vivo by imaging. Antibody labels or markers for in vivo imaging of MLN 50, 51, 62 or 64 protein include those detectable by X-radiography, NMR or ESR. For X-radiography, suitable labels include radioisotopes such as barium or caesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

An antibody or antibody fragment which has been labeled with an appropriate detectable imaging moiety, such as a radioisotope (for example, $^{131}I$, $^{112}In$, $^{99m}Tc$), a radio-opaque substance, or a material detectable by nuclear magnetic resonance, is introduced (for example, parenterally, subcutaneously or intraperitoneally) into the mammal to be examined for breast cancer. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain the protein. In vivo tumor imaging is described in S. W. Burchiel et al., *Immunopharmacokinetics of Radiolabelled Antibodies and Their Fragments*, in TUMOR IMAGING: THE RADIOCHEMICAL DETECTION OF CANCER (S. W. Burchiel and B. A. Rhodes, eds., Masson Publishing Inc. (1982)).

Antibodies for use in the present invention can be raised against the intact MLN 50, 51, 62 or 64 protein or an antigenic polypeptide fragment thereof, which may presented together with a carrier protein, such as an albumin, to an animal system (such as rabbit or mouse) or, if it is long enough (at least about 25 amino acids), without a carrier. As used herein, the term "antibody" (Ab) or "monoclonal antibody" (Mab) is meant to include intact molecules as well as antibody fragments (such as, for example, Fab and F(ab')$_2$ fragments) which are capable of specifically binding to the MLN 50, 51, 62 or 64 protein. Fab and F(ab')$_2$ fragments lack the Fc fragment of intact antibody, clear more rapidly from the circulation, and may have less non-specific tissue binding of an intact antibody (Wahl et al., *J. Nucl. Med* 24:316–325 (1983)). Thus, these fragments are preferred.

The antibodies of the present invention may be prepared by any of a variety of methods. For example, cells expressing the MLN 50, 51, 62 or 64 protein or an antigenic fragment thereof can be administered to an animal in order to induce the production of sera containing polyclonal antibodies. In a preferred method, a preparation of MLN 50, 51, 62 or 64 is prepared and purified to render it substantially free of natural contaminants. Such a preparation is then introduced into an animal in order to produce polyclonal antisera of greater specific activity.

In the most preferred method, the antibodies of the present invention are monoclonal antibodies (or MLN 50, 51, 62 or 64-binding fragments thereof). Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., MONOCLONAL ANTIBODIES AND T-CELL HYBRIDOMAS, 563–681 (Elsevier, N.Y., 1981)). In general, such procedures involve immunizing an animal (preferably a mouse) with a MLN 50, 51, 62 or 64 antigen or, more preferably, with a cell expressing the antigen. Suitable cells can be recognized by their capacity to bind anti-MLN 50, 51, 62 or 64 antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 μg/l of nonessential amino acids, about 1,000 U/ml of penicillin, and about 100 μml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$O), available from the American Type Culture Collection, Rockville, Md. After fusion, the resulting hybridoma cells are selectively maintained in HAT medium, and then cloned by limiting dilution as described by Wands et al., *Gastroenterology* 80:225–232 (1981). The hybridoma cells obtained through such a selection are then assayed to identify clones which secrete antibodies capable of binding the MLN 50, 51, 62 or 64 antigen.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, antigen binding fragments can be produced through the application of recombinant DNA technology or through synthetic chemistry.

Where in vivo imaging is used to detect levels of MLN 50, 51, 62 or 64 protein in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

D52/D53 Gene Expression as a Marker to Distinguish Different Types of Leukemia

The present inventors have further discovered that the relative expression levels of the D52 and D53 genes can be used to distinguish between different types of leukemia. In particular, the inventors have observed that the D52 gene is expressed in leukemia cells that have myelocytic characteristics (such as HL-60 cells) but not in leukemia cells having erythroid characteristics (such as K 562 cells); whereas the inverse is true for D53 gene expression. Thus, the invention further provides a diagnostic method for distinguishing between different types of leukemia, which involves assaying leukemia cells for D52 or D53 gene expression; whereby, the presence of D52 gene expression or the lack of D53 gene expression indicates that the leukemia cells have myelocytic characteristics and the presence of D53 gene expression or the lack of D52 gene expression indicates that the leukemia cells have erythroid characteristics. Preferably, the method is used to distinguish different types of acute myeloid leukemia. As indicated, the method of the invention can be performed by assaying for the presence or absence of either D52 or D53 gene expression. However, preferably, the expression of both genes is assayed.

The human (h) D52 gene is described in detail in Byrne, J. A., et al., *Cancer Research* 55:2896–2903 (1995) and the mD52 gene is described below. The hD53 gene is also described below. Methods for detecting D52 and D53 gene expression in leukemia cells are described in detail above and in the Examples below. As above, D52 and D53 gene expression can be assayed by detecting either the corresponding mRNA or protein.

MLN 50, 51, 62, 64 and D53 Nucleic Acid Molecules, Polypeptides and Fragments Thereof Using the information provided herein, such as the nucleotide sequences of MLN 62, 50, 64, 51, D53, or mD52 as set out in FIGS. 6(A–B), 14(A–B), 16(A–C), 21(A–E) 24(B) and 25(B), respectively (SEQ ID NOS:1, 3, 5, 7, 9 and 11, respectively), an isolated nucleic acid molecule of the present invention may be obtained using standard cloning and screening procedures, such as those for cloning cDNAs using mRNA as starting material.

By "isolated" nucleic acid molecules(s) is intended a nucleic acid molecule, DNA or RNA, which has been removed from its native environment. For example, recombinant DNA molecules contained in a vector are considered isolated for purposes of the invention as are recombinant DNA molecules maintained in heterologous host cells or purified (partially or substantially) DNA molecules in solution. Isolated RNA molecules include in vitro RNA transcripts of the DNA molecules of the present invention. By "isolated" polypeptide or protein is intended a polypeptide or protein removed from its native environment. For example, recombinantly produced polypeptides and proteins expressed in host cells are considered isolated for purposes of the invention, as are native or recombinant polypeptides which have been partially or substantially purified by any suitable technique such as, for example, the single-step purification method disclosed in Smith and Johnson, *Gene* 67:31–40 (1988). Isolated nucleic acid molecules and polypeptides also include such compounds produced synthetically.

As indicated, nucleic acid molecules of the present invention may be in the form of RNA, such as mRNA, or in the form of DNA, including, for instance, cDNA and genomic DNA obtained by cloning or produced synthetically. The DNA may be double- or single-stranded. Single-stranded DNA may be the coding strand, also known as the sense strand, or it may be the noncoding strand, also referred to as the antisense strand.

The MLN 50, 51, 62, 64 genes and the D53 gene were deposited on Jun. 14, 1996, at the American Type Culture Collection, 10801 University Boulevard, Manassas, Va. 20110 and given the accession numbers indicated herein.

The MLN 50, 51, 62, 64, D53 and mD52 nucleic acid molecules of the present invention are discussed in more detail below.

MLN 62

The present invention provides isolated nucleic acid molecules comprising a polynucleotide encoding the CART1 polypeptide (corresponding to the MLN 62 cDNA clone) whose amino acid sequence is shown FIG. 6 (SEQ ID NO:2) or a fragment of the polypeptide. Such isolated nucleic acid molecules include DNA molecules comprising an open reading frame (ORF) whose initiation codon is at position 85–87 of the nucleotide sequence shown in FIG. 6 (SEQ ID NO:1) and further include DNA molecules which comprise a sequence substantially different than all or part of the ORF whose initiation codon is at position 85–87 of the nucleotide sequence of FIG. 6 (SEQ ID NO:1) but which, due to the degeneracy of the genetic code, still encode the CART1 polypeptide or a fragment thereof. Of course, the genetic code is well known in the art. Thus, it would be routine for one skilled in the art to generate the degenerate variants described above.

The invention further provides isolated nucleic acid molecules encoding the CART1 polypeptide having an amino acid sequence as encoded by the cDNA of the clone deposited as ATCC Deposit No. 97610 on Jun. 14, 1996.

The invention further provides an isolated nucleic acid molecule having the nucleotide sequence shown in FIG. 6 (SEQ ID NO:1) or the nucleotide sequence of the CART1 gene contained in the above-described deposited cDNA, or a fragment thereof. Such isolated DNA molecules and fragments thereof are useful as DNA probes for gene mapping by in situ hybridization with chromosomes and for detecting expression of the CART1 gene in human tissues (including breast and lymph node tissues) by Northern blot analysis. Of course, as discussed above, if a DNA molecule includes the ORF whose initiation codon is at position 85–87 of FIG. 6 (SEQ ID NO:1), then it is also useful for expressing the CART1 polypeptide or a fragment thereof.

MLN 50

Figure 14A:
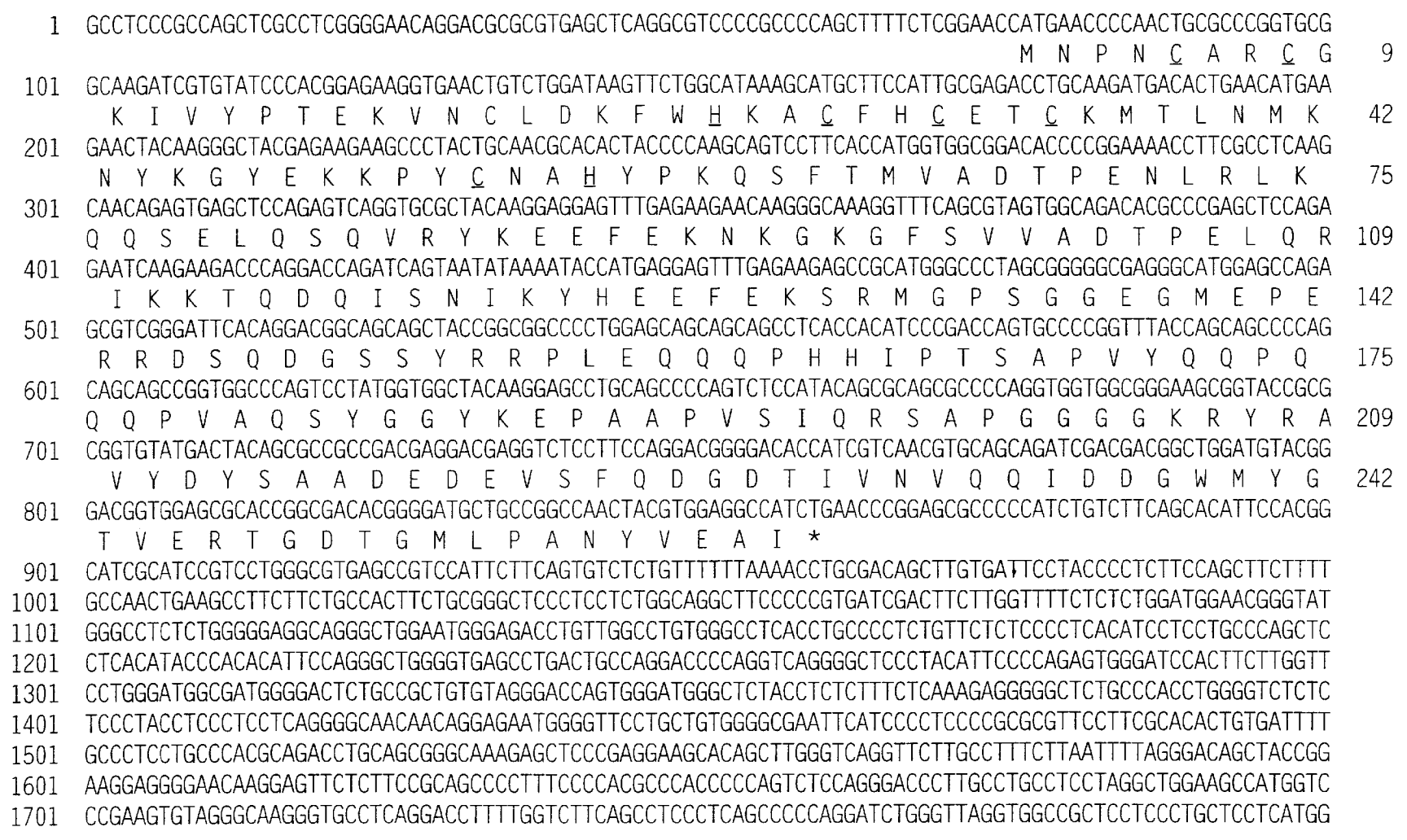
Figure 14C:
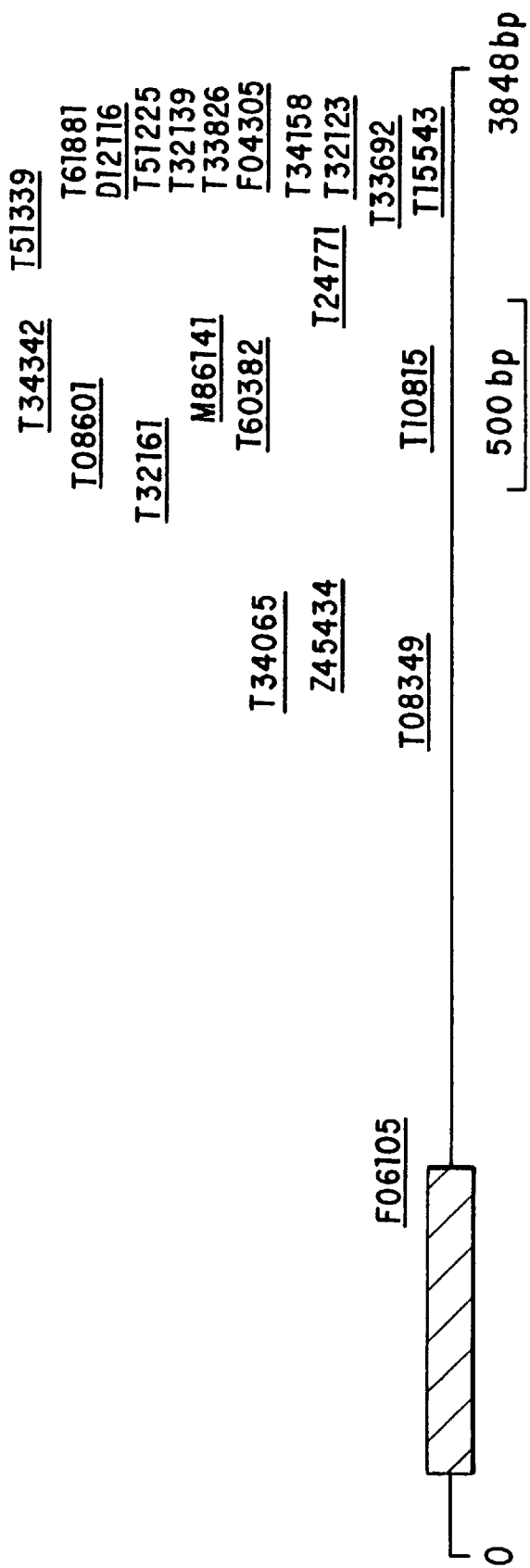
FIG. 14. Nucleotide and Amino Acid Sequences of Human Lasp-1 . (A–B) Nucleotide sequence (SEQ ID NO:3) and amino acid sequence (SEQ ID NO:4) of human Lasp-1. Nucleotides and amino acid residues are numbered on the left and right, respectively. The consensus residues involved in the LIM domain are underlined and bolded and in the SH3 domain re-bolded. Putative tyrosine residues in tyrosine kinase phosphorylation are underlined. An asterisk denotes the termination codon. The signal for polyadenylation is underlined. (C) Structure of Lasp-1 cDNA. The shaded box indicates the protein-coding region. The position of the different expressed sequences tags with homology to Lasp-1 are indicated with their corresponding length and accession numbers.

The present invention also provides isolated nucleic acid molecules comprising a polynucleotide encoding the Lasp-1 polypeptide (corresponding to the MLN 50 cDNA clone) whose amino acid sequence is shown in FIG. 14(A–B) (SEQ ID NO:4) or a fragment of the polypeptide. Such isolated nucleic acid molecules include DNA molecules comprising an open reading frame (ORF) whose initiation codon is at position 76–78 of the nucleotide sequence of FIG. 14(A–B) (SEQ ID NO:3) and further include DNA molecules which comprise a sequence substantially different than all or part of the ORF whose initiation codon is at position 76–78 of the nucleotide sequence of FIG. 14(A–B) (SEQ ID NO:3) but which, due to the degeneracy of the genetic code, still encode the Lasp-1 polypeptide. Of course, the genetic code is well known in the art. Thus, it would be routine for one skilled in the art to generate the degenerate variants described above.

The invention further provides isolated nucleic acid molecules encoding the Lasp-1 polypeptide having an amino acid sequence as encoded by the cDNA of the clone deposited as ATCC Deposit No. 97608 on Jun. 14, 1996.

The invention further provides an isolated nucleic acid molecule having the nucleotide sequence shown in FIG. 14(A–B) (SEQ ID NO:3) or the nucleotide sequence of the Lasp-1 gene contained in the above-described deposited cDNA, or a fragment thereof. Such isolated DNA molecules and fragments thereof are useful as DNA probes for gene mapping by in situ hybridization with chromosomes and for detecting expression of the Lasp-1 gene in human tissues (including breast and lymph node tissues) by Northern blot analysis. Of course, as discussed above, if a DNA molecule includes the ORF whose initiation codon is at position 76–78 of FIG. 14(A–B) (SEQ ID NO:3), then it is also useful for expressing the Lasp-1 polypeptide or a fragment thereof.

MLN 64

The present invention also provides isolated nucleic acid molecules comprising a polynucleotide encoding the MLN 64 polypeptide whose amino acid sequence is shown FIG. 16 (SEQ ID NO:6) or a fragment of the polypeptide. Such isolated nucleic acid molecules include DNA molecules comprising an open reading frame (ORF) whose initiation codon is at position 169–171 of the nucleotide sequence of FIG. 16 (SEQ ID NO:5) and further include DNA molecules which comprise a sequence substantially different than all or part of the ORF whose initiation codon is at position 169–171 of the nucleotide sequence of FIG. 16 (SEQ ID NO:5) but which, due to the degeneracy of the genetic code, still encode the MLN 64 polypeptide or a fragment thereof. Of course, the genetic code is well known in the art. Thus, it would be routine for one skilled in the art to generate the degenerate DNA molecules above.

The invention further provides isolated nucleic acid molecules encoding the MLN 64 polypeptide having an amino acid sequence as encoded by the cDNA of the clone deposited as ATCC Deposit No. 97609 on Jun. 14, 1996.

The invention further provides an isolated DNA molecule having the nucleotide sequence shown in FIG. 16 (SEQ ID NO:5) or the nucleotide sequence of the MLN 64 gene contained in the above-described deposited cDNA, or a fragment thereof. Such isolated DNA molecules and fragments thereof are useful as DNA probes for gene mapping by in situ hybridization with chromosomes and for detecting expression of the MLN 64 gene in human tissues (including breast and lymph node tissues) by Northern blot analysis. Of course, as discussed above, if a DNA molecule includes the ORF whose initiation codon is at position 169–171 of FIG. 16 (SEQ ID NO:5), then it is also useful for expressing the MLN 64 polypeptide or a fragment thereof.

MLN 51

The present invention also provides isolated nucleic acid molecules comprising a polynucleotide encoding the MLN 51 polypeptide whose amino acid sequence is shown FIG. 21(A–E) (SEQ ID NO:8) or a fragment thereof. Such isolated nucleic acid molecules include DNA molecules comprising an open reading frame (ORF) whose initiation codon is at position 234–236 of the nucleotide sequence of FIG. 21(A–E) (SEQ ID NO:7) and further include DNA molecules which comprise a sequence substantially different than all or part of the ORF whose initiation codon is at position 234–236 of the nucleotide sequence of FIG. 21(A–E) (SEQ ID NO:7) but which, due to the degeneracy of the genetic code, still encode the MLN 51 polypeptide or a fragment thereof. Of course, the genetic code is well known in the art. Thus, it would be routine for one skilled in the art to generate the degenerate DNA molecules above.

The invention further provides isolated nucleic acid molecules encoding the MLN 51 polypeptide having an amino acid sequence as encoded by the cDNA of the clone deposited as ATCC Deposit No. 97611 on Jun. 14, 1996.

The invention further provides an isolated DNA molecule having the nucleotide sequence shown in FIG. 21(A–E) (SEQ ID NO:7) or the nucleotide sequence of the MLN 51 gene contained in the above-described deposited cDNA, or a fragment thereof. Such isolated DNA molecules and fragments thereof are useful as DNA probes for gene mapping by in situ hybridization with chromosomes and for detecting expression of the MLN 51 gene in human tissues (including breast and lymph node tissues) by Northern blot analysis. Of course, as discussed above, if a DNA molecule includes the ORF whose initiation codon is at position 234–236 of FIG. 21(A–E) (SEQ ID NO:7), then it is also useful for expressing the MLN 51 polypeptide or a fragment thereof.

D53

The present invention also provides isolated nucleic acid molecules comprising a polynucleotide encoding the D53 polypeptide whose amino acid sequence is shown FIG. 24(B) (SEQ ID NO:10) or a fragment thereof. Such isolated nucleic acid molecules include DNA molecules comprising an open reading frame (ORF) whose initiation codon is at position 181–183 of the nucleotide sequence of FIG. 24(B) (SEQ ID NO:9) and further include DNA molecules which comprise a sequence substantially different than all or part of the ORF whose initiation codon is at position 181–183 of the nucleotide sequence of FIG. 24(B) (SEQ ID NO:9) but which, due to the degeneracy of the genetic code, still encode the D53 polypeptide or a fragment thereof. Of course, the genetic code is well known in the art. Thus, it would be routine for one skilled in the art to generate the degenerate DNA molecules above.

The invention further provides isolated nucleic acid molecules encoding the D53 polypeptide having an amino acid sequence as encoded by the cDNA of the clone deposited as ATCC Deposit No. 97607 on Jun. 14, 1996.

The invention further provides an isolated DNA molecule having the nucleotide sequence shown in FIG. 24(B) (SEQ ID NO:9) or the nucleotide sequence of the D53 gene contained in the above-described deposited cDNA, or a fragment thereof. Such isolated DNA molecules and fragments thereof are useful as DNA probes for gene mapping by in situ hybridization with chromosomes and for detecting expression of the D53 gene in human tissue (including breast and lymph node tissues) by Northern blot analysis. Of course, as discussed above, if a DNA molecule includes the ORF whose initiation codon is at position 181–183 of FIG. 24(B) (SEQ ID NO:9), then it is also useful for expressing the D53 polypeptide or a fragment thereof.

Murine D52

The present invention also provides isolated nucleic acid molecules comprising a polynucleotide encoding the murine D52 polypeptide whose amino acid sequence is shown FIG. 25(B) (SEQ ID NO:12) or a fragment thereof. Such isolated nucleic acid molecules include DNA molecules comprising an open reading frame (ORF) whose initiation codon is at position 22–24 of the nucleotide sequence of FIG. 25(B) (SEQ ID NO:11) and further include DNA molecules which comprise a sequence substantially different than all or part of the ORF whose initiation codon is at position 22–24 of the nucleotide sequence of FIG. 25(B) (SEQ ID NO:11) but which, due to the degeneracy of the genetic code, still encode the D52 polypeptide or a fragment thereof. Of course, the genetic code is well known in the art. Thus, it would be routine for one skilled in the art to generate the degenerate DNA molecules above.

The invention further provides an isolated DNA molecule having the nucleotide sequence shown in FIG. 25(B) (SEQ ID NO:11) or a fragment thereof. Such isolated DNA molecules and fragments thereof are useful as DNA probes for gene mapping by in situ hybridization with chromosomes and for detecting expression of the murine or human D52 gene in mouse or human tissue (including breast and lymph node tissues) by Northern blot analysis. Of course, as discussed above, if a DNA molecule includes the ORF whose initiation codon is at position 22–24 of FIG. 25(B) (SEQ ID NO:11), then it is also useful for expressing the murine D52 polypeptide or a fragment thereof.

Fragments, Derivatives and Variants of the Isolated Nucleic Acid Molecules of the Invention By "fragments" of an isolated DNA molecule having the nucleotide sequence shown in FIGS. 6(A–B), 14(A–B), 16(A–C), 21(A–E), 24(B), or 25(B) (SEQ ID NO:1, 3, 5, 7, 9, or 11, respectively) are intended DNA fragments at least 15 bp, preferably at least 20 bp, and more preferably at least 30 bp in length which are useful as DNA probes as discussed above. Of course, larger DNA fragments of about 50–2000 bp in length are also useful as DNA probes according to the present invention as are DNA fragments corresponding to most, if not all, of the nucleotide sequence shown in FIGS. 6(A–B), 14(A–B, 16(A–C), 21(A–E), 24(B), or 25(B) (SEQ ID NO:1, 3, 5, 7, 9, or 11, respectively). By a fragment at least 20 bp in length, for example, is intended fragments which include 20 or more contiguous bases from the nucleotide sequence of the deposited cDNA or the nucleotide sequence shown in FIGS. 6, 14, 16, 21(A–D), 24(B), or 25(B) (SEQ ID NO:1, 3, 5, 7, 9, or 11, respectively). As indicated, such fragments are useful diagnostically either as a probe according to conventional DNA hybridization techniques or as primers for amplification of a target sequence by the polymerase chain reaction (PCR).

For example, the present inventors have constructed a labeled DNA probe corresponding to the full length human cDNA (nucleotides 1–2004) to detect CART1 gene expression in human tissue using Northern blot analysis (see infra, Example 2). Further, the present inventors have constructed a labeled DNA probe corresponding to a 1.0 kb BamHI fragment to detect Lasp-1 gene expression in human tissues using Northern blot analysis (see infra, Example 3). The present inventors have also constructed a labeled DNA probe corresponding to nucleotides 1 to 2008 of FIG. 16 (SEQ ID NO:5) to detect MLN 64 gene expression in human tissues using Northern blot analysis (see infra, Example 4). Still further, a 5' probe of MLN 64 was obtained using an amplified (by PCR) DNA fragment (nucleotides 1–81 of FIG. 16 (SEQ ID NO:5)), as was a 3' probe corresponding to an EcoRI fragment (nucleotides 60–2073 of FIG. 16 (SEQ ID NO:5)). Finally, the present inventors have also labeled the 842 bp insert of clone 116783 (FIG. 1(A)) to isolate the U1 clone (now D53), as well as to detect D53 expression in human tissues using Northern blot analysis (see infra, Example 5).

Since the MLN 62, 50, 64, 51 genes and the D53 gene have been deposited and the nucleotide sequences shown in FIGS. 6, 14, 16, 21(A–D), 24(B) and 25(B), respectively (SEQ ID NO:1, 3, 5, 7, 9, or 11, respectively) are provided, generating such DNA fragments of the present invention would be routine to the skilled artisan. For example, restriction endonuclease cleavage or shearing by sonication could easily be used to generate fragments of various sizes. Alternatively, the DNA fragments of the present invention could be generated synthetically according to known techniques.

Preferred nucleic acid molecules of the present invention will encode the mature form of the MLN 62, 50, 64, 51, mD52 or D53 protein and/or additional sequences, such as those encoding the leader sequence, or the coding sequence of the mature polypeptide, with or without the aforementioned additional coding sequences, together with additional, noncoding sequences, including for example, but not limited to introns and noncoding 5' and 3' sequences such as the transcribed, nontranslated sequences that play a role in transcription, mRNA processing (including splicing and polyadenylation signals), ribosome binding, and mRNA stability; and additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for example, hexa-histidine provides for convenient purification of the fusion protein. The HA tag corresponds to an epitope derived of influenza hemagglutinin protein, which has been described by Wilson et al., *Cell* 37:767 (1984).

The present invention further relates to variants of the isolated nucleic acid molecules of the present invention, which encode fragments, analogs or derivatives of the MLN 62, 50, 64, 51, mD52 or D53 protein. Variants may occur naturally, such as an allelic variant. Non-naturally occurring variants may be produced using art-known mutagenesis techniques, which include those produced by nucleotide substitutions, deletions or additions. Especially preferred among these are silent or conservative substitutions, additions and deletions, which do not alter the properties and activities of the MLN 62, 50, 64, 51, mD52 or D53 protein or fragment thereof.

Further embodiments of the invention include isolated nucleic acid molecules that are at least 90% identical, and more preferably at least 95%, 97%, 98% or 99% identical to the above-described isolated nucleic acid molecules of the present invention. In particular, the invention is directed to isolated nucleic acid molecules at least 90%, 95%, 97%, 98%, or 99% identical to the nucleotide sequences contained in the deposited cDNAs or in FIGS. 6(A–B), 14(A–B), 16(A–C), 21(A–E), 24(B) or 25(B) (SEQ ID NO:1, 3, 5, 7, 9 or 11, respectively).

By the invention, "% identity" between two nucleic acid sequences can be determined using the "fastA" computer algorithm (Pearson, W. R. & Lipman, D. J., *Proc. Natl. Acad. Sci. USA* 85:2444 (1988)) with the default parameters. Uses of such 95%, 97%, 98%, or 99% identical nucleic acid molecules of the present invention include, inter alia, (1) isolating the MLN 62, 50, 64, 51, mD52, hD52, or D53 gene or allelic variants thereof in a cDNA library; (2) in situ hybridization (FISH) to metaphase chromosomal spreads to provide precise chromosomal location of the MLN 62, 50, 64, 51, mD52, hD52 or D53 gene as described in Verma et al., HUMAN CHROMOSOMES: A MANUAL OF BASIC TECHNIQUES (Pergamon Press, New York, 1988); and (3) Northern Blot analysis for detecting MLN 62, 50, 64, 51, mD52, hD52 or D53 mRNA expression in specific tissues.

Guidance concerning how to make phenotypically silent amino acid substitutions is provided in Bowie, J. U. et al., *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U., et al., *Science* 247:1306–1310 (1990), and the references cited therein.

The invention is further related to nucleic acid molecules capable of hybridizing to a nucleic acid molecule having a sequence complementary to or hybridizing directly to one of the deposited cDNAs or the nucleic acid sequence shown in FIGS. 6(A–B), 14(A–B), 16(A–C), 21(A–E), 24(B) or 25(B) (SEQ ID NO:1, 3, 5, 7, 9 or 11, respectively) under stringent conditions. By "stringent conditions" is intended overnight incubation at 42° C. in a solution comprising: 50% formamide, 5× SSC (150 mM NaCl, 15 mM trisodium citrate), 50 mM sodium phosphate (pH 7.6), 5× Denhardt's solution, 10% dextran sulfate, and 20 µg/ml denatured, sheared salmon sperm DNA (ssDNA), followed by washing the filters in 0.1× SSC at about 65° C.

Examples of variant nucleic acid molecules made according to the present invention are discussed below. The present inventors have cloned and identified a number of MLN 64 gene variants resulting from nucleotide substitutions, deletions and/or insertions. Interestingly, the modifications principally occurred at exon/intron boundaries, suggesting that the MLN 64 variants result from defective splicing processes. These variations of the MLN 64 gene are described in Table VI below and include the following: two substitutions, of a C to T at nucleotide 262 and of an A to G at nucleotide 518, changing Leu to Phe at amino acid 32 and Gln to Arg at amino acid 117, respectively (Table VI, variants A and B); a 99 bp deletion of nucleotides 716 to 814, leading to a 33 amino acid deletion in the MLN 64 protein (i.e., a deletion of amino acids 184–216, giving a 412 amino acid variant protein) (Table VI, variant C); a 51 bp insertion between nucleotides 963–964, generating a stop codon 48 bp downstream of the insertion site and giving rise to a 281 amino acid chimeric C-terminal truncated protein containing 16 aberrant amino acids at the C-terminus (Table VI, variant D); a 657 bp insertion between nucleotides 963–964, generating a 285 amino acid chimeric C-terminal truncated protein containing 20 aberrant amino acids at the C-terminus (Table VI, variant E); the 99 bp deletion described above and a 13 bp deletion of nucleotides 531–543, generating a frameshift leading to 247 amino acid chimeric C-terminal truncated protein containing the 121 N-terminal amino acids of MLN 64 and 126 aberrant amino acids at the C-terminal part (Table VI, variant F); and a 137 bp deletion of nucleotides 115–251 leading to a loss of the initiating ATG codon, the 13 bp deletion described above and a 199 bp insertion downstream of nucleotide 715 encoding an N-terminal truncated protein containing the 138 C-terminal amino acids of MLN 64 (Table VI, variant G).

Based on the above description, generating these seven distinct variants A–G and the polypeptides they encode would be routine for one skilled in the art. For example, as discussed in detail in Example 4, below, the present inventors have cloned these variants from cDNA libraries obtained from metastatic axillary lymph node tissue, an SKBR3 breast cancer cell line, and nontransformed placenta tissue. Moreover, several variants could also be generated by site-directed mutagenesis of the MLN 64 gene whose sequence is shown in FIG. 16 (SEQ ID NO:5).

In a further aspect, the present invention is directed to polynucleotides having a nucleotide sequence complementary to the nucleotide sequence of any of the polynucleotides discussed above.

Expressed Sequence Tags

Figure 22:
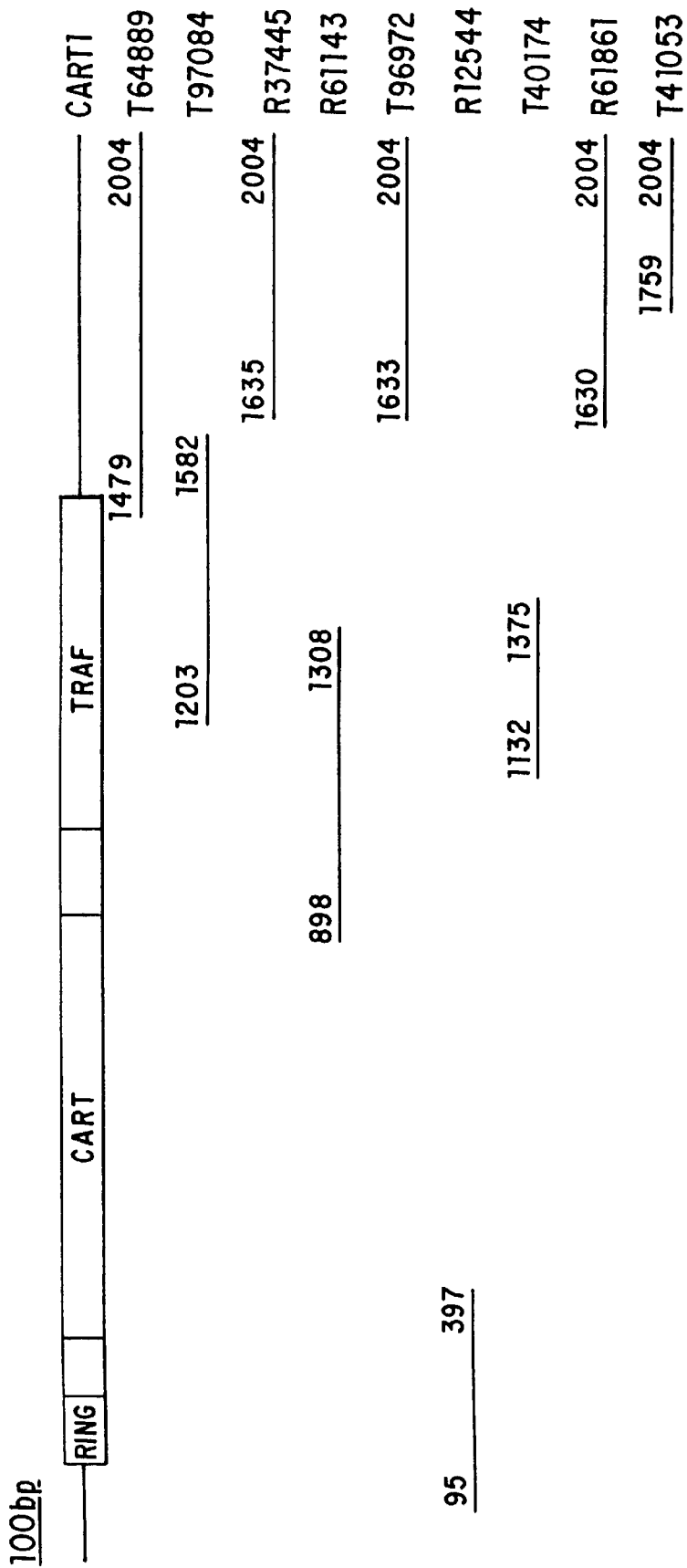
FIG. 22. Alignment of Expressed Sequence Tags (ESTs) with Homology to the CART1 cDNA Sequence. Nine ESTs with homology to part of the CART1 nucleotide sequence were identified in GenBank. The accession number and alignment relative to the CART1 gene are indicated. The CART1 ORF is boxed.

An expressed sequence tag (EST) is a segment of a sequence from a randomly selected cDNA clone that corresponds to a mRNA (Adams, M. D. et al., *Science* 252:1651–1656 (1991); Adams, M. D. et al., *Nature* 355:632–634 (1992); Adams, M. D. et al., *Nat. Genet.* 4:373–380 (1993)). Nine ESTs with at least partial homology to a portion of the CART1 (MLN 62) nucleotide sequence were identified by the present inventors in GenBank (Accession Nos. T64889 (SEQ ID NO;102), T97084 (SEQ ID NO:103), R37445 (SEQ ID NO:104), R61143 (SEQ ID NO:105), T96972 (SEQ ID NO:106), R12544 (SEQ ID NO:107), T40174 (SEQ ID NO:108), R61861 (SEQ ID NO:109) and T41053 (SEQ ID NO:110)). The alignment of these ESTs relative to the CART1 nucleotide sequence is provided in FIG. 22.

Twenty-two ESTs with at least partial homology to a portion of the Lasp-1 (MLN 50) nucleotide sequence were identified by the present inventors in GenBank (Accession Nos. T15543 (SEQ ID NO:74), T33692 (SEQ ID NO:75), T32123 (SEQ ID NO:76), T34158 (SEQ ID NO:77), F04305 (SEQ ID NO:78), T33826 (SEQ ID NO:79), T32139 (SEQ ID NO:80), T51225 (SEQ ID NO:81), D12116 (SEQ ID NO:82), T61881 (SEQ ID NO:83), T51339 (SEQ ID NO:84), T24771 (SEQ ID NO:85), T10815 (SEQ ID NO:86), T60382 (SEQ ID NO:87), M86141 (SEQ ID NO:88), T34342 (SEQ ID NO:89), T08601 (SEQ ID NO:90), T32161 (SEQ ID NO:91), T34065 (SEQ ID NO:92), Z45434 (SEQ ID NO:93), T08349 (SEQ ID NO:94) and F06105(SEQ ID NO:95)). The alignment of these ESTs relative to the Lasp-1 nucleotide sequence is provided in FIG. 14(C).

Fourteen ESTs with at least partial homology to a portion of the MLN 64 nucleotide sequence were identified by the present inventors in GenBank (Accession Nos. M85471 (SEQ ID NO:111), T49922 (SEQ ID NO:112), T85470 (SEQ ID NO:113), T85372 (SEQ ID NO:114), R02020 (SEQ ID NO:115), S70803 (SEQ ID NO:116), R02021 (SEQ ID NO:117), R17500 (SEQ ID NO:118), R41043 (SEQ ID NO:119), R36697 (SEQ ID NO:120), R37545 (SEQ ID NO:121), R42594 (SEQ ID NO:122), R48774 (SEQ ID NO:123) and R48877 (SEQ ID NO:124)).

Three ESTs with at least partial homology to a portion of the MLN 51 nucleotide sequence were identified by the present inventors in GenBank (Accession Nos. Z25173 (SEQ ID NO:96), D19971 (SEQ ID NO:97) and D11736 (SEQ ID NO:98)). The alignment of these ESTs relative to the MLN 51 nucleotide sequence is provided in FIG. 23.

Three ESTs with at least partial homology to a portion of the D53 nucleotide sequence were identified by the present inventors in GenBank (Accession Nos. T89899 (SEQ ID NO:99), T68402 (SEQ ID NO:100) and T93647 (SEQ ID NO:101)).

Isolated RNA Molecules

The present invention further provides isolated RNA molecules which are in vitro transcripts of one of the deposited cDNAs described above, a nucleic acid sequence shown in FIGS. 6(A–B), 14(A–B), 16(A–C), 21(A–D), 24(B) or 25(B) (SEQ ID NO:1, 3, 5, 7, 9 or 11, respectively) or a fragment thereof. Such RNA molecules are useful as antisense RNA probes for detecting CART1, Lasp-1, MLN 64, MLN 51, mD52, hD52 or D53 gene expression by in situ hybridization. For example, the present inventors have generated a labeled antisense RNA probe by in vitro transcription of a BglII fragment (corresponding to nucleotides 279–1882 of FIG. 6 (SEQ ID NO:1)) of the CART1 cDNA. The RNA probe was used to detect CART1 gene expression in malignant epithelial cells and invasive carcinomas (see infra, Example 2). The present inventors also generated a labeled antisense RNA probe specific for the human MLN 64 cDNA by in vitro transcription. This RNA probe was used to detect MLN 64 gene expression in malignant epithelial cells and invasive carcinomas (see infra, Example 4).

Polypeptides and Fragments Thereof

CART1 Polypeptide

The invention further provides an isolated CART1 polypeptide having an amino acid sequence as encoded by the cDNA deposited as ATCC Deposit No. 97610, or as shown in FIG. 6 (SEQ ID NO:2), or a fragment thereof. The CART1 polypeptide, which the inventors have shown is localized in the nucleus of breast carcinoma cells, is an about 470-residue protein exhibiting three main structural domains. First, a cysteine-rich domain was located at the N-terminal part of the protein (amino acid residues 18–57 of FIG. 6 (SEQ ID NO:2)) which corresponds to an unusual RING finger motif, presumably involved in protein-protein binding. Second, an original cysteine-rich domain was located at the core of the protein (amino acid residues 83–282 of FIG. 6 (SEQ ID NO:2)) and is constituted by three repeats of an HC3HC3 consensus motif, possibly involved in nucleic acid and/or protein-protein binding, that has been designated as the CART motif. Third, the C-terminal part of the CART1 protein corresponds to a TRAF domain (amino acid residues 308–470 of FIG. 6 (SEQ ID NO:2)) known to be involved in protein/protein interactions.

Similar association of RING, CART and TRAF domains has been observed in the art in the human CD40-binding protein and in the mouse tumor necrosis factor (TNF) receptor-associated factor 2 (TRAF2), both involved in signal transduction mediated by TNF receptor family and, in the developmentally regulated *Dictyostelium discoideum* DG17 protein. This suggests that, together with CART1, these structurally related proteins are members of a new protein family and, that CART1 may be involved in TNF-related cytokine signal transduction during breast cancer progression. Thus, since the CART1 DNA sequence is provided in FIG. 6 (SEQ ID NO:1) as are the regions which encode the RING, CART and TRAF domains, it would be well within the purview of the skilled artisan to generate recombinant constructs similar or equivalent to those listed below.

As discussed above, the present inventors have discovered that the CART1 polypeptide is a prognostic marker of breast cancer. Thus, this polypeptide and its fragments can be used to generate polyclonal and monoclonal antibodies as discussed above for use in prognostic assays such as immunohistochemistry and RIA on cytosol. For example, the present inventors have substantially purified recombinantly produced CART1 and injected it into mice to raise monoclonal antibodies. Moreover, a polypeptide fragment of CART1, corresponding to the sequence $Q^{393}$ to $D^{411}$ of FIG. 6 (SEQ ID NO:2), has been injected into rabbits to raise a polyclonal antibody.

Lasp-1 Polypeptide

The invention further provides an isolated Lasp-1 polypeptide having an amino acid sequence as encoded by the cDNA deposited as ATCC Deposit No. 97608, or as shown in FIG. 14(A–B) (SEQ ID NO:4), or a fragment thereof. The present inventors have discovered that the Lasp-1 polypeptide is an about 261-residue protein exhibiting two main structural domains. First, one copy of a cysteine-rich LIM/double zinc finger-like motif is located at the N-terminal part of the protein (amino acids 1–51 of FIG. 14 (SEQ ID NO:4)). Second, a SH3 (Src homology region 3) domain is located at the C-terminal part of the protein (amino acids 196–261 of FIG. 14(A–B) (SEQ ID NO:4)). Lasp-1 is the first protein exhibiting associated LIM and SH3 domains and thus constitutes the first member of a new protein family. Thus, since the Lasp-1 DNA sequence is provided in FIG. 14(A–B) (SEQ ID NO:3) as are the regions which encode the LIM and SH3 domains, it would be well within the purview of the skilled artisan to generate recombinant constructs similar or equivalent to those listed below.

As discussed above, the present inventors have discovered that the Lasp-1 polypeptide is a prognostic marker of breast cancer. Thus, this polypeptide and its fragments can be used to generate polyclonal and monoclonal antibodies as discussed above for use in prognostic assays such as immunohistochemistry and RIA on cytosol.

MLN 64 Polypeptide

The invention further provides an isolated MLN 64 polypeptide having an amino acid sequence as encoded by the cDNA deposited as ATCC Deposit No. 97609, or as shown in FIG. 16 (SEQ ID NO:6), or a fragment thereof. The invention also provide polypeptides encoded for by the seven variants A–G discussed above. These variations of the MLN 64 protein are discussed in detail in Example 4, below. The present inventors have discovered that the MLN 64 protein shown in FIG. 16 (SEQ ID NO:6) is an about 445-residue protein exhibiting two potential transmembrane domains (at residues 1–72 and 94–168) and several potential leucine zipper and leucine-rich repeat structures. Amino acid composition analysis showed 11.5% aromatic residues (Phe, Trp and Tyr) and 26% aliphatic residues (Leu, Ile, Val and Met). Thus, since the MLN 64 DNA sequence is provided in FIG. 16 (SEQ ID NO:5), it would be well within the purview of the skilled artisan to generate recombinant constructs similar or equivalent to those listed below.

The present inventors have discovered that the MLN 64 polypeptide is a prognostic marker of breast cancer. Thus, this polypeptide, its fragments, and the polypeptide variants discussed above can be used to generate polyclonal and monoclonal antibodies for use in prognostic assays such as immuno-histochemistry and RIA on cytosol.

For example, a polypeptide fragment of the MLN 64 protein, 16 amino acids in length located in the C-terminal part of the MLN 64 protein, was synthesized by the inventors in solid phase using Fmoc chemistry and coupled to ovalbumin through an additional NH2-extra-terminal cysteine residue, using the bifunctional reagent MBS. This synthetic MLN 64 fragment was injected into BALB/c mice periodically until obtention of positive sera. Spleen cells were removed and fused with myeloma cells according to St. Groth & Scheidegger, *J. Immunol. Meth.* 35:1–21 (1980). Culture supernatants were screened by ELISA using the unconjugated peptide fragment as antigen. Positive culture media were tested by immunocytofluorescence and Western blot analysis on MLN 64 cDNA transfected COS-1 cells. Several hybridomas, found to secrete monoclonal antibodies specifically recognizing MLN 64 protein, were cloned twice on soft agar. Monoclonal antibodies directed against the synthetic MLN 64 peptide fragment were employed in an immunohistochemical analysis which showed MLN 64 protein staining restricted to transformed epithelial cells (see infra, Example 4).

MLN 51 Polypeptide

The invention further provides an isolated MLN 51 polypeptide having an amino acid sequence as encoded by the cDNA deposited as ATCC Deposit No. 97611, or as shown in FIG. 21(A–E) (SEQ ID NO:8), or a fragment thereof. The present inventors have discovered that the MLN 51 polypeptide is an about 534-residue protein. Thus, since the MLN 51 DNA sequence is provided in FIG. 21(A–E) (SEQ ID NO:7), it would be well within the purview of the skilled artisan to generate recombinant constructs similar or equivalent to those listed below.

As discussed above, the present inventors have discovered that the MLN 51 polypeptide is a prognostic marker of breast cancer. Thus, this polypeptide, its fragments, and the polypeptide variants discussed above can be used to generate polyclonal and monoclonal antibodies for use in prognostic assays such as immunohistochemistry and RIA on cytosol.

D53 Polypeptide

The invention further provides an isolated D53 polypeptide having an amino acid sequence as encoded by the cDNA deposited as ATCC Deposit No. 97607, or as shown in FIG. 24(B) (SEQ ID NO:10), or a fragment thereof. The present inventors have discovered that the D53 polypeptide is about 204 amino acids in length and have identified a single coiled-coil domain in hD53, as well as in the hD52 homolog and mouse D52, towards the N-terminus of each protein, which is predicted to end at $Leu^{71}$ in all 3 proteins. This coiled-coil domain overlaps with the leucine zipper predicted in hD52/N8 using helical wheel analysis. The presence of a coiled-coil domain in D52 family proteins indicates that specific protein-protein interactions are required for the functions of these proteins. The present inventors have identified the presence of 2 candidate PEST domains in the three proteins, hD53, hD52 and mD52, indicating that their intracellular abundances may be in part controlled by proteolytic mechanisms. Interestingly, the extent of the N-terminally located PEST domain overlaps that of the coiled-coil domain in both D52 and D53 proteins. It could thus be envisaged that interactions via the coiled-coil domain could mask this PEST domain, in accordance with the hypothesis that PEST sequences may act as conditional proteolytic signals in proteins able to form complexes (Rechsteiner, M., *Adv. Enzyme Reg.* 27:135–151 (1988)). Also, the sequences of the three proteins contain an uneven distribution of charged amino acids; while approximately the first and last 50 amino acids of each protein exhibits a predominant negative charge, the central portion of each protein exhibits an excess of positively charged residues. Finally, the present inventors have identified similar potential post-translational modification sites in the three proteins.

The present inventors have discovered that the D53 polypeptide is a tumor marker in breast cancer. Moreover, relative hD52/hD53 gene expression levels are useful as a marker for distinguishing between different forms of leukemia.

Murine D52 Polypeptide

The invention further provides an isolated mD52 polypeptide having an amino acid sequence as shown in FIG. 25(B) (SEQ ID NO:12), or a fragment thereof. The present inventors have discovered that the mD52 polypeptide is an about 185 amino acid residue protein having domain features as described above.

Polypeptide Fragments and Variants

Fragments of CART1, Lasp-1, MLN 64, MLN 51, mD52 or D53 other than those described above capable of raising both monoclonal and polyclonal antibodies will be readily apparent to one of skill in the art and will generally be at least 10 amino acids, and preferably at least 15 amino acids, in length. For example, the "good antigen" criteria set forth in Van Regenmortel et al., *Immunol. Letters* 17:95–108 (1988), could be used for selecting fragments of the CART1, Lasp-1, MLN 64, MLN 51, mD52 or D53 protein capable of raising monoclonal and polyclonal antibodies.

It will be recognized in the art that some amino acid sequences of CART1, Lasp-1, MLN 64, MLN 51, mD52 or D53 can be varied without significant effect on the structure or function of the protein. If such differences in sequence are contemplated, it should be remembered that there will be critical areas on the protein which determine activity. Such areas will usually comprise residues which make up the binding site, or which form tertiary structures which affect the binding site. In general, it is possible to replace residues which form the tertiary structure, provided that residues performing a similar function are used. In other instances, the type of residue may be completely unimportant if the alteration occurs at a noncritical region of the protein.

Thus, the present invention further includes variations of the CART1, Lasp-1, MLN 64, MLN 51, mD52 or D53 protein which show substantial protein activity or which include regions of the CART1, Lasp-1, MLN 64, MLN 51, mD52 or D53 protein such as the protein fragments discussed above capable of raising antibodies useful in immunohistochemical or RIA assays. Such mutants include deletions, insertions, inversions, repeats and type-substitutions (e.g., substituting one hydrophilic residue for another, but not strongly hydrophilic for strongly hydrophobic as a rule). Small changes or such "neutral" amino acid substitutions will generally have little effect on activity.

Typically seen as conservative substitutions are as follows: the replacements, one for another, among the aliphatic amino acids, Ala, Val, Leu and Ile; interchange of the hydroxyl residues, Ser and Thr; exchange of the acidic residues, Asp and Glu; substitution between the amide residues, Asn and Gln; exchange of the basic residues, Lys and Arg; and replacements among the aromatic residues, Phe, Tyr. As indicated in detail above, further guidance concerning which amino acid changes are likely to be phenotypically silent (i.e., are not likely to have a significant deleterious effect on a function) can be found in Bowie, J. U. et al., *Science* 247:1306–1310 (1990).

Preferably, such variants will be at least 90%, 95%, 97%, 98% or 99% identical to the CART1, Lasp-1, MLN 64, MLN 51, mD52 or D53 polypeptides described above and also include portions of such polypeptides with at least 30 amino acids and more preferably at least 50 amino acids. By the invention, "% identity" between two polypeptides can be determined using the "fastA" computer algorithm with the default parameters (Pearson, W. R. & Lipman, D. J., *Proc. Natl. Acad. Sci. USA* 85:2444 (1988)).

The isolated CART1, Lasp-1, MLN 64, MLN 51, mD52, or D53 polypeptide, or a fragment thereof, are preferably provided in an isolated form, and preferably are substantially purified. Of course, purification methods are known in the art. In preferred embodiment, a recombinantly produced version of the CART1, Lasp-1, MLN 64, MLN 51, mD52 or D53 polypeptide is substantially purified by the one-step method described in Smith and Johnson, *Gene* 67:31–40 (1988). The CART1, Lasp-1, MLN 64, MLN 51, mD52 or D53 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be nonglycosylated. In addition, polypeptides of the invention may also include an initial modified methionine residue, and in some cases as a result of host-mediated processes.

Vectors and Hosts

The present invention also relates to vectors which include an isolated DNA molecule(s) of the present invention, host cells which are genetically engineered with the vectors, and the production of CART1, Lasp-1, MLN 64, MLN 51, mD52 or D53 polypeptide(s), or fragments thereof, by recombinant techniques.

A DNA molecule, preferably a cDNA, encoding the CART1, Lasp-1, MLN 51, MLN 64, mD52 or D53 polypeptide or a fragment thereof, may easily be inserted into a suitable vector. Ideally, the vector has suitable restriction sites for ease of insertion, but blunt-end ligation, for example, may also be used, although this may lead to uncertainty over reading frame and direction of insertion. In such an instance, it is a matter of course to test transformants for expression; 1 in 6 of which should have the correct reading frame.

The CART1, Lasp-1, MLN 51, MLN 64, mD52 or D53 polypeptide(s), or fragments thereof, can be expressed in any suitable host cell. The extent of expression may be analyzed by SDS polyacrylamide gel electrophoresis (Laemmelli, et al., *Nature* 227:680–685 (1970)). Cultures useful for production of such polypeptides include prokaryotic, eukaryotic and yeast expression systems. Preferred systems includes *E. coli*, Streptomyces and *Salmonella typhimurium* and yeast, mammalian or plant cells. Mammalian hosts include HeLa, COS, and Chinese Hamster Ovary (CHO) cells. Yeast hosts include *S. cerevisiae*. Insect cells include Drosophila S2 and Spodoptera Sf9 cells. Appropriate culture mediums and conditions for the above-described host cells are known in the art. Vectors capable of directing expression in the above-mentioned host cells are also known in the art.

The present inventors have designed the following recombinant DNA expression constructs which encode either the entire CART1 protein or fragments of the CART1 protein corresponding to the individual domains discussed above. Bacterial expression systems are as follows: pGEX-CART1; pGEX-RING; pGEX-CART; pGEX-CART-TRAF; and pGEX-TRAF. Yeast expression systems are as follows: pBTMN-CART-TRAF; pBTMN-CART; pBTMN-TRAF; pVP-CART-TRAF; pVP-CART; and pVP-TRAF. Eukaryotic expression systems are as follows: pSG5-CART1, pAT3-CART1; pAT4-CART1; pBC-CART1; and pCMV-CART1.

For example, by pAT4-CART1, is intended the pAT4 vector containing the entire CART1 DNA coding sequence as an insert. Similarly, by pBTMN-CART-TRAF, is intended the pBTMN vector containing the DNA sequence encoding the CART and TRAF regions of the CART1 protein. The remaining constructs listed above are to be interpreted in a like-manner. The pGEX, pBTMN, pVP, pSG5, pAT3, pAT4, pBC and pCMV vectors are known in the art and publicly available.

The present inventors have designed the following recombinant DNA expression constructs which encode either the entire Lasp-1 protein or fragments of the Lasp-1 protein. Bacterial expression systems are as follows: pGEX-LASP1; pGEX-LIM; and pGEX-SH3. Yeast expression systems are as follows: pBTMN-LASP1; pBTMN-LIM; pBTMN-SH3; pVP-LASP1; pVP-LIM; and pVP-SH3. Eukaryotic expression systems are as follows: pSG5-LASP1; pBC-LASP1; and pCMV-LASP1. The pGEX, pBTMN, pVP, pSG5, pBC and pCMV vectors are known in the art and publicly available.

The present inventors have designed the following recombinant DNA expression constructs which encode the MLN 64 protein. Bacterial expression systems include pGEX-MLN 64. Eukaryotic expression systems include pSG5-MLN 64 and pBC-MLN 64. The pGEX, pSG5 and pBC vectors are known and publicly available.

Having generally described the invention, the same will be more readily understood through reference to the following examples which are provided by way of illustration and are not intended to be limiting.

EXPERIMENTS

EXAMPLE 1

Identification of Four Novel Human Genes Amplified and Overexpressed in Breast Carcinoma and Located to the q11-q21.3 Region of Chromosome 17

Introduction

Despite earlier detection and a lower size of the primary tumors at the time of diagnosis (Nyström, L. et al., *Lancet* 341:973–978 (1993); Fletcher, S. W. et al., *J. Natl. Cancer Inst.* 85:1644–1656 (1993)), associated metastases remain the major cause of breast cancer mortality (Frost, P. & Levin, R., *Lancet* 339:1458–1461 (1992)). Therefore, defining the mechanisms involved in the formation and growth of metastases is still major challenge in breast cancer research (Rusciano, D. & Burger, M. M., *BioEssays* 14:185–194 (1992); Hoskins, K. & Weber, B. L., *Curr. Opin. Oncol.* 6:554–559 (1994)). The processes leading to the formation of are complex (Fidler, I. J., *Cancer Res.* 50:6130–6138 (1990); Liotta, L. et al., *Cell* 64:327–336 (1991)), and identifying the related molecular events is thus critical for the selection of optimal treatments.

The initial steps of transformation characterized by the malignant cell escape from normal cell cycle controls, are driven by the expression of dominant oncogenes and/or the loss of tumor suppressor genes (Hunter, T. & Pines, J., *Cell* 79:573–582 (1994)). Tumor progression can be considered as the ability of the malignant cells to leave the primary tumoral site and, after migration through lymphatic or blood vessels, to grow at a distance in host tissue and form a secondary tumor (Fidler, I. J., *Cancer Res.* 50:6130–6138 (1990); Liotta, L. et al., *Cell* 64:327–336 (1991)). Progression to metastasis is dependent not only upon transformation but also upon the outcome of a cascade of interactions between the malignant cells and the host cells/tissues. These interactions may reflect molecular modification of synthesis and/or of activity of different gene products both in malignant and host cells. Several genes involved in the control of tumoral progression have been identified and shown to be implicated in cell adhesion, extracellular matrix degradation, immune surveillance, growth factor synthesis and/or angiogenesis (reviewed in, Hart, I. R. & Saini, A., *Lancet* 339:1453–1461 (1992); Ponta, H. et al., B.B.A. 1198:1–10 (1994); Bernstein, L. R. & Liotta, L. A., *Curr. Opin. Oncol.* 6:106–113 (1994); Brattain, M. G. et al., *Curr. Opin. Oncol.* 6:77–81 (1994); Fidler, I. J. & Ellis, L. M., *Cell* 79:185–188 (1994)).

In order to identify and clone genes which could be involved in the cancer progression, we performed a differential screening of a cDNA library established from breast cancer derived metastatic axillary lymph nodes (MLN). In breast cancer, axillary lymph nodes are usually the earliest sites for metastasis formation, and they are routinely removed for diagnostic purposes (Carter, C. L. et al., *Cancer* 63:181–187 (1989)). Systemic metastases will usually occur later on in the disease, principally in bone, brain and visceres (Rusciano, D. & Burger, M. M., *BioEssays* 14:185–194 (1992)) and, because there is no benefit in terms of survival for the patients, they are rarely removed. Similar differential screening protocols have already permitted the identification of several genes possibly involved in tumor progression, including the stromelysin-3 gene which is overexpressed in most invasive breast carcinomas (Basset, P. et al., *Nature* 348:699–704 (1990)) and the maspin gene, whose expression is reduced in breast cancer cell lines (Zou, Z. et al., *Science* 263:526–529 (1994)). In the present study, the screening of the MLN cDNA library was performed using two probes representative of malignant (MLN) and of non-malignant (fibroadenomas; FA) breast tissues, respectively. Metastatic samples were obtained from patients harboring clinical and histological characteristics associated with a poor prognosis and a high propensity of metastatic spreading. FAs, which are benign tumors, have been selected as control tissues since, although nonmalignant, they are proliferating tissues, thereby minimizing the probability to identify mRNAs characteristic of cellular growth, but unrelated to the malignant process.

Here we report the identification of four novel genes, co-localized on the chromosome 17 long arm, and amplified and overexpressed in malignant breast tissues.

Materials and Methods

Tissues and Cell Cultures

Surgical specimens obtained at the Hôpitaux Universitaires de Strasbourg, were frozen in liquid nitrogen for RNA extraction. Adjacent sections were fixed in 10% buffered formalin and paraffin embedded for histological examination.

The cell lines (ZR75-1, MCF7, SK-BR-3, BT-20, BT474, HBL-100, MDA-MB231 and T47D) are described and available in the American Type Culture Collection (ATCC, Rockville, Md.). The lines MCF7, ZR75-1, BT474 and T47D are estrogen receptor positive, whereas BT-20, SK-BR-3 and MDA-MB-231 were estrogen receptor negative. Cells were routinely maintained in our laboratory and were cultured at confluency in Dulbecco's modified Eagle's medium supplemented with 10% fetal calf serum.

RNA Preparation and Analysis

Surgical specimens were homogenized in the guanidinium isothiocyanate lysis buffer and purified by centrifugation through cesium chloride cushion (Chirgwin, J. M. et al., *Biochemistry* 18:52–94 (1979)). PolyA$^+$ RNA was purified using oligodT cellulose chromatography (Aviv, H. & Leder, P., *Proc. Natl. Acad. Sci. USA* 69:1408–1412 (1977)). RNAs from cultured cell lines were extracted using the single-step procedure of Chomczynski, P. & Sacchi, N., *Anal. Biochem.* 162:156–159 (1987)). RNAs were fractionated by electrophoresis on 1% agarose, 2.2M formaldehyde gels (Lehrach, H. et al., *Biochemistry* 16:4743–4751 (1977)), transferred to nylon membrane (Hybond N, Amersham Corp., Arlington Heights, Ill.) and immobilized by baking for 2 hrs at 80° C.

cDNA Library Construction

PolyA$^+$ RNA from four independent surgical specimens of breast cancer MLNs were pooled. The cDNA was synthesized using MMLV reverse transcriptase (Superscript™, Gibco BRL, Gaithersburg, Md.) and oligodT (Pharmacia Fine Chemicals, Piscataway, N.J.) as primer. Second strand synthesis was performed by RNaseH replacement (Gubler, U. & Hoffman, B. J., *Gene* 25:263–269 (1983)). After blunt-ending using T4 DNA Polymerase I, EcoRI adaptors were added. After ligation, excess of adaptors and molecules less than 300 bp were removed by gel filtration chromatography on Biogel A50m (Bio-Rad, Richmond, Calif.). Size selected cDNAs were ligated in the EcoRI cloning site of lambda ZAPII (Stratagene Inc., La Jolla, Calif.).

Probe Preparation

In order to obtain a MLN specific probe (plus probe), 3 μg of polyA$^+$ RNA purified from MLN were subjected to first strand cDNA synthesis and 370 ng of cDNA were obtained by oligodT priming. RNA molecules were removed by NaOH hydrolysis and single-stranded cDNA was hybridized to 7 μg of polyA$^+$ RNA purified from a breast FA (19× excess). After hybridization for 24 hrs at 68° C. (Hedrick, S. M. et al., *Nature* 308:149–153 (1984); Rhyner, T. A. et al., *J. Neurosci. Res.* 16:167–181 (1986)), single-stranded material (12% of the starting cDNA) was purified by hydroxylapatite chromatography (Bio-Rad, Richmond, Calif.). The minus probe, derived from a breast FA, was similarly obtained from 5 μg of polyA$^+$ RNA which were converted into 560 ng of single-stranded cDNA and hybridized to 7 μg of normal colon and liver (20× excess). After hydroxylapatite chromatography, 14% of the cDNA remained single-stranded. In both cases, single-stranded cDNAs were concentrated and washed with $T_{10}E_1$ using Centricon 30 (Amicon, Beverly, Mass.). Twenty ng and 40 ng of plus and minus probes were obtained, respectively. The $^{32}$P-random labeling (Feinberg, A. P. & Vogelstein, B., *Anal. Biochem.* 112:195–203 (1983)) of 10 ng of single-stranded cDNA gave $2\times10^9$ and $3\times10^9$ cpm/μg of plus and minus probes, respectively.

cDNA Library Screening

One hundred thousand pfu from the MLN library were plated, and nylon filter replica (Biodyne A transfer membrane, Pall Europe Limited, Portsmouth) were hybridized at 42° C. in 50% formamide, 5× SSC, 0.4% ficoll, 0.4% polyvinylpyrrolidone, 20 mM sodium phosphate, pH 6.5, 0.5% SDS, 10% dextran sulfate and 100 μg/ml denatured salmon sperm DNA, for 36–48 hrs, with the $^{32}$P-labeled plus or minus probes diluted to $0.5–1\times10^6$ cpm/ml. Stringent washings were performed at 60° C. in 0.1× SSC and 0.1% SDS. Filters were autoradiographed at –80° C. for 24–72 hrs. Plaques giving differential signals with the plus and minus probes were picked up and subjected to a secondary screening using the same hybridization conditions.

Plasmid Recovery and Southern Blot Analysis

Pure plaques were directly recovered as bacterial colonies using the pBluescript/λZAPII in vivo excision system (Stratagene Inc., La Jolla, Calif.). Small scale plasmid extractions were performed (Zhou, C. et al., *Biotechniques* 8:172–173 (1990)) and approximately ⅟₁₀ of the material (200 ng) was digested with EcoRI and loaded on 2 agarose gels, run in parallel. After electrophoresis, gels were blotted onto nylon membranes (Hybond N$^+$, Amersham Corp.) and membranes were hybridized to the plus and minus probes. Inserts from selected clones were purified from agarose gel and $^{32}$P-labeled by random priming, and used for Northern and Southern blot analyses and cross-hybridizations.

Sequencing and Computer Analysis

Plasmid templates, prepared as previously described, were treated with RNaseA (10 μg/ml) for 30 min, then precipitated by 0.57 volume of polyethylene glycol NaCl (20%, 2M), washed with ethanol, vacuum-dried and resuspended at 200 ng/μl in $T_{10}E_1$. The double-stranded DNA templates were sequenced with Taq polymerase and either pBluescript universal or internal primers, using dye-labeled ddNTPs for detection on an Applied Biosystems 373A automated sequencer. Sequence analyses were performed using the GCG sequence analysis package (Wisconsin package, version 8.0, Genetics Computer Group, Madison, Wis.). Sequence homologies were identified using the FastA and Blast programs by searching the complete combined GenBank/EMBL databanks (release 84.0/39.0) and in the case of translated sequences, by searching the complete SwissProt database (release 29.0).

Genomic DNA Extraction and Southern Blot Analysis

Cells were grown in 75 mm$^2$ flasks at confluency, and washed with 1× PBS. After addition of 2 ml of extraction buffer (10 mM Tris-HCl, pH 8.0, 0.1 M Na$_2$EDTA, pH 8.0, 20 μg/ml RNaseA, 0.5% SDS, 100 μg/ml proteinase K), the flasks were incubated at 42° C. for 12 hrs. Genomic DNA was recovered by precipitation with 1 volume of isopropanol. After washing in 70% ethanol, DNA was air-dried and dissolved in $T_{10}E_1$ at 4° C. For DNA amplification studies, 10 μg of cell line genomic DNA were BamHI digested until completion. For chromosomal localization, DNA extracted from human/rodent somatic cell hybrids (NIGMS Mapping panel #2; Coriell Cell Repositories, Camden, N.J.) digested with BamHI or EcoRI until completion was used. In both cases, BamHI or EcoRI digested genomic DNA was fractionated on 0.8% agarose gel and blotted onto Hybond N$^+$ membranes. Quantitation of MLN gene copy number in breast cell lines was determined by dotblot analysis. Genomic DNA (2.5 μg) was denatured in 0.4M NaOH at 65° C. for 1 hr and 2-fold serial dilutions were spotted onto Hybond N$^+$ membranes. Hybridization and washing were performed as described for cDNA library screening. Control probe p53 corresponded to a 2.0 kb BamHI fragment released from php53B (ATCC No. 57254). RNA loading control suitable for human cells and tissues was an internal (0.7 kb) PstI fragment of 36B4 (Masiakowski, P. et al., *Nucleic Acids Res.* 10:7895–7903 (1982)).

Gene Mapping

Chromosomal assignment of genes MLN 50, 51, 62 and 64 was carried out by in situ hybridization on chromosome preparations obtained from phytohemagglutinin-stimulated human lymphocytes, cultured for 72 hrs.

5-Bromodeoxyuridine (60 μg/ml) was added to the medium for the final 7 hrs of culture to ensure posthybridization chromosomal banding of good quality. cDNA probes were $^3$H-labeled by nick-translation to a specific activity of 1.5× $10^8$ dpm/ml. The radiolabeled probes were hybridized to metaphases spreads at a final concentration of 25 ng/ml of hybridization solution, as previously described (Mattei, M. G. et al., *Human Genet.* 69:268–271 (1985)). After the slides were coated with nuclear track emulsion (NTB2; Kodak, Rochester, N.Y.), they were exposed for 19 days at 4° C. before development. To avoid any slipping of silver grains during the banding procedure, chromosome spreads were first stained with buffered Giemsa solution, and metaphases were photographed. R-banding was then performed by the fluorochrome-photolysis-Giemsa method, and metaphases were rephotographed before analysis.

Results

Differential Screening of the MLN cDNA Library

Four patients with ductal breast carcinomas were selected according to their age (below 50 years of age), the large size and high histological grade of their primary tumor (Bloom, H. J. G. & Richardson, W. W., *Brit. J. Cancer* 11:359–366 (1957)) and the presence of MLN (Table I). Because of the high heterogeneity of breast tumors (Lönn, U. et al., *Intl. J. Cancer* 58:40–45 (1994) and refs. therein), RNAs were extracted from metastatic samples coming from the four patients and pooled in relative equal amounts, in order to prepare a representative breast MLN cDNA library. Histological examination of the selected MLN samples revealed above 80% of metastatic tissue. However, in order to avoid dilution of rare differential transcripts, we prepared the enriched plus probe using MLNs exclusively obtained from patient C. This patient had 17 involved lymph nodes (Table I), and, in addition, her primary tumor exhibited two poor prognostic factors which were an estradiol and progesterone receptor negative status (Osborne, C. K. et al., *Receptors*, in BREAST DISEASES 301–325 (2nd ed., Harris, J. R. et al., eds. J. B. Lippincott, Philadelphia, Pa. 1991)) and a c-erbB-2 overexpression (Slamon, D. J. et al., *Science* 244:707–712 (1989); Borg, A. et al., *Oncogene* 6:137–143 (1991); Toikkanen, S. et al.,*J. Clin. Oncol.* 8:103–112 (1992); Muss, H. B. et al., *N. Engl. J. Med.* 300:1260–1266 (1994)).

A total of $10^5$ recombinants from the MLN cDNA library were differentially screened using two enriched probes. The plus probe was derived from MLN cDNAs and deprived of sequences expressed in a FA. The "minus" probe was derived from FA cDNAs and deprived of sequences expressed in normal liver and colon (see Materials and Methods). Comparison of the patterns obtained with these two probes allowed for the detection of 195 "differential plaques" which were positive with the "plus" probe and negative with the "minus" probe. Twenty four differential plaques were subjected to a second screening and plasmid DNAs recovered from pure plaques were tested for the presence of "differential inserts" by Southern blot analysis (see Materials and Methods). Identified differential inserts were $^{32}$P-labeled and used to reprobe the MLN cDNA library lifts and the Southern blots in order to identify related cDNA clones. The same protocol was used to characterize the remaining "differential plaques" and finally, ten independent families of differential clones were identified. The longest cDNA insert of each family (MLN 4, 10, 19, 50, 51, 62, 64, 70, 74 and 137) were selected for further studies.

Expression Analysis of the Ten MLN Genes

In order to test the differential expression of the genes corresponding to these clones, Northern blots were prepared using MLN, FA and normal axillary lymph node (NLN) RNAs. Filters were hybridized with the ten $^{32}$P-labeled MLN cDNAs. As shown in FIG. 1, all detected mRNAs were preferentially observed in MLN (lanes 1) whereas no signal or only a faint signal was observed in NLN and FA (lanes 2 and 3). The mRNA sizes, detected by the ten probes, varied from 0.5 kb (MLN 70) up to 5 kb (MLN 74) indicating that our screening protocol did not favor a preferential transcript size. Although the expression levels differed, they remained relatively high, even for the least abundant of them (MLN 62) (FIG. 1).

cDNA and Putative Protein Sequences of the Ten MLN Genes

In a first step, cDNAs were partially sequenced on both extremities using universal primers for the pBluescript vector. These partial sequences were compared to the combined GenBank/EMBL DNA databanks. MLN 74, 19, 10 and 4 corresponded to the already known genes fibronectin (Accession Nos. X02761, K00799, K02273, X00307 and X00739; Kornblihtt, A. R. et al., *EMBO J.* 3:221–226 (1983)), c-erbB-2 (Accession No. M11730; Coussens, L. et al., *Science* 230:1132–1139 (1985)), nonspecific cross-reacting antigen (NCA, Accession No. M18728; Tawaragi, Y. et al., *Biochem. Biophys. Res. Commun.* 150:89–96 (1988)) and calcyclin (Accession Nos. M14300 and J02763; Calabretta, B. et al., *J. Biol. Chem.* 26:12628–12632 (1986)), respectively. Altogether they were the most abundant clones recovered in this screening since, as indicated in Table II, they represented 75% of the differential clones. The relationship of these genes to cancer and, for some of them to metastasis, has been already reported.

In a second step, when no sequence homology was initially found, the complete cDNA sequences were established and the putative corresponding protein sequences were compared to those present in the SwissProt databank. MLN 70 (Accession No. X80198) and MLN 137 (Accession No. X80197) showed homologies with proteins from other species and could be classified in the S100 and keratin families (Kligman, D. & Hilt, D. C., *Trends Biol. Sci.* 13:437–443 (1988); Donato, R., *Cell Calcium* 12:713–726 (1991); Smack, D. P. et al., *J. Amer. Acad. Dermatol.* 30:85–102 (1994)), respectively. The 30 amino acid long ZF-1 pig cysteine-rich peptide (Accession No. P80171, Sillard, R. et al., *Eur. J. Biochem.* 211:377–380 (1993)) showed 100% identity to the N-terminal part of the MLN 50 putative protein (Accession No. X82456). In addition, several sequence homologies were found with various expressed sequence tags (ESTs; Adams, M. D. et al., *Nature* 335:632–634 (1992)) within the 3' noncoding regions of the MLN 50 (Accession Nos. T08349, T08601 and M86141, Adams, M. D. et al., *Nature* 335:632–634 (1992); Adams, M. D. et al.,*Nat. Genet.* 4:373–380 (1993); T10815, Bell, G. I. & Takeda, J., *Hum. Mol. Genet.* 2:1793–1798 (1993); D12116, Okubo, K. et al., *Nat. Genetics* 2:173–179 (1992)) and MLN 51 (Accession No. X80199; EST Accession Nos. Z25173 and D19971, Okubo, K. et al., *Nat. Genetics* 2:173–179 (1992)) cDNA sequences. Surprisingly, we observed 100% homology with part (129 bp) of an 401 bp long EST (Accession No. M85471, Adams, M. D. et al., *Nature* 335:632–634 (1992)) and the 5' coding region of MLN 64 (Accession No. X80198), suggesting that this EST could correspond to a chimera or to an unspliced RNA. Since most homologies observed for MLN 50, 51 and 64 were restricted to small noncoding DNA sequences and since no homology was found for MLN 62 (Accession No. X80200), we assumed that they belong to new protein families and further characterizations were undertaken.

Chromosomal Assignment of MLN 50, 51, 62 and 64 Genes

Southern blots were constructed by loading EcoRI or BamHI digest of genomic DNAs from human somatic cell hybrids, corresponding to individual human chromosome in a rodent background. MLN 51 and 64 probes showed an unique hybridization signal on chromosome 17, whereas MLN 50 and 62 probes showed a strong hybridization to chromosome 17 and a faint signal on chromosomes 3 and 16, and on chromosome 5, respectively (Table III). Since the four probes showed hybridization with chromosome 17, the same Southern blot was reprobed with MLN 19 corresponding to the c-erbB-2 oncogene, previously localized on the chromosome 17 (Fukushige, S. I. et al., *Mol. Cell. Biol.* 6:955–958 (1986)). As expected, MLN 19 showed a hybridization restricted to this chromosome (Table III).

Figure 2B:
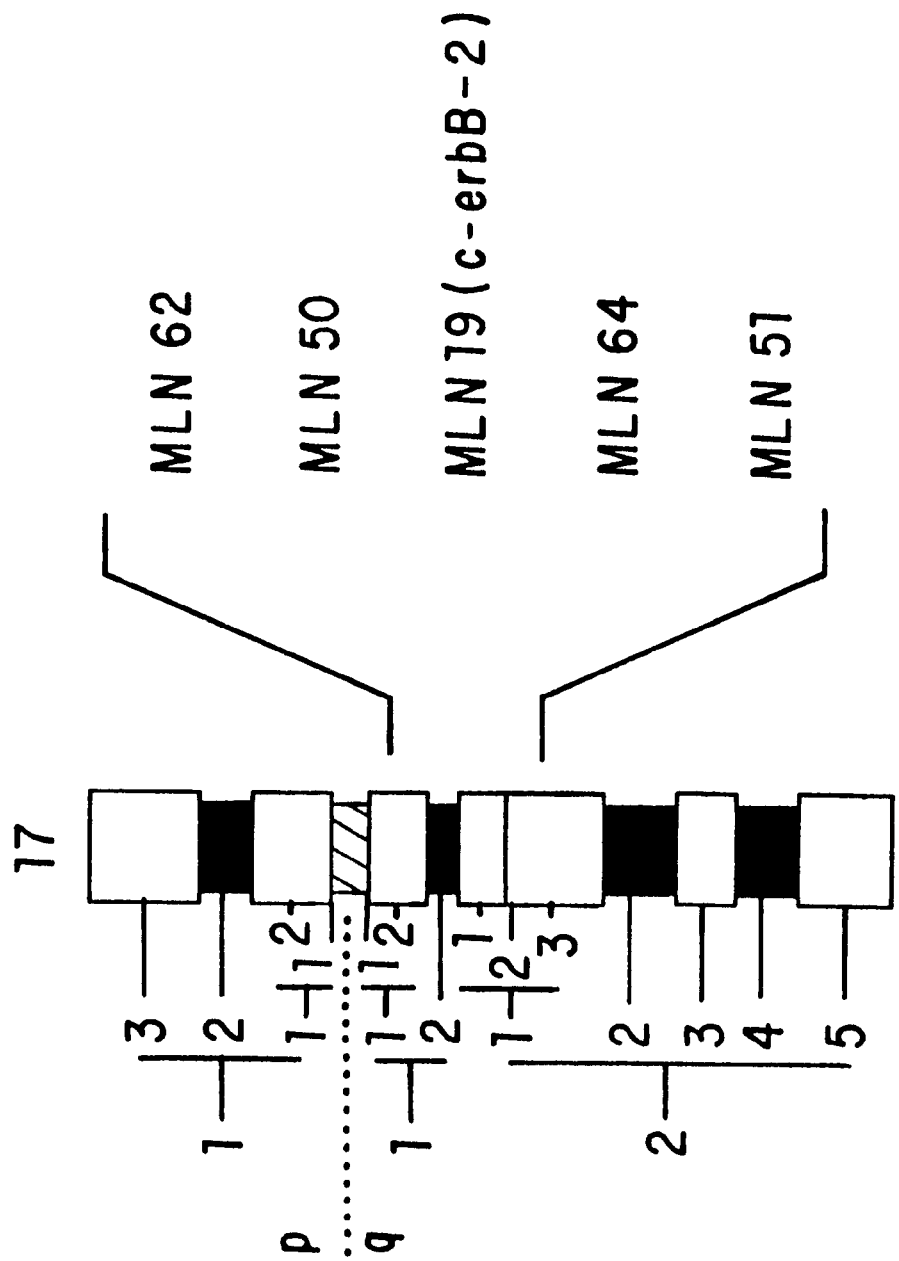

In order to define the precise location of the four new genes on chromosome 17, we carried out chromosomal in situ hybridization. Using MLN 50, 100 metaphase cells were examined. 276 silver grains were associated with the chromosomes and 83 of these (30%) were located on chromosome 17. The distribution of grains was not random: 65/83 (78.3%) of them mapped to the q11-q21 region of the long arm of chromosome 17 (FIG. 2(A)). Two secondary sites were detected, at 3p22-3p21.3 (36/276, 13% of total grains) and at 16q12.1 (26/276, 9.4% of total grains). Using MLN 51, 100 metaphase cells were examined. 176 silver grains were associated with the chromosomes and 60 of these (34.1%) were located on chromosome 17. The distribution of grains was not random: 49/60 (81.6%) of them mapped to the q12-q21.3 region of the long arm of chromosome 17 (FIG. 2(A)). Using MLN 62, 150 metaphase cells were examined. 204 silver grains were associated with the chromosomes and two sites of hybridization were detectable. 20.1% were located on chromosome 17 and 82.9% of them mapped to the q11-q12 region of the long arm (FIG. 2(A)). 16.6% were located on chromosome 5. The distribution of grains was not random: 79.4% mapped to the (q31-q32) region of chromosome 5 long arm. Using MLN 64, 150 metaphase cells were examined. 247 silver grains were associated with chromosomes and 64 of these (25.9%) were located on chromosome 17. The distribution of grains was not random: 73.4% of them mapped to the q12-q21 region of the long arm of chromosome 17 with a maximum in the q21.1 band (FIG. 2(A)). These results are in good agreement with the findings previously obtained by Southern blot hybridization and suggest that, along the long arm of the chromosome 17, MLN 50 and 62 and MLN 51 and 64 are centromeric and telomeric to MLN 19 (c-erbB-2), respectively (FIG. 2(B)).

Amplification and Expression of MLN 50, 51, 62 and 64 Genes

Figure 3:
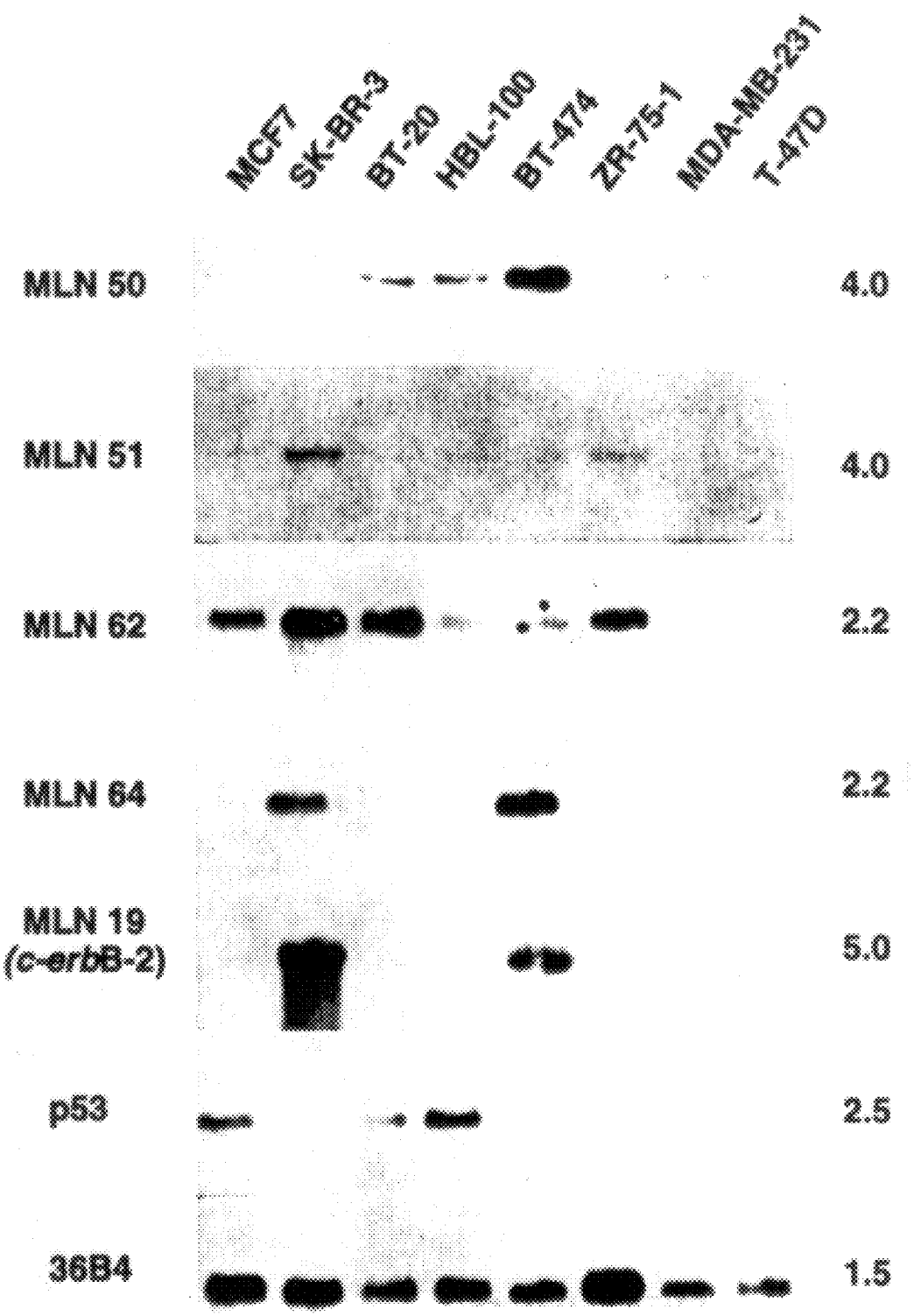
FIG. 3. Expression Analysis of MLN 50, 51, 62 and 64 Genes Among Breast Cancer Cell Lines. Ten μg of total RNA from breast cancer cell lines were loaded in each lane. Hybridizations were carried out successively with probes corresponding to MLN 50, 51, 62 and 64. Control hybridizations were performed with MLN 19 (c-erbB-2), p53 and 36B4. Approximate sizes of the mRNAs are indicated in kb (right).

Five of the cDNA clones isolated in this study corresponded to genes located on the chromosome 17, namely MLN 50, 51, 62, 64 and 19. Moreover, they are all localized on the long arm of chromosome 17 in the q11-q21.3 region. Since it is known that c-erbB-2 overexpression in breast carcinomas is mostly dependent on gene amplification (Slamon, D. J. et al., *Science* 235:177–182 (1987); van de Vijver, M. et al., *Mol. Cell Biol.* 7:2019–2023 (1987)), we looked for MLN 50, 51, 62 and 64 gene amplification. Each of them showed amplification in 10–20% of sporadic breast carcinomas (data not shown). Nevertheless, amplification does not always correlate with gene overexpression. Then, in order to study the relationship between MLN gene amplification and expression, we have performed genomic DNA and RNA analyses of a panel of human breast cancer cell lines, including MCF7, TO-47D, BT-474, SKBR-3, MDA-MB-231, BT-20 and ZR-75-1, and the immortalized breast epithelial cell line HBL-100. MLN amplification and expression patterns were compared to those of c-erbB-2 and of p53, a gene located on the short arm of chromosome 17 and frequently mutated or lost but never amplified in breast carcinoma (Baker, S. J. et al., *Science* 244:217–221 (1989)). Hybridization of Southern blots containing a BamHI digest of genomic DNAs extracted from these cell lines showed that the c-erbB-2, MLN 50, 51 and 64 genes were amplified in some cell lines, whereas the MLN 62 and p53 genes were not (Table IV). Moreover, in order to quantify the level of amplification, dot blots containing serial dilutions of cell genomic DNAs were performed. As summarized in Table IV, MLN 64 and c-erbB-2 genes were found to be co-amplified in SK-BR-3 (8 and 16 copies, respectively) and BT-474 (16 and 32 copies, respectively). MLN 50 gene was only amplified in BT-474 (8 copies) and MLN 51 gene in SK-BR-3 (4 copies). Northern blots containing RNAs extracted from the same cell lines were hybridized to the MLN cDNA probes (FIG. 3). MLN 64 and 19 (c-erbB-2) genes were overexpressed in SK-BR-3 and BT-474, MLN 50 gene in BT-474 and MLN 51 gene in SK-BR-3. These results clearly showed that, in cell lines, MLN 50, 51 and 64 overexpression were related to their gene amplification. Overexpression above basal level was observed for MLN 62 in SK-BR-3 and BT-20, and for p53 in MCF7 and HBL-100, independently of gene amplification.

Amplification patterns observed in breast cancer cell lines suggested that MLN 50 (co-amplified with c-erbB-2, but not with MLN 62) and MLN 64 (co-amplified with c-erbB-2 in two cell lines, whereas MLN 51 was only in one cell line) should be located closer to c-erbB-2 than MLN 62 and 51, respectively. Thus, according to their chromosomal assignments and amplification patterns, the five locus framework order cen-MLN 62-MLN 50-c-erbB-2-MLN 64-MLN 51-tel could be proposed (FIG. 2(B)).

Discussion

In the present study, we report the identification of cDNAs by differential screening of a breast cancer MLN cDNA library with two subtracted cDNA probes, representative of malignant (MLN) and nonmalignant (FA) breast tissues.

The identified cDNAs corresponded to ten distinct genes expressed in MLNs, but not in normal lymph nodes or FAs. 75% of these cDNAs corresponded to known genes, namely the c-erbB-2, NCA, fibronectin and calcyclin genes, which have been previously shown to be involved in metastatic processes. c-erbB-2 overexpression has been demonstrated in 15–30% of breast carcinomas and has been associated with shorter survival, particularly in patients with invaded lymph nodes (Slamon, D. J. et al., *Science* 244:707–712 (1989); Borg, A. et al., *Oncogene* 6:137–143 (1991); Toikkanen S. et al., *J. Clin. Oncol.* 8:103–112 (1992); Muss, H. B. et al., *N. Engl. J. Med.* 300:1260–1266 (1994)). NCA belongs to the carcinoembryonic antigen (CEA) family. CEA expression is elevated in 50–80% of patients with metastatic breast cancer and is used as a circulating marker to detect disease recurrence (Loprinzi, C. et al., *J. Clin. Oncol.* 4:46–56 (1986)). A modulation of fibronectin expression by alternative splicing has been reported in malignant tumors (Carnemolla, B. et al., *J. Cell Biol.* 108:1139–1148 (1989); Humphries, M. J., *Semin. Cancer Biol.* 4:293–299 (1993)). Calcyclin, a member of the S100 $Ca^{++}$ binding protein family, is a cell cycle related protein and has been shown to be overexpressed in highly metastatic human melanoma cell lines (Weterman, M. A. et al., *Cancer Res.* 52:1291–1296 (1992)). About half of the last 25% of identified cDNAs corresponded to two novel members of the S100 and keratin protein families, respectively. Finally, the remaining differential clones (MLN 50, 51, 62 and 64) corresponded to cDNAs which did not belong to any previously characterized gene or protein family.

The four genes corresponding to these cDNAs were co-localized to the q11-q21.3 region of the chromosome 17 long arm. Several genes implicated in breast cancer progression have already been assigned to the same portion of this chromosome, notably the oncogene c-erbB-2 in q12 (Fukushige, S. I. et al., *Mol. Cell. Biol.* 6:955–958 (1986)) and the recently cloned tumor suppressor gene BRCA1 in q21 (Hall J. M. et al., *Science* 250:1684–1689 (1990); Miki, Y. et al., *Science* 266:66–71 (1994) and refs. therein). According to their chromosomal assignments, we mapped the four novel genes proximal (MLN 62 and 50) and distal (MLN 64 and 51) to the c-erbB-2 gene, and, most probably, proximal to the BRCA1 gene.

In vivo, the four MLN genes showed amplification in 10–20% of breast carcinomas. Moreover, in breast cancer cell lines, MLN 64 exhibited an amplification pattern identical to that of c-erbB-2 showing a clear amplification in BT-474 and SK-BR-3. However, MLN 50 and 51 gene amplification was restricted to BT-474 and SK-BR-3, respectively, and, any cell lines showed MLN 62 amplification. Altogether, these results support the concept that c-erbB-2 amplicon nature and size are variable from one malignant cell line to another (Muleris, M. et al., *Genes Chrom. Cancer* 10:160–170 (1994)), exemplifying the breast cancer heterogeneity (Lönn, U. et al., *Intl. J. Cancer* 58:40–45 (1994) and refs. therein). Finally, in breast cancer cell lines, MLN 50, 51 and 64 gene overexpression was correlated with gene amplification.

It is assumed that DNA amplification plays a crucial role in tumor progression by allowing cancer cells to upregulate numerous genes (Kallioniemi, A. et al., *Proc. Natl. Acad. Sci. USA* 91:2156–2160 (1994); Lönn, U. et al., *Intl. J. Cancer* 58:40–45 (1994)). Frequency of gene amplification as well as gene copy number increase during breast cancer progression, notably in patients who do not respond to treatment, suggesting that overexpression of the amplified target genes confers a selective advantage to malignant cells (Schimke, R. T., *J. Biol. Chem.* 263:5989–5992 (1988); Lönn, U. et al., *Intl. J. Cancer* 58:40–45 (1994); Guan, X. Y. et al., *Nat. Genet.* 8:155–161 (1994)). Recently, amplified loci, distinct from those of currently known oncogenes, have been mapped, using comparative genomic hybridization (Kallioniemi, A. et al., *Proc. Natl. Acad. Sci. USA* 91:2156–2160 (1994); Muleris, M. et al., *Genes Chrom. Cancer* 10:160–170 (1994)), suggesting the presence of unknown genes whose expression contributes to breast cancer. As we report here, the use of differential screening could be an efficient methodology for the identification of such unknown genes, since it allows for the direct cloning of amplified and overexpressed genes. Although amplification involves large regions of chromosomal DNA, it is known to target oncogenes (Schwab, M. & Amler, L., *Genes Chrom. Cancer* 1:181–193 (1990)). The correlation between amplification and overexpression is necessary to identify the targeted gene. Thus, within the 17q12 amplicon, c-erbB-2 is often co-amplified with c-erbA but c-erbA overexpression was never observed (van de Vijver, M. et al., *Mol. Cell. Biol.* 7:2019–2023 (1987)). A similar finding was observed within the 11q13 amplicon where the cyclinD/PRAD1 gene is linked to int-2 and hst-1 two fibroblast growth factor related genes and only PRAD1 is overexpressed in the carcinomas (Lammie, G. A. et al., *Oncogene* 6:439–444 (1991)). In this context the fact that the four novel genes identified in the present study are not only amplified but also overexpressed, suggests that they may contribute to the genesis and/or the progression of breast tumors.

TABLE I

Clinical and Histological Characteristics of the Breast Carcinomas

| Patient | Age (yrs.) | Tumor size (cm) | Histological grade | Number of involved lymph nodes |
|---|---|---|---|---|
| A | 40 | 2 × 1.5 × 1.5 | III | 1/15 |
| B | 35 | 2.5 × 1.8 × 1.6 | II | 5/14 |
| C | 50 | 2.7 × 2.0 × 1.5 | II | 17/19 |
| D | 40 | 3.5 × 3.0 × 2.0<br>2.0 × 1.5 × 2.0 | III | 2/10 |

TABLE II

Characteristics of the 10 Differential cDNAs Identified in the MLN cDNA Library

| Clone | Frequency[a] % | cDNA size Kb | Similarity/ Identity | Reference or GeneBank/EMBL accession number |
|---|---|---|---|---|
| MLN 4 | 5 | 0.6 | calcyclin | (Calabretta, B. et al., J. Biol. Chem. 26:12628–12632 (1986) |
| MLN 10 | 12 | 3.2 | NCA | (Tawaragi, Y. et al., Biochem. Biophys. Res. Commun. 150: 89–96 (1988) |
| MLN 19 | 28 | 3.0 | c-erbB-2 | (Coussens, L. et al. Science 230:1132–1139 (1985) |
| MLN 50 | 7 | 3.8 | porcine ZF-1 peptide[c] | X82456[b] |
| MLN 51 | 3 | 3.2 | — | X80199[b] |
| MLN 62 | 2 | 2.0 | — | X80200[b] |
| MLN 64 | 2 | 2.0 | — | X80198[b] |
| MLN 70 | 9 | 0.5 | S100 protein family | X80201[b] |
| MLN 74 | 30 | 5.6 | fibronectin | (Kornblihtt, A. R. et al. EMBO J. 3:221–226 (1983) |
| MLN 137 | 2 | 1.2 | keratin protein family | X80197[b] |

[a]The frequency was estimated as the number of identified clones relative to the total number of differential clones in the MLN cDNA library.
[b]Accession numbers for the novel cDNAs identified in the present study.
[c]Homology is resticted to the 30 amino acids of the ZF-1 peptide (Sillard, R. et al., Eur. J. Biochem. 211:377–380 (1993)).

TABLE III

Chromosomal Assignment of MLN 50, 51, 62, and 64 Genes

Hybridization to Human/Rodent Cell Hybrid DNA[a] Specific for Chromosome

| Clone | X | Y | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|---|---|
| MLN 50 | – | – | – | – | + | – | – | – | – | – | – | – | – | – | – | – | – | + | ++ | – | – | – | – |
| MLN 51 | – | – | – | – | – | – | – | – | – | – | – | – | – | – | – | – | – | – | ++ | – | – | – | – |
| MLN 62 | – | – | – | – | – | – | + | – | – | – | – | – | – | – | – | – | – | – | ++ | – | – | – | – |
| MLN 64 | – | – | – | – | – | – | – | – | – | – | – | – | – | – | – | – | – | – | ++ | – | – | – | – |
| MLN 19 c-erbB-2 | – | – | – | – | – | – | – | – | – | – | – | – | – | – | – | – | – | – | ++ | – | – | – | – |

[a]Mapping panel #2 from NIGMS, Coriell Cell Repositories (Camden, N.J., U.S.A.)
– no weak, ++ strong signals

TABLE IV

MLN 50, 51, 62 and 64 Gene Amplification Among Breast Cancer Cell Lines

| Gene | MCF7 | SK-BR-3 | BT-20 | HBL-100 | BT-474 | ZR75-1 | MDA-MB-23I | T-47D | Human leucocyte |
|---|---|---|---|---|---|---|---|---|---|
| MLN 19 (c-erbB-2) | — | (16) | — | — | (32) | — | — | — | — |
| MLN 64 | — | (8) | — | — | (16) | — | — | — | — |
| MLN 62 | — | — | — | — | — | — | — | — | — |
| MLN 50 | — | — | — | — | (8) | — | — | — | — |
| MLN 51 | — | (4) | — | — | — | — | — | — | — |
| p53 | — | — | — | — | — | — | — | — | — |

— no amplification could be detected; estimated copy numbers are indicated in parenthesis.

EXAMPLE 2

CART1, a Gene Expressed in Human Breast Carcinoma, Encodes a Novel Member of the Tumor Necrosis Factor Receptor-Associated Protein Family Introduction Human CART1 cDNA corresponds to the MLN 62 cDNA clone discussed above in Example 1. The clone was identified through a differential screening performed by using two subtractive probes, respectively representative of metastatic and nonmalignant breast tissues and was mapped on chromosome 17, at the q11-q12 locus, a locus which includes the oncogene c-erbB-2 whose overexpression is correlated with a shorter overall and disease free survival for breast cancer patients (Slamon, D. J. et al., *Science* 235:177–182 (1987); Muss, H. B. et al., *N. Engl. J. Med.* 330:1260–1266 (1994)).

In this example, we investigated the CART1 gene expression in a panel of normal and malignant human tissues and characterized the CART1 cDNA protein and gene organization. CART1 was specifically expressed in epithelial breast cancer cells. The amino acid sequence of CART1 reveals structural domains similar to those present in TNF receptor associated proteins, suggesting that CART1 is implicated in signal transduction for TNF-related cytokines.

Materials and Methods

Tissues Collection

Depending on subsequent analysis, tissues were either immediately frozen in liquid nitrogen (RNA extraction), or fixed in formaldehyde and paraffin embedded (in situ hybridization). Frozen tissues were stored at −80° C. whereas paraffin-embedded tissues were stored at 4° C.

The mean age of the 39 patients included in the present study was 55 years. The main characteristics of the breast carcinomas were as followed: SBR grade I (13%), grade II (38%), grade III (49%); estradiol receptor positive (25%), negative (75%); lymph nodes without invasion (39%), with invasion (61%).

RNA Isolation and Analysis

Total RNA prepared by a single-step method using guanidinium isothiocyanate (Chomczynski, P. & Sacchi, N., *Anal. Biochem.* 162:156–159 (1987)) was fractionated by agarose gel electrophoresis (1%) in the presence of formaldehyde. After the transfer, RNA was immobilized by heating (12 hr, 80° C.). Filters (Hybond N; Amersham Corp.) were acidified (10 min, 5% $CH_3COOH$) and stained (10 min, 0.004% methylene blue, 0.5M $CH_3COONa$, pH 5.0) prior to hybridization.

A CART1 probe corresponding to the full-length human cDNA (nucleotides 1 to 2004), cloned into pBluescript II SK vector (Stratagene) was $^{32}P$-labeled using random priming (~$10^6$ cpm/ng DNA) (Feinberg, A. P. & Vo Vogelstein, B., *Anal. Biochem.* 132:6 (1983)). Filters were prehybridized for 2 hrs at 42° C. in 50% formamide, 5× SSC, 0.1% SDS, 0.5% PVP, 0.5% Ficoll, 50 mM sodium pyrophosphate, 1% glycine and 500 μg/ml ssDNA. Hybridization was for 18 hrs under stringent conditions (50% formamide, 5× SSC, 0.1% SDS, 0.1% PVP, 0.1% Ficoll, 20 mM sodium pyrophosphate, 10% dextran sulfate, 100 μg/ml ssDNA; 42° C.). Filters were washed for 30 min in 2× SSC, 0.1% SDS at room temperature, followed by 30 min in 0.1× SSC, 0.1% SDS at 55° C.

In Situ Hybridization

In situ hybridization was performed using a $^{35}S$-labeled antisense RNA probe (5×$10^8$ cpm/μg), obtained after in vitro transcription of a BglII fragment (nucleotides 279–1882) of the human CART1 cDNA. Formaldehyde-fixed paraffin-embedded tissue sections (6 μm thick) were deparaffined in LMR, rehydrated and digested with proteinase K (1 μg/ml; 30 min, 37° C.). Hybridization was for 18 hrs, followed by RNase treatment (20 μg/ml; 30 min, 37° C.) and stringently washed twice (2× SSC, 50% formamide; 60° C., 2 hrs). Autoradiography was for 2 to 4 weeks using NTB2 emulsion (Kodak). After exposure, the slides were developed and counterstained using toluidine blue. $^{35}$S-labeled sense transcript from CART1 was tested in parallel as a negative control.

CART1 Genomic DNA Cloning

Fifty μg of human genomic DNA was partially digested with Sau3A. After size selection on a 10–30% sucrose gradient, inserts (16–20 kb) were subcloned at the BamHI replacement site in lambda EMBL 301 (Lathe, R. et al., *Gene* 57:193–201 (1987)). 2.5×10$^6$ recombinant clones were obtained and the library was amplified once. One million pfu were analyzed for the presence of genomic CART1 DNA, using the full-length CART1 cDNA probe. Thirty clones gave a positive signal. After a second screening, four of these clones were subcloned into pBluescript II SK-vector (Stratagene), sequenced and positioned with respect to the CART1 cDNA sequence.

Sequencing Reactions

CART cDNA clones and genomic subclones prepared as described (Zhou, C. et al., *Biotechniques* 8:172–173 (1990)) were further purified with RNaseA treatment (10 μg/ml; 30 min, 37° C.) followed by PEG/NaCl precipitation (0.57 vol.; 20%, 2M) and ethanol washing. Vacuum dried pellets were resuspended at 200 ng/μl in TE. Double-stranded DNA templates were then sequenced with Taq polymerase, using either pBluescript universal primers and/or internal primers, and dye-labeled dNTPs for detection on an Applied Biosystems 373A automated sequencer.

Computer Analysis

Sequence analysis were performed using the GCG sequence analysis package (Wisconsin Package, version 8, Genetic Computer Group). The CART1 cDNA sequence and its deduced putative protein were used to search the complete combined GenBank/EMBL databases and the complete SwissProt database respectively, with BLAST (Altschul, S. F. et al., *J. Mol. Biol.* 215:403–410 (1990)) and FastA (Pearson, W. R. & Lipman, D. J., *Proc. Natl. Acad. Sci. USA* 85:2444–2448 (1988)) programs. The RING finger motif and consensus sequences of CART1 protein were further identified by the Motifs program in the PROSITE dictionary (release 12). The sequence alignments were obtained automatically by using the program PileUp (Feng, D. F. & Doolittle, R. F., *J. Mol. Evol.* 25:351–360 (1987)).

Results

Expression of the CART1 Gene

Figure 4:
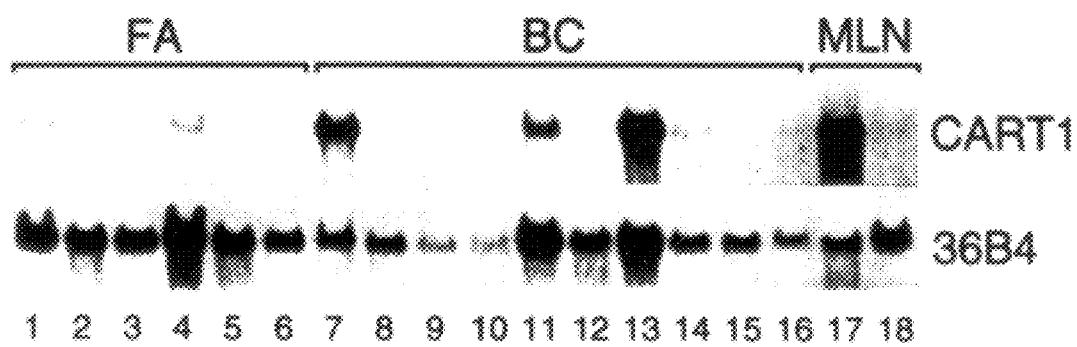
FIG. 4. Northern Blot Analysis of CART1 mRNA in Human Breast Fibroadenomas, Carcinomas and Lymph Node Metastases. Each lane contained 10 μg of total RNA. From left to right, RNA samples from breast fibroadenomas (FA, lanes 1–6), carcinomas (BC, lanes 7–16) and metastatic lymph nodes (MLN, lanes 17 and 18) were loaded. Hybridization was carried out using $^{32}P$ cDNA probe for CART1. A 2000-base long CART1 transcript was expressed, at various levels, in some carcinomas (lanes 7, 11 and 13), and in one metastatic sample (lane 17). The 36B4 probe (Masiakowski, P. et al., *Nucl. Acids Res.* 10:7895–7903 (1982)) was used as positive internal control. Autoradiography was for 2 days for hybridization of CART1, whereas 36B4 hybridization was exposed for 16 hrs.

Using Northern blot analysis, we have studied CART1 gene expression in benign (16 fibroadenomas) and malignant (39 carcinomas and 5 metastatic axillary lymph nodes) human breast tissues. Hybridization with a CART1 cDNA probe gave a positive signal corresponding to CART1 transcripts with an apparent molecular weight of 2 kb, in 4 carcinomas and 2 metastases (FIG. 4, lanes 7, 11, 13 and 17, and data not shown). The fibroadenomas did not show CART1 expression above the basal level (FIG. 4, lanes 1–6). No CART1 transcripts were observed in normal human axillary lymph node, skin, lung, stomach, colon, liver kidney and placenta (data not shown).

Figure 5A:
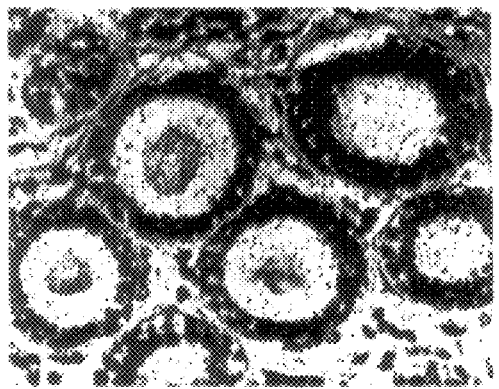
FIG. 5. In Situ Hybridization of CART1 mRNA in Human Breast Carcinoma and Axillary Lymph Node Metastasis. Sections of normal breast (A), in situ carcinoma (C), invasive carcinoma (B) and metastatic lymph node (D) were hybridized with antisense $^{35}S$ RNA probe specific for CART1. CART1 was strongly expressed in the tumoral epithelial cells, whereas the stromal part of the tumor was totally negative (B). CART1 transcripts were homogeneously distributed throughout the positive areas (B–D). Normal ducts were devoid of CART1 signal (A). No significant labeling above background was found when using sense human CART1 RNA probe (data not shown). Bright field (A–D).
Figure 5B:
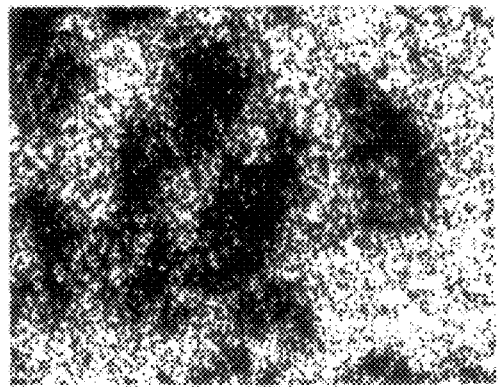
Figure 5C:
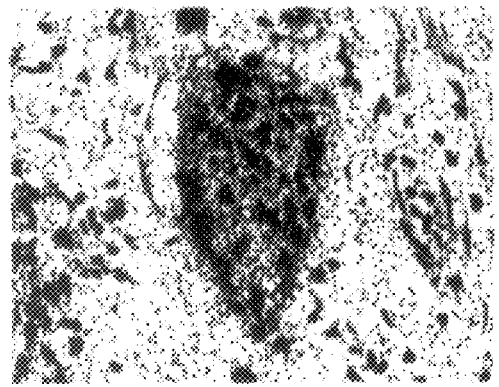
Figure 5D:
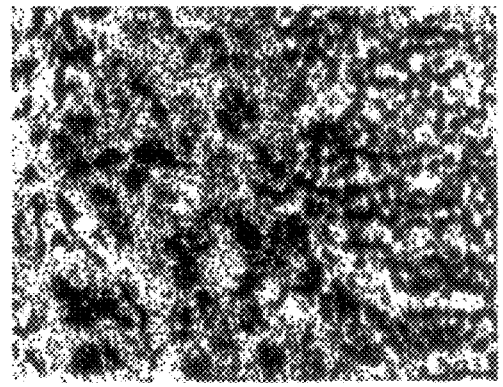

In situ hybridization, using an antisense CART1 RNA probe, was performed on primary breast carcinomas and axillary lymph node metastases. CART1 was expressed in malignant epithelial cells (FIG. 5(C)) and invasive carcinomas (FIG. 5(B)), whereas tumoral stromal cells were negative. CART1 transcripts were homogeneously distributed among the positive areas. Normal epithelial cells did not express the CART1 gene, even when located at the prox- imity of invasive carcinomatous areas (FIG. 5(A) and data not shown). A similar pattern of CART1 gene expression was observed in metastatic axillary lymph nodes from breast cancer patients with expression limited to cancer cells whereas noninvolved lymph node areas were negative (FIG. 5(D) and data not shown).

Determination of Human CART1 cDNA and Putative Protein Sequences

The complete CART1 cDNA sequence has been established from three independent cDNA clones. Both sense and antisense strands have been sequenced. The longest cDNA clone contained 2004 bp, a size consistent with the previously observed 2 kb transcript suggesting that this cDNA corresponded to a full-length CART1 cDNA (FIG. 6) (SEQ ID NO:1). The first ATG codon (at nucleotide position 85) had the most favorable context for initiation of translation (Kozak, M., *Nucl. Acids Res.* 15:8125–8149 (1987)), and a classical AATAAA poly(A) addition signal sequence (Wahle, E. & Keller, W., *Annu. Rev. Biochem.* 61:419–440 (1992)) was located 18 bp upstream of the poly(A) stretch. Thus, the open reading frame was predicted to encode a 470-residue protein (FIG. 6) (SEQ ID NO:2), with a molecular weight of 53 KD and a pHi of 8. The putative protein showed several consensus sequences, and notably two potential nuclear localization signals (NLS), a monopartite KPKRR (residues 11–15 of FIG. 6, SEQ ID NO:2) (Dang, C. V. & Lee. W. M. F., *J. Biol. Chem.* 264:18019–18023 (1989)) and a bipartite RR-X$_{11}$-KRRLK (residues 123–140 of FIG. 6, SEQ ID NO:2) (Dingwall, C. & Laskey, R. A., *Trends Biochem. Sci.* 16:478–480 (1991)). The molecule also contained potential sites (reviewed in, Kemp, B. E. & Pearson, R. B., *Trends Biochem. Sci.* 15:342–346 (1990)) specific of N-glycosylation (NGS, residues 355–357 of FIG. 6, SEQ ID NO:2), phosphorylation by casein kinase I (EELS, residues 300–303; SVGS, residues 303–306; ECFS, residues 331–334; all of FIG. 6, SEQ ID NO:2) and casein kinase II (SEE, residues 86–88; SRRD, residues 122–125; SGE, residues 149–151; SHE, residues 155–157; TSE, residues 185–187; TKE, residues 199–201; SGE, residues 357–359; SLLD, residues 389–392; SLDE, residues 426–429; SHQD, residues 441–444; all of FIG. 6, SEQ ID NO:2), proline-dependent phosphorylation (FSPA, residues 333–336 of FIG. 6, SEQ ID NO:2) and cAMP-dependent phosphorylation (RRVT, residues 384–387 of FIG. 6, SEQ ID NO:2). Moreover, two cystein-rich (C-rich) regions were identified, one located at the N-terminal part of the protein (residues 18–57) and the other at the core of the molecule (residues 83–282). Finally, the C-terminal part of the CART1 protein corresponded to the recently described TRAF domain (Rothe, M. et al., *Cell* 78:681–692 (1994)) (FIG. 6).

CART1 Contains an Unusual N-terminal RING Finger Motif

Figure 7:
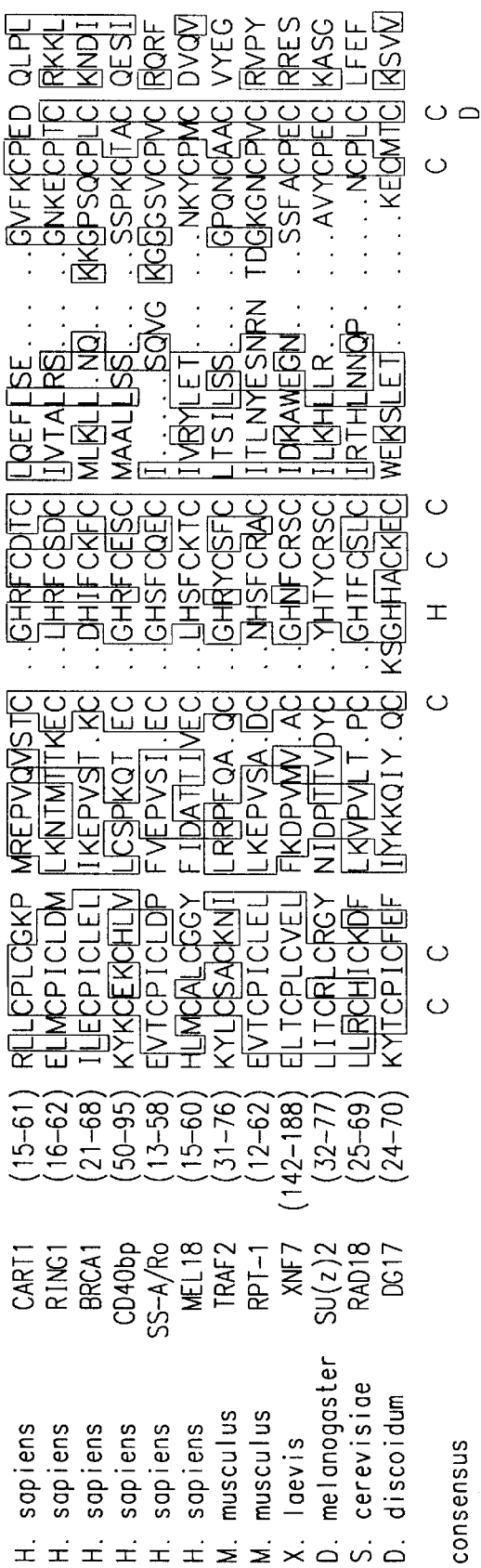
FIG. 7. Primary Structure of the CART1 C3HC3D Motif and Comparison with RING Finger Proteins from Various Species. These sequences are aligned to each other using the PileUp program (Feng, D. F. & Doolittle, R. F., *J. Mol. Evol.* 25:351–360 (1987)). Bracket numbers indicate the respective position of the motif in each protein. Residues identical in all sequences are bold-typed, and the conservative residues (R/K; I/V/L; Y/F; D/E; N/Q; S/T) are grey-boxed. Gaps are used to optimize alignment: H,Homo (CART1 (SEQ ID NO:2), RING1 (SEQ ID NO:13), BRCA1 (SEQ ID NO:14), CD40bp (SEQ ID NO:15), SS-A/Ro (SEQ ID NO:16), MEL18 (SEQ ID NO:17)); M,Mus (TRAF2 (SEQ ID NO:18), RPT-1 (SEQ ID NO:19)); X,Xenopus (XNF7 (SEQ ID NO:20)); D, Drosophila (SU(z)2 (SEQ ID NO:21)); S, Saccharomyces (RAD18 (SEQ ID NO:22)); D,Dictyostelium (DG17 (SEQ ID NO:23).

The N-terminal C-rich structure of the putative CART1 protein contained a CX$_2$CX$_{12}$CX$_1$HX$_2$CX$_2$CX$_{11}$CX$_2$D (C$_3$HC$_3$D) motif (residues 18–57 of FIG. 6, SEQ ID NO:2) reminiscent of the C3HC4 consensus sequence (Freemont, P. S. et al., *Cell* 64:483–484 (1991); FIG. 7). This sequence, located either at the N- or at the C-terminal part of proteins, could potentially give rise to two zinc fingers and has been named the RING finger motif (Freemont, P. S., *Ann. N.Y. Acad. Sci.* 684:174–192 (1993) and refs. therein). The proteins which share such a structure often exhibit DNA or RNA binding properties, and have been reported to be implicated during development such as DG17 (Driscoll, D. M. & Williams, J. G., *Mol. Cell. Biol.* 7:4482–4489 (1987)) and SU(z)2 (Van Lohuizen, M. et al., *Nature* 353:353–355

Figure 8A:
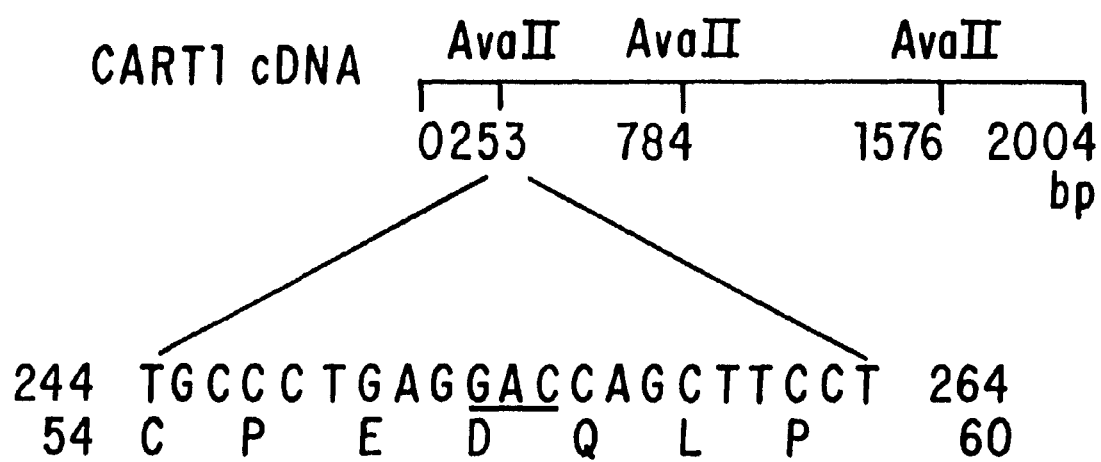
FIG. 8. Pattern of AvaII Digestion of the Full-Length CART1 cDNA. (A) Positions and sequence of AvaII sites (bold-typed) in the full-length CART1 cDNA (SEQ ID NO:1). Corresponding protein sequence from residues 54 to 60 of SEQ ID NO:2 is indicated using one letter code. D is bold-typed. (B) Ethidium bromide staining of gel electrophoresis of the CART1 AvaII digest. Molecular weight (m.w.) and CART1 fragments sizes are given on the left and right sides, respectively.
Figure 8B:
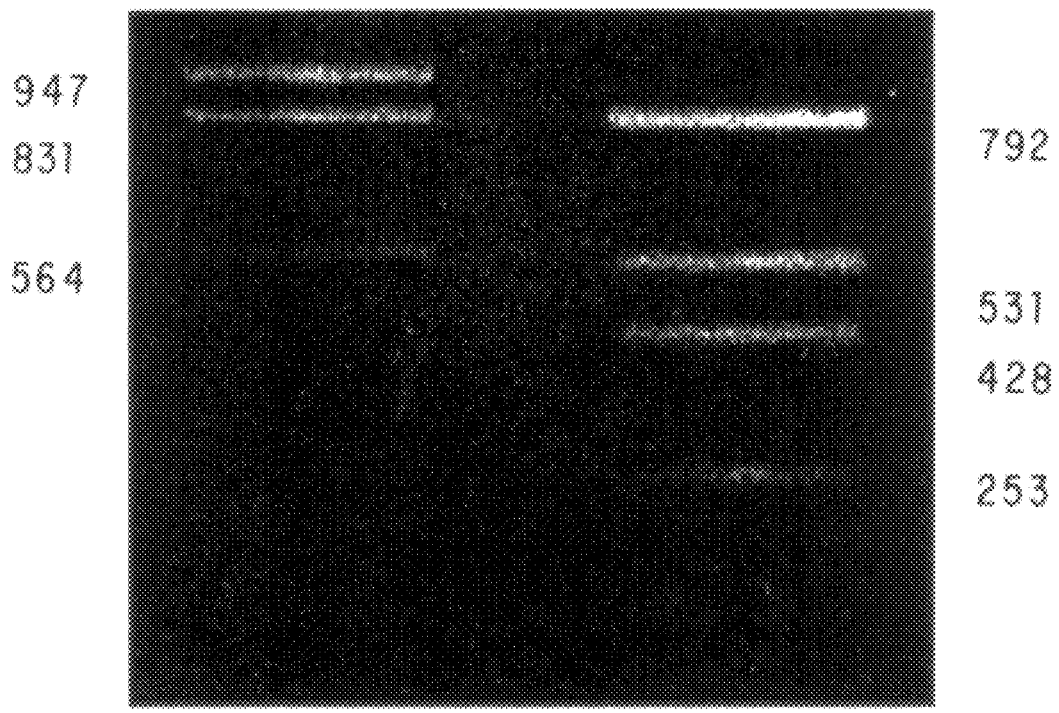

(1991)), gene transcription such as RPT-1 (Patarca, R. et al., *Proc. Natl. Acad. Sci. USA* 85:2733–2737 (1988)), SS-A/Ro (Chan, E. K. L. et al., *J. Clin. Invest.* 87:68–76 (1991)), XNF7 (Reddy, B. et al., *Dev. Biol.* 148:107–116 (1991)) and RING1 (Lovering, R. et al., *Proc. Natl. Acad. Sci USA* 90:2112–2116 (1993)), DNA repair such as RAD-18 (Jones, J. S. et al., *Nucl. Acids Res.* 16:7119–7131 (1988)), cell transformation such as MEL-18 (Tagawa, M. et al., *J. Biol. Chem.* 265:20021–20026 (1990); Goebl, M. G., *Cell* 66:623 (1991)), tumor suppression such as BRCA1 (Miki, Y. et al., *Science* 266:66–71 (1994)), or signal transduction such as CD40-binding protein (CD40-bp) (Hu, H. M. et al., *J. Biol. Chem.* 269:30069–30072 (1994)) and TRAF2 (Rothe, M. et al., *Cell* 78:681–692 (1994)). The distribution of C- and H-residues is highly conserved in all these RING fingers (FIG. 7). However, CART1 contained an aspartic acid (D-) residue instead of the last C-residue of the C3HC4 motif (FIG. 7). In order to confirm the presence of this D-residue, and since D-codon sequence lead to an AvaII restriction site (FIG. 8(A)), an AvaII digestion was performed on the full-length CART1 cDNA. Gel electrophoresis showed the presence of four bands (253, 428, 531 and 792 bp, respectively), a pattern consistent with the presence of a D-codon (FIG. 8(B)). However, since the CART1 cDNA was cloned from a cDNA library established using malignant tissues, we could not exclude the possibility that the D-residue resulted from an alteration occurring during carcinogenesis (Bishop, J. M, *Cell* 64:235–348 (1991)). Thus, in order to identify the physiological residue, we sequenced CART1 DNA from a normal leukocyte genomic library (see Materials and Methods). This analysis confirmed the presence of a D-residue, and consequently the C3HC3D motif. Data bank library analysis did not reveal any other protein sharing an identical RING finger motif.

Identification and Characterization of a Novel C-rich Motif, the CART Motif

The second C-rich region expanded from residues 83 to 282 and constituted almost half of the protein (FIG. 6) (SEQ ID NO:2). It contained 23 C- and 12 H-residues, corresponding to 96% and 67% of the remaining C- and H-residues, respectively. A careful examination of spacing of these C/H residues allowed the detection of an ordonnance giving rise to three $HX_3CX_6CX_3CX_{11-12}HX_4CH_6CH_{2-6}CH_{11}$ (HC3HC3) repeats. The most N-terminal of them (residues 101–154) contained the potential bipartite NLS (FIGS. 6 and 9). Homologies between these repeats were not restricted to the C/H residues and to the spacer sizes. Alignment of the three CART1 HC3HC3 motifs showed around 50% similarity and 30% identity with each other (FIG. 9).

Homology searches in the protein database revealed the presence of one copy of an analogous motif (residues 193–250) in the *Dictyostelium discoideum* DG 17 protein (FIG. 9) (SEQ ID NO:28) (Driscoll, D. M. & Williams, J. G., *Mol. Cell. Biol.* 7:4482–4489 (1987)), and of two copies in the human CD40-bp (FIG. 9) (residues 134–189 and 190–248, SEQ ID NOS:24 and 25, respectively) (Hu, H. M. et al., *J. Biol. Chem.* 269:30069–30072 (1994)) and in the mouse TRAF2 (FIG. 9) (residues 124–176 and 177–238, SEQ ID NOS:26 and 27) (Rothe, M. et al., *Cell* 78:681–692 (1994)). It should be noted that the sequences of the two N-terminal CART1 HC3HC3 motifs were most similar to those of the N-terminal motifs of CD40-bp (50% and 40%, respectively) and of TRAF2 (52% and 46%, respectively). The C-terminal CART1 HC3HC3 motif however was most similar to the C-terminal motifs of CD40-bp (58%) and of TRAF2 (55%), and to that of DG17 (51%) (FIG. 9). From these comparisons, the $HX_{3-4}CX_6CX_{2-4}CX_{11-12}HX_{3-4}CX_6CX_{2/6}CX_{11}$ consensus sequence was proposed for this novel motif that we named the CART motif for "C-rich motif Associated to RING and TRAF domains" (see, infra) (FIG. 9).

CART1 Contains a C-terminal TRAF Domain

The TRAF domain, recently identified in the TNF receptor-associated factors 1 (TRAF1) and 2 (TRAF2), is involved in TNF signal transduction pathway. TRAF domains encompass the 230 C-terminal residues of these proteins and share 53% identity (Rothe, M. et al., *Cell* 78:681–692 (1994)). The TRAF motif was also reported in the CD40-bp which associates with the cytoplasmic tail of CD40, another member of the TNF receptor family (Hu, H. M. et al., *J. Biol. Chem.* 269:30069–30072 (1994)). The C-terminal part of CART1 (residues 267–470) showed two degrees of homology with the TRAF domain. Thus, residues 267 to 307 showed a weak homology (12–23% identity). From structural predictions, this N-terminal part of CART1 TRAF domain is supposed to give rise to an alpha helix (Chou, P. Y. & Fasman, G. D., *Annu. Rev. Biochem.* 47:251–276 (1978)). Such a structure, already proposed for the corresponding regions of TRAF1, TRAF2 and CD40-bp is supposed to be involved in protein/protein interactions (Rothe, M. et al., *Cell* 78:681–692 (1994); Hu, H. M. et al., *J. Biol. Chem.* 269:30069–30072 (1994)). The C-terminal part of CART1 TRAF domain (residues 308–470) of SEQ NO ID:2 showed high degree of similarity and identity with the corresponding part of TRAF1 (60% and 42%) (SEQ ID NOS: 30 and 34), TRAF2 (69% and 47%) (SEQ ID NOS:31 and 35) and CD40-bp (62% and 43%) (SEQ ID NOS:29 and 33), thus defining a "restricted TRAF domain" (FIG. 10). Finally, since DG17 already contained a N-terminal RING finger and a CART motif we looked for the presence of a restricted TRAF domain in its C-terminal part. We observed 55% similarity and 30% identity between the last 150 residues of CART1 and DG17 (data not shown). However, the protozoan DG17 protein showed numerous mismatches with the restricted TRAF consensus motif derived from human and mouse proteins (FIG. 10), suggesting that DG17 contains a primitive TRAF domain.

CART1 Gene Organization

Figure 11:
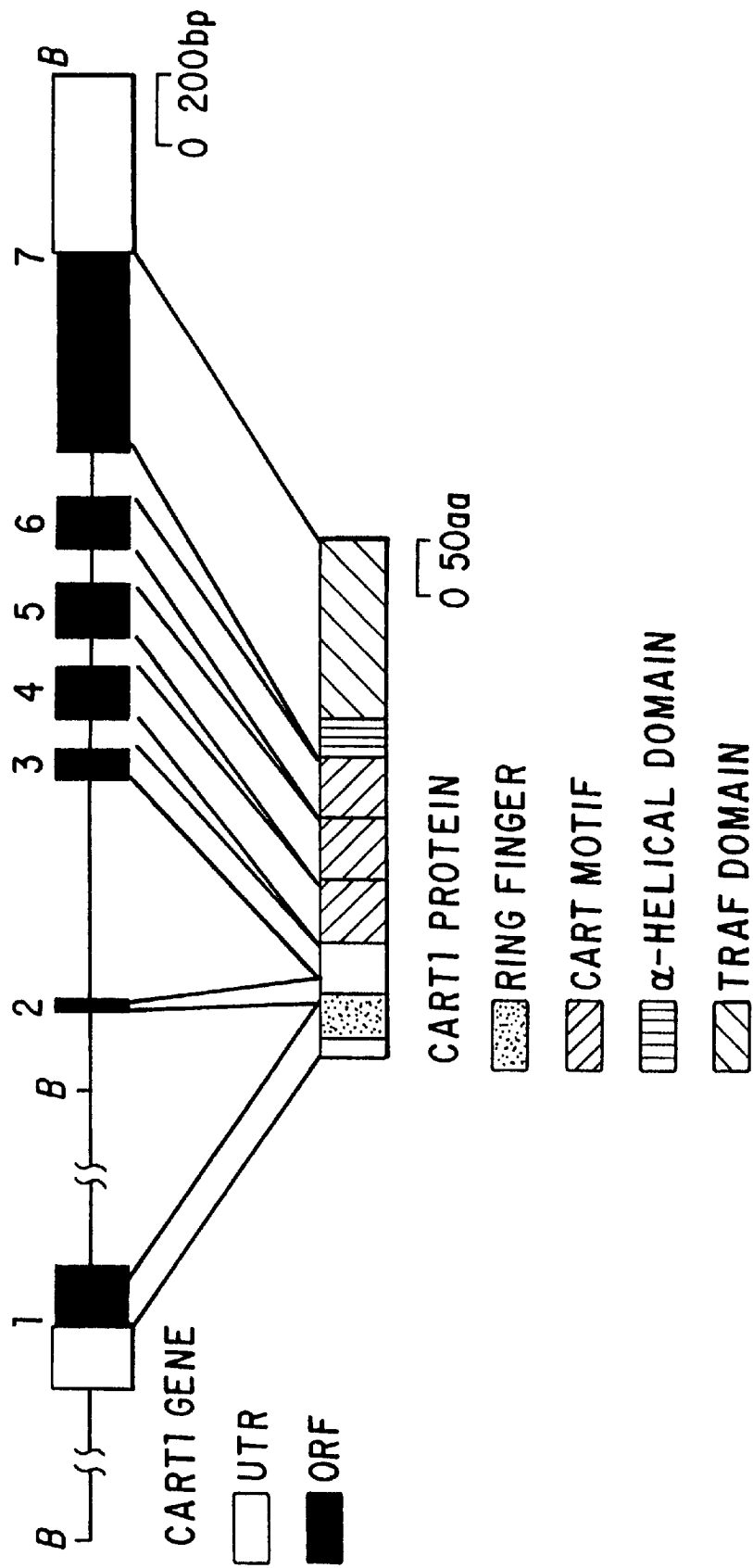
FIG. 11. Organization of the Human CART1 Gene and Protein. Schematic representation of the CART1 gene exon/intron organization. Exons are numbered from 1 to 7. The correspondence between DNA coding sequences and protein domains are indicated (B, BamHI; ORF, open reading frame; UTR, untranslated region).

Two independent clones have been selected from a screening of a human leukocyte genomic library using the full-length CART1 cDNA probe. These clones contained 3 and 3.2 kb BamHI fragments which have been subcloned and partially sequenced in order to map splicing sites. The human CART1 gene was found to be split into 7 exons (FIG. 11 and Table V (exon/intron Nos. 1–6 corresponding to SEQ ID NOS:52–57, respectively). Comparison of the intron/exon boundaries showed that each corresponded to a canonical splice consensus sequence (Breathnach, R. & Chambon, P., *Annu. Rev. Biochem.* 50:349–383 (1981)). The total length of the CART1 gene is approximately 5.5 kb (FIG. 11). Analysis of the genomic structure of the RING finger domain revealed that it is encoded by two exons separated by the presence of an intronic sequence located between nucleotides 226–227 (FIG. 4). Thus, the C3HC2 and the CD parts of the C3HC3D motif are encoded by exons 1 and 2, respectively (FIG. 11). The three CART motifs were encoded by three separate exons of 161 (exon 4) (SEQ ID NO:55),161 (exon 5) (SEQ ID NO:56) and 156 (exon 6) (SEQ ID NO:57) bp, respectively (FIG. 11 and Table V). In addition to their similar size, the three exons exhibited about 40% identity with each other, suggesting they have arisen by duplication of an ancestral exon. Finally, the a-helix and the restricted TRAF domain were encoded by exon 7 which also encoded for the 3' untranslated region.

CART1 Protein Subcellular Localization—CART1 subcellular localization was performed on paraffin-embedded sections from a human invasive breast carcinoma using a rabbit polyclonal antibody. The antibody specificity was established by Western blot analysis of CART1 recombinant protein (data not shown). Consistent with our findings using in situ hybridization, CART1 immunoperoxidase staining (brown staining) was observed in malignant epthelial cells. Moreover, CART1 protein appeared to be located in the nucleus showing that almost one of the CART1 nuclear localization signals was functional. The intensity of staining was variable from one cell to another, even within a given area of the section.

Discussion

We characterized a cDNA and corresponding putative protein encoded by a novel gene that we call the CART1 gene (identified as MLN 62 in Example 1) by screening a breast cancer metastatic lymph node cDNA library. CART1 was overexpressed in 10% of primary breast carcinomas and 50% of metastatic axillary lymph nodes, whereas the corresponding nonmalignant tissues did not. CART1 transcripts were specifically detected in malignant epithelial cells and homogeneously distributed throughout the carcinomatous areas. No CART1 expression was observed in a panel of normal human tissues including skin, lung, stomach, colon, liver, kidney and placenta. This expression pattern, restricted to some malignant tissues, suggests that CART1 is involved in processes leading to the formation and/or progression of primary carcinomas and metastases. The putative CART1 protein sequence, deduced from the cDNA open reading frame, exhibited several structural domains. The CART1 N-terminal part contained a C-rich domain characterized by the presence of a RING finger (Freemont, P. S., *Ann. N.Y. Acad. Sci.* 684:174–192 (1993)). The RING finger protein family presently comprises more than 70 members involved in the regulation of cell proliferation and differentiation (reviewed in, Freemont, P. S., *Ann. N.Y. Acad. Sci.* 684:174–192 (1993)). Interestingly, one of the recently identified members of the family is the tumor suppressor gene BRCA1, responsible for about 50% of inherited breast cancers (Miki, Y. et al., *Science* 266:66–71 (1994)). RING finger motif is assumed to fold into two zinc fingers and to be involved in protein/nucleic acid interaction(s) (Schwabe, J. W. R. & Klug, A., *Nature Struc. Biol.* 1:345–349 (1994) and refs. therein). In CART1 RING finger, the last C-residue is substituted by a D-residue giving rise to a C3HC3D motif instead of the usual C3HC4 motif. Since aspartic acid has already been described as a potential zinc coordinating residue (Vallee, B. L. & Auld, D. S., *Biochem.* 29:5647–5659 (1990)), we assume that the C3HC3D motif may efficiently bind metal atoms through the zinc finger structure. Consistent with this hypothesis, aspartic acid has already been reported to be functional in another type of zinc finger motif, the LIM domain (Sanchez-Garcia, I. & Rabbits, T. H., *Trends Genet.* 9:315–320 (1994) and refs. therein).

CART1 RING finger is encoded by two exons coding for the C3HC2 and CD part of the C3HC3D motif, respectively, a genomic organization slightly different from that previously described for the consensus MEL-1 8 RING finger which results from two exons encoding the C3H and C4 putative zinc finger, respectively (Asano, H. et al., *DNA Sequence* 3:369–377 (1993)).

CART1 also contained an original C-rich region, located more centrally within the protein and composed of three repeats of an HC3HC3 motif corresponding to a novel protein signature and that we designated the CART motif These three repeats were encoded by distinct exons homologous with each other, suggesting that they derived from an ancestral exon. CART motifs were only found, in variable copy numbers, in three RING finger proteins, the human CD40-bp (two copies), the mouse TRAF2 (two copies) and the *Dictyostelium discoideum DG*17 protein (one copy) (Hu, H. M. et al., *J. Biol. Chem.* 269:30069–30072 (1994); Rothe, M. et al., *Cell* 78:681–692 (1994); Driscoll, D. M. & Williams, J. G., *Mol. Cell. Biol.* 7:4482–4489 (1987)). The corresponding C-rich regions of CD40-bp, TRAF2 and DG17 have been previously reported to be partially arranged in pattern resembling either the CHC3H2 "B box" motif or the C2H2 *Xenopus laevis* transcription factor III A motif (Freemont, P. S., *Ann. N.Y. Acad. Sci.* 684:174–192 (1993); Hu, H. M. et al., *J. Biol. Chem.* 269:30069–30072 (1994); Rothe, M. et al., *Cell* 78:681–692 (1994); Driscoll, D. M. & Williams, J. G., *Mol. Cell. Biol.* 7:44824489 (1987)). The CART motif, as defined in the present study, encompasses almost the totality of the C-rich region observed in CART1, CD40-bp, TRAF2 and DG17. The function of the CART domain remains to be determined. Preliminary protein studies (C.R., unpublished results) indicate that the correct folding of the CART motif is depending on the presence of zinc, supporting the hypothesis that CART corresponds to a novel zinc binding motif presumably involved in nucleic acid binding (Schwabe, J. W. R. & Klug, A., *Nature Struc. Biol.* 1:345–349 (1994); Schmiedeskamp, M. & Klevit, R. E., *Curr. Opin. Struc. Biol.* 4:28–35 (1994)).

The C-terminal part of CART1 corresponded to a TRAF domain previously identified in TRAF 1, TRAF2 and CD40-bp. This motif is involved in protein/protein interaction and TRAF2 and CD40-bp have been reported to specifically interact with the cytoplasmic domain of two members of the TNF-receptor family, TNF-R2 and CD40, respectively (Rothe, M. et al., *Cell* 78:681–692 (1994); Hu, H. M. et al., *J. Biol. Chem.* 269:30069–30072 (1994)). The TRAF domain is composed of two structural domains, a N-terminally located domain which corresponds to a weakly conserved alpha helix and a C-terminally located domain which is highly conserved and corresponds to what we called the "restricted TRAF domain," since it includes only part of the previously described TRAF domains (Rothe, M. et al., *Cell* 78:681–692 (1994); Hu, H. M. et al., *J. Biol. Chem.* 269:30069–30072 (1994)). Both structural motifs were encoded by the same exon of the CART1 gene. Homology was also observed with the C-terminal part of the protozoan DG17 protein which, although less conserved, could be considered as a TRAF domain.

Figure 12:
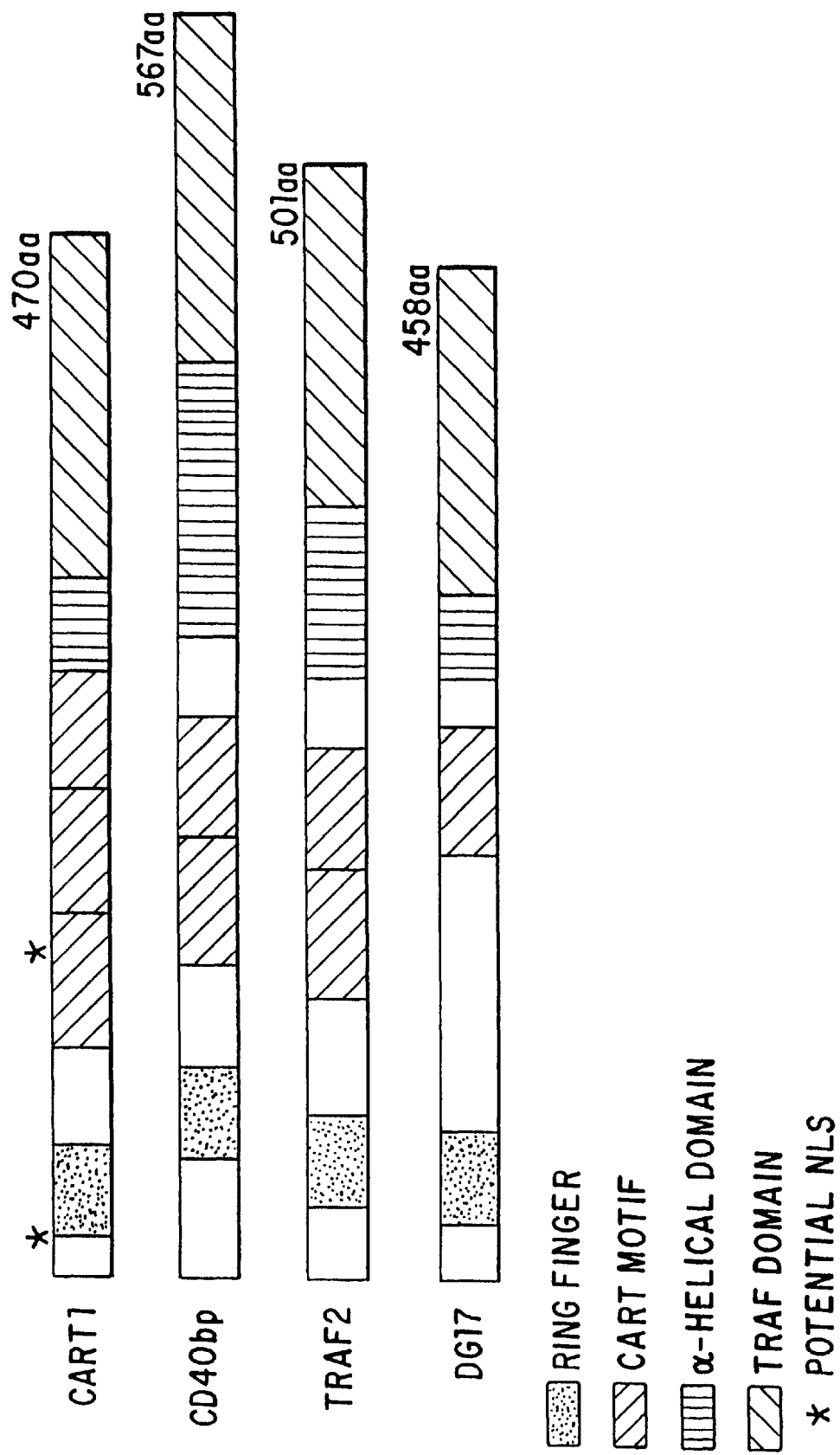
FIG. 12. Comparison of CART1, CD40-bp, TRAF2 and DG17 Protein Structural Organization. The size and position of RING finger, CART motif, α helix and restricted TRAF domain are represented for each of these proteins, highlighting the similarity of their protein organization.

Thus, CART1 shared a protein organization similar to that of the human CD40-bp, the mouse TRAF2 and protozoan DG17, including a N-terminal RING finger, one to three central CART motifs and a C-terminal TRAF domain (FIG. 12). These results suggest that these structurally related proteins belong to the same protein family and may exhibit analogous function. DG17 is expressed during *Dictyostelium discoideum* aggregation which occurs under stress conditions in order to permit cell survival through a differentiated multicellular organism. The precise function of DG17 function remains unknown (Driscoll, D. M. & Williams, J. G., *Mol. Cell. Biol.* 7:4482–4489 (1987)). However, both CD40-bp and TRAF2 have been previously shown to be involved in TNF-related cytokine signal transduction (Hu, H. M. et al., *J. Biol. Chem.* 269:30069–30072 (1994); Rothe, M. et al., *Cell* 78:681–692 (1994)). In contrast to growth factor receptors, cytokine receptors generally do not contain kinase activity in their cytoplasmic region, and their signal transduction mechanisms remain elusive (reviewed in, Taga, T. & Kishimoto, T., *FASEB J.* 6:3387–3396 (1993)). To date, the TNF and TNF receptor families contain 8 and 12 members, respectively. The lack of sequence homology among TNF-receptor cytoplasmic domains, required for signal transduction, suggests the existence of specific signaling pathway for each receptor (reviewed in, Smith, C. A. et al., *Cell* 65:959–962 (1994)). Recently, it has been proposed that signal transduction through CD40 and TNF-R2 involved the interaction of their cytoplasmic domain with two cytoplasmic proteins, CD40-bp and TRAF2, respectively (Rothe, M. et al., *Cell* 78:681–692 (1994); Hu, H. M. et al., *J. Biol. Chem.* 269:30069–30072 (1994)). Thus, CD40-bp and TRAF2 could be latent cytoplasmic transcription factors, which would be translocated to the nucleus under receptor activation by their respective ligands. A similar system has already been proposed for the protein family of signal transducers and activators of transcription (STAT) involved in gene activation pathways triggered by interferons (Darnell, J. E. et al., *Science* 264:1415–1421 (1994)). This system implies a direct signal transduction pathway through STAT migration from cytoplasm to nucleus, presumably triggered by STAT phosphorylation following receptor activation (Ihle, J.N. et al., *Trends Biochem. Sci.* 19:222–227 (1994); Darnell, J. E. et al., *Science* 264:1415–1421 (1994)). From all these observations, it is tempting to speculate that CART1, which not only shares a structural arrangement of RING, CART and TRAF domains identical to that observed in two TNF receptor associated proteins, but also exhibits putative NLS and phosphorylation sites, may exert similar function for TNF-related cytokine signal transduction.

TNF ligand family members have been shown to induce pleiotropic biological effects, including cell differentiation, proliferation, activation or death, all processes involved during carcinogenesis and tumor progression (Smith, C. A. et al., *Cell* 65:959–962 (1994), and refs. therein). In breast carcinomas, p55 and p75 TNF receptors have been shown to be expressed in malignant tissues, and a dramatic increase of the secretion of their corresponding TNFαligand has been associated with metastatic step of the disease (Pusztai, L. et al., *Brit. J. Cancer* 70:289–292 (1994), and refs. therein). Our observation of CART1 overexpression in breast carcinomas suggests that, CART1 may be involved in signal transduction pathway either involving p55/p75 or another member of the TNF-receptor family. The nature of TNF receptor as well as the nature of protein(s) which may interact with CART1 are now under characterization.

EXAMPLE 3

Lasp-1 (MLN 50), Encodes the First Member of a New Protein Family Characterized by the Association of LIM and SH3 Domains Introduction In Example 1 above, we describe the isolation of MLN 50 (Lasp-1) cDNA from a breast cancer derived metastatic lymph node cDNA library by differential hybridization using malignant (metastatic lymph node) versus nonmalignant (fibroadenoma and normal lymph node) breast tissue. Chromosomal mapping allowed us to map the Lasp-1 gene to the q12-q21 region of the chromosome 17 long arm. This region is known to be altered in 20 to 30% of breast cancers leading to the amplification of the proto-oncogene c-erbB-2 (Fukushige, S. I. et al., *Mol. Cell Biol.* 6:955–958 (1986); Slamon, D. J. et al., *Science* 244:707–712 (1989)). In breast cancer cell lines, we found that Lasp-1 RNA overexpression was correlated with its gene amplification and to c-erbB-2 amplification/overexpression suggesting that Lasp-1 and c-erbB-2 belong to the same amplicon. In the present example, we determined the frequency of Lasp-1 overexpression in human breast cancer and characterized the encoded protein.

Materials and Methods

Tissue and Cell Cultures

Surgical specimens obtained at the Hopitaux Universitaires de Strasbourg, were frozen in liquid nitrogen for RNA extraction. Adjacent sections were fixed in 10% buffered formalin and paraffin embedded for histological examination.

The cell lines (SK-BR-3, BT-474, MCF-7) are available from the American Type Culture Collection (ATCC, Rockville, Md.). Cells were routinely maintained in our laboratory and cultured at confluency in Dulbecco's modified Eagle's medium supplemented with 10 % fetal calf serum (SK-Br-3) and with 10 μg/ml of insulin (MCF-7), and in RPMI supplemented with 10% fetal calf serum and 10 μg/ml of insulin (BT-474).

RNA Preparation and Analysis

Surgical specimens were homogenized in the guanidinium isothiocyanate lysis buffer and purified by centrifugation through cesium chloride cushion (Chirgwin, J. M. et al., *Biochem.* 18:52–94 (1979)). RNAs from cultured cell lines were extracted using the single-step procedure of Chomczynski, P. & Sacchi, N., *Anal. Biochem* 162:156–159 (1987). RNAs were fractionated by electrophoresis on 1% agarose, 2.2 M formaldehyde gels (Lehrach, H. et al., *Biochem.* 16:4743–4751 (1977)), transferred to nylon mem-

TABLE V

Exon/Intron Organization of the CART1 Gene

| EXON | | | | INTRON | | |
|---|---|---|---|---|---|---|
| N° | size (bp) | 5' splice donor | 3' splice acceptor | N° | size (bp) | SEQ ID NO. |
| 1 | ~500 | CCTCAG gtgctg . . . | . . . tatcag TGAAGG | 1 | ~2100 | 52 |
| 2 | 52 | GCCAAG gtgcag . . . | . . . ccccag ATCTAC | 2 | 581 | 53 |
| 3 | 105 | CTACAG gtgagg . . . | . . . caccag GGCCAC | 3 | 69 | 54 |
| 4 | 161 | TATGAG gtgggt . . . | . . . ttccag AGCCAT | 4 | 83 | 55 |
| 5 | 161 | ATCCAG gtgagg . . . | . . . ccccag AGCCAC | 5 | 87 | 56 |
| 6 | 155 | CACAGG gtgaga . . . | . . . caacag TGCCCT | 6 | 150 | 57 |
| 7 | 1140 | | | | | |

Exon sequences are indicated in capital letters, and intron sequences in small letters.

brane (Hybond N, Amersham Corp.) and immobilized by baking for 2 hrs at 80° C.

Probe Preparation and Hybridization

Lasp-1 probe corresponded to a 1.0 kb BamHI fragment released from MLN 50 subcloned into pBluescript. The RNA loading control probe 36B4 was an internal 0.7 kb PstI fragment (Masiakowski, P. et al., *Nucleic Acids Res.* 10:7895–7903 (1982)).

Northern blots were hybridized at 42° C. in 50% formamide, 5× SSC, 0.4% ficoll, 0.4% polyvinylpyrrolidone, 20 mM sodium phosphate pH 6.5, 0.5% SDS, 10% dextran sulfate and 100 μg/ml denatured salmon sperm DNA, for 36–48 hrs with the $^{32}$P-labeled probe diluted to $0.5$–$1.10^6$ cpm/ml. Stringent washings were performed at 60° C. in 0.1× SSC and 0.1% SDS. Blots were autoradiographed at −80° C. for 24 hrs.

Sequence Analysis

Sequence analyses were performed using the GCG sequence analysis package (Wiskonsin package version 8.0, Genetics computer Group, Madison, Wis.). The Lasp-1 cDNA and amino acid sequences were used to search the complete combined GenBank/EMBL database and the complete SwissProt database with BLAST (Altschul, S. F. et al., *J. Mol. Biol.* 215:403–410 (1990)) and FastA (Pearson, W. R. & Lipman, D. J., *Proc. Natl. Acad Sci. USA* 85:2444–2448 (1988)) programs, respectively. The LIM motif and consensus sequences of Lasp-1 were further identified by the motif program in the PROSITE dictionary (release 12). The sequence alignments were obtained automatically by using the program PileUp (Feng, D. F. & Doolittle, R. F., *J. Mol. Evol.* 25:351–360 (1987)).

Results and Discussion

To determine Lasp-1 mRNA distribution we carried out Northern blot analysis using the cDNA as a probe. A single 4.0 kb mRNA band was detected at low level in all the human tissue and cell lines studied (FIG. 13 and data not shown). Lasp-1 mRNA overexpression was found in 8% (5/61) primary breast cancers (FIG. 13(A), lane 8) and in 40% (2/5) breast cancer derived metastatic lymph nodes (FIG. 13(A), lanes 1 and 2). No expression (0/15) above the basal level was found in nonmalignant breast tissues (FIG. 13(A), lanes 13–17, fibroadenomas; lane 18, hyperplastic breast) nor in normal adult tissues (FIG. 13(B), lanes 1–6 and data not shown). By comparison with c-erbB-2 overexpression, Lasp-1 was found to be coexpressed in most (FIG. 13(A), lanes 1, 2 and 8; FIG. 13(B), lane 8) but not in all (FIG. 13(A), lane 12; FIG. 13(B), lane 7) human breast cancer and cell lines. These results suggest that Lasp-1 is quite ubiquitous at the RNA level, with an increased expression in some breast cancer tissue and derived metastatic lymph nodes which is probably caused by gene amplification centered around the c-erbB-2 locus.

The complete Lasp-1 cDNA sequence was established from four independent cDNA clones. Both sense and antisense strands were sequenced. The longest cDNA clone contained 3848 bp, a size consistent with the transcript size suggesting that this clone should correspond to the full length cDNA (FIG. 14(A–B)) (SEQ ID NO:3). At the nucleotide level, sequence homologies were found with 22 expressed sequences tags (ESTs) (Weinstock et al., *Curr. Opin. Biotech.* 5:599–603 (1994), and refs. therein). Some of these sequences are redundant and they were mostly located on the 3' untranslated end of the molecule (FIG. 14(C)). Most of these ESTs were established from different human cDNA libraries established using normal tissues (fetal brain, white blood cells, prostate gland, liver, pancreatic islet cells and fetal spleen). The presence of Lasp-1 transcripts in all these samples is in good agreement with our finding of ubiquitous expression of Lasp-1 mRNA (FIG. 13 and data not shown).

The first ATG codon (nucleotide position 76 of FIG. 14(A–B) (SEQ ID NO:3)) had a favorable context for initiation of translation (Kozak, M., *Nucl. Acids Res.* 15:8125–8149 (1987)), and a classical AATAAA poly(A) addition signal sequence (Wahle, E. & Keller, W., *Annu. Rev. Biochem.* 61:419–440 (1992)) was located 13 bp upstream of the poly(A) stretch (FIG. 14(A–B) (SEQ ID NO:3)). The deduced open reading frame encoded a 261 amino acid protein, with a molecular weight of 30 KD and a pHi of 6.5 (FIG. 14(A–B) (SEQ ID NO:4)). The protein showed several consensus sequences: an amidation site (GGKR, residues 203–206 of FIG. 14(A–B), SEQ ID NO:4), several phosphorylation sites by cAMP and cGMP dependent protein kinase (RRDS, residues 141–144 of FIG. 14(A–B), SEQ ID NO:4), casein kinase II (SGGE, 139–136; SAAD, 213–216; SFQD, 221–224; all of FIG. 14(A–B), SEQ ID NO:4), protein kinase C (TEK, 14–16; TCK, 33–35; SYR, 150–152; all of FIG. 14(A–B), SEQ ID NO:4)) and tyrosine kinase (KKGYEKKPY, 38–45; KDSQDGSSY, 137–144; all of FIG. 14(A–B), SEQ ID NO:4). Moreover, a cystein rich region was identified as a LIM (Sànchez-Garcia, I. & Rabbits, T. H., *Trends Genet.* 9:315–320 (1994)) domain in the N-terminal part and a SH3 (Musacchio et al., *FEBS Lett.* 307:55–61 (1992)) domain at the C-terminal portion of the protein.

The deduced primary sequence of Lasp-1 contains two likely tyrosine phosphorylation sites (underlined in FIG. 14 (SEQ ID NO:4); these residues are followed by short tripeptides demonstrating homology to the predicted SH2 binding motif (Songyang et al., *Cell* 72:767–778 (1993)).

A Single LIM Domain is Present at the N- part of Lasp-1

The LIM domain is an arrangement of seven cysteine and histidine residues (C—X$_2$—C—X$_{16/23}$—H—X$_2$—C—X$_2$—C—X$_2$—C—X$_{16/21}$—C—X$_{2/3}$—C/D/H)2,3—C/D/A/H) present in a number of invertebrate and vertebrate proteins. The generic name was given for the product of the three firstly identified LIM genes (lin-11, lsl-1 and mec-3). The family of LIM containing proteins is continuously increasing and could be subdivided in distinct groups (Sànchez-Garcia, I. & Rabbits, T. H., *Trends Genet* 9:315–320 (1994)). One group designated LIM-HD, includes protein having two LIM domains associated with a homeodomain (lin-11, lsl-1, mec-3). Another group designated LIM-only, includes proteins exhibiting a single (CRIP), two (CRP, TSF3, RBTN1, RBTN2, RBTN3) or three (zyxin) LIM domains. Recently, a new group designated LIM-K, including proteins having two LIM domains associated with a kinase domain, had been described (Sànchez-Garcia, I. & Rabbits, T. H., *Trends Genet.* 9:315–320 (1994); Mizuno et al., *Oncogene* 9:1605–1612 (1994)). The LIM domain defines a zinc binding structure and zinc binding is necessary for the proper folding of the domain.

Sequence alignments of LIM proteins with Lasp-1 showed a best score alignment with the *C. elegans* YLZ4 putative protein (Accession No. P34417). Although the overall homology is low (36% identity and 55% similarity), it is high within the LIM domain (66% identity and 80% similarity). The protein YLZ4 was identified in the whole sequencing of the *C. elegans* chromosome III (Wilson, R. et at, *Nature* 368:32–38 (1994)). The LIM domain of YLZ4 does perfectly fit the LIM consensus, the first two cysteines are spaced by four instead of two residues, leading to a gap in the alignment (FIG. 15(A)) (SEQ ID NO:37). Among other LIM containing proteins besides the LIM consensus sequence, additive homologies were found in the human cysteine-rich protein CRP (Liebhaber, et al., *Nucl. Acids Res.* 18:3871–3879 (1990)), the rat cysteine-rich intestinal protein CRIP and the physiological function of these proteins is not yet known, although a role for CRIP in intestinal zinc absorption has been suggested and CRP was identified as a binding partner for a LIM-only protein zyxin. The interaction between these two proteins, believed to have regulatory or signaling functions in focal adhesion plaques (Crawford et al., *J. Cell Biol.* 116:1381–1393 (1992); Crawford et al., *J. Cell Biol.* 124:117–127 (1994); Sadler et al., *J. Cell Biol.* 119:1573–1587 (1992)), is mediated by sequence-specific interactions between their LIM domains (Shmeichel & Beckerle, *Cell* 79:211–219 (1994)). The LIM domain can be considered as a protein/protein modular binding interface similarly to SH2 and SH3 domains (Shmeichel & Beckerle, *Cell* 79:211–219 (1994)). Our findings showing a strong conservation for Lasp-1 LIM domain across a wide range of different species mammals, nematodes and plant suggest an important function for this domain.

Lasp-1 Contains a SH3 Domain at the C-terminal Part

The SH3 (src homology region 3) is a small protein domain of 60 amino acids, first identified as a conserved sequence in the N-terminal noncatalytic part of the src protein tyrosine kinase (Sadowski et al., *Mol. Cell. Biol.* 6:4396–4408 (1986); Mayer et al., *Nature* 332:272–275 (1988)). A number of proteins involved in the tyrosine kinases signal transduction pathway contain SH3 domains (Schlessinger, *Curr. Opin. Genet. Develop.* 4:25–30 (1994)), this domain could also been found in proteins of unrelated functions such as cytoskeleton associated proteins (Musacchio et al., *FEBS Lett.* 307:55–61 (1992)). The function of the SH3 domain remains unclear; however, SH3 containing proteins are usually located close to the plasmic membrane suggesting a role for this domain in the targeting of protein to this cellular compartment (Musacchio et al., *FEBS Lett.* 307:55–61 (1992)). Direct evidences of the adaptor molecule Grb2, SH3 domain targeting properties, were provided (Bar-Sagi et al., *Cell* 74:83–91 (1993)). Hints to the function were achieved by the resolution of several different SH3 domains, showing that the overall structure is conserved and independently folded. Also, several protein ligands for the SH3 domains of oncogenic tyrosine kinases have been isolated, leading to the definition of specific proline-rich regions required for the binding to SH3 domains (Alexandropoulos et al., 92:3110–3114 (1995) and refs. therein).

Sequence *Proc. Natl. Acd. Sci. USA* alignment revealed homology of the Lasp-1 C-terminal part with several SH3 containing proteins (FIG. 15(B)), including in the SH3 domain of EMS 1 (SEQ ID NO:44) (Schuuring et al., *Oncogene* 7:355–361 (1992)) a human homolog of the src tyrosine kinase substrate cortactin (Wu et al., *Mol. Cell Biol.* 11:5113–5124 (1991)). The strongest conservation was found with the YLZ3 (SEQ ID NO:43) putative protein of *C elegans* (Accession No. P34416), the overall homology is low (23% identity and 40% similarity) but significant within the SH3 domain (57% identity and 74% similarity). This protein was deduced from the whole *C elegans* chromosome III sequencing. Interestingly, on the F42HlO.3 cosmid the gene encoding YLZ3 lies next to the gene encoding YLZ4 which contained a LiM domain strongly homolog with that of Lasp-1 (FIG. 15(A)) (SEQ ID NO:4). This may reflect modular evolution processes leading to join in the same protein functional domains separated in proteins from primitive organisms.

In conclusion, Lasp-1 carries a LIM domain and a SH3 domain. These domains are involved in protein/protein interactions occurring in different cellular processes including development, transcription, transformation and cell signaling. LIM domains have been shown to be associated with two distinct functional domains, the homeo and kinase domains. SH3 domains are often found in association with SH2, pleckstrin homology (PH) and kinase domains. A link between LIM and SH3 domains was found by the interaction of the cytosquelettal protein paxillin (LIM only protein) with SH2 and SH3 domains of vinculin and the focal adhesion kinase (ppl25$^{fak}$). To date Lasp-1 is the first protein containing both domains and could represent the first member of a new protein family of adaptor molecules involved in cell signaling. The ubiquitous expression of Lasp-1 in human adult tissues suggests a basic cellular function for this protein, moreover its overexpression though genetic amplification in 10 to 15% of human breast cancer suggests that Lasp-1 could be implicated in carcinogenesis or tumor progression.

EXAMPLE 4

MLN 64, a Gene Co-Expressed with the c-erbB2 Oncogene in Malignant Cells and Tissues Introduction In Example 1 above, we describe isolating human MLN 64 cDNA from a metastatic breast cancer cDNA library. This clone was identified through a differential screening performed by using two subtractive probes, respectively representative of metastatic and nonmalignant breast tissues, in order to identify new genes susceptible to be specifically involved in breast cancer.

We mapped MLN 64 at the q12-q21 region of the long arm of chromosome 17 with a maximum in the q21.1 band (see, supra, Example 1). This region already includes two genes known to be involved in breast cancer disease, the oncogene c-erbB-2 (Slamon, D. J. et al., *Science* 235:177–182 (1987)) in q12 and the tumor suppressor gene BRCAI (Hall, J. M. et al., *Science* 250: 1684–1689 (1990); Brown & Solomon, *Curr. Opin. Genet. Dev.* 4:439–445 (1994), and refs. therein) in q21. c-erbB-2 overexpression is correlated with a shorter overall and disease free survival for breast cancer patients (Muss, H. B. et al., *N. Engl. J. Med.* 300:1260–1266 (1994), and refs. therein). Moreover, c-erbB-2 overexpression has been shown to be dependent of gene amplification during carcinogenesis (van de Vijver, M. et al., *Mol. Cell Biol.* 7:201–223 (1987)). We established in Example 1 that the MLN 64 gene was co-amplified with the c-erbB-2 gene in SKBR3 and BT474 breast cancer cell lines. It is assumed that DNA amplification plays a crucial role in tumor progression by allowing cancer cells to upregulate numerous genes (Lönn, U. et al., *Intl. J. Cancer* 58:4045 (1994); Kallioniemi, A. et al., *Proc. Natl. Acad Sci. USA* 4 91:2156–2160 (1994)), and notably oncogenes. Frequency of gene amplification as well as gene copy number increase during breast cancer progression, notably in patients who do not respond to treatment, suggesting that overexpression of the amplified target genes confers a selective advantage to malignant cells (Schwab, M. & Amler, L., *Genes. Chrom. Cancer* 1:181–193 (1990); Lönn, U. et al., *Intl. J. Cancer* 58:4045 (1994); Guan, X. Y. et al., *Nat. Genet.* 8:155–161 (1994)).

BRCAI is responsive for about half of the inherited forms of breast carcinomas, suggesting that other tumor suppressor gene(s) could be implicated (Miki, Y. et al., *Science* 266:66–71 (1994)). BRCAI has been shown to exhibit various possible disease-causing alterations including frameshifts and nonsense mutations (Castilla et al., *Nat. Genet.* 8:387–391 (1994); Friedman et al., *Nat. Genet.* 8:399404 (1994); Simard et al., *Nat. Genet.* 8:392–398 (1994)).

Finally, in sporadic primary breast carcinomas, various sites of DNA mutation, deletion or amplification have been reported in the q12-q21 region of the chromosome 17 (Kirchweger et al., *Intl. J. Cancer* 56:13–19 (1994); Futreal et al., *Science* 266:120–122 (1994); Guan, X. Y. et al., *Nat. Genet.* 8:155–161 (1994)). In this context, MLN 64, which is located in q12-q21 region of the chromosome 17 and amplified and overexpressed in breast cancer cell lines, may be involved in molecular processes leading to breast cancer development and/or progression.

In the present Example, we characterized the MLN 64 cDNA, protein and gene organization, and investigated the MLN 64 gene expression in a panel of normal and malignant human tissues.

Materials and Methods

Tissue and Cell Line Collections

Depending on subsequent analysis, tissues were either immediately frozen in liquid nitrogen (RNA extraction), or fixed in formaldehyde and paraffin embedded (in situ hybridization and immunohistology). Frozen tissues were stored at −80° C. whereas paraffin-embedded tissues were stored at 4° C.

The mean age of the 39 patients included in the present study was 55 years. The main characteristics of the breast carcinomas were as followed: SBR grade I (13%), grade II (38%), grade III (49%); estradiol receptor positive (25%), negative (75%); lymph nodes without invasion (39%), with invasion (61%).

RNA Isolation and Analysis

Total RNA prepared by a single-step method using guanidinium isothiocyanate (Chomczynski, P. & Sacchi, N.,*Anal. Biochem.* 162:156–159 (1987)) was fractionated by agarose gel electrophoresis (1%) in the presence of formaldehyde. After transfer, RNA was immobilized by heating (12 hrs, 80° C.). Filters (Hybond N; Amersham Corp.) were acidified (10 min, 5% $CH_3COOH$) and stained (10 min, 0.004% methylene blue, 0.5M $CH_3COONa$, pH 5.0) prior to hybridization.

The MLN 64 probe described in Example 1 corresponding to the full-length human cDNA (nucleotides 1–2008), cloned into pBluescript II SK-vector (Stratagene) was $^{32}P$-labeled using random priming (~10 $^6$cpm/ng DNA) (Feinberg, A. P. & Vogelstein, B., *Anal. Biochem.* 137:266–267 (1984)). Filters were prehybridized for 2 hrs at 42° C. in 50% formamide, 5× SSC, 0.1% SDS, 0.5% PVP, 0.5% Ficoll, 50 mM sodium pyrophosphate, 1% glycine, 500 μg/ml of ssDNA. Hybridization was for 18 hrs under stringent conditions (50% formamide, 5× SSC, 0.1% SDS, 0.1% PVP, 0.1% Ficoll, 20 mM sodium pyrophosphate, 10% dextran sulfate, 100 μg/ml ssDNA; 42° C.). Filters were washed 30 min in 2× SSC, 0.1% SDS at room temperature, followed by 30 min in 0.1% SSC, 0.1% SDS at 55° C. After dehybridization, filters were rehybridized with a c-erbB-2 specific probe. The 36B4 probe (Masiakowski, P. et al., *Nucleic S Acids Res.* 10:7895–7903 (1982)) was used as positive internal control. Autoradiography was for 2 days for hybridizations of MLN 64 and c-erbB-2 whereas 36B4 hybridization was exposed for 16 hrs.

Genomic DNA Isolation and Analysis

Genomic DNAs (10 mg) from human leucocytes and from monkey, pig, rabbit, rat, hamster, mouse, chicken, fly and worm were digested with EcoR1 or TaqI, fractionated by agarose gel electrophoresis (0.8%), and transferred to nylon membranes (Hybond $N^+$, Amersham Corp.). The hybridization conditions for Southern blots were identical to those previously described for Northern blots.

Preparation of Monoclonal Antibodies and Immunohistochemistry

The synthetic peptide PC94 corresponding to 16 AA (amino acid(s)) located in the C-terminal part of the putative MLN64 protein (FIG. 16) was synthesized in solid phase using Fmoc chemistry (Model 43 1A peptide synthesizer, Applied Biosystems, Inc., Foster City, Calif.), verified by amino acid analysis (Model 420A-920A-130A analyzer system; Applied Biosystems, Inc.) and coupled to ovalbumin (Sigma Chemical Co., St. Louis, Mo.) through an additional NH2-extraterminal cysteine residue, using the bifunctional reagent MBS (Aldrich Chemical Co., Milwaukee, Wis.).

Two 8-weeks-old female BALB/c mice were injected intraperitoneally with 100 μg of coupled antigen every two weeks until obtention of positive antisera. Four days before the fusion, the mice received a booster injection of antigen (100 μg), and then 10 μg intravenous and 10 μg intraperitoneal route every day until spleen removal. The spleen cells were fused with Sp2/0-Ag14 myeloma cells according to St. Groth & Scheidegger, *J. Immunol. Meth.* 35:1–21 (1980). Culture supernatants were screened by ELISA using the unconjugated peptide as antigen. Positive culture media were then tested by immunocytofluorescence and Western blot analysis on MLN64 cDNA transfected COS-1 cells. Five hybridomas, found to secrete antibodies specifically recognizing MLN 64, were cloned twice on soft agar. They all corresponded to IgG1, k subclass of immunoglobulins (Isotyping kit, Amersham Corp.).

Immunohistochemical analysis was performed as previously described (Rio, M. C. et al., *Proc. Natl. Acad Sci. USA* 84:9243–9247 (1987)) using paraffin-embedded tissue sections. Hybridoma supernatant was diluted 2-fold and a peroxidase-antiperoxidase system (DAKO, Carpinteria, Calif.) was used for the revelation.

In Situ Hybridization

In situ hybridization was performed using a $^{35}S$-labeled antisense RNA probe ($5\times10^8$ cpm/μg) specific of the human MLN 64 cDNA. Formaldehyde-fixed paraffin-embedded tissue sections (6 μm thick) were deparaffined in LMR, rehydrated and digested with proteinase K (1 μg/ml; 30 min, 37° C.). Hybridization was for 18 hrs, followed by RNase treatment (20 μg/ml ; 30 min, 37° C.) and stringently washed twice (2× SSC, 50% formamide; 60° C., 2 hrs). Autoradiography was for 2 to 4 weeks using NTB2 emulsion (Kodak). After exposure, the slides were developed and counterstained using toluidine-blue. $^{35}S$-labeled sense transcript from MLN 64 was tested in parallel as a negative control.

MLN 64 Genomic DNA Cloning

Fifty μg of human genomic DNA was partially digested with Sau3A. After size selection on a 10–30% sucrose gradient, inserts (16–20 kb) were subcloned at the BamHI replacement site in lambda EMBL 301 (Lathe, R. et al., *Gene* 57:13–201 (1987)). $2.5\times10^6$ recombinant clones were obtained and the library was amplified once. One million pfu were analyzed in duplicate for the presence of genomic MLN 64 DNA, using a 5' and a 3' end specific MLN 64 probes. The 5' probe was obtained using amplified DNA fragment (nucleotides 1 to 81) and the 3' probe corresponded to an EcoR1 fragment encompassing MLN 64 XYZbp (nucleotides 60 to 2073). Ten and 18 clones gave a positive signal with the 5' and 3' probe, respectively. After a second screening, 4 clones, hybridizing with the two probes, were subcloned into pBluescript 11 SK- vector (Stratagene), sequenced and positioned with respect to the MLN 64 cDNA sequence.

RT-PCR - Sequencing Reactions

MLN 64 cDNA clones and genomic subclones prepared as described (Zhou, C. et al., *Biotechniques* 8:172–173 (1990)) were further purified with RNaseA treatment (10 μg/ml; 30 min, 37° C.) followed by PEG/NaCl precipitation (0.57 vol., 20%, 2 M) and ethanol washing. Vacuum dried pellets were resuspended at 200 ng/μl in TE. Double-stranded DNA templates were then sequenced with Taq polymerase, using either pBluescript universal primers and/or internal primers, and dye-labeled ddNTPs for detection on an Applied Biosystems 373A automated sequencer.

Computer analysis

Sequence analyses were performed using the GCG sequence analysis package (Wisconsin Package, version 8, Genetic Computer Group). The MLN 64 cDNA sequence and its deduced protein were used to search the complete combined GenBank/EMBL databases and the complete SwissProt database respectively, with BLAST (Altschul, S. F. et al., *J. Mol. Biol.* 215:403410 (1990)) and FastA (Pearson, W. R. & Lipman, D. J., *Proc. Natl. Acad Sci. USA* 85:2444–2448 (1988)) programs.

Results

Determination of Human MLN 64 cDNA and Putative Protein Sequences

The complete MLN 64 cDNA sequence has been established from six independent cDNAs, coming from a tissular cDNA library constructed using human metastatic axillary lymph nodes (Example 1). For each clone, both sense and antisense strands have been sequenced. The full-length MLN 64 cDNA contained 2073 bp (FIG. 16) (SEQ ID NO:5). The first ATG codon (nucleotides 169–171) had the most favorable context for initiation of translation (Kozak, M., *Nucl. Acids Res.* 15:8125–8148 (1987)), and an AAT-TAAA poly(A) addition signal sequence (nucleotides 2050–2056 of SEQ ID NO:5) (Wahle, E. & Keller, W., *Annu. Rev. Biochem.* 61:41–40 (1992)) was located 24 bp upstream of the poly(A) stretch. Thus, the open reading frame encodes a 445 amino acid (AA) protein (FIG. 16) (SEQ ID NO:6), with a molecular weight of 50 KD and a pHi of 8.2. DNA database searches reveal homology with various human expressed sequence tags (ESTs) identified in libraries established using either adult (heart), postnatal (brain) or embryo (placenta, liver, spleen and brain). Moreover, 75% homology was observed with the cDNA sequence (606 bp) of the clone p10.15, recently identified through differential screening of a rat osteosarcoma cell line cDNA library (Waye & Li *J. Cell Biochem.* 54:273–280 (1994)), suggesting that MLN 64 could correspond to the human homolog of the rat p10.15.

Surprisingly, protein alignment revealed that the homology between the two putative proteins was restricted to the last 21 C-terminal AA of MLN 64 which were identical to 21AA located at the core of the p10.15 protein (Waye & Li, *J. Cell Biochem.* 54:273–280 (1994)). A careful examination of both putative proteins has been performed and showed that they result from different open reading frames including only 21 codons in common (Waye & Li, *J. Cell Biochem.* 54:273–280 (1994s). MLN 64 exhibited 29% identity and 55% similarity with the *Caenorhabditis elegans* U12964 putative protein of unknown function (Waterston R., direct submission). The putative MLN 64 protein analysis showed potential sites (reviewed in, Kemp, B. E. & Pearson, R. B., *Trends Biochem. Sci.* 15:342–346 (1990)) specific of N-glycosylation (NESD, residues 219–222; NKTV, residues 311–314; both of FIG. 16, SEQ ID NO:6), phosphorylation by casein kinase II (SFFD, residues 94–97; SPPE, residues 209–212; SDNE, residues 217–220; SDEE, residues 221–224; SAQE, residues 232–235; SPRD, residues 343–346; TMFE, residues 426429; all of FIG. 16, SEQ ID NO:6), protein kinase C (SPR, residues 343–345; SAK, residues 370–372; THK, residues 375–377; all of FIG. 16, SEQ ID NO:6), amidation (AGKK, residues 226–229; FIG. 6, SEQ ID NO:6). Moreover, structural analysis revealed two potential transmembrane domains (residues 1–72 and 94–168 of FIG. 16, SEQ ID NO:6). MLN 64 amino acid composition showed 11.5% of aromatic residues (Phe, Trp and Tyr) and 26% of aliphatic residues (Leu, Ile, Val and Met). A careful examination of spacing of these aliphatic residues has been performed in order to detect a possible ordonnance of them. The Leu residues are principally distributed in the 200 N-terminal AA (37 Leu), between AA285 and AA328 (7Leu/43AA) and AA406 and AA441 (7Leu/35AA). No consensus leucine zipper (reviewed in, Busch & Sassone-Corsi, *Trends Genet.* 6:36–40 (1990)) nor leucine-rich repeats (Kobe & Deiserhofer, *Trends Biochem. Sci.* 11:415421 (1994)) could be drawn.

MLN 64 variants

The tissular cDNA library was constructed using metastatic axillary lymph nodes coming from four distinct patients. Six independent MLN 64 (SEQ ID NO:5) cDNAs have been cloned from this library and sequenced. We observed a high degree of variability between their sequences. Thus, we observed two substitutions, of a C to T (nucleotide 262) and A to G (nucleotide 518), changing Leu to Phe (AA32) and Gln to Arg (AA117), respectively (Table VI, variants A and B). Another cDNA presented a 99 bp deletion (nucleotides 716–814) leading to the deletion of 33 AA (AA184-AA216) and to a 412 AA putative protein (Table VI, variant C). Finally, one clone exhibited a 51 bp insertion (between nucleotides 963–964) generating a stop codon 48 bp downstream of the insertion site and giving rise to a 281 AA chimeric C-terminal truncated protein containing 16 aberrant AAs at its C-terminal part (Table VI, variant D). These results showed that, at least 4 modifications occur in the MLN 64 open reading frame. Since genes exhibiting genetic and epigenetic DNA alterations leading to protein modifications and presumably to loss of function could play a role in transformation and/or cancer progression (Joensen et al., *Amer. J Pathol.* 143:867–874 (1993); Katagiri et al., *Cytogenet. Cell Genet.* 68:3944 (1995)) and in order to avoid the possibility that the observed variations result from cDNA library artifacts, we decided to redone MLN 64 cDNAs from a second library established using SKBR3 breast cancer cell line (unpublished data).

Twenty-five new MLN 64 cDNAs were cloned and MLN 64 specific primers were designed in order to identify, using PCR, the presence of insertion/deletion variants identical to those previously isolated from the tissular library. Among the 25 clones, 6 showed modified sizes consistent with already identified deletion/insertion events whereas the 19 remaining clones showed a size identical to that of the wild type MLN 64 cDNA (data not shown). Sequence analyses of the 6 variant clones showed that they all contained a C at nucleotide 262 position and an A to G substitution at nucleotide 518 position (Table VI variant B), suggesting that single nucleotide variations observed in the MLN 64 clones isolated from the tissular library could correspond to individual polymorphism since the library was established using tissues from 4 patients. Four clones presented a 99 bp deletion (nucleotides 716–814), a modification previously observed in cDNAs cloned from the metastatic library (Table VI, variant C). In addition to the 99 bp deletion, one clone exhibited a 13 bp deletion (nucleotides 531–543) generating a frameshift and giving rise to a 247 AA chimeric C-terminal truncated protein containing the 121 N-terminal AAs of MLN 64 and 126 aberrant AAs at the C-terminal part (Table VI, variant F). A 657 bp insertion (between nucleotides 963 and 964) was observed in another clone which results in a 285 AA C-truncated protein (Table VI, variant E). The remaining clone showed three modifications, a 137 bp deletion (nucleotides 115–251) leading to the loss of the initiating ATG codon, the already described 13 bp deletion (nucleotides 531–543) and a 199 bp insertion (downstream nucleotide 715). Since the first potential ATG codon is located at nucleotides 1087 to 1089, this clone could possibly encode a N-terminal truncated protein containing the 139 C-terminal AA of the MLN 64 (Table VI, variant G). Thus, in addition to the variants previously observed in the tissular cDNA library, we observed 3 novel MLN 64 variants in the cellular cDNA library. All studied clones presented a polyA+ excluding the possibility that insertions could correspond to unspliced pre-messenger RNAs. The identification of 2 identical variants (Table VI variants B and C) isolated from the 2 distinct libraries, showed that they are not due to cDNA library artefacts but to cDNA modifications specific of the MLN 64 gene. The putative nonsense protein sequences present in variants D, E and F showed no homology with already known protein sequences contained in databases.

In order to determine if these variants were specific of malignancy and since MLN 64 was expressed in placenta (see, infra), we used a human cDNA placenta library (J. M. Garnier, unpublished data) to search for variants using the same PCR protocol as for the previously described SKBR3 library screening. Nine independent clones have been identified and checked for alternative splicing events. The incidence of variants was lower than in transformed tissues since only one variant corresponding to the insertion of 199 bp, already identified in malignant tissue, was found.

MLN 64 Gene Organization

A human leukocyte genomic library was screened using two probes corresponding to nucleotides 1–81 (FIG. 16; SEQ ID NO:5) obtained by PCR amplification and to the almost full-length MLN 64 cDNA (nucleotides 60–2073), respectively (see Materials and Methods). One hundred and six clones were hybridized, leading to the obtention of a positive signal with one of the two probes. No clones showed simultaneous hybridization with both probes. Four clones hybridized with the smallest probe. They all contained a 6 kb insert which was sequenced using internal primers in order to determine the exon/intron boundaries. Four other clones hybridized to the longest probe. BamHI digestion of the inserts gave two fragments (3.5 and 6 kb) which were subcloned and sequenced using various primers in order to map splicing sites. The sizes of the introns were estimated by sequencing or PCR amplification of genomic subclones using primers located within the cDNA and at exon boundaries. The human MLN 64 gene whose total length was approximately 20 kb, was found to be split into 15 exons (FIG. 17 and Table VII (exon/intron Nos. 1–14 corresponding to SEQ ID NOS:58–71)). Exon 1 and part of exons 2 and 15 contain 5' and 3' untranslated regions of the MLN 64 gene. Translated cDNA sequence starts at nucleotide 55 of exon 2. Intron/exon boundaries analysis showed that the 5' splice donor sequences related to exons 2 (SEQ ID NO: 59), 3 (SEQ ID NO:60), 4 (SEQ ID NO:61), 6 (SEQ ID NO:63), 9 (SEQ ID NO:66) and 13 (SEQ ID NO:70), and the 3' splice acceptor sequences related to exons 2 (SEQ ID NO:59), 3 (SEQ ID NO:60), 6 (SEQ ID NO:63), 11 (SEQ ID NO:68) and 12 (SEQ ID NO:69) did not correspond to the canonical splice consensus sequence (Breathnach, R. & Chambon, P., *Annu. Rev. Biochem.* 50:349–383 (1981)) (Table VII).

Figure 17:
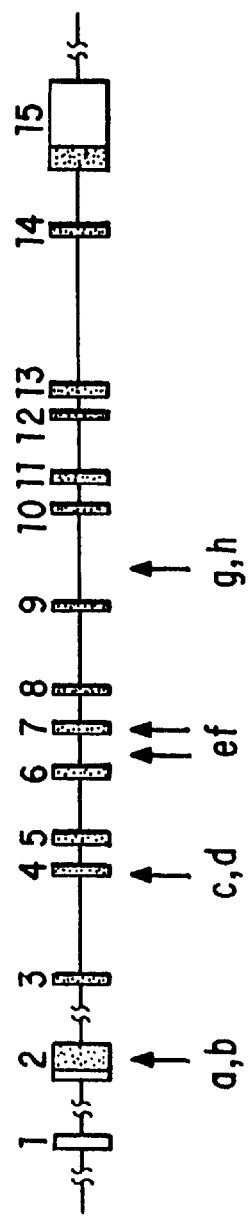
FIG. 17. Organization of the Human MLN 64 Gene and Protein. Schematic representation of the MLN 64 gene exon/intron organization. Exons are numbered from 1 to 15 (hatched and open boxes for coding and noncoding exons, respectively). Arrows indicate the nucleotide substitution, exon deletion and intron insertion sites (a: exon 2, C/T substitution, b: exon 2, 137 bp 5' end deletion, c: exon 4, A/G substitution, d: exon 4, 13 bp 3' end deletion, e: intron 6, 199 bp 5' end insertion, f: complete exon 7 deletion, g and h: intron 9, 51 bp and 657 bp 5' end insertion).

The cDNA modifications leading to the protein variants were all distributed from exon 2 to intron 9. Single nucleotide substitutions were observed in exon 2 and 4 (FIGS. 17, *a* and *c*). The 137 bp and 13 bp deletions occurred at the 5' end of the exon 2 (FIG. 17, *b*) and at the 3' end of the exon 4 (FIG. 17, *d*), respectively. The 99 bp deletion concerned the entire exon 7 (FIG. 17, *f*). The 199 bp insertion corresponded to the 5' end of the intron 6 (FIG. 17, *e*), and the 51 bp or 657 bp insertions to the 5' end or to the entire intron 9 (FIGS. 17, *g* and *h*). Thus, the deletion/insertion events occurred at the boundaries of intron I/exon 2 (SEQ ID NO:58/SEQ ID NO:59), exon 4/intron 4 (SEQ ID NO:61, exon 6/intron 6 (SEQ ID NO:63), intron 6/exon 7 (SEQ ID NO:63/SEQ ID NO:64) and exon 9/intron 9 (SEQ ID NO:66), presumably due to the low degree of conservation of these splicing sites (Table VII).

Moreover, we looked for the conservation of MLN 64 gene, using a zooblot containing either EcoRI or BamHI digested genomic DNAs from worms, fly, hamster, mouse, rat, pig and human. MLN 64 cDNA hybridization gave faint and strong signals with invertebrates and vertebrates, respectively (data not shown), indicating that MLN 64 is well conserved throughout evolution suggesting an important function for this protein.

MLN 64 is Overexpressed in Human Malignant Tissues

Figure 18:
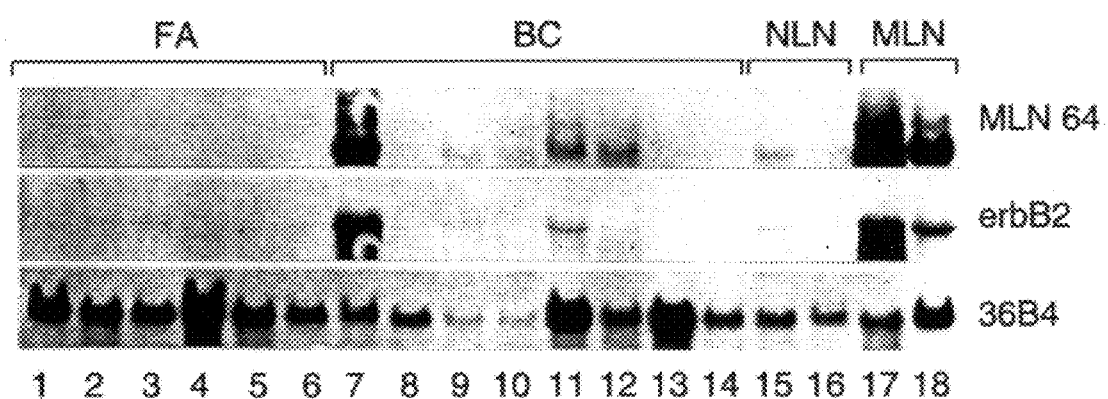
FIG. 18. Northern Blot Analysis of MLN 64 mRNA in Human Breast Fibroadenomas, Carcinomas and Lymph Node Metastases. Each lane contained 10 μg of total RNA. From left to right, RNA samples from breast fibroadenomas (lanes 1–6), carcinomas (lanes 7–14), normal lymph nodes (lanes 15 and 16) and metastatic lymph nodes (lanes 17 and 18) are loaded. Hybridization was carried out using $^{32}$P cDNA probe for MLN 64. A 2000-base long MLN 64 transcript is expressed, at various levels, in some carcinomas (lanes 6, 10 and 11), and in the metastatic samples (lanes 16 and 17). The same pattern of expression was observed using an erbB-2 probe. The 36B4 probe (Masiakowski, P. et al., Nucl. Acids Res. 10:7895–7903 (1982)) was used as positive internal control. Autoradiography was for 2 days for hybridization of MLN 64 and erbB-2, whereas 36B4 hybridization was exposed for 16 hrs.
Figure 19A:
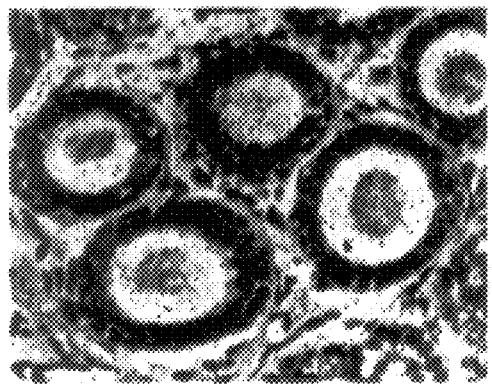
FIG. 19. In Situ Hybridization of MLN 64 mRNA in Human Breast Carcinoma and Axillary Lymph Node Metastasis. Sections of normal breast (A), in situ carcinoma (C), invasive carcinoma (B) and metastatic lymph node (D) were hybridized with antisense $^{35}$S RNA probe specific for MLN 64. MLN 64 is strongly expressed in the tumoral epithelial cells, whereas the stromal part of the tumor is totally negative (B). MLN 64 transcripts are homogeneously distributed throughout the positive areas (B–D). Normal ducts are devoid of MLN 64 signal (A). No significant labeling above background was found when using sense human MLN 64 RNA probe (data not shown). Bright field (A–D).
Figure 19B:
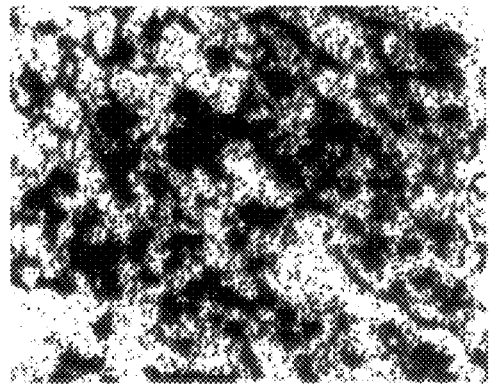
Figure 19C:
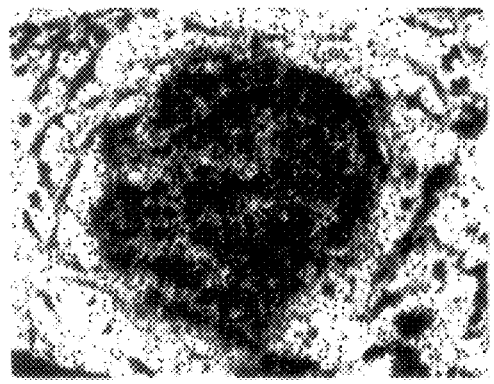
Figure 19D:
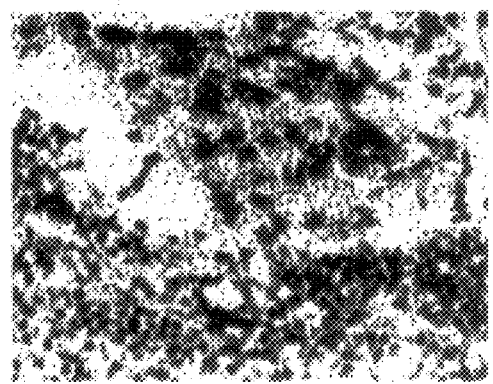
Figure 20A:
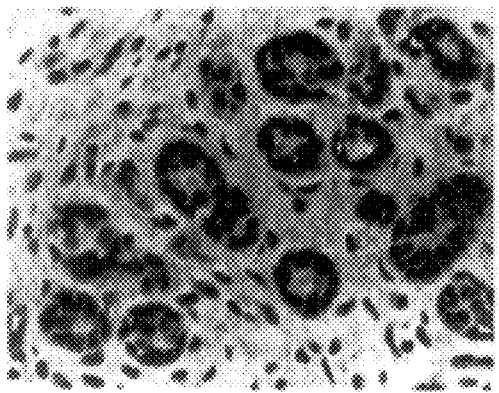
FIG. 20. Immunohistochemistry of Human Breast Carcinoma and Axillary Lymph Node Metastasis. Sections of normal breast (A), in situ carcinoma (C), invasive carcinoma (B) and metastatic lymph node (D) were studied for the presence of MLN 64 protein, using a monoclonal antibody (see Materials and Methods). MLN 64 is strongly expressed in the tumoral epithelial cells, whereas the stromal part of the tumor is totally negative (B). MLN 64 protein was located in cytoplasmic bundles like structures (B–D). Normal ducts are devoid of MLN 64 staining (A).
Figure 20B:
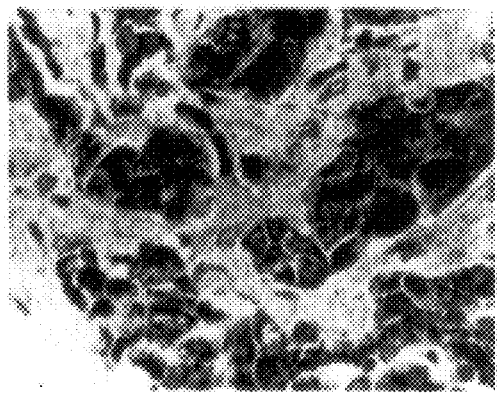
Figure 20C:
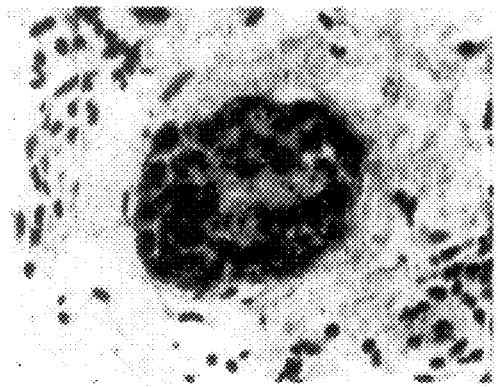
Figure 20D:
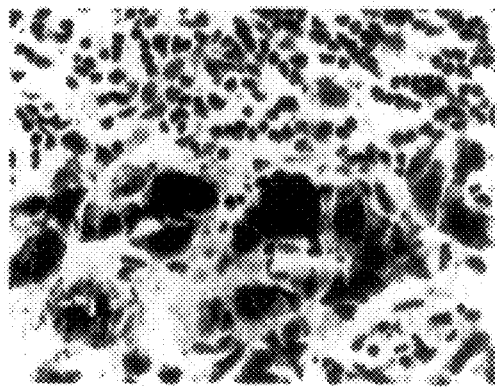

Northern blot hybridization with the MLN 64 cDNA probe (see Materials and Methods) gave a positive signal corresponding to MLN 64 transcripts with an apparent molecular weight of 2 kb (FIG. 18, lanes 11, 12, 17, 18 and data not shown). Moreover, a longer transcript of 3 kb was also detected in samples which contain the higher amount of the 2 kb transcripts (FIG. 18, lanes 7, 17, 18 and data not shown). After longer autoradiography, two additional species of mRNA became visible. Polyadenylated RNA extracted from BT474 cell line exhibited identical pattern of hybridization (data not shown).

Using Northern blot analysis, MLN 64 overexpression was observed in malignant tumors of breast (14/93 cases), brain (2/3 cases), lung (2/23 cases) whereas colon (4 cases), intestine (1 case), skin (5 cases), thyroid (2 cases) and head and neck (25 cases) were negative ((FIG. 18, lanes 7, 11, 12, and data not shown). Moreover, metastatic lymph nodes derived from breast (2/6 cases), liver (1/2 cases) and head and neck (1/16 cases) cancers expressed MLN 64, whereas those from skin (7 cases), lymphoma (3 cases) and kidney (1 case) cancers were MLN 64 negative (FIG. 18, lanes 17, 18, and data not shown). Three liver metastes derived from breast cancer (1/1 case) and colon cancer (2/7 cases) also expressed the MLN 64 whereas one skin and one epiploon metastases derived from breast and ovary cancer, respectively, did not (data not shown). No MLN 64 transcripts were observed in normal human breast, axillary lymph node, stomach, colon, liver and kidney, whereas faint signal was observed in skin, lung, head and neck epidermoid tissues and placenta (FIG. 18, lanes 15 and 16 and data not shown). Moreover, the breast fibroadenomas (13 cases studied), which are benign tumors, did not show MLN 64 expression above the basal level (FIG. 18, lanes 1–6). Altogether, these results showed that MLN 64 could be overexpressed in the primary tumors or metastases of a wide panel of tissues including breast, colon, liver, lung, brain and head and neck. Nevertheless, the level of MLN 64 overexpression observed in carcinomas of breast origin was 3–5 fold higher than in cancer of other tissues.

Since in breast cancer cell lines, the MLN 64 overexpression was always correlated with those of the erbB-2 oncogene, successive hybridizations of the same filters with a c-erbB-2 cDNA probe have been performed. In all MLN 64 positive malignant tissues, we observed an overexpression of the erbB-2 oncogene (FIG. 18, lanes 6, 10, 11, 16 and 17, and data not shown). Thus, as in cell lines, the two genes were co-expressed in vivo.

MLN 64 Expression is Restricted to Malignant Epithelial Cells

In situ hybridization, using an antisense MLN 64 RNA probe, was performed on primary breast carcinomas and axillary lymph node metastases. MLN 64 was expressed in the malignant epithelial cells, in in situ (FIG. 19) and invasive (FIG. 19) carcinomas, whereas tumor stromal cells were negative. MLN 64 transcipts were homogeneously distributed among the positive areas. Normal epithelial cells did not express the MLN 64 gene, even when located at the proximity of invasive carcinomatous areas (FIG. 19 and data not shown). A similar pattern of MLN 64 gene expression was observed in metastatic axillary lymph nodes from breast cancer patients with expression limited to cancer cells whereas noninvolved lymph node areas were negative (FIG. 19 and data not shown).

Using monoclonal antibody directed against a MLN 64 synthetic peptide (see Materials and Methods), breast carcinoma immunohistochemical analysis showed MLN 64 staining restricted to the transformed epithelial cells. Moreover, the MLN 64 protein showed a particular distribution with cytoplasmic condensation sites, suggesting an organite localization for MLN 64 (FIG. 20). Identical pattern was observed using the BT474 breast cancer cell line (FIG. 20).

Discussion

In the present Example, we characterized the MLN 64 cDNA and its corresponding protein. In Example 1 above, MLN 64 cDNA was identified by differential screening of a breast cancer metastatic lymph node cDNA library. The MLN 64 protein which contains 445 AA, showed two potential transmembrane domains and several potential leucine zipper and leucine-rich repeat structures previously identified in a number of diverse proteins involved in protein-protein interaction and signal transduction (Busch & Sassone-Corsi, *Genet.* 6:36–40 (1990); Kobe & Deisenhofer, *Trends. Biochem. Sci.* 11:415–421 (1994)). Although the MLN 64 cDNA presented a high degree of homology with the rat p10.15 cDNA, no homology was observed between the two predicted proteins with the exception of 21 AA (Waye & Li, *J. Cell. Biochem.* 54:273–280 (1994)). The highest degree of homology was for the *Caenorhabditis elegans* U12964 putative protein of unknown function.

MLN 64 gene contains 15 exons and the coding region encompasses from the 3' end of the exon 2 to the 5' end of the exon 15. In Example 1 above, we observed that no obvious rearrangements, insertions or deletions affected the MLN 64 gene in a panel of breast cancer cell lines. In these cell lines, the MLN 64 gene expression was always correlated with MLN 64 gene amplification.

In the present Example, in breast cancer cell and/or tissue, we identified and characterized 7 distinct MLN 64 cDNAs, resulting from nucleotide substitutions, deletions and/or insertions. Interestingly, the cDNA modifications principally occurred at exon/intron boundaries, suggesting that the MLN 64 variants result from defective splicing processes. Consistently, almost all the concerned splicing site sequences were defective (Breathnach, R. & Chambon, P., *Annu. Rev. Biochem.* 50:349–383 (1981)).

Two variants lead to AA substitution and 5 variants encode N- or C-truncated MLN 64 proteins. In addition, 3 of them lead to chimeric proteins containing additive nonsense protein sequences of 16, 20 and 126 AA, respectively. Using RT-PCR, 1 MLN 64 mRNA containing the intron 6 sequence has been detected in placenta, showing that, at least in this case, MLN 64 alternative splicing was not a transformation specific event. It remains to be seen, using antibodies directed against appropriate epitopes, if all MLN 64 variant RNAs are effectively translated, specifically in cancerous-tissues and/or naturally occurring. In both physiological and/or pathological conditions, alternative splicing have been reported to occur in transcription of a panel of genes including those coding for the oestradiol receptor (Miksicek, *Semin. Cancer Biol.* 5:369–379 (1994) and refs. therein), the ubiquitous cell surface glycoprotein CD44 (Arch et al., *Science* 257:682–685 (1992); Joensen et al., *Amer. J Pathol.* 143:867–874 (1993)), the metalloprotease/disintegrin-like protein MDC (Katagiri et al., *Cytogenet. Cell Genet.* 68:39–44 (1995)) and the tumor suppressor p53 (Han & Kulesz-Martin, *Nucl. Acids Res.* 20:179–181 (1992)). Although the biological significance of these variants was not always well established, their presence in transformed tissues is usually associated with a poor prognosis and a high metastatic potentiality (Miksicek, *Semin. Cancer Biol.* 5:369–379 (1994).

Using Northern blots, we observed two major messenger sizes at 2 kb consistent with the wild type ARNm, and at 3 kb, only observed in the tissues highly expressing the 2 kb mRNA. Human normal skin, lung, head and neck and placenta expressed MLN 64 at a low level, whereas breast, lymph nodes, stomach, colon, liver, kidney and breast fibroadenomas did not. Interestingly, skin, lung and head and neck are all epidermoid tissues, suggesting that MLN 64 protein could play a physiological role in tissues of this origin. MLN 64 was overexpressed in breast, colon, brain, liver, lung, and head and neck primary malignant tumors and/or metastases, the highest level of expression being observed in breast malignant tissues. Thus, MLN 64 which is observed in a wide panel of transformed tissues, should be involved in basic process occurring in carcinogenesis and/or tumoral progression.

In both breast primary tumor and metastasis, MLN 64 transcripts were homogeneously distributed throughout the carcinomatous areas, whereas normal tissues were negative. Moreover, MLN 64 is expressed in in situ tumors, suggesting that it may be involved in precocious events leading to tumor invasion. Monoclonal antibody, directed against a C-terminally located MLN 64 synthetic peptide, permitted us to localize the MLN 64 protein in vesicle-like structures in the cytoplasm of the malignant epithelial cells. Using Western blot, MLN 64 was found in both BT474 cell and culture medium extracts. Thus, despite the absence of a hydrophobic secretion signal at the N-terminal part of the molecule, the MLN 64 is probably translocated across the endoplasmic reticulum membrane via a nonclassical mechanism. The MLN 64 positive bundles also contain F-actine, suggesting that MLN 64 is related to the cytoskeleton of the transformed cells, possibly to podosomes. Podosomes are close contact cell-adhesive structures regarded as a key structure in invasive processes.

We showed in Example 1 that, in breast cancer cell lines, MLN 64 overexpression is correlated with MLN 64 gene amplification and with oncogene erbB-2 amplification suggesting that both genes, which are co-localized in q12-q21 on the long arm of the chromosome 17, belong to the same amplicon. Consistently, we have now observed, in vivo, a coexpression of the two genes. erbB-2 amplification is one of the most common genetic alteration occurring in breast carcinomas (reviewed in, Devilee & Cornelisse *Biochim. Biophys. Acta* 118:113–130 (1994) and refs. therein) and is associated with a poor prognosis (Slamon, D. J. et al., *Science* 244:707–712 (1989); Muss, H. B. et al., *N. Engl. J Med.* 330:1260–1266 (1994)). It is currently admitted that gene amplification/overexpression confers a preferential growth to the cells and concerned the oncogenes (Schwab, M. & Amler, L., *Genes. Chrom. Cancer* 1:181–193 (1990); Kallioniemi, A. et al., *Proc. Natl. Acad Sci. USA* 91:2156–2160 (1994)), whereas, the variants resulting in dramatic modification of the protein permit a growth of the cells by inactivation of proteins including tumor suppressor genes (Kulesz-Martin et al., *Mol. Cell Biol* 14:1698–1708 (1994); Katagiri et al., *Cytogenet. Cell Genet.* 68:39–44 (1995)). In this context, it may be paradoxical that the MLN 64 gene which is amplified showed numerous variant species. What could be the efficiency of amplification if the product of the target amplified gene is defective? Whatever the mechanism(s), since genes showing amplification leading to overexpression or alternative splicing leading to defective proteins (Miksicek, *Semin. Cancer Biol.* 5:369–379 (1994)) are most often strongly related to cancerous processes, our results suggest that MLN 64 may participate in carcinogenesis and/or tumor progression. Since it has recently been proposed that the oncogenic properties of erbB-2 could be increased by the overexpression of downstream signaling molecules possibly co-localized on the chromosome 17, such as GRB7, it is tempting to speculate that MLN 64 could be involved in the erbB-2 signaling pathway.

TABLE VI

MLN 64 Variants in SKBR3 and Metastatic Breast Cancer cDNA Libraries

| Variant | Nucleotide | Nucleotide change | Gene location | Coding effect | Putative variant protein | Incidence in library Tissular | Cellular |
|---|---|---|---|---|---|---|---|
| A | 262 (SEQ ID NO: 5) | CTC-->TTC | exon 2 | missense | AA 32: substitution Leu/Phe | 1/6 | 0/6 |
| B | 518 (SEQ ID NO: 5) | CAG-->CGG | exon 4 | missense | AA 117: substitution Gln/Arg | 1/6 | 6/6 |
| C | 715 (SEQ ID NO: 5) | 99 bp deletion | exon 7 | deletion | 412 AA: 184–216 deletion | 1/6 | 3/6 |
| D | 963 (SEQ ID NO: 5) | 51 bp insertion | intron 9 | nonsense | 281 AA: C-truncated 16 nonsense AA | 1/6 | 0/6 |
| E | 963 (SEQ ID NO: 5) | 657 bp insertion | intron 9 | nonsense | 285 AA: C-truncated 20 nonsense AA | 0/6 | 1/6 |
| F | 530 (SEQ ID NO: 5) 715 (SEQ ID NO: 5) | 13 bp deletion 99 bp deletion | exon 4 exon 7 | frameshift | 247 AA: C-truncated 126 nonsense AA | 0/6 | 1/6 |
| G | 114 (SEQ ID NO: 5) 530 (SEQ ID NO: 5) 715 (SEQ ID NO: 5) | 137 bp deletion 13 bp deletion 199 bp insertion | exon 2 exon 4 intron 6 | deletion | 139 AA: N-truncated | 0/6 | 1/6 |

TABLE VII

Exon/Intron Organization of the MLN 64 Gene. Exon Sequences Are Indicated in Capital Letters, and Intron Sequences in Small Letters.

| EXON N° | size (bp) | 5' splice | donor | 3' splice | acceptor | INTRON N° | size (bp) | SEQ ID NO. |
|---|---|---|---|---|---|---|---|---|
| 1 | 114 | ATGGAG | .. | ..cgcccc | CAGCCC | 1 | >10000 | 58 |
| 2 | 273 | CTGAAT | gtgagt.. | ..tcacag | ACCACC | 2 | ⁻3000 | 59 |
| 3 | 78 | ATCTTT | gtgagt.. | ..caccag | GTCCTG | 3 | ⁻750 | 60 |
| 4 | 78 | ATTGCG | gtaaga.. | ..gggcag | GTCACG | 4 | 120 | 61 |
| 5 | 54 | TCTGAG | gtcagt.. | ..tcacag | CTGCTC | 5 | 378 | 62 |
| 6 | 118 | AGCGAT | gtgagt.. | ..ctccag | GGTATC | 6 | 199 | 63 |
| 7 | 99 | TTGCAG | gtgagg.. | ..ctgcag | GGTCTG | 7 | 230 | 64 |
| 8 | 56 | GGTCAG | gtattt.. | ..gtccag | GAGCGG | 8 | ⁻550 | 65 |
| 9 | 93 | AATAAT | gtaaga.. | ..ccatag | GAATAT | 9 | 657 | 66 |
| 10 | 63 | CTGAAG | gtgagt.. | ..tcccag | ACCTTC | 10 | 157 | 67 |
| 11 | 96 | TGCCAG | gtgagc.. | ..cctcag | ATCCTG | 11 | ⁻400 | 68 |
| 12 | 80 | CCCAAG | gtgagt.. | ..ccgcag | GGACTT | 12 | 91 | 69 |
| 13 | 105 | TGTCCG | gtgagc.. | ..ccatag | GGGAGA | 13 | ⁻1100 | 70 |
| 14 | 94 | CTCAAG | gtgggg.. | ..ccccag | GGCCGC | 14 | 460 | 71 |
| 15 | 672 | | | | | | | |

EXAMPLE 5

Definition of the D52 Gene/Protein Family through Cloning of a D52 Homolog, D53

Introduction

The human D52 (hD52) cDNA was cloned through differential screening of a breast carcinoma cDNA library (Byrne, J. A. et al., *Cancer Res.* 55:2896–2903 (1995)). The hD52 gene is overexpressed in approximately 40% of human breast carcinomas, where it is specifically expressed in the cancer cells. The hD52 locus has been mapped to chromosome 8q21, a region which is frequently amplified in breast carcinoma (Kallioniemi, A. et al., *Proc. Natl. Acad Sci. USA* 91:2156–2160 (1994); Muleris, M. et al., *Genes Chrom. Cancer* 10:160–170 (1994)), in cancers of the prostate (Cher, M. L. et al., *Genes Chrom. Cancer* 11:153–162 (1995)) and bladder (Kallioniemi, A. et al., *Genes Chrom. Cancer* 12: 213–219 (1995)), and in osteosarcoma (Tarkkanen, M. et al., *Cancer Res.* 55:1334–1338 (1995)). Accordingly, we noted hD52 gene amplification in the breast carcinoma cell line SK-BR-3 (Byrne, J. A. et al., *Cancer Res.* 55:2896–2903 (1995)), which has been previously reported to harbor a chromosome 8q21 amplification (Kallioniemi, A. et al., *Proc. Natl. Acad Sci. USA* 91:2156–2160 (1994)). The predicted hD52 amino acid sequence is highly novel, possessing very little homology with sequences thus far reported (Byme, J. A. et al., *Cancer Res.* 55:2896–2903 (1995)). Using the differential display technique (Liang, P. & Pardee, A. B., *Science* 257:967–971 (1992)), a hD52 cDNA (known as N8) was also recently cloned through its differential expression between normal and tumorous lung-derived cell lines.

Comparing the hD52 protein sequence with translated nucleotide sequences in genetic databases identified several expressed sequence tag (EST) sequences which when translated, showed 48 to 67% identity with 24 to 40 amino acid regions of the hD52 sequence. These sequences derived from human cDNA clones isolated from adult liver and fetal liver/spleen cDNA libraries by the Washington University-Merck EST project. Two such cDNA clones were provided by the IMAGE consortium at the Lawrence Livermore National Laboratory (Livermore, Calif.), and the insert of one was used to screen a breast carcinoma cDNA library. This allowed us to isolate a 1347 bp cDNA whose coding sequence predicts a 204 amino acid protein which is 52% identical to hD52. On the basis of this homology and similarities existing between putative domains in the 2 proteins, we have called this novel gene D53, and propose that this represents a second member of the D52 gene/protein family.

Materials and Methods cDNA Library Screening

Two cDNAs (clones 83289 and 116783, corresponding to GenBank Accession Nos. T68402 and T89899, respectively) were gifts from the IMAGE consortium at the Lawrence Livermore National Laboratory (Livermore, Calif.). The random-primed $^{32}$P-labeled insert of clone 116783 was used to screen 500,000 plaque forming units (pfus) from a breast carcinoma cDNA library (Byrne, J. A. et. al., *Cancer Res.* 55:2896–2903 (1995)) which had been transferred to duplicate nylon filters (Hybond N, Amersham Corp.). Screening was performed basically as previously described (Basset P. et al., *Nature* 348:699–704 (1990)), with identified λZAP II clones being replated at densities allowing the isolation of pure plaques, and submitted to secondary screening. Clone inserts were rescued in the form of pBluescript SK- plasmids using the in vivo excision system, according to the manufacturer's instructions (Stratagene).

For the isolation of mD52 cDNAs, a cDNA library was used which was constructed by C. Tomasetto (IGBMC, Illkirch, France) using polyA+ RNA isolated from apoptotic mouse mammary gland. OligodT-primed cDNAs were ligated with the ZAP-cDNA linker-adaptor, and cloned into the Uni-ZAp™ XR vector according to the manufacturer's protocol (Stratagene). A total of 850,000 pfus were screened using an EcoRI restriction fragment from the hD52 cDNA (containing 91 bp of 5'-UTR and 491 bp of coding sequence (Byrne, J. A. et al., *Cancer Res.* 55:2896–2903 (1995)) at reduced stringency, with final filter washes being performed using 2× SSC and 0.1% SDS at room temperature for 30 min. A single clone (F1) was identified. After purification and insert rescue using in vivo excision, the $^{32}$P-labeled F1 insert was used to rescreen the same cDNA library filters using the same conditions, in order to identify a full-length cDNA (clone C1).

DNA Sequencing

Mini-preparations of plasmid DNA which had been further purified by NaCl and polyethylene glycol 6000 precipitation were sequenced with Taq polymerase and either T3 and/or T7 universal primers, or internal primers, and dye-labeled ddNTPs for detection on an Applied Biosystems 373 A automated sequencer.

Sequence Analyses

Nucleic acid and amino acid sequence analyses were performed using the following programs available in the GCG sequence analysis package: BLAST and FastA, for sequence homology searches; gap, for further sequence alignments; Isoelectric, for the calculation of pI values; Motifs, for the identification of recognized protein motifs; and Pepcoil, for the identification of coiled-coil domains, according to the algorithm of Lupas, A. et al., *Science* 252:1162–1164 (1991). PEST sequences were assigned using the PEST-FIND algorithm (Rogers, S. et al., *Science* 234:364–368 (1986)), which was a gift from Dr. Martin Rechsteiner, University of Utah, U.S.A. Other predictions of secondary structure were performed using the MSEQ (Black, S. D. & Glorioso, J. C., *BioTech.* 4:448–460 (1986)), PHD (Rost, B. & Sander, C., *Proteins* 19:55–72 (1994)) and PSA (Stultz, C. M. et al., *Prot. Sci.* 2:305–314 (1993)) software.

Chromosomal Localization

Chromosomal localization of the hD53 gene was performed using chromosome preparations obtained from phytohemagglutinin stimulated lymphocytes. Cells were cultured for 72 hrs, with 60 μg/ml 5-bromodeoxyuridine having been added during the final 7 hrs of culture to ensure a posthybridization chromosomal banding of good quality. For the mD52 gene, in situ hybridization experiments were carried out using metaphase spreads from a WMP strain male mouse, in which all autosomes except 19 were in the form of metacentric Robertsonian translocations. The 116783 (hD53) clone containing an insert of 842 bp in a modified pT7T3D plasmid vector (Pharmacia), and the C1 (mD52) clone containing an insert of 2051 bp in pBluescript SK- (Stratagene), were $^3$H-labeled using nick-translation to final specific activities of 8×10$^7$ dpm/μg, and hybridized to metaphase spreads at final concentrations of 200 ng/ml (116783) and 100 ng/ml (C1) of hybridization solution as described (Mattei, M. G. et al., *Human Genet.* 69:268–271 (1985)). Autoradiography was performed using NTB2 emulsion (Kodak) for 21 days (116783) and 20 days (C1) at 4° C. To avoid any slippage of silver grains during the banding procedure, chromosome spreads were first stained with buffered Giemsa solution and the metaphases were photographed. R-banding was performed using the fluorochromephotolysis-Giemsa method and metaphases were rephotographed before analysis.

Cell Culture

BT-20, BT-474 and MCF7 breast carcinoma cell lines, and the leukemic cell lines HL-60 and K-562 are as described in the American Type Culture Collection catalogue (7th ed.). Cell culture media were for BT-20, MEM supplemented with 10% fetal calf serum (FCS), 2 mM pyruvate, 2 mM glutamine, 10 μg/ml insulin and 1% non-essential amino acids; for BT474, RPMI 1640 supplemented with 10% FCS, 2 mM glutamine, and 10 μg/ml insulin; for MCF7, DMEM supplemented with 10% FCS, and 0.6 μ/ml insulin; for HL60, RPMI 1640 supplemented with 10% FCS; and for K-562, RPMI 1640 supplemented with 10% heat-inactivated FCS and 2 mM glutamine. All cells were cultured in the presence of antibiotics (0.1 mg/ml streptomycin, 500 U/ml penicillin and 40 μg/ml gentamycin) at 37° C. with 5% $CO_2$/95% air in a humidified incubator.

For exaperiments in which breast carcinoma cell lines were cultured in the estradiol supplemented or depleted media, cells were seeded into four 75 $cm^2$ flasks at low density. These were cultured for one day before normal growth media were replaced (3 flasks) or not (one flask) by phenol red-free DMEM supplemented with 0.6 μg/ml insulin and 10% FCS which had been treated with dextran-coated charcoal to deplete endogenous steroids. Cells were cultured for 2 days in steroid-depleted media before this was supplemented (2 flasks), or not (one flask), with $10^{-8}$ M or $10^{-9}$ M estradiol. Cell culture was continued for 3 days, at which point cells were approaching confluency.

For experiments in which HL-60 and K-562 cells were induced to differentiate using 12-O-tetradecanoylphorbol-13-acetate (IPA), cells were diluted to a density of $2\times10^5$ cells/ml and 10 ml volumes were seeded into 85 mm diameter culture dishes. At the start of each experiment, one culture dish was immediately harvested for RNA extraction. Media were then supplemented, or not, with 16 nM or 160 nM TPA, and cells were cultured for periods of up to 48 hrs before harvest for RNA extraction.

RNA Extraction and Northern Blot Analyses

Human surgical specimens were obtained from the Hôpitaux Universitaires de Strasbourg, being frozen and stored in liquid nitrogen. Total RNA was isolated from tissues and cultured cells as previously described (Rasmussen, U. B. et al., *Cancer Res.* 53:40964101 (1993)). Northern analyses were performed with 10 μg of total RNA which were electrophoresed through 1.0% denaturing agarose gels and transferred to nylon filters (Hybond N, Amersham Corp.) using 20× SSC.

Northern hybridizations were performed using $^{32}$P-labeled inserts from the 116783 hD53 cDNA and the hD52 cDNA (Byrne, J. A. et al., *Cancer Res.* 55:2896–2903 (1995)). To verify the effectiveness of estrogen treatments in breast carcinoma cell lines, and of TPA treatments in leukemic cell lines, we also rehybridized filters with $^{32}$P-labeled cDNA inserts corresponding to the estrogen-inducible gene pS2 (Rio, M. C. et al., *Proc. Nail. Acad Sci. USA* 84:9243–9247 (1987)), and the transferrin receptor gene (Kuhn, L. C. et al., *Cell* 37:95–103 (1984)), in these respective cases. All filters were rehybridized with a $^{32}$P-labeled internal PstI fragment of the 36B4 cDNA (Masiakowski, P. et al., *Nucl. Acids Res.* 10:7895–7903 (1982)), representing a ubiquitously expressed gene. Hybridizations and washing steps were performed essentially as described (Basset, P. et al., *Nature* 348:699–704 (1990)).

Results

Isolation and Sequencing of the Human D53 cDNA

The existence of a hD52 homolog was originally predicted from 3 EST sequences (GenBank Accession Nos. T68402, T89899 and T93647) which when translated, showed 24–40 amino acid regions which were 48–67% identical with regions between amino acids 130–180 of hD52. These ESTs derived from human cDNA clones isolated from adult liver and fetal liver/spleen cDNA libraries by the Washington University-Merck EST project, and 2 of these cDNA clones (clones 83289 and 116783, corresponding to GenBank Accession Nos. T68402 and T89899, respectively) were kindly provided by the IMAGE consortium at the Lawrence Livermore National Laboratory. Sequencing of clones 83289 and 116783 in both directions indicated that they consist of 1626 bp and 842 bp, respectively (FIG. 24(A)). Within their regions of overlap (714 bp), their sequences were identical, except for a deletion of 100 bp in clone 83289 (corresponding to nucleotides 567–666, FIG. 24(B) (SEQ ID NO:9)), and a single T/G polymorphism at nucleotides 254 and 371 of clones 83289 and 116783, respectively (nucleotide 865, FIG. 24(B) (SEQ ID NO:9)).

Clones 83289 and 116783 were found to possess open reading frames extending from their 5'-ends, encoding 60 and 99 amino acids, respectively, and terminating with the same stop codon (FIG. 24(A)). However, because of the sequence deletion present in the 83289 clone, the first 18 amino acids of the 83289 amino acid sequence are frame-shifted with respect to those encoded by the corresponding DNA sequence of the 116783 clone. Thus, the first methionine residue present in the 116783 amino acid sequence ($Met^{128}$, FIG. 24(B) (SEQ ID NO:10), which is present in a moderately favorable context for translation initiation) is no longer in-frame in the 83289 amino acid sequence. For this reason, and also because the lengths of these apparently partial length cDNA clones did not correspond with the observed transcript size of 1.5 kb (see, infra), a breast carcinoma cDNA library was screened with the 116783 clone insert in order to isolate additional clones. The shorter 116783 clone was chosen for screening, because of the presence of an Alu sequence in the extended 83289 3'-UTR (FIG. 24(A)).

Of the 14 positive clones thus identified, 11 remained positive upon secondary screening, and of these, 2 (U1 and S1) possessed additional sequences at their 5' ends with respect to the 116783 sequence. The insert of the longest clone, U1, was sequenced in both directions. This indicated that the U1 clone possessed 494 additional bp with respect to the 5' extent of clone 116783, and that this sequence included a strong Kozak consensus sequence (nucleotides 175–184; FIG. 24(B); SEQ ID NO:9). Thus the U1 sequence was noted to consist of 180 bp of 5'-UTR, a coding sequence of 615 bp and a 3'-UTR of 552 bp, including a 22 bp polyA sequence. The hD52 and U1 coding sequences were found to be well conserved (62% identical) over much of their lengths, but the predicted 5'-UTRs were poorly conserved. It should be noted that as for hD52 (13Byrne, J. A. et al., *Cancer Res.* 55:2896–2903 (1995)), there is no in-frame stop codon present in the U1 5' ULR sequence. However, if the reading frame is continued in a 5' direction from the proposed hD52 and U1 translation initiation sites, the resulting protein sequences encoded show no homology to each other. This contrasts with the protein sequences encoded after the proposed initiation of translation sites (see, infra), where 60% identity/78% conservation of homology is observed between the first 170 amino acids of hD52 and the corresponding region of U1. We thus decided to term the novel gene corresponding to the U1 cDNA D53, which is predicted to encode a protein of 204 amino acids (FIG. 24(B); SEQ ID NO:10) having a molecular mass of 22.5 KD.

Isolation and Sequencing of a Mouse D52 cDNA

Figure 25A:
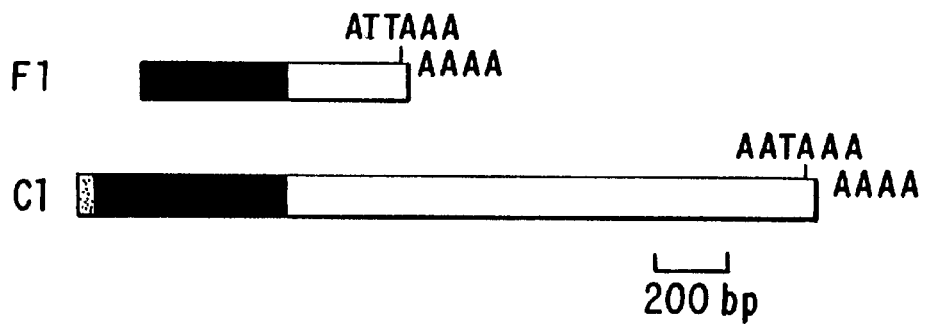
FIG. 25 (A)–(B). Diagrammatic Representation of Two mD52 cDNAs. (A) Diagrammatic representation of two mD52 cDNAs isolated from the apoptotic mouse mammary gland cDNA library. Shaded regions indicate 5'-UTR sequence, solid regions indicate coding sequence and open regions indicate 3'-UTR sequence. The polyadenylation signals associated with polyA sequences are indicated. (B) Nucleotide sequence (SEQ ID NO:11) and amino acid sequence (SEQ ID NO:12) determined for the mD52 Cl cDNA. The predicted coding sequence is translated using the one letter code (in bold), with numbering in italics referring to the translated product, and all other numbering referring to the nucleotide sequence. Within the 3'-UTR, two polyadenylation signals (ATTAAA, nucleotides 976–981, and AATAAA, nucleotides 2014–2019, both of SEQ ID NO:11) are shown underlined and in bold, as are the corresponding sites of polyA addition (nucleotides 1012 and 2033 of SEQ ID NO:11).

In order to further define the D52 family and the degree to which these sequences may be conserved during evolution, a mouse homolog of the hD52 cDNA was cloned from an apoptotic mouse mammary gland cDNA library. The identity of the initially isolated 735 bp murine F1 cDNA (FIG. 25(A)) as a D52 homolog was shown by a high level of homology noted between its incomplete coding sequence and that of hD52 (Byrne, J. A. et al., *Cancer Res* 55:2896–2903 (1995)). Of four longer cDNAs subsequently identified using the F1 cDNA, the longest (C1, 2051 bp; FIG. 25(B); SEQ ID NO: 11) appeared to contain a full-length, 558 bp coding sequence when compared with that of hD52. The predicted hD52 and mD52 coding sequences are 82% identical., with the latter encoding a protein of 185 amino acids (FIG. 25(B); SEQ ID NO: 12). The remaining 1482 bp of the C1 cDNA represents 3'-UTR sequence, which is approximately 69% identical to the corresponding region of the hD52 3'-UTR (Byrne, J. A. et al., *Cancer Res.* 55:2896–2903 (1995)). This homology ends at the polyadenylation signal., whose sequence and position is conserved in the hD52 sequence, and where its use gives rise to a minor 2.2 kb hD52 transcript (Byrne, J. A. et al., *Cancer Res.* 55:2896–2903 (1995)). The C1 cDNA thus appears to represent a mouse homolog to this minor hD52 transcript, its structure having apparently been conserved between hD52 and mD52 genes.

Domain Features Commonly Identified in D52 Protein Family Members

The identity of the U1 cDNA as a D52 homolog (termed hD53) was confirmed upon aligning the predicted hD53 amino acid sequence (SEQ ID NO:10) with those of hD52 (SEQ ID NO:50) and mD52 (SEQ ID NO: 12), as shown in FIG. 26(A). The 204 amino acids of hD53 are 52% identical/66% conserved with respect to hD52, and human and murine D52 homologs are 86% identical/91% conserved. The hD53, mD52 and hD52 sequences were further examined using a number of sequence analysis programs in order to further evaluate the significance of these homologies. Due to the previous identification of a central region displaying 7-amino acid periodicities of apolar amino acids in hD52 (Byrne, J. A et al., *Cancer Res.* 55:2896–2903 (1995)), a program was used which statistically compares query sequences with known coiled-coil domains (Lupas, A. et al., *Science* 252:1162–1164 (1991)). Coiled-coil domains are amphipathic (α-helical domains characterized by hydrophobic residues at positions a and d of an abcdefg heptad repeat pattern, and frequently also by charged residues at positions e and g (reviewed in, Adamson, J. G. et al., *Curr. Opin. Biotechnol.* 4:428–437 (1993)). Coiled-coil structures, which represent protein dimerization domains, are formed between 2 coiled-coil domains which adopt a supercoil structure such that their nonpolar faces are continually adjacent, and both hydrophobic and ionic interactions are important for their formation and stability (Adamson, J. G. et al., *Curr. Opin. Biotechnol.* 4:428–437 (1993)). Putative coiled-coil domains of 40–50 amino acids were identified towards the N-terminus of hD53, mD52 and hD52 sequences, and are predicted to comprise amino acids 22–71 in hD53 (SEQ ID NO:10) and hD52 (SEQ ID NO:51), and amino acids 29–71 in mD52 (SEQ ID NO: 12), as shown in FIG. 26(B). It can be noted that not all a and d positions of the heptad repeats in these predicted coiled-coil domains are occupied by hydrophobic residues (FIG. 26(B)). This reflects the fact that certain deviations from the previously mentioned sequence characteristics of coiled-coil domains are not incompatible with the formation of coiled-coil structures (Lupas, A. et al., *Science* 252:1162–1164 (1991); Adamson, J. G. et al., *Curr. Opin. Biotechnol* 4:428–437 (1993)).

Visual inspection of these 3 amino acid sequences followed by computated analysis identified a second domain type predicted to be present in each protein, this being the PEST domain (Rogers, S. et al., *Science* 234:364–368 (1986)). PEST domains are considered to be proteolytic signals, having been identified in proteins known to have short intracellular half-lives (Rechsteiner, M., *Semin. Cell Biol.* 1:433–440 (1990)). They are enriched in Pro, Glu, Asp, Ser and Thr residues, and are flanked by Lys, Arg or His residues, although in the absence of these, the N- or C-terminus protein end is also a permitted flank (Rogers, S. et al., *Science* 234:364–368 (1986)). PEST domains can be objectively found and assessed using an algorithm which assigns a so-called PEST score, giving a measure of the strength of a particular PEST sequences candidature. We used this algorithm to identify PEST signals, and their sequences and associated PEST scores are listed in Table VIII (hD52 (AA10–40) (SEQ ID NO:72); mD52 (AA10–40) (SEQ ID NO: 12); hD53 (AA1–37) (SEQ ID NO:10); hD52 (AA152–179) (SEQ ID NO:73); mD52 (AA152–185) (SEQ ID NO: 12); hD53 (AA169–190) (SEQ ID NO: 10)). Almost all putative PEST signals identified have associated PEST scores of greater than zero, which is considered to define a PEST sequence (Rechsteiner, M., *Semin. Cell Biol.* 1:433–440 (1990)), with only the C-terminally located PEST domain of hD53 representing a weaker PEST candidate.

A third feature which is common between the 3 sequences is an uneven distribution of charged amino acids within these. All 3 proteins are predominantly acidic, with pIs of 4.70, 4.75, and 5.58 for mD52, hD52 and hD53, respectively. However, while approximately the first and last 50 amino acids of each protein exhibits a predominant negative charge (due in part to the presence of PEST domains), the central portion of each protein exhibits an excess of positively charged residues, with the most frequently occurring charged amino acid residue being Lys in all cases (FIG. 26(A)).

Finally, mD52, hD52 and hD53 proteins possess sites for similar potential posttranslational modifications, although the frequency and positions of these sites are not identical in the 3 sequences. All 3 proteins may be subject to N-glycosylation, since in both mD52 and hD52, $Asn^{167}$ is a potential glycosylation site, with $Asn^{163}$ being a second potential site in mD52, whereas $Asn^{82}$ is a potential site in hD53. A number of potential phosphorylation sites were originally noted in hD52 (Byrne, J. A. et al., *Cancer Res.* 55:2896–2903 (1995)), and a similar analysis of the potential phosphorylation sites present in mD52 and hD53 reveals that hD53 includes a greater density of potential phosphorylation sites (14 potential sites) than either mD52 or hD52 (8 and 9 potential sites, respectively). Moreover, the distribution of these sites in hD53 differs from the pattern observed in mD52 and hD52, which is largely conserved between these 2 molecules. Of 14 potential phosphorylation sites in hD53, 4 are also found in both mD52 and hD52, and the remainder are distinct to hD53 (FIG. 26(A) (SEQ ID NO:10)). Most interestingly, $Tyr^{130}$ of hD53, which is located within a 13 amino acid insertion with respect to the aligned mD52 and hD52 sequences, is predicted to be phosphorylated by tyrosine kinase, whereas no such site exists in either mD52 or hD52.

Homologies Between D52 Protein Family Members and Other Amino Acid Sequences

In contrast to the degree of homology present between hD53 and h/mD52, the predicted hD53 amino acid sequence (FIG. 24(B); SEQ ID NO: 10) shows relatively little homology with sequences of described proteins, as initially observed for hD52 (Byrne, J. A. et al., *Cancer Res.* 55:2896–2903 (1995)). Homology can be identified between the coiled-coil domain of hD53 and similar domains of other proteins, such as yeast ZIPI (Sym, M. et al., *Cell* 72:365–378 (1993)). Lower levels of amino acid sequence identity are observed between more extensive regions of hD53, and proteins of the cytoskeleton, or other homologous proteins. For example, weak homology (20% identity, 34% conservation) was noted over 172 amino acids of hD53 with moesin from the pig (Lankes, W. T. et al., *Biochim. Biophys. Acta* 1216:479–482 (1993)), the human (Lankes, W. T. & Furthmayr, H., *Proc. Natl. Acad Sci. USA* 88:8297–8301 (1991)) and the mouse (Sato, N., *J. Cell Sci.* 103:131–143 (1992)). Somewhat higher levels of sequence identity (31–36% identity, 45–51% homology) were noted between amino acids 139–177, and histone H1 sequences from maize (Razafimahatratra, P. et al., *Nucl. Acids Res.,* 19:1491 (1991)) and wheat (Yang, P. et al., *Nucl. Acids Res.* 19:5077 (1991)).

Recently, we noted a significantly higher degree of homology between h/mD52 and hD53 sequences and that of the putative protein F13E6.1 encoded between nucleotides 5567–6670 of the *Caenorhabditis elegans* chromosome X cosmid F13E6 (EMBL Accession No. Z68105; Wilson, R. et al., *Nature* 368:32–38 (1994)). At 257 amino acids in length, the putative F13E6.1 protein is somewhat longer than D52 and D53, with 42 amino acids (amino acids 121–167) corresponding to predicted exon 4 of the F13E6.1 gene not being present in D52 or D53 sequences. F13E6.1 is most similar to hD52, where aligning the 2 sequences using the programme gap indicates 36.2% identity/45.4% conservation of homology over the 185 amino acids of hD52. The existence of transcripts deriving from this or a similar gene is indicated by EST sequences deriving from cDNA clones from *Caenorhabditis elegans* (GenBank Accession Nos. D73047, D73326, D76021 and D76362) and the parasitic nematode *Strongyloides stercoralis* (GenBank Accession No. N21784). In summary, it is possible that a D52 homolog or ancestral gene exists in nematodes.

Chromosomal Localizadons of D52 and D53 Genes

Previous gene mapping studies have indicated a single hD52 locus at chromosome 8q21 (Byrne, J. A. et al., *Cancer Res.* 55:2896–2903 (1995)). Thus in the present study we similarly determined the chromosomal localizations for hD52 and mD52, in order to determine whether human gene members of the proposed D52 family are clustered on chromosome 8q, and whether this/these loci may be syntenically conserved in other species.

Figure 27A:
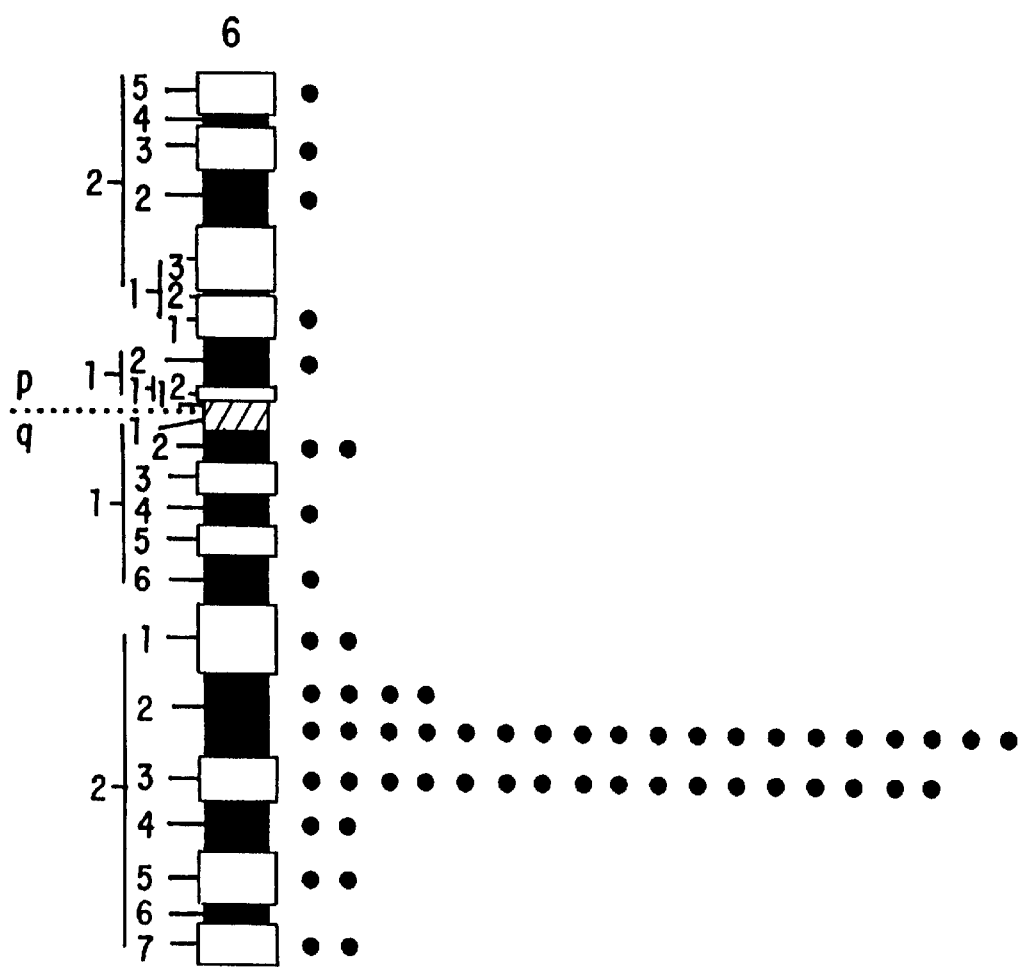
FIG. 27 (A)–(B). (A) Ideogram of the human G-banded chromosome 6 illustrating the distribution of labeled sites with the 116783 hD53 probe. (B) Localization of the mD52 gene to mouse chromosomes 3 and 8 by in situ hybridization. Diagrams of WMP mouse Rb (3;12) and Rb (8;9) chromosomes, indicating the distributions of labeled sites on chromosomes 3 and 8.

In the 100 metaphase cells examined after in situ hybridization using the hD53 116783 probe, there were 172 silver grains associated with chromosomes, and 57 of these grains (33.1%) were located on chromosome 6. The distribution of grains on this chromosome was not random, 40/57 (70.2%) of these mapping to the q22-q23 region (FIG. 27(A)). These results allow us to map the hD53 locus to the 6q22-q23 bands of the human genome, thus demonstrating that independent loci on separate chromosomes exist for the hD52 and hD53 genes.

Figure 27B:
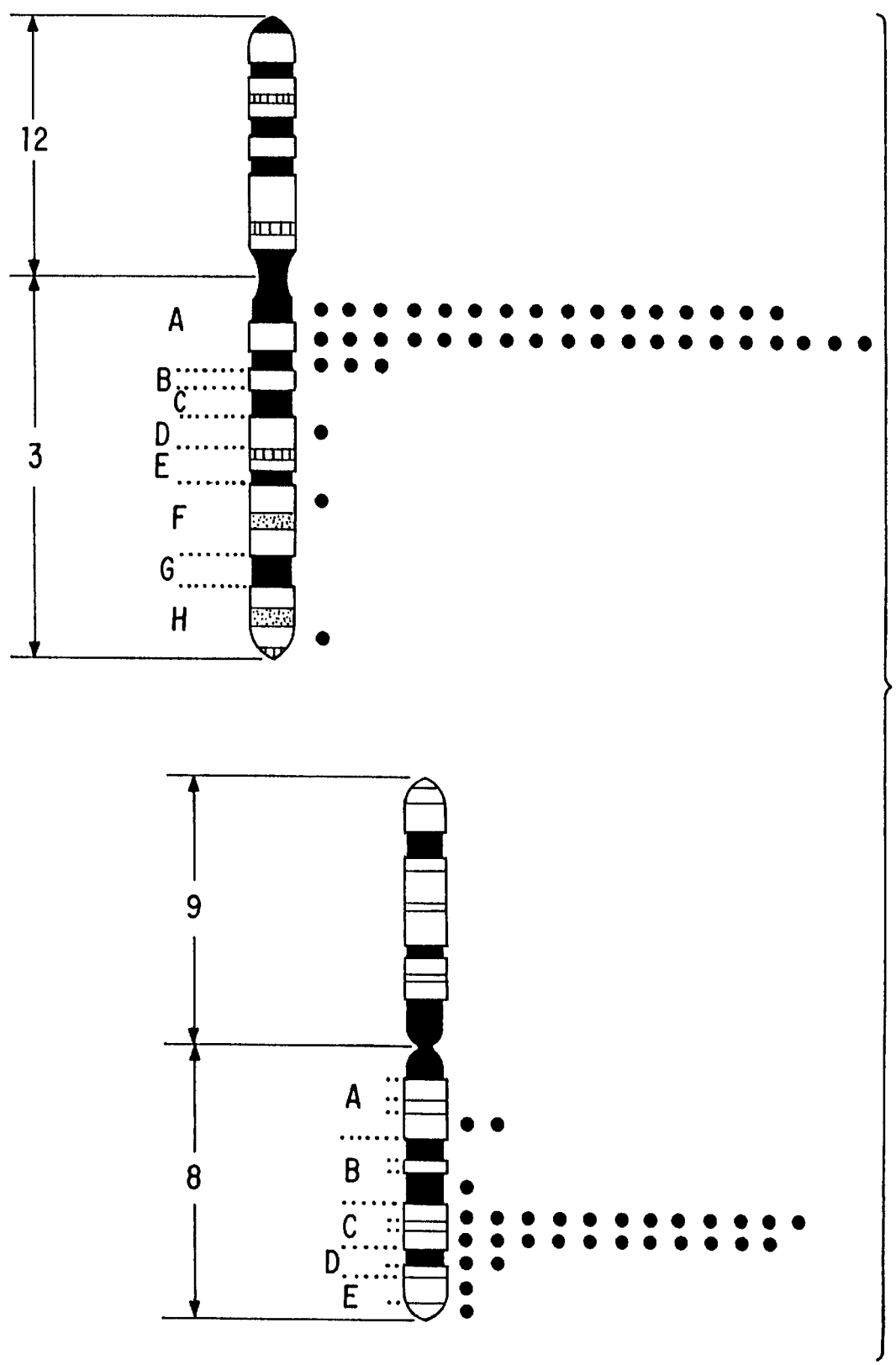

Using the mD52 C1 probe, 153 silver grains were associated with chromosomes in the 100 metaphase cells examined after in situ hybridization. Forty-one of these grains (26.8%) were located on chromosome 3. The distribution of grains on this chromosome was not random, 35/41 (85.3%) of these mapping to the A1-A2 region (FIG. 27(B)). A secondary hybridization peak was detectable on chromosome 8, since 30 of the total grains were located on this chromosome (19.6%), and the distribution of grains on this chromosome was not random, 23/30 of these mapping to the C band. Thus, we were able to define 2 mD52 loci on chromosome 3A1-3A2, and chromosome 8C of the mouse genome, a result which was somewhat unexpected given the existence of a single hD52 locus.

The mouse chromosome 3A1-3A2 region has been reported to be syntenic with regions of human chromosome 8q (O'Brien, S. J. et al., *Report of the Committee on Comparative Gene Mapping*, in HUMAN GENE MAPPING 846 (1993); Lyon, M. F. & Kirby, M. C., *Mouse Genome* 93:23–66 (1995)), including band 8q22 adjacent to the hD52 gene at 8q21. This suggests that the chromosome 3A1-3A2 locus is the major mD52 locus, and corresponds with the distribution of silver grains between the 2 sites, 22.9% of all grains associated with chromosomes being found at chromosome 3A1-A,2, compared with 15.0%/o associated with chromosome 8C. The significance of the dual mouse D52 loci is currently unknown. The chromosome 8C locus may represent a mD52 pseudogene, or another highly mD52-homologous gene. While it is currently not possible to distinguish between these possibilities, it would appear from the existence of a single 1D52 locus that either secondary loci do not exist in the human, or that they are co-localized with the primary hD52 locus at human chromosome 8q21.

Figure 28:
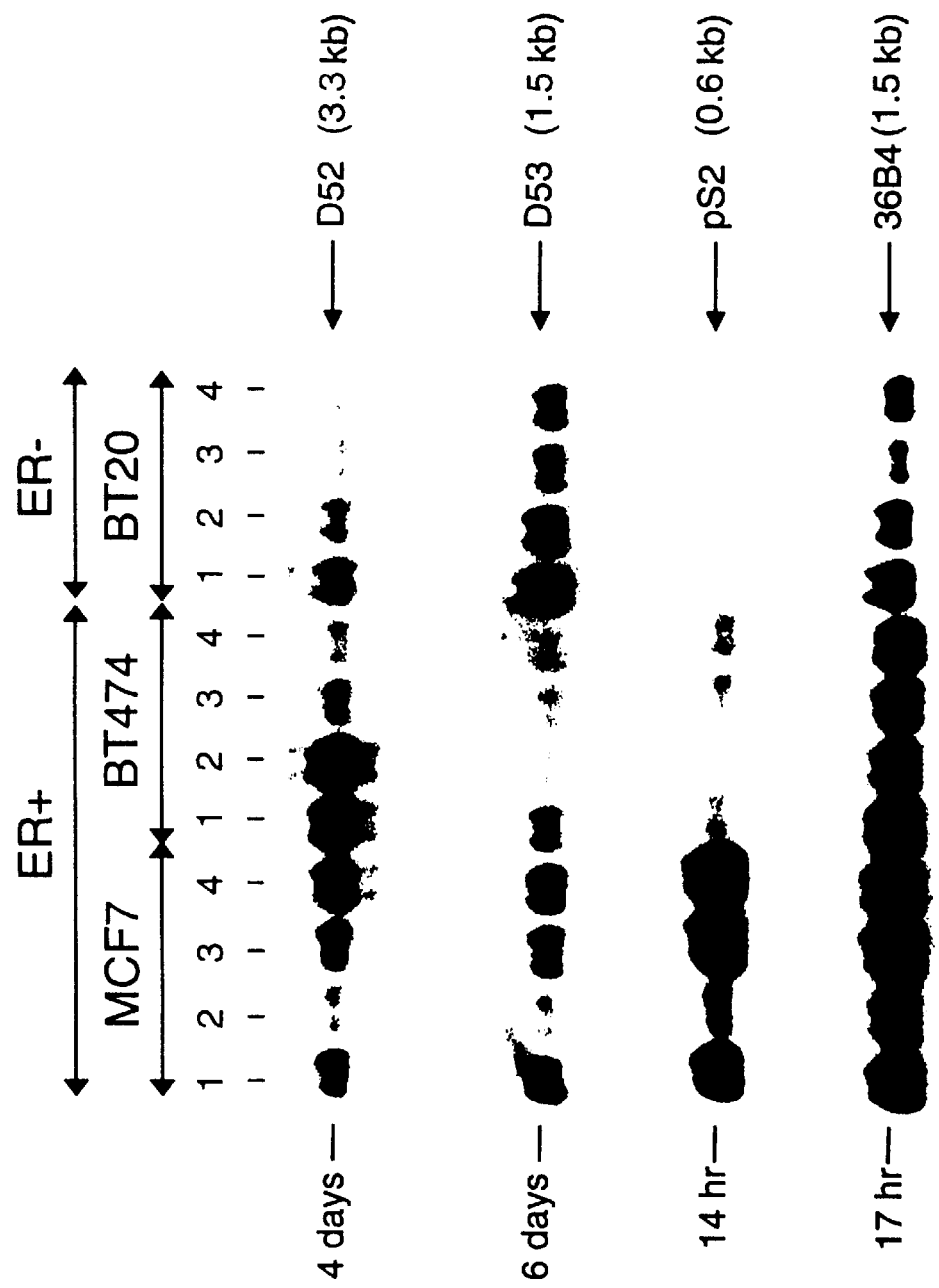
FIG. 28. The Effects of Estradiol Treatment on hD52 and hD53 Transcript Levels in Human Breast Carcinoma Cell Lines. Northern blot analyses were performed using 10 μg total RNA for each sample. The identity and size (in parenthesis) of each transcript is indicated to the right of each panel, whereas the corresponding duration of autoradiographic exposure is shown on the left. For each cell line, lane 1 indicates total RNA from cells grown for 6 days in normal media (see Materials and Methods), lane 2 indicates total RNA from cells grown for 1 day in normal media and for 5 days in phenol red-free DMEM with 10% steroid-depleted FCS and 0.6 μg/ml insulin, lane 3 is as for lane 2 except that for the last 3 days of culture, media were supplemented with $10^{-9}$ M estradiol, and lane 4 is as for lane 2 except that for the last 3 days of culture, media were supplemented with $10^{-8}$ M estradiol. ER+/ER− indicates the presence/absence of the estrogen receptor in the cell line(s) shown below. The hD52 and hD53 transcripts were co-expressed in the 3 cell lines, and transcript levels for both genes were similarly affected by estradiol stimulation/deprivation in MCF7 cells, and were not affected by the same treatments in BT-20 cells. Differing effects on hD52 and hD53 transcript levels were noted in the experiment using BT-474 cells. The estrogen-inducible pS2 gene was used as a control for the effectiveness of estradiol supplementations/deprivations. As expected, the presence of estradiol induced pS2 expression in ER+ cell lines, but not in the ER+ cell line BT-20. For all 3 cell lines, similar results were obtained in at least one other experiment performed on a separate occasion.

Comparative Expression Patterns of hD52 and hD53 in Human Breast Tissues and Breast Cancer Cell Lines The expression pattern of hD53 was evaluated in normal adult human tissues, breast carcinomas and fibroadenomas, and a number of cell lines using Northern blot analysis. A single 1.5 kb hD53 transcript was detected in all samples positive for hD53 expression (FIG. 28 and data not shown). Of those normal tissues examined, the hD53 transcript was detected in kidney and very weakly in skin, but not in liver, stomach, colon, kidney or placenta. In breast tumors, the hD53 transcript was detected in 4/9 carcinomas and in 1/3 fibroadenomas, hD53 transcript levels being noted to be similar in these 5 tumors (data not shown). All tissue and tumor samples in which the hD53 transcript was detected also contained detectable levels of hD52 transcripts. However, the hD53 gene appeared to be less widely expressed than hD52 at the level of sensitivity offered by Northern blot analysis, since only a proportion of those tissues expressing hD52 transcripts showed detectable levels of hD53 (data not shown).

Initial results from Northern blot analyses of hD53 expression in breast carcinoma cell lines indicated that hD52 transcript levels were higher in estrogen receptor-positive cell lines than in those considered not to express the estrogen receptor (Byrne, J. A. et al., *Cancer Res.* 55:2896–2903 (1995)). Thus, we undertook to examine whether hD52 and/or hD53 transcript levels could be influenced by the presence/absence of estradiol in growth media. Hybridization of hD52 and hD53 probes with RNA samples from human breast carcinoma cell lines indicated that mRNAs corresponding to both genes were detectable in MCF7 and BT474 cells (which express the estrogen receptor), and in BT-20 cells (which do not express the estrogen receptor)

(FIG. 28). However the relative transcript levels for hD52 and hD53 were not identical in these cell lines, hD52 being relatively strongly expressed in BT-474 cells, and relatively weakly expressed in BT-20 cells, whereas the inverse was true for hD53.

In MCF7 cells, removal of estrogen from the culture medium coincided with reduced hD53 and hD52 transcript levels, whereas supplementation of the media to estradiol concentrations of $10^{-9}/10^{-8}$ M restored control hD52 or hD53 transcript levels (FIG. 28). In the BT-474 cell line, culturing cells for 5 days in steroid-depleted media did not alter hD52 transcript levels, and estradiol supplementation of depleted media to $10^{-9}$ or $10^{-8}$ M coincided with decreased hD52 transcript levels. The hD53 transcript levels were altered in BT474 cells in a different way, in that these decreased in cells cultured in estrogen-depleted media, and were not restored by subsequent estradiol supplementation (FIG. 28). In BT-20 cells, the presence or absence of estradiol resulted in no appreciable changes in hD52 or hD53 transcript levels compared with 36B4 mRNA levels noted in the same samples (FIG. 28).

The effectiveness of estradiol deprivation and supplementation was assessed through rehybridizing the same blots with a probe to human pS2, a gene whose transcription is directly controlled by estrogen in MCF7 cells (Brown, A.M.C. et al., *Proc. Natl. Acad Sci. USA* 81:6344–6348 (1984)). Levels of pS2 mRNA have been shown to increase for up to 3 days of estradiol treatment, by which time the magnitude of induction is as much as 30-fold (Westley, B. et al., *J. Biol. Chem.* 259:10030–10035 (1984)). Accordingly, in MCF7 and BT-474 cells, pS2 transcript levels were either low or undetected in steroid depleted media, whereas estraiol treatments resulted in inductions of pS2 gene expression. However, pS2 mRNA was undetected in estrogen receptor-negative BT-20 cells, in agreement with previous findings (May, F.E.B. & Westley, B. R., *J. Biol. Chem.* 263:12901–12908 (1988)).

Figure 29A:
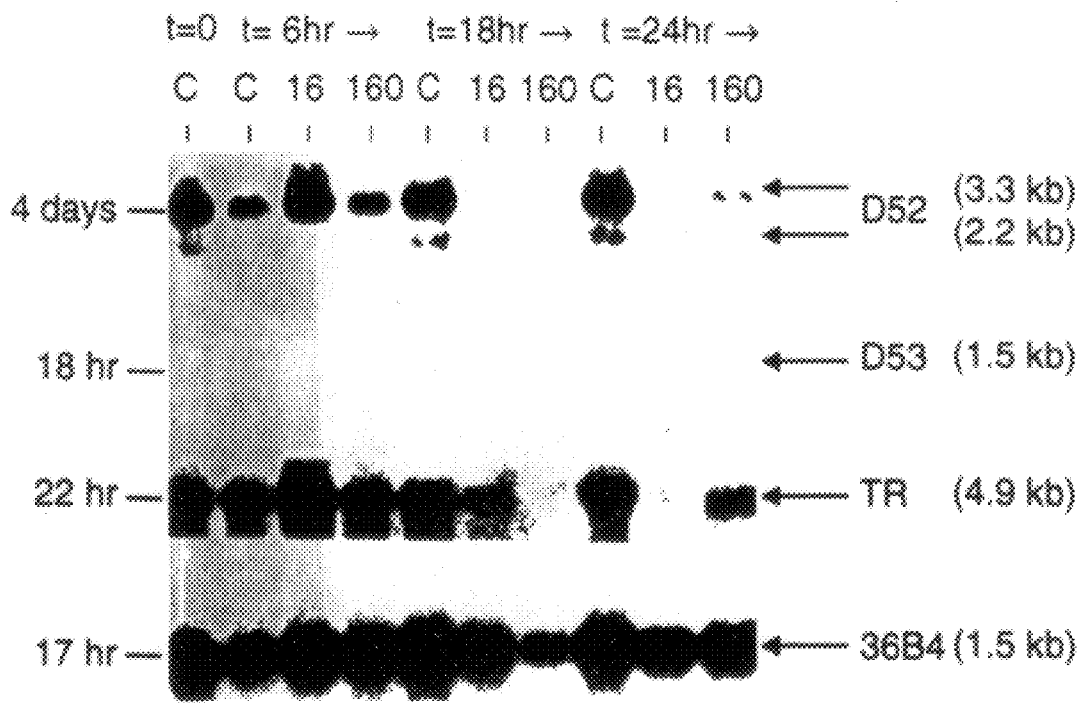
FIG. 29. The Effects of TPA Treatment on hD52 or hD53 Transcript Levels in Human Leukemia Cell Lines. Northern blot analyses were performed using 10 μg total RNA for each sample. The identity and size (in parenthesis) of each transcript is indicated to the right of each panel, whereas the corresponding duration of autoradiographic exposure is shown on the left. Lanes marked (C) indicate total RNA from cells grown in normal media (see Materials and Methods), lanes marked (16) indicate total RNA from cells grown in media supplemented with 16 nM TPA, and lanes marked (160) indicate total RNA from cells grown in media supplemented with 160 nM TPA. Times shown above the lanes indicate when cells were harvested after the start of each experiment. (A) TPA treatment of HL-60 cells was found to decrease hD52 and transferrin receptor (TR) transcript levels after 18 hrs TPA treatment. hD53 transcripts were not detected in HL-60 cells. Similar results were obtained in at least one other experiment performed on a separate occasion. (B) TPA treatment of K-562 cells was found to decrease hD53 and transferrin receptor (TR) transcript levels after 24 hrs TPA treatment. hD52 transcripts were not detected in K-562 cells.

Reduction in hD52 or hD53 mRNA Levels Upon Induction of Differentiation in Leukemic Cell Lines Initial results from Northern blot analyses had previously indicated that hD52 transcripts were detectable in HL-60 myelocytic leukemia cells, but not in K-562 proerythroblastic leukemia cells (Byrne, J. A. et al., *Cancer Res.* 55:2896–2903 (1995)), and we thus decided to examine the expression of hD53 in these same cell lines. In cells cultured under normal conditions (see Materials and Methods), we noted reciprocal patterns of expression for the hD52 and hD53 genes in these cell lines, in that hD52 transcripts were detected in HL-60 cells, but not in K-562 cells, whereas hD53 transcripts were detected in K-562 cells, but not in HL-60 cells (FIG. 29(A) and (B)).

Figure 29B:
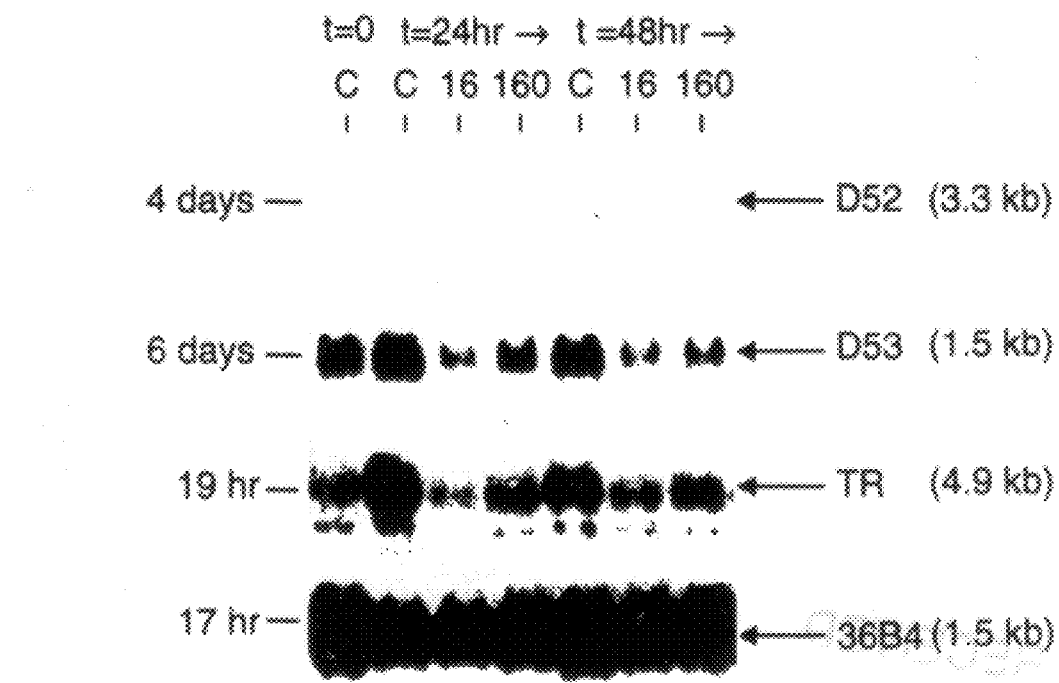

The proliferative and differentiation responses of HL-60 cells and K-562 cells to chemical agents such as TPA have been thoroughly characterized (reviewed in, Harris, P. & Ralph, P., *J Leuk. Biol.* 37:407–422 (1985); Sutherland, J. A. et al., *J. Biol. Resp. Modif.* 5:250–262 (1986)), with TPA promoting differentiation along monocyte/macrophage pathway in both cell lines. Culturing cells in the presence of 16 nM or 160 nM TPA resulted in decreased hD52 transcript levels in treated HL-60 cells (FIG. 29(A)), and decreased hD53 transcript levels in treated K-562 cells (FIG. 29(B)), after periods of 18–24 hrs. As a molecular control for the efficacy of TPA treatments, filters were rehybridized with a transferrin receptor cDNA insert (Kühn, L. C. et al., *Cell* 37:95–103 (1984)), since reduced transferrin receptor transcript levels have been reported for both HL60 cells (Ho, P. T. C. et al., *Cancer Res.* 49:1989–1995 (1989)) and K-562 cells (Schonhorn, J. E., *J. Biol. Chem.* 270:3698–3705 (1995)) after TPA treatment. The kinetics with which decreased transferrin receptor transcript levels were noted in TPA-treated cells (FIG. 29(A) and (B)) are in good agreement with those previously reported (Ho, P. T. C. et al., *Cancer Res.* 49:1989–1995 (1989); Schonhorn, J. E., *J. Biol. Chem.* 270:3698–3705 (1995)). Interestingly, parallel decreases (with respect to both their magnitudes and kinetics) were observed for transferrin receptor and hD52 or hD53 transcripts in HL-60 cells (FIG. 29(A)) and K-562 cells (FIG. 29(B)), respectively.

Discussion

We report the cloning of a novel human cDNA termed hD53, and of the mouse D52 cDNA homolog, due to the clear similarity between these sequences and hD52 (Byrne, J. A. et al., *Cancer Res.* 55:2896–2903 (1995)). The high conservation of homology between h/mD52 and hD53 sequences, combined with the low levels of homology existing between these sequences and those of other characterized proteins, lead us to propose the existence of the novel D52 gene/protein family. The fact that mD52 and hD52 sequences are 86% identical/91% conserved, combined with the possible existence of a D52 homolog or ancestral gene in nematodes, suggest basic cellular functions for D52 family proteins, which are as yet unknown. However, the results of sequence analyses and of further experiments presented here have allowed us to form hypotheses regarding their functions.

A central hD52 region of approximately 110 amino acids displaying 7-amino acid periodicities of apolar amino acids was previously identified by virtue of low levels of homology with cytoskeletal protein regions Byrne, J. A. et al., *Cancer Res.* 55:2896–2903 (1995)). Using the so-called Lupas algorithm (Lupas, A. et al., *Science* 252:1162–1164 (1991)), we have now identified a single coiled-coil domain in hD52, mD52 and hD53 towards the N-terminus of each protein, and which is predicted to end at $Leu^{71}$ in all 3 proteins. This coiled-coil domain overlaps with the leucine zipper predicted in hD52/N8 using helical wheel analysis. The presence of a coiled-coil domain in D52 family proteins indicates that specific protein-protein interactions are required for the functions) of these proteins. Similarly, the presence of 2 candidate PEST domains in D52 proteins indicates that their intracellular abundances may be in part controlled by proteolytic mechanisms. Interestingly, the extent of the N-terminally located PEST domain overlaps that of the coiled-coil domain in both D52 and D53 proteins. It could thus be envisaged that interactions via the coiled-coil domain could mask this PEST domain, in accordance with the hypothesis that PEST sequences may act as conditional proteolytic signals in proteins able to form complexes (Rechsteiner, M., *Adv. Enyme Reg.* 27:135–151 (1988)).

At present, the cellular distribution pattern of hD53 transcripts in tissues is unknown and thus the significance of hD52 and hD53 co-expression in tissues cannot be evaluated. However, the results obtained for hD52 and hD53 expression in breast carcinoma cell lines indicate that the 2 genes may be expressed in the same cell type, with co-expression of hD52 and hD53 transcripts being demonstrated in 3/5 cell lines examined (BT-20, BT474 and MCF7). In a remaining 2 cell lines (HBL100 and ZR-75-1), only hD52 transcripts were detectable (Byrne, J. A. et al., *Cancer Res.* 55:2896–2903 (1995); Byrne, J. A., unpublished results), and thus hD52 may be more frequently or abundantly expressed than hD53 in breast carcinoma cells. Since neither hD52 nor hD53 transcripts were detected in HFL1 fibroblasts (Byrne, J. A. et al., *Cancer Res.* 55:2896–2903 (1995); Byrne, J. A., unpublished results), we thus currently hypothesize that hD53, like hD52 (Byrne, J. A. et al., *Cancer Res.* 55:2896–2903 (1995)), represents an epithelially-derived marker.

Estradiol stimulation/deprivation experiments performed in MCF7 cells indicate that the hD52 and hD53 transcript levels normally measured in MCF7 cells cultured with FCS are dependent upon estradiol. At present, the mechanism by which estradiol induces the accumulation of hD52 and hD53 transcripts in MCF7 cells is unknown. It is possible that fluctuations in hD52/hD53 transcript levels may be secondary to the mitogenic effects of estrogen on MCF7 cells, and not directly produced by estradiol per se. However, estradiol stimulation/deprivation experiments performed in a second estrogen receptor-positive breast carcinoma cell line, BT-474, gave different results from those observed in MCF7 cells. The hD52 transcript level present in BT-474 cells cultured with FCS was not estrogen dependent, and indeed supplementing steroid-depleted media with $10^{-9}$ M and $10^{-8}$ M estradiol resulted in significantly decreased hD52 transcript levels. Such differing effects in 2 estrogen receptor-positive breast carcinoma cell lines may indicate multiple mechanisms by which the estradiol-estrogen receptor complex may influence hD52 gene expression in breast carcinoma cells, or the existence of different, cell-specific factors in BT474 and MCF7 cells which cooperate with the receptor complex in this process (Parker, M. G., *Curr. Opin. Cell Biol.* 5:499–504 (1993); Cavailles, V. et al., *Proc. Natl. Acad Sci. USA* 91:10009–10013 (1994)). Furthermore, estradiol deprivation/supplementation had different effects on hD52 and hD53 transcript levels in BT-474 cells. Decreased hD53 transcript levels were observed in cells cultured for 5 days in steroid-depleted media, whether or not this media had been subsequently supplemented with estradiol for the last 3 days of culture. We interpret these results as indicating that the absence of factor(s) in the steroid-depleted media resulted in decreased hD53 transcript levels, and that in this case the factor was not estradiol.

While hD52 and hD53 were found to be co-expressed in 3/5 breast carcinoma cell lines, corresponding findings in leukemic cells confirm that co-expression of these genes is not obligatory. HL-60 cells are myelocytic leukemia cells, and can be induced to differentiate along granulocytic or macrophage pathways (Harris, P. & Ralph, P., *J. Leuk. Biol.* 37:407–422 (1985)), whereas K-562 leukemia cells have erythroid characteristics, and can be induced to express features characteristic of granulocytic, macrophagic and megakaryocytic differentiation (Sutherland, J. A. et al., *J. Biol. Resp. Modif.* 5:250–262 (1986)). The present study has provided another molecular distinction between these 2 cell lines, since hD52 transcripts were detected in HL-60 cells but not in K-562 cells, whereas hD53 transcripts were detected in K-562 cells but not in HL-60 cells. This suggests that hD52/hD53 gene expression status may find future use as a marker to distinguish between different forms of leukemia.

Treatment of HL-60 and K-562 cells with TPA was found to have similar effects in reducing hD52 and hD53 transcript levels, respectively. This provides a second example of similar regulation of gene expression for these 2 different genes, this time in 2 different cell lines, and could be considered further proof of a functional relationship between the hD52 and hD53 genes. The mechanism by which hD52 and hD53 transcript levels are reduced in HL-60 and K-562 cells by TPA treatment is currently unknown. It is possible that reduced hD52 or hD53 transcript levels arise as an indirect consequence of TPA treatment, which is known to result in a marked cessation of proliferation, and an induction of macrophagic differentiation in both HL-60 and K-562 cells. However, the fact that hD52/hD53 and transferrin receptor transcript levels decreased in parallel fashions in TPA-treated cells indicates that a common stimulus might be responsible for these events.

In summary, we have demonstrated the existence of a new gene/protein family, the D52 family, which is presently comprised of D52 and D53. The presence of an acidic coiled-coil domain in both D52 and D53 proteins indicates that specific protein-protein interactions may form an important component of D52 and D53 function. This, combined with the fact that hD52 and hD53 transcripts are coexpressed in some human cell lines, leads us to speculate that hD52 and hD53 may be able to interact in vivo. However, our observations in HL-60 and K-562 cell lines, where the 2 genes were not co-expressed judging from Northern blot data, indicate that if indeed hD52 and hD53 are cellular partners, that this partnership is not obligatory. Other partners may exist for each of these proteins, and it is tempting to speculate that under certain conditions, the formation of homodimers may be favored.

TABLE VIII

Candidate PEST Domains Identified in hD52 and hD53 Amino Acid Sequences

| Sequence | Amino acids | PEST domain sequence | PEST score | SEQ ID NO. |
|---|---|---|---|---|
| hD52 | 10–40 | RTDPVPEEGEDVAATISATETLSEEEQEELR[a] | 15.8 | 72 |
| mD52 | 10–40 | KTEPVAEEGEDAVTMLSAPEALTEEEQEELR | 11.8 | 12 |
| hD53 | 1–37 | MEAQAQGLLETEPLQGTDEDAVASADFSSMLSEEEK | 5.8 | 10 |
| hD52 | 152–179 | KPAGGDFGEVLNSAANASATTTEPLPEK | 0.6 | 73 |
| mD52 | 152–185 | KPAGGDFGEVLNSTANATSTMTTEPPPEQMTESP* | 9.0 | 12 |
| hD53 | 164–184 | KVGGTNPNGGSFEEVLSSTAH | −6.0 | 10 |

[a]Positively charged amino acids and protein termini are underlined, whereas PEDS residues are showh in bold. Amino acid residues are indicated using the one letter code.

EXAMPLE 6

Two Distinct Amplified Regions Involved at 17q11-q21 in Human Primary Breast Cancer Introduction Gene amplification has been shown to play an important part in the pathogenesis and prognosis of various solid tumors including breast cancer, probably because overexpression of the amplified target gene confers a selective advantage. The first technique to detect gene amplification was cytogenetic analysis. Thus amplification of several chromosomal regions, visualized as either extrachromosomal double minutes (dmin) or integrated homogeneously staining regions (hsrs) are among the major visible cytogenetic abnormalities found in breast tumors (Gebhart, E. et al., *Breast Cancer Res. Treat.* 8:125–138 (1986); Dutrillaux, B. et al., *Cytogenet.* 49:203–217 (1990)). Other techniques such as comparative genomic hybridization (CGH) and a novel strategy based upon chromosome microdissection and fluorescence in situ hybridization have also been applied to broad searches for regions of increased DNA copy number in tumor cells (Guan, X. Y. et al., *Nat. Genet.* 8:155–161 (1994); Muleris, M. et al., *Genes Chrom. Cancer* 10:160–170 (1994)). These different techniques have revealed some 20 amplified chromosomal regions in breast tumors. These amplified regions results in 5- to 100-fold amplification of a small number of genes, few of which are thought to contribute in a dominant manner to the malignant phenotype. Positional cloning efforts begin to identify the critical gene(s) in each amplified region. To date, genes documented to be amplified in breast cancers include, FGFRI (8p12), MYC (8p24), FGFR2 (10q26), CCND1, GSTP1 and EMS1 (11q13), IGFR and FES (15q24-q25), and ERBB2 (17q12-q21) (reviewed in, Brieche, I. & Lidereau, R, *Genes Chrom. Cancer* 14:227–251 (1995)). DNA amplification at segment q11-q21 of chromosome 17 seems one of the most commonly amplified region in human breast carcinomas. FISH, CGH and chromosome microdissection shown a high increase in DNA-sequence copy-number of this region (Kallioniemi, O. et al., *Proc. Natl. Acad Sci. USA* 89:5321–5325 (1992); Guan, X. Y. et al., *Nat. Genet.* 8:155–161 (1994); Muleris, M. et al., *Genes Chrom. Cancer* 10: 160–170 (1994)). Amplification of 17q12 was originally discovered in breast carcinoma using a probe to the ERBB2 gene (Slamon, D. J. et al., *Science* 235:177–182 (1987)). Quickly other tumor types followed including cancers of the ovary, stomach and bladder, and less frequently lung and colon carcinomas. Interestingly, the presence of amplification at 17q12-q21 has been related to be a clinical relevance in breast cancer, where independent studies have shown association with an increased risk of relapse (Slamon, D. J. et al., *Science* 235:177–182 (1987); Ravdin, P. M & Chamness, G. C., *Gene* 159:19–27 (1995)). To date, only one gene, ERBB2, has been proposed to be responsible for the emergence of this amplicon. The ERBB2 proto-oncogene belongs to the ERBB family, the first identified member of which (ERBB1) encodes the EGF (epidermal growth factor) receptor (Dougall, W. C. et al., *Oncogene* 9:2109–2123 (1994)). ERBB2 amplification is associated with overexpression of its product. This gene is a good candidate for a role in breast cancer because of its transforming potency (DiFiore, P. P. et al., *Science* 237:178–182 (1987)) and that transgenic mice carrying the ERBB2 gene show altered mammary cell proliferation and high incidence of mammary adenocarcinomas (Muller, W. J. et al., *Cell* 54:105–115 (1988)).

All these initial reports emphasized a potential role for the ERBB2 proto-oncogene at 17q12-q21 in human breast carcinomas. However, four novel genes (called MLN 50, 51, 62 and 64) from this chromosomal region have recently been identified by a differential screening of a cDNA library established from breast cancer-derived metastatic axillary lymph nodes (Tomasetto, C. et al., *Genomics* 28(3):367–376 (1995)). MLN 51 and MLN 64 genes showed little homology with others already described. MLN 62 gene (also known as CART1 or TRAF4) is a novel member of the tumor necrosis factor receptor-associated protein family Régnier, et al., *Journal of Biological Chemistry* 270 (43):25715–25721 (1995)), while MLN 50 gene (also named Lasp-1) defines a new LIM protein subfamily characterized by the association of LIM motif and a domain of region 3 Src homology (SH3) at the N- and C-terminal parts of the protein, respectively (Tomasetto, C. et al., *Genomics* 28(3):367–376 (1995)).

These four genes have been found amplified and overexpressed in breast cancer cell lines. Therefore, amplification of 17q11-q21DNA sequences may be more complex than firstly suspected, and the number and the identity of target gene(s) remain open questions.

In the present study we have investigated a large series of primary breast tumors for amplification of ERBB2 gene and the four novel genes. We report that 25.5% of the breast tumors show amplification of one or more of these genes. Preliminary mapping of the amplicons suggests the involvement of two distinct amplified regions at 17q11-q21 in human primary breast cancer. Moreover, we suggest three genes (MLN 62, ERBB2 and MLN 64) as likely targets of the amplification event at these two chromosomal regions.

Materials and Methods

Tumor and Blood Samples

Samples were obtained from 98 primary breast tumors surgically removed from patients at the Centre Rene Huguenin (France); none of the patients had undergone radiotherapy or chemotherapy. Immediately following surgery, the tumor samples were placed in liquid nitrogen and stored at −70° C. until extraction of high-molecular-weight DNA and RNA. A blood sample was also taken from each patient.

DNA Probes

A pMAC117 probe (a 0.8 Kb AccI fragment DNA fragment from a genomic clone of ERBB2) was used to detect ERBB2 (ATCC No. 53408). The four novel clones (MLN 50, 51, 62 and 64) were described in detail in Tomasetto et at (1995). These five probes were previously positioned and ordered by in situ hybridization (Tomasetto, C. et al., *Genomics* 28(3):367–376 (1995).

For Southern-blot analysis, the control probes used were the human β-globin (Wilson, J. T. et al., *Nucl. Acids Res.* 5:563–581 (1978)) and the MOS proto-oncogene (ATCC No. 41004).

For Northern-blot analysis, the control probe used was a 0.7-kb PstI fragment of the 36B4 cDNA, as described by Masiakowski, P. et al., *Nucl. Acids Res.* 10:7895 (1982).

DNA Analysis

DNA was extracted from tumor tissue and blood leucocytes, according to standard methods (Maniatis, T. et at, MOLECULAR CLONING: A LABORATORY MANUAL (2nd ed., Cold Spring Harbor, N.Y. (1989)). Ten $\mu$g of TaqI-restricted DNAs were separated by electrophoresis in agarose gel (leucocyte and tumor DNA samples from each patient were run in adjacent lanes), and blotted onto nylon membrane filters (Hybond N+, Amersham Corp.), according to standard techniques. The membrane filters were hybridized with nick-translated $^{32}$P-labeled probes, washed, and autoradiographed at −70° C. for an appropriate period.

Determination of DNA Amplification

Restriction enzyme-digested tumor DNAs were compared with matching lymphocyte DNA in the same agarose gels. Blots of these gels were first hybridized with ERBB2 and the four MLN probes. Rehybridization of the same blots with the MOS and the β-globin probes provided a control for the amount of DNA transferred onto the nylon membranes. The proto-oncogene and control gene autoradiographs were first scored by visual inspection and then determined by densitometry. Only the signals with an intensity of two copies or more were considered to represent amplification. Amplification level was quantified by serial dilutions of tumor DNA to obtain a Southern hybridization signal similar to that obtained with leucocyte DNA samples.

RNA Analysis

RNA was extracted from normal and tumoral breast tissue by using the LiCl/urea method (Auffray, C. & Rougeon, F., *Eur. J Biochem.* 107:303–314 (1980)). Ten micrograms of RNA was fractionated by electrophoresis on 1.2% agarose gels containing 6% formaldehyde, and analyzed by blot hybridization after transfer onto nylon membrane filters (Hybond N, Amersham Corp.). The same filters were first hybridized with ERBB2 and the four MLN nick-translated $^{32}$P-labeled probes in 50% formamide at 42° C. Membranes were washed under stringent conditions in 0.1× SSPE, 0.1% SDS at 50° C. and subjected to autoradiography for various periods at −80° C. Membranes were also rehybridized with a 36B4 cDNA probe corresponding to a ubiquitous RNA. The signal obtained was used to check the amount of RNA loaded on the gel in each experiment. The 36B4 signal also showed that the RNA samples were not extensively degraded.

Evaluation of RNA Overexpression

Relative intensities of the mRNA bands were assessed by visual examination and confirmed by means of densitometry taking the ubiquitous 36B4 bands into account. Increase in expression of at least 2-fold relative normal breast tissues expression were scored as positive. Overexpression was quantified by serial dilution of tumor RNA to obtain a Northern hybridization signal similar to that obtained with normal breast tissue.

Results

Normal DNA (peripheral blood lymphocytes) and autologous tumor DNA from 98 breast cancer patients were screened on Southern blots for amplification of 5 different genes (ERBB2, MLN 50, 51, 62 and 64) located at 17q11-q21.

Amplification occurred in at least one locus in 25 of the 98 tumors (25.5%).

Densitometrical analysis revealed that amplification levels varied not only from case to case but in some tumors also from gene to gene. Amplification ranged from 2- to more than 30-fold.

17q11-q21 Anplicon Maps in Breast Carcinomas

Figure 30:
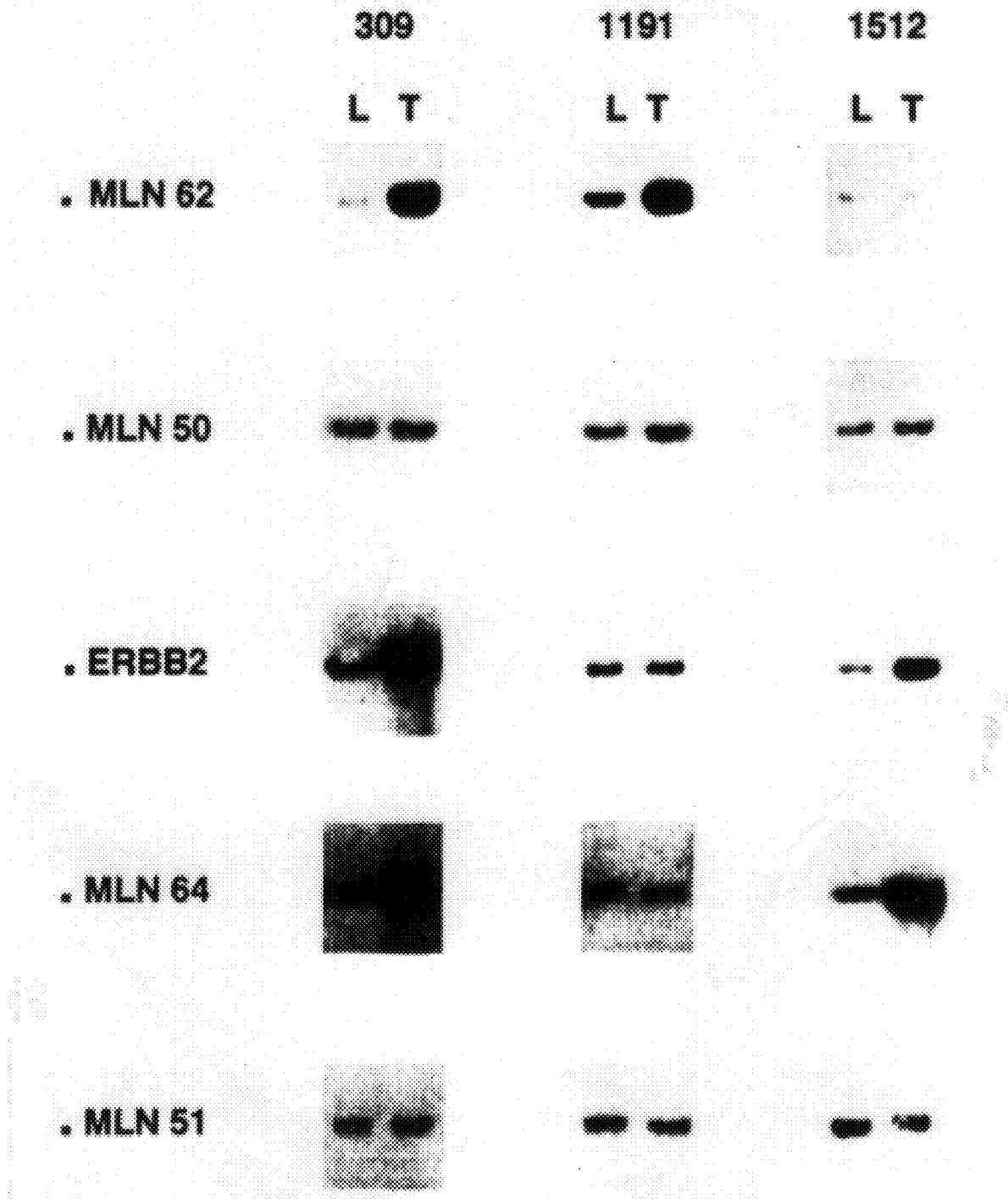
FIG. 30. Southern Blot Analysis of Three Representative Breast Cancer Tumor DNAs with Amplifications of Chromosomal Region 17q11-q21. (L) and (T) indicate matched TaqI-digested DNA samples isolated from peripheral leukocytes and tumor tissue, respectively. Hybridizations were carried out successively with probes MLN 50, 51, 62, 64 and ERBB2. Case 309 shows amplifications for MLN 62, ERBB2 and MLN64. Case 1191 shows amplification for only MLN 62. Case 1512 shows amplifications for ERBB2 and MLN 64.
Figure 31:
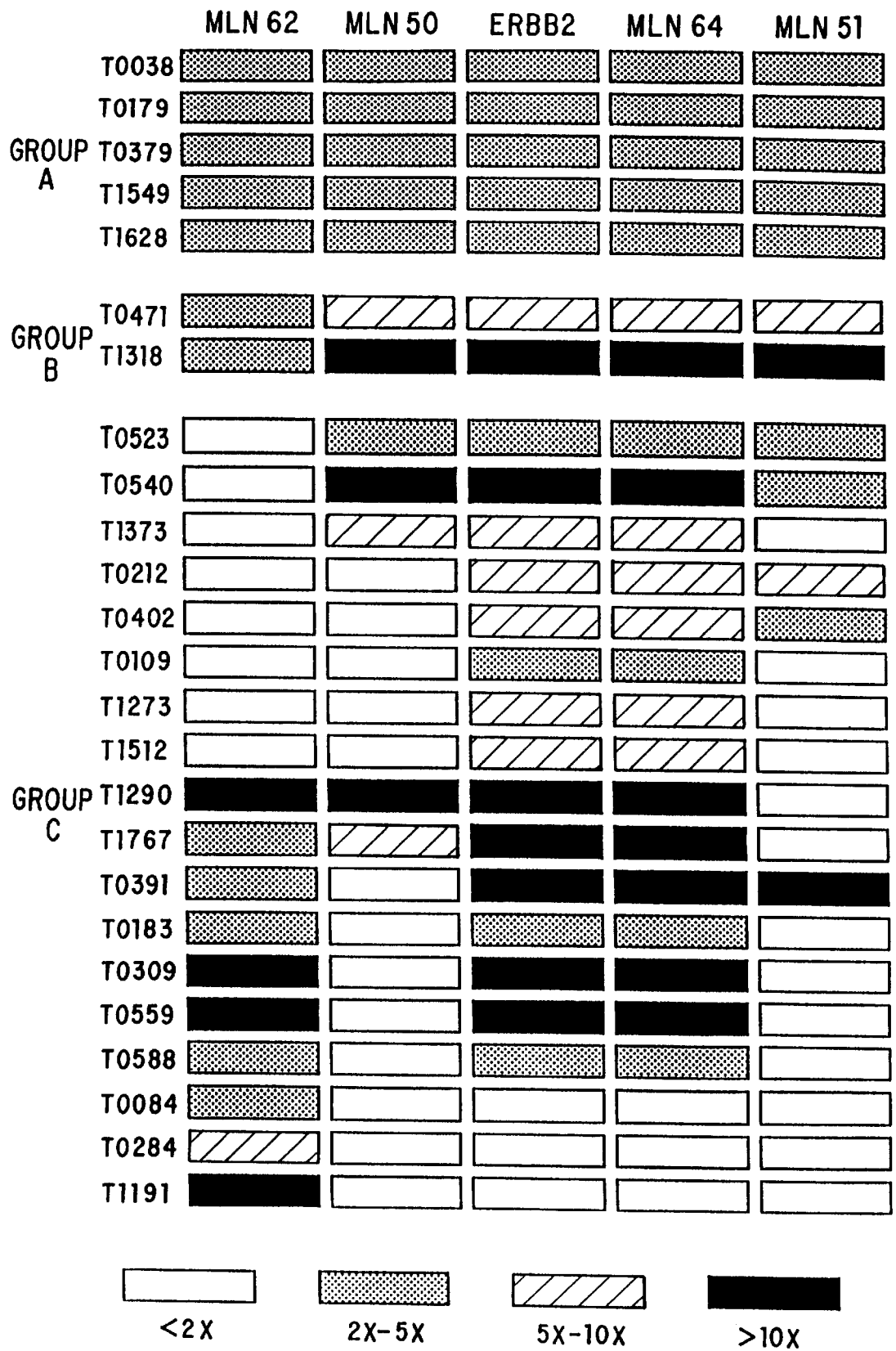
FIG. 31. 17q11-q21 Amplicon Maps in Human Breast Cancer. Lines correspond to each tumor sample, columns to each marker. The densitometrically determined gene dosages (amplification levels) were subdivided into four categories. White boxes represent a normal copy number, shaded boxes 2–5 times amplification, dark shaded boxes 6–10 times amplification, and black boxes > ten times amplification. The loci from 17q11-q21 are ordered according to their chromosomal location, from the most centromeric locus (MLN 62) to the most telomeric locus (MLN 51).

The 25 amplified tumors were subdivided into three groups on the basis of pattern and level of amplification: A, tumors with amplification of all genes with similar amplification levels; B, amplification of all genes with varied amplification levels; and C, amplification of some of these genes. FIG. 30 shows examples of the most common patterns of genetic changes. FIG. 31 summarizes data in the form of amplification maps.

The group A (5 cases) corresponds to the existence of a single but large amplicon at 17q11-q21. For these five tumors, amplification levels were always low (2–5×), suggesting polysomies of the entire long arm of chromosome 17. This first group is not of great interest to identify the candidate genes responsible for the emergence of amplicons.

The two other groups (groups B and C; 12 and 18 cases, respectively) show that the size and the amplification level varied from tumor to tumor. Tumors T0084, T0284 and T1191 had the smallest amplicon involving only MLN 62. With the exception of these three tumors, the amplicons in all the other 17 tumors included ERBB2 and MLN 64. Interestingly, ERBB2 and MLN 64 were always coamplified to similar levels. In 3 cases (T0109, T1273, T1512), these are the only genes amplified at 17q11-q21. In 5 others tumors (T0391, T0183, T0309, T0559 and T0588) the amplicons were discontinuous between MLN 62 and the two loci ERBB2 and MLN 64. In these tumors MLN 50 showed no evidence of amplification.

Our finding suggests the existence of two distinct amplified regions at 17q11-q12 and 17q12-q21 in human primary breast cancer, one includes MLN 62 locus and the other ERBB2 and MLN 64 loci, respectively.

Expression of ERBB2 and the Four MLN Genes in Breast Carcinomas

Whether the amplification of ERBB2 and the four MLN genes contributed to an elevated expression was determined by comparison of RNA expression with DNA amplification. This was performed on a total of 20 tumor samples for which total RNA was available; 10 samples among the 25 tumors amplified in at least one locus and 10 unamplified tumors.

Figure 32:
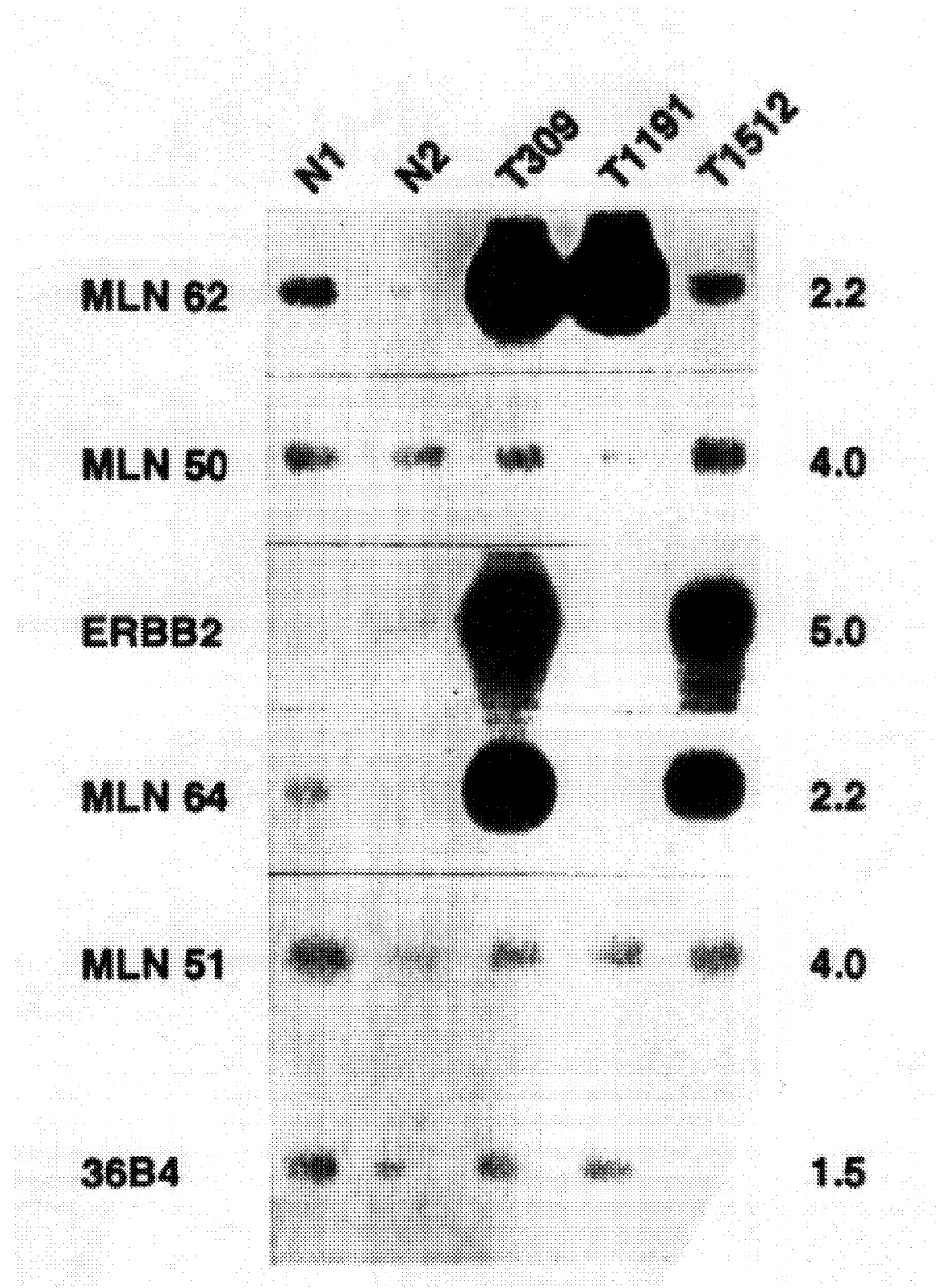
FIG. 32. Northern Blot Analysis of MLN 50, 51, 62, 64 and ERBB2 in Normal and Tumoral Breast Tissues. N1 and N2, normal breast tissues; T309, T1191 and T1512, breast tumor tissues. Hybridizations were carried out successively with probes MLN 50, 51, 62, 64 and ERBB2. Control hybridizations with the 36B4 probe showed that similar amounts of mRNA were loaded in each case. Right, approximate sizes of the mRNAs are indicated in kb. Case 309 shows overexpressions for MLN62, ERBB2 and MLN64, compared with normal breast tissues. Case 1191 shows overexpression for only MLN62. Case 1512 shows overexpressions for ERBB2 and MLN64.

FIG. 32 shows examples of some overexpressed tumors, evaluated by Northern blot analysis. No gross alteration in the size of the mRNA was detected in any samples. We observed a perfect overlap between RNA overexpression and DNA amplification. Amplified tumors were always overexpressed for amplified genes, and the five genes were never overexpressed in the 10 unamplified tumor DNA specimens. Despite the technical difficulty of obtaining quantitative data from Northern blot analyses, a correlation seems observed between levels of RNA and the degree of DNA amplification. The tumors with high amplified levels showed higher mRNA levels, irrespectively of analyzed genes.

Discussion

There are various approaches to search genes whose amplification may be responsible for tumorigenesis. Cytogenetic analysis, CGH and chromosome microdissection have allowed the localization of distinct amplified chromosomal regions which might harbor genes contributing to tumorigenesis. Studies using pulsed field electrophoresis have shown that amplicons in human tumor cells usually comprise large regions of genomic DNA which can be up to several megabases in length and contain several genes (Brookes, S. et al., *Genes Chrom. Cancer* 6:222–231 (1993)). Fine-scale molecular mapping of amplified regions is needed to locate such genes precisely. Thus, coamplification of genes located in a limited chromosomal region have been described in human tumors. Examples include the complex coamplification of multiple genes from 11q13 in human breast cancer (Karlseder, J. et al., *Genes Chrom. Cancer* 9:42–48 (1994)) as well as from 12q13-q14 in human malignant gliomas (Reifenberger, G. et al., *Cancer Res.* 54:4299–4303 (1994)).

Several authors observed amplification of the ERBB2 gene from 17q11-q21 in human breast cancer (Slamon, D. J. et al., *Science* 235:177–182 (1987); Ali, I.U. et al., *Oncogene Res.* 3:139–146 (1988); Borg, A. et al., Oncogene 6:137–143 (1991); Paterson, M. C. et al., *Cancer Res.* 51:556–567 (1991)). As four novel genes from this chromosomal segment have recently been identified and three of them have been found amplified and overexpressed in breast cancer cell lines (Tomasetto, C. et al., *Genomics* 28(3)

:367–376 (1995)), we decided to further characterize the 17q11-q21 region in breast cancer biopsies by studying amplification of these four novel genes, in addition to the ERBB2 gene in a large series of tumor DNAs. The aim was to identify the genes within this amplification, to determine their frequency and their level of amplification, and thereby to more precisely define the actual driver gene(s) in this amplicon(s).

Twenty-five (25.5%) of 98 tumors showed at least one of the five genes amplified. Amplification of these five genes is systematically accompanied by mRNA overexpression. However, it is also known that some tumors with single-copy of an oncogene may overexpress the corresponding mRNA. In the present study, we also examined the expression at RNA level of ERBB2 and the four MLN genes in 10 tumors of the breast, which do not show amplification. We did not observed any unamplified tumor overexpressed for these 5 tested genes. So, it seem that the four MLN genes, like ERBB2 gene, could not be activated by mechanisms other than gene amplification in breast carcinoma such as, for example, alteration of the regulatory sequence of the genes.

In the majority of the altered tumors, amplification encompassed not all the tested loci. The two genes most frequently amplified on 17q11-q21 in our series were ERBB2 and MLN 64 (22.5%) which were systematically coamplified and overexpressed at similar levels. The invariable coamplification of ERBB2 and MLN 64 seen in our study indicates that both genes are likely to be located in close proximity to each other at 17q12-q21. In consequence, the amplification and consequent overexpression of MLN 64 as well as ERBB2 gene could be of pathogenetic significance for breast neoplastic growth. A third gene, MLN 62, can be regarded as the possible target selected for a second amplicon. This gene is located centromeric to MLN 64 and ERBB2 genes at 17q11-12. Although MLN 62 gene was less frequently amplified (17.5%) than MLN 64 and ERBB2 genes, it has been found with high levels of amplification in most tumors which showed two distinct amplified regions at 17q11-q21 and was the only amplified and overexpressed gene in three tumors (T0084, T0284 and T1191). These findings suggest that in some tumors amplification of MLN 62 may provide a selective growth advantage. Even if the amplicons observed in our breast tumor series frequently contained MLN 50 and MLN 51, the amplification maps suggest that these two genes are not the target genes of the amplification, they were invariably coamplified with MLN 64 and ERBB2 and never showed the highest amplification level in individual tumors. Four other ERBB2 neighboring genes have previously been observed coamplified with ERBB2 in 10–50% of ERBB2 amplified tumors, including THRA1 (van de Vijver, M. et al., *Mol. Cell Biol* 7:2019–2023 (1987)), RARA (Keith, W. N. et al., *Eur. J. Cancer* 29a:1469–1475 (1993)), GRB-7 (Stein, D. et al., *EMBO J.* 13:1331–1340 (1994)) and TOP2A (Smith, K. et al., *Oncogene* 8:933–938 (1993)). These four genes were never amplified alone without ERBB2 amplification. Our data, together with these other results therefore suggest that MLN 50 and MLN 51, as well as THRA1, RARA, GRB-7 and TOP2A, are just incidentally included in some 17q12-q21 amplicons.

To date, little is known about the physiological and pathological functions of MLN 62 and MLN 64. If MLN 64 gene showed little homology with others described, MLN 62/CART1/TRAF4 encodes a protein exhibiting 3 domains also observed in the CD40-binding protein and in the tumor necrosis factor (TNF) receptor-associated factor 2 (TRAF2), both involved in signal transduction mediated by the TNF receptor family. So, MLN 62/CART1/TRAF4 gene may be involved in TNF-related cytokine signal transduction in breast carcinoma.

In conclusion, the present study shows that DNA amplification is frequently observed in two different regions at 17q11-q21 in human breast cancer. This suggests that several genes in these two regions are involved in the initiation and/or progression of human breast cancer. Our preliminary mapping of these 17q11-q21 amplicons in 25 amplified breast tumors shows that they consistently include either MLN 62/CART1TRAF4 (17q11-q12) or MLN 64 and ERBB2 (17q12-q21). The two new genes are good candidates for a role in breast cancer because, like ERBB2, their amplification leads to their overexpression. The main conclusion drawn from our data is that, although ERBB2 remains a good candidate as one of genes under selection in the 17q11-q21 amplicons, two novel candidate genes have been identified as driver genes of these amplicons. Thus, the elucidation of the physiological and pathological significance of MLN 62/CART1/TRAF4 and MLN 64 would confirm the involvement of these two genes in breast carcinogenesis.

It will be appreciated to those skilled in the art that the invention can be performed within a wide range of equivalent parameters of composition, concentrations, modes of administration, and conditions without departing from the spirit or scope of the invention or any embodiment thereof.

The disclosure of all references, patent applications and patents recited herein are hereby incorporated by reference.

What is claimed is:

1. An isolated nucleic acid molecule comprising a polynucleotide selected from the group consisting of:

(a) a polynucleotide encoding a polypeptide having an amino acid sequence as shown in SEQ ID NO:4;

(b) a polynucleotide encoding a polypeptide having an amino acid sequence as encoded by the MLN50 cDNA contained in ATCC Deposit No. 97068;

(c) a polynucleotide having a nucleotide sequence at least 90% identical to the nucleotide sequence of the polynucleotide of (a) or (b);

(d) a polynucleotide having a nucleotide sequence complementary to the nucleotide sequence of any of the polynucleotides of (a)–(c);

(e) a polynucleotide encoding a polypeptide having an amino acid sequence as shown in SEQ ID NO:8;

(f) a polynucleotide encoding a polypeptide having an amino acid sequence as encoded by the MLN51 cDNA contained in ATCC Deposit No. 97611;

(g) a polynucleotide having a nucleotide sequence at least 90% identical to the nucleotide sequence of the polynucleotide of (e) or (f);

(h) a polynucleotide having a nucleotide sequence complementary to the nucleotide sequence of any of the polynucleotides of (e)–(g);

(i) a polynucleotide encoding a polypeptide having an amino acid sequence as shown in SEQ ID NO:10;

(j) a polynucleotide encoding a polypeptide having an amino acid sequence as encoded by the D53 cDNA contained in ATCC Deposit No. 97607;

(k) a polynucleotide having a nucleotide sequence at least 90% identical to the nucleotide sequence of the polynucleotide of (i) or (j); and (l) a polynucleotide having a nucleotide sequence complementary to the nucleotide sequence of any of the polynucleotides of (i)–(k).

2. The isolated nucleic acid molecule of claim 1, which is a DNA molecule.

3. The isolated nucleic acid molecule of claim 2, wherein said polynucleotide is cDNA.

4. A method for making a recombinant vector comprising inserting the isolated nucleic acid molecule of claim 1 into a vector.

5. A recombinant vector produced by the method of claim 4.

6. A method of making a recombinant host cell comprising introducing the recombinant vector of claim 5 into a host cell.

7. A recombinant host cell produced by the method of claim 6.

8. A recombinant method for producing a polypeptide comprising culturing a recombinant host cell wherein said recombinant host cell comprises the isolated nucleic acid molecule of (a), (b), (d), (e), (f), (h), (i), (j), or (l) of claim 1.

9. An isolated nucleic acid molecule comprising a nucleic acid sequence encoding any one of the MLN 64 variants A–G disclosed in Table VI.

10. An isolated polypeptide selected from the group consisting of:

(a) a polypeptide having the amino acid sequence as shown in SEQ ID NO:4;

(b) a polypeptide having the amino acid sequence as encoded by the MLN50 cDNA contained in ATCC Deposit No. 97608;

(c) a polypeptide having the amino acid sequence as shown in SEQ ID NO:8;

(d) a polypeptide having the amino acid sequence as encoded by the MLN51 cDNA contained in ATCC Deposit No. 97611;

(e) a polypeptide having the amino acid sequence as shown in SEQ ID NO:10; and (f) a polypeptide having the amino acid sequence as encoded by the D53 cDNA contained in ATCC Deposit No. 97607.

11. An isolated polypeptide which is any one of the MLN 64 variants A–G disclosed in Table VI.

12. An isolated nucleic acid fragment of a polynucleotide shown in SEQ ID NO:3 or a fragment of the MLN50 cDNA contained in ATCC Deposit No. 97608, wherein said fragment is at least 50 bp in length and does not have a sequence described in GenBank Accession No. T15543 SEQ ID NO:74, T33692 SEQ ID NO:75, T32123 SEQ ID NO:76, T34158 SEQ ID NO:77, F04305 SEQ ID NO:78, T33826 SEQ ID NO:79, T32139 SEQ ID NO:80, T51225 SEQ ID NO:81, D12116 SEQ ID NO:82, T61881 SEQ ID NO:83, T51339 SEQ ID NO:84, T24771 SEQ ID NO:85, T10815 SEQ ID NO:86, T60382 SEQ ID NO:87, M86141 SEQ ID NO:88, T34342 SEQ ID NO:89, T08601 SEQ ID NO:90, T32161 SEQ ID NO:91, T34065 SEQ ID NO:92, Z45434 SEQ ID NO:93, T08349 SEQ ID NO:94, or F06105 SEQ ID NO:95.

13. The isolated nucleic acid fragment of claim 12, which is contained in a recombinant vector.

14. An isolated nucleic acid fragment comprising a nucleotide sequence encoding 50 contiguous amino acids of SEQ ID NO:8 or 50 contiguous amino acids as encoded by the MLN51 cDNA contained in ATCC Deposit No. 97611, wherein said fragment does not have a sequence described in GenBank Accession No. Z25173 SEQ ID NO:96, D19971 SEQ ID NO:97 or D11736 SEQ ID NO:98.

15. The isolated nucleic acid fragment of claim 14, which is contained in a recombinant vector.

16. An isolated nucleic acid molecule comprising a polynucleotide selected from the group consisting of:

(a) a polynucleotide encoding a polypeptide having an amino acid sequence as shown in SEQ ID NO:2;

(b) a polynucleotide encoding a polypeptide having an amino acid sequence as encoded by the MLN62 cDNA contained in ATCC Deposit No. 97610;

(c) a polynucleotide having a nucleotide sequence at least 90% identical to the nucleotide sequence of the polynucleotide of (a) or (b); and (d) a polynucleotide having a nucleotide sequence complementary to the nucleotide sequence of any of the polynucleotides of (a)–(c).

17. The isolated nucleic acid molecule of claim 16, which is a polynucleotide encoding a polypeptide having an amino acid sequence as shown in SEQ ID NO:2.

18. The isolated nucleic acid molecule of claim 16, which is a polynucleotide encoding a polypeptide having an amino acid sequence as encoded by the MLN62 cDNA contained in ATCC Deposit No. 97610.

19. The isolated nucleic acid molecule of claim 16, which is a polynucleotide having a nucleotide sequence at least 90% identical to the nucleotide sequence of the polynucleotide of (a) or (b).

20. The isolated nucleic acid molecule of claim 16, which is a polynucleotide having a nucleotide sequence complementary to the nucleotide sequence of any of the polynucleotides of (a)–(c).

21. The isolated nucleic acid molecule of claim 16, which is a DNA molecule.

22. The isolated nucleic acid molecule of claim 21, wherein said polynucleotide is cDNA.

23. A method for making a recombinant vector comprising inserting the isolated nucleic acid molecule of claim 16 into a vector.

24. A recombinant vector produced by the method of claim 23.

25. A method of making a recombinant host cell comprising introducing the recombinant vector of claim 24 into a host cell.

26. A recombinant host cell produced by the method of claim 25.

27. A recombinant method for producing a polypeptide comprising culturing a recombinant host cell wherein said recombinant host cell comprises the isolated nucleic acid molecule of (a), (b), or (d) of claim 16.

28. An isolated polypeptide selected from the group consisting of:
 (a) a polypeptide having the amino acid sequence as shown in SEQ ID NO:2; and
 (b) a polypeptide having the amino acid sequence as encoded by the MLN62 cDNA contained in ATCC Deposit No. 97610.

29. The isolated polypeptide of claim 28, which is a polypeptide having the amino acid sequence as shown in SEQ ID NO:2.

30. The isolated polypeptide of claim 28, which is a polypeptide having the amino acid sequence as encoded by the MLN62 cDNA contained in ATCC Deposit No. 97610.

31. An isolated nucleic acid molecule comprising a polynucleotide selected from the group consisting of:
 (a) a polynucleotide encoding a polypeptide having an amino acid sequence as shown in SEQ ID NO:6;
 (b) a polynucleotide encoding a polypeptide having an amino acid sequence as encoded by the MLN64 cDNA contained in ATCC Deposit No. 97609;
 (c) a polynucleotide having a nucleotide sequence at least 90% identical to the nucleotide sequence of the polynucleotide of (a) or (b);
 (d) a polynucleotide fragment encoding 50 contiguous amino acids of SEQ ID NO:6 or 50 contiguous amino acids as encoded by the MLN64 cDNA contained in ATCC Deposit No. 97609, wherein said fragment does not have a sequence described in GenBank Accession No. M85471 SEQ ID NO:111, T49922 SEQ ID NO:112, T85470 SEQ ID NO:113, T85372 SEQ ID NO:114, R02020 SEQ ID NO:115, S70803 SEQ ID NO:116, R02021 SEQ ID NO:117, R17500 SEQ ID NO:118, R41043 SEQ ID NO:119, R36697 SEQ ID NO:120, R37545 SEQ ID NO:121, R42594 SEQ ID NO:122, R48774 SEQ ID NO:123 or R48877 SEQ ID NO:124; and
 (e) a polynucleotide having a nucleotide sequence complementary to the nucleotide sequence of any of the polynucleotides of (a)–(d).

32. The isolated nucleic acid molecule of claim 31, which is a polynucleotide encoding a polypeptide having an amino acid sequence as shown in SEQ ID NO:6.

33. The isolated nucleic acid molecule of claim 31, which is a polynucleotide encoding a polypeptide having an amino acid sequence as encoded by the MLN64 cDNA contained in ATCC Deposit No. 97609.

34. The isolated nucleic acid molecule of claim 31, which is a polynucleotide having a nucleotide sequence at least 90% identical to the nucleotide sequence of the polynucleotide of (a) or (b).

35. The isolated nucleic acid molecule of claim 31, which comprises a polynucleotide fragment encoding 50 contiguous amino acids of SEQ ID NO:6 or 50 contiguous amino acids as encoded by the MLN64 cDNA contained in ATCC Deposit No. 97609, wherein said fragment does not have a sequence described in GenBank Accession No. M85471 SEQ ID NO:111, T49922 SEQ ID NO:112, T85470 SEQ ID NO:113, T85372 SEQ ID NO:114, R02020 SEQ ID NO:115, S70803 SEQ ID NO:116, R02021 SEQ ID NO:117, R17500 SEQ ID NO:118, R41043 SEQ ID NO:119, R36697 SEQ ID NO:120, R37545 SEQ ID NO:121, R42594 SEQ ID NO:122, R48774 SEQ ID NO:123 or R48877 SEQ ID NO: 124.

36. The isolated nucleic acid molecule of claim 31, which is a polynucleotide having a nucleotide sequence complementary to the nucleotide sequence of any of the polynucleotides of (a)–(d).

37. The isolated nucleic acid molecule of claim 31, which is a DNA molecule.

38. The isolated nucleic acid molecule of claim 37, wherein said polynucleotide is cDNA.

39. A method for making a recombinant vector comprising inserting the isolated nucleic acid molecule of claim 31 into a vector.

40. A recombinant vector produced by the method of claim 39.

41. A method of making a recombinant host cell comprising introducing the recombinant vector of claim 40 into a host cell.

42. A recombinant host cell produced by the method of claim 41.

43. A recombinant method for producing a polypeptide comprising culturing a recombinant host cell wherein said recombinant host cell comprises the isolated nucleic acid molecule of (a), (b), (d), or (e) of claim 31.

44. An isolated polypeptide selected from the group consisting of:
 (a) a polypeptide having the amino acid sequence as shown in SEQ ID NO:6;
 (b) a polypeptide having the amino acid sequence as encoded by the MLN64 cDNA contained in ATCC Deposit No. 97609; and
 (c) a polypeptide fragment of (a) or (b), wherein said fragment is at least 50 amino acids in length.

45. The isolated polypeptide of claim 44, which is a polypeptide having the amino acid sequence as shown in SEQ ID NO:6.

46. The isolated polypeptide of claim 44, which is a polypeptide having the amino acid sequence as encoded by the MLN64 cDNA contained in ATCC Deposit No. 97609.

47. The isolated polypeptide of claim 44, which is a polypeptide fragment of (a) or (b), wherein said fragment is at least 50 amino acids in length.

48. An isolated polypeptide comprising a polypeptide fragment selected from the group consisting of:
 (a) a polypeptide fragment of a polypeptide having the amino acid sequence as shown in SEQ ID NO:4, or as encoded by the MLN50 cDNA contained in ATCC Deposit No. 97608, wherein said fragment is at least 50 amino acids in length; and
 (b) a polypeptide fragment of a polypeptide having the amino acid sequence as shown in SEQ ID NO:8, or as encoded by the MLN51 cDNA contained in ATCC Deposit No. 97611, wherein said fragment is at least 50 amino acids in length.

* * * * *